United States Patent [19]
Totani et al.

[11] Patent Number: 5,770,108
[45] Date of Patent: Jun. 23, 1998

[54] PYRIMIDINE COMPOUND AND LIQUID CRYSTAL COMPOSITION AND LIQUID CRYSTAL ELEMENT USING THE SAME

[75] Inventors: Yoshiyuki Totani, Yokohama; Motokazu Hirao, Kabato-gun; Atsuo Otsuji, Yokohama; Tsutomu Ishida, Yokohama; Hiroe Kayashima, Yokohama; Masakatsu Nakatsuka, Yokohama, all of Japan

[73] Assignee: Mitsui Toatsu Chemicals, Inc., Tokyo, Japan

[21] Appl. No.: 668,157

[22] Filed: Jun. 21, 1996

[30] Foreign Application Priority Data

Jun. 28, 1995 [JP] Japan .................... 7-162099
Aug. 15, 1995 [JP] Japan .................... 7-207960

[51] Int. Cl.$^6$ .................... C09K 19/34; C09K 19/32; C07D 69/76; C07D 239/02

[52] U.S. Cl. .................... 252/299.61; 252/299.62; 252/299.63; 568/647; 568/630; 568/632; 568/634; 560/100; 546/339; 546/342; 544/298

[58] Field of Search .................... 252/299.61, 299.62, 252/299.63, 299.01; 544/298; 560/100; 546/339, 342; 568/630, 632, 634, 647, 633

[56] References Cited

U.S. PATENT DOCUMENTS

| 5,072,021 | 12/1991 | Nakatsuka et al. | 560/56 |
| 5,290,478 | 3/1994 | Satoh et al. | 252/299.62 |
| 5,496,500 | 3/1996 | Toyne et al. | 252/299.61 |
| 5,589,103 | 12/1996 | Yamada et al. | 252/299.61 |

FOREIGN PATENT DOCUMENTS

| 643119 | 3/1995 | European Pat. Off. . |
| 4236102 | 4/1994 | Germany . |
| 4240041 | 6/1994 | Germany . |
| 56-107216 | 8/1981 | Japan . |
| 59-118744 | 7/1984 | Japan . |
| 61-195187 | 8/1986 | Japan . |
| 6-25055 | 2/1994 | Japan . |
| 6-25060 | 2/1994 | Japan . |
| 6-122875 | 5/1994 | Japan . |
| 6-228057 | 8/1994 | Japan . |
| 7-233109 | 9/1995 | Japan . |

OTHER PUBLICATIONS

Noel A. Clark et al, *Appl. Phys. Lett.*, "Submicrosecond Bistable Electro–Optic Switching in Liquid Crystals", vol. 36, No. 11, pp. 899–901 (1980).
L.A. Beresnev et al, *Mol. Cryst. Liq. Cryst.*, vol. 89, pp. 327–338 (1982).

*Primary Examiner*—C. H. Kelly
*Attorney, Agent, or Firm*—Burns, Doane, Swecker & Mathis

[57] ABSTRACT

A novel pyrimidine compound represented by the following Formulas (1) and (2), a liquid crystal composition containing said compound and a liquid crystal element having excellent characteristics such as high speed response, orientation and high contrast ratio.

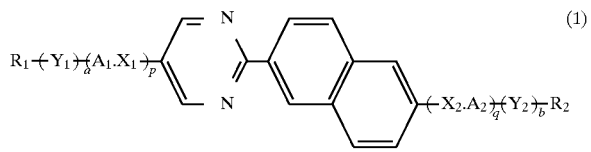

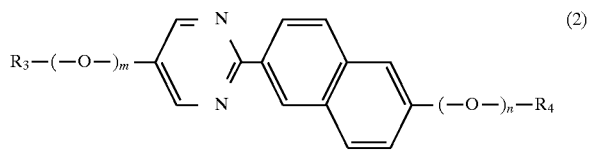

wherein $R_1$ and $R_2$ each represent a linear or branched alkyl or alkenyl group, an alkoxyl or alkenyloxy group; $R_3$ and $R_4$ each represent a linear or branched alkyl group or alkenyl group; $A_1$ and $A_2$ each represent a substituted or unsubstituted 1,4-phenylene group, a pyridine-2,5-diyl or trans-1,4-cyclohexylene group; $X_1$ and $X_2$ each represent a single bond, —COO—, —OCO—, —OCH$_2$ or —CH$_2$O— group; $Y_1$ and $Y_2$ each represent —COO— or —OCO— group; and a, b, p, q, m and n each represent 0 or 1, provided that a+b+p+q is not 0.

16 Claims, 2 Drawing Sheets

PYRIMIDINE COMPOUND AND LIQUID CRYSTAL COMPOSITION AND LIQUID CRYSTAL ELEMENT USING THE SAME

BACKGROUND OF THE INVENTION (1) Field of the Invention

The present invention relates to a novel pyrimidine compound, more specifically to a novel pyrimidine compound useful as a component for a liquid crystal composition used for a liquid crystal display element, a liquid crystal composition containing said compound, and a liquid crystal element using the liquid crystal composition.

(2) Description of the Related Art

A TN (twisted nematic) type display element is most widely used as a liquid crystal display element at present. This TN type display system is inferior in a response time as compared with a light-emitting type element (cathode tube, electroluminescence, plasma display, and the like). Accordingly, an STN (super twisted nematic) type display element in which the twisted angle is controlled to 180° to 270° has been developed, but the response time is still inferior. Thus, while various efforts for the improvement have been made, the TN type liquid crystal display element having a shorter response time has not yet been achieved.

However, a novel display system using a ferroelectric liquid crystal which is actively investigated in recent years has a possibility to improve markedly in a response time [N. A. Clark et al, Applied Phys. Lett., 36, 899 (1980)].

This system makes use of a chiral smectic phase such as a chiral smectic C phase showing ferroelectricity. It is known that a phase showing ferroelectricity is not only the chiral smectic C phase, but chiral smectic F, G, H and I phases also are ferroelectric liquid crystal phases showing ferroelectricity. These smectic liquid crystal phases belong to tilt series chiral smectic phases. Among them, a chiral smectic C phase having a low viscosity is preferred in terms of practical use.

Various liquid crystal compounds showing the chiral smectic C phase have so far been investigated, and a lot of compounds have already been found and produced. At present, however, a single compound can not meet the optimization of many characteristics (high speed response, orientation, high contrast ratio, memory stability, and temperature dependency of these various characteristics) which are required when actually applying liquid crystal compounds to ferroelectric liquid crystal display elements, and therefore ferroelectric liquid crystal compositions obtained by blending several liquid crystal compounds are used.

A ferroelectric liquid crystal composition does not always comprise only compounds showing ferroelectric liquid crystal phases, and it is disclosed in Japanese Patent Application Laid-Open No. 61-195187 (1986) that compositions showing ferroelectric liquid crystal phases as a whole can be obtained by employing compounds or compositions showing non-chiral smectic C, F, G, H and I phases for fundamental materials and blending them with one or plural compounds showing ferroelectric liquid crystal phases. Further, it is reported that ferroelectric liquid crystal compositions can be obtained as a whole by employing compounds or compositions showing phases such as a smectic C phase for fundamental materials and blending them with one or plural compounds which are optically active but do not show ferroelectric liquid crystal phases [Mol. Cryst. Liq. Cryst., 89, 327 (1982)].

It can be found from the summary of the above facts that regardless of showing a ferroelectric liquid crystal phase, ferroelectric liquid crystal compositions can be constituted by blending one or plural compounds which are optically active with compounds showing phases such as non-chiral smectic C phases.

Thus, various compounds can be used as structural components for liquid crystal compositions. Practically, however, desired are liquid crystal compounds or mixtures thereof showing smectic C phases or chiral smectic C phases in a wide temperature range including room temperatures. Known as components for these smectic C liquid crystal compositions are phenyl benzoate series liquid crystal compounds, biphenyl series liquid crystal compounds, phenyl pyrimidine series liquid crystal compounds, and tolan series liquid crystal compounds. However, it is not reasonable to say that liquid crystal compositions containing these compounds as components have sufficiently satisfactory characteristics.

A lot of chiral smectic C liquid crystal compositions which have so far been investigated have a chevron layer structure (a layer structure in which a layer is bent), and this prevents response of spontaneous polarization to an applied electric field from being efficiently made, which in turn increases response time and lowers contrast ratio due to a defect in zig-zag orientation in some cases.

Accordingly, liquid crystal materials having non-chiral or chiral smectic C phases of a book shelf layer structure or a structure close thereto are desired.

Compounds having naphthalene rings and liquid crystal compositions containing them are known as liquid crystal compounds and compositions having book shelf layer structures (Japanese Patent Application Laid-Open No. 6-122875 (1994), etc.), and various compounds having naphthalene rings have been synthesized and investigated [U.S. Pat. No. 4,585,575, Japanese Patent Application Laid-Open No. 6-25055 (1994), Japanese Patent Application Laid-Open No. 6-25060, Japanese Patent Application Laid-Open No. 6-40985, Japanese Patent Application Laid-Open No. 6-228057 (German Patent Publication Laid-open No. 4240041), and the like].

However, problems still remain in these compounds as shown below:

(1) because of inferior compatibility in blending various liquid crystal compounds used for liquid crystal compositions, that is, inferior compatibility in blending several kinds of compounds used for liquid crystal compositions, some specific components are deposited from a crystal liquid phase in the form of crystals, or a liquid crystal temperature region which liquid crystal compounds have is notably reduced by blending;

(2) optimization of a tilt angle θ (the contrast ratio is maximized at θ=22.5° based on a relational expression of an incident light intensity $I_o$ with a transmitted light intensity I in a liquid crystal element making use of birefringence of liquid crystal [$I/I_o = \sin^2 4\theta \cdot \sin^2 (\pi d \Delta n/\lambda)$], wherein d represents a cell thickness, and Δn represents a refractive index anisotropy and Δ represents a wavelength of incident light]); and (3) orientation characteristics on various oriented films (removal of orientation defects such as a zig-zag orientation defect, and uniformity of orientation).

Accordingly, it is required at present to test various materials showing smectic C phases or chiral smectic C phases to optimize response time, memory stability, a layer structure in smectic C phase, a tilt angle, orientation characteristics on oriented films, and compatibility between liquid crystal compounds when blending them into crystal liquid compositions.

SUMMARY OF THE INVENTION

An object of the present invention is to provide a liquid crystal compound or a compound useful as a component for a liquid crystal composition which is suited to improve various characteristics such as high speed response, orientation, and high contrast ratio when the liquid crystal compound is blended into a ferroelectric liquid crystal composition in order to put a ferroelectric liquid crystal element into practical use, a liquid crystal composition containing said compounds and a liquid crystal element using the liquid crystal composition.

First, the present invention relates to a pyrimidine compound represented by the following Formula (1):

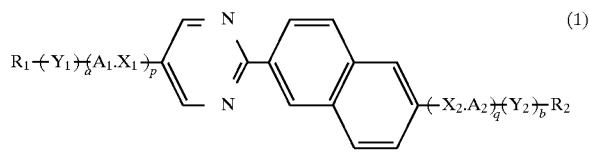

wherein $R_1$ and $R_2$ each represent a linear or branched alkyl group or alkoxyl group having 1 to 24 carbon atoms or a linear or branched alkenyl group or alkenyloxy group having 2 to 24 carbon atoms and each group may be substituted with halogen atoms; the —$CH_2$— groups (provided that the adjacent —$CH_2$— groups and the —$CH_2$— groups bonded to $Y_1$, $Y_2$ or an aromatic ring are excluded) which are present in said alkyl group, alkoxyl group, alkenyl group and alkenyloxy group may be substituted with an oxygen atom, a sulfur atom, a —CO— group, a —COO— group, or a —COO— group; $R_1$ and $R_2$ may have asymmetric carbon atoms, and said asymmetric carbon atoms may be optically active; $A_1$ and $A_2$ each represent a substituted or unsubstituted 1, 4-phenylene group, a pyridine-2, 5-diyl group or a trans-1, 4-cyclohexylene group; $X_1$ and $X_2$ each represent a connecting group selected from a single bond, a —COO— group, a —OCO— group, a —OCH$_2$— group, and a —CH$_2$O— group; $Y_1$ and $Y_2$ each represent a —COO— group or a —OCO— group (provided that when $Y_1$ is a —OCO— group, $R_1$ is not a linear or branched alkoxyl group or alkenyloxy group, and when $Y_2$ is a —COO— group, $R_2$ is not a linear or branched alkoxyl group or alkenyloxy group); and a, b, p and q each represent 0 or 1, provided that a+b+p+q is not 0.

The present invention also relates to a pyrimidine compound represented by the following Formula (2):

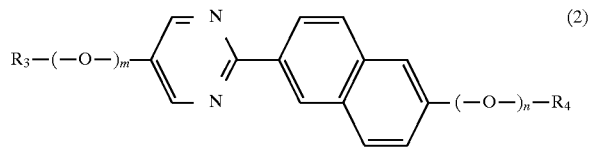

wherein $R_3$ and $R_4$ each represent a linear or branched alkyl group or alkenyl group having 3 to 24 carbon atoms and each group may be substituted with halogen atoms; m and n each represent 0 or 1; at least one —$CH_2$— group (provided that the adjacent —$CH_2$— groups and the —$CH_2$— groups bonded to oxygen atoms or aromatic rings are excluded) present in the alkyl group or alkenyl group of at least one of $R_3$ and $R_4$ is substituted with an oxygen atom; and the branched alkyl group or alkenyl group may have asymmetric carbon atoms, and the asymmetric carbon atoms may be optically active.

Further, the present invention relates to a pyrimidine compound represented by the following Formula (3) or (4):

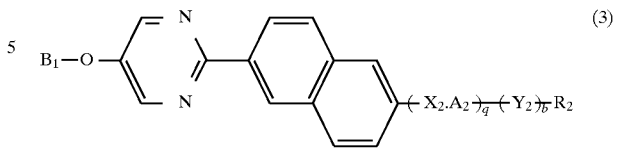

wherein $B_1$ represents a hydrogen atom or a benzyl group; $R_2$ represents a linear or branched alkyl group or alkoxyl group having 1 to 24 carbon atoms or a linear or branched alkenyl group or alkenyloxy group having 2 to 24 carbon atoms and each group may be substituted with halogen atoms; the —$CH_2$— groups (provided that the adjacent —$CH_2$— groups and the —$CH_2$— groups bonded to $Y_1$, $Y_2$ or an aromatic ring are excluded) which are present in said alkyl group, alkoxyl group, alkenyl group and alkenyloxy group may be substituted with an oxygen atom, a sulfur atom, a —CO— group, a —COO— group and a —OCO— group; $R_2$ may have asymmetric carbon atoms, and the asymmetric carbon atoms may be optically active; $A_2$ represents a substituted or unsubstituted 1,4-phenylene group, a pyridine-2,5-diyl group or a trans-1,4-cyclohexylene group; $X_2$ represents a connecting group selected from a single bond, a —COO— group, a —OCO— group, a —OCH$_2$— group and a —CH$_2$O— group; $Y_2$ represents a —COO— group or a —OCO— group (provided that when $Y_2$ is a —COO— group, $R_2$ is not a linear or branched alkoxyl group or alkenyloxy group); and b and q each represent 0 or 1, provided that b+q is not 0;

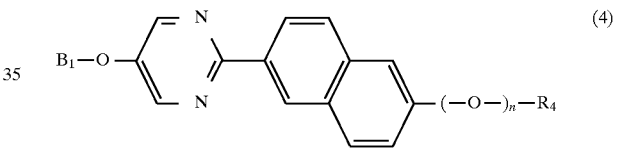

wherein $B_1$ represents a hydrogen atom or a benzyl group; $R_4$ represents a linear or branched alkyl group or alkenyl group having 3 to 24 carbon atoms and each group may be substituted with halogen atoms; n represents 0 or 1; at least one —$CH_2$— group (provided that the adjacent —$CH_2$— groups and the —$CH_2$— groups bonded to oxygen atoms or aromatic rings are excluded) present in the alkyl group or alkenyl group of $R_4$ is substituted with an oxygen atom; and the branched alkyl group or alkenyl group may have asymmetric carbon atoms, and the asymmetric carbon atoms may be optically active.

Further, the present invention relates to a liquid crystal composition characterized by containing at least one pyrimidine compound represented by Formula (1) or (2), and a liquid crystal element using the liquid crystal composition.

The pyrimidine compound of the present invention is excellent particularly in orientation characteristics and has an excellent compatibility with other liquid crystal compounds and a large tilt angle, which make it possible to provide a pyrimidine compound effective for improving the response time.

Figure 1:
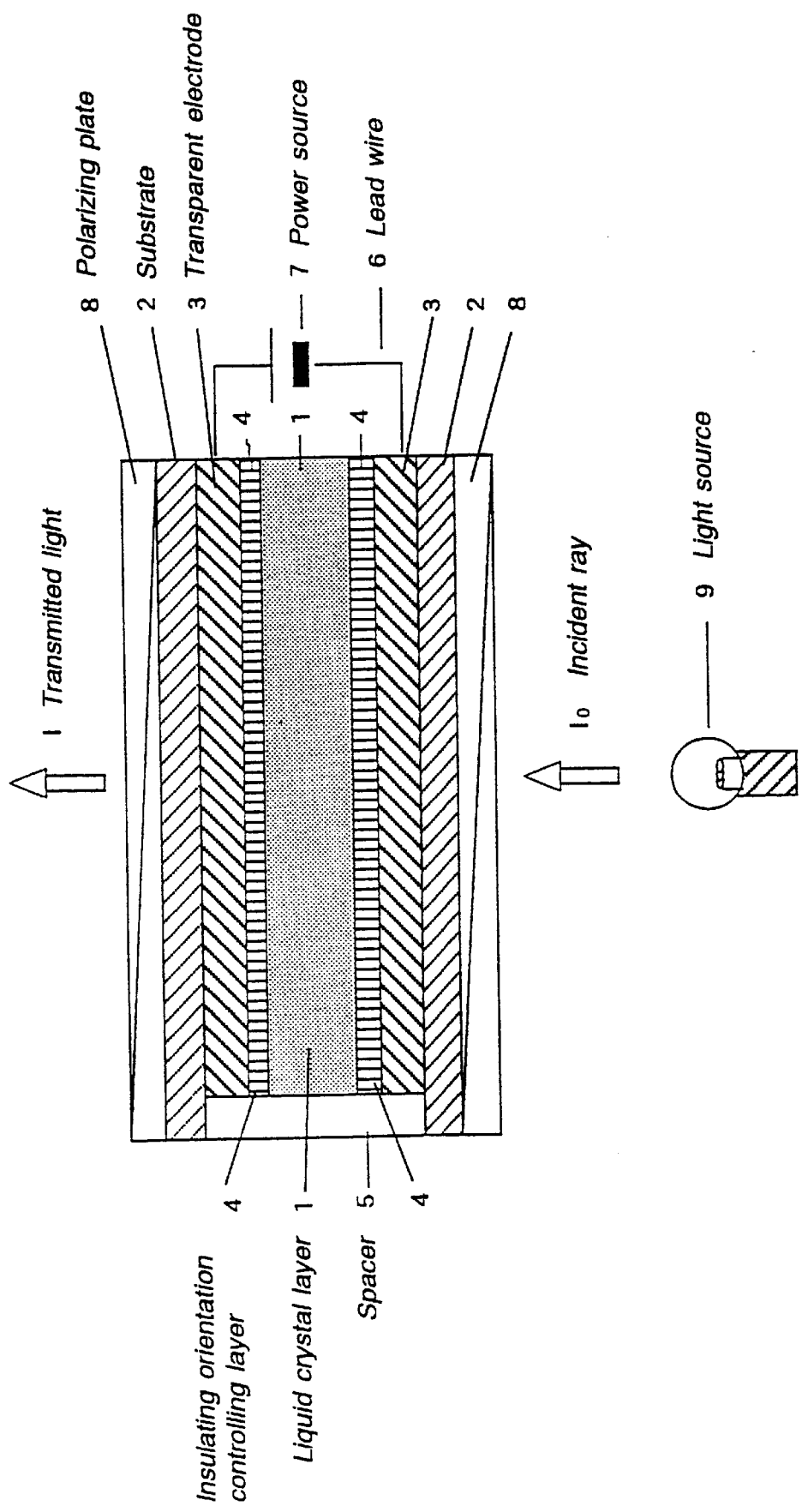
FIG. 1 is a schematic, cross-sectional drawing of one example of a liquid crystal element using a liquid crystal showing a chiral smectic phase.

DETAILED DESCRIPTION OF THE PREFERRED EMBODIMENTS
The present invention will be explained below in detail.
The pyrimidine compound of the present invention represented by Formula (1) has any of four structures of (1-A), (1-B), (1-C), and (1-D) when p and q each are 0 or 1:
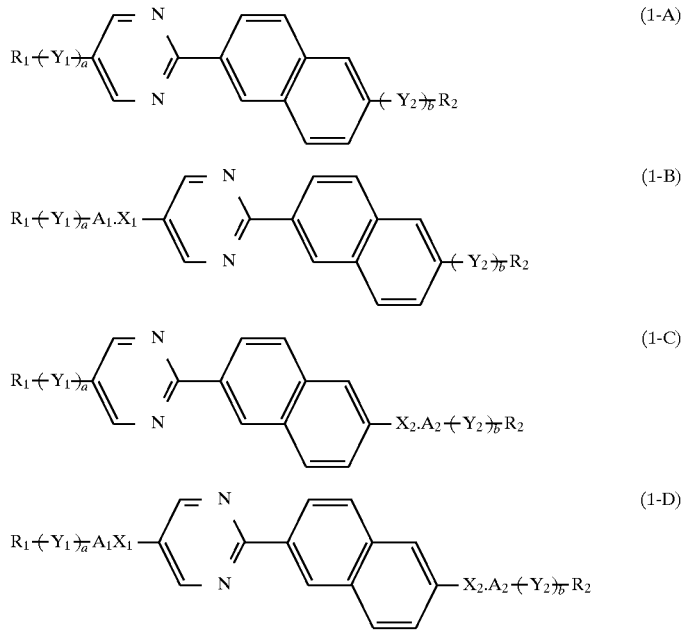
Further, the compound in which a and b each are 0 or 1 in (1-A), (1-B), (1-C), and (1-D) has any of the structures of (1-A1 to 1-A3), (1-B1 to 1-B4), (1-C1 to 1-C4), and (1-D1 to 1-D4):
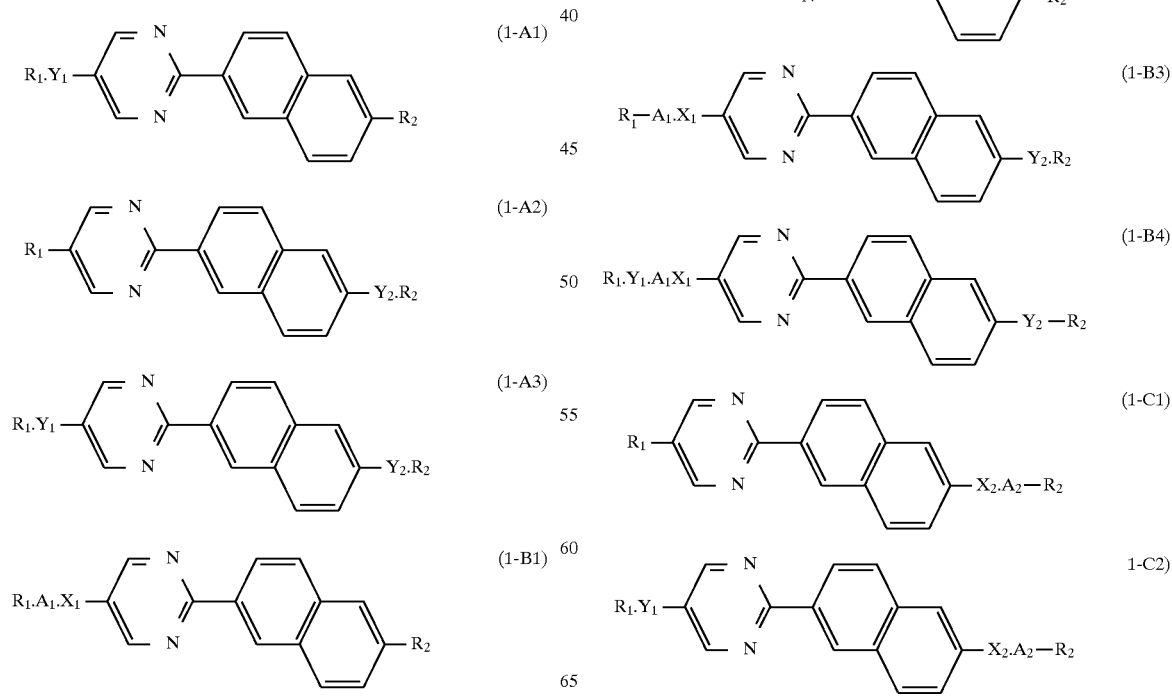

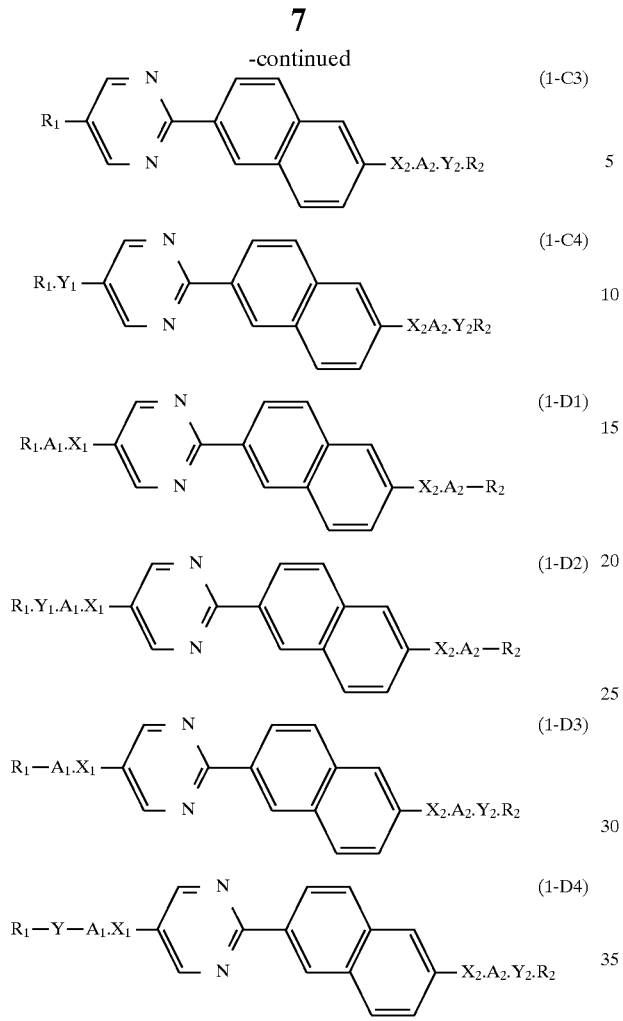

Among these structures, preferred is (1-A), (1-B) or (1-C), and more preferred is (1-A1), (1-A2), (1-A3), (1-B1), (1-B3), (1-C1), or (1-C3).

In the pyrimidine compound of the present invention represented by Formula (1), $R_1$ and $R_2$ each represent a linear or branched alkyl group or alkoxyl group having 1 to 24 carbon atoms or a linear or branched alkenyl group or alkenyloxy group having 2 to 24 carbon atoms, and $R_1$ and $R_2$ may have asymmetric carbon atoms which may be optically active.

The —$CH_2$— groups (provided that the adjacent —$CH_2$— groups and the —$CH_2$— groups bonded to $Y_1$, $Y_2$ or an aromatic ring are excluded) which are present in the above alkyl group, alkoxyl group, alkenyl group and alkenyloxy group may be substituted with an oxygen atom, a sulfur atom, a —CO— group, a —COO— group, and a —OCO— group.

$R_1$ and $R_2$ include, for example:
(1) a linear or branched alkyl group or alkoxyl group (hereinafter, abbreviated as an alkyl group and an alkoxyl group),
(2) a linear or branched alkyl group or alkoxyl group in which hydrogen atoms are substituted with halogen atoms (hereinafter, abbreviated as a haloalkyl group and a haloalkoxyl group),
(3) a linear or branched alkyl group or alkoxyl group in which a —$CH_2$— group is substituted with an oxygen atom (hereinafter, abbreviated as an alkoxyalkyl group and an alkoxyalkoxyl group),
(4) a linear or branched alkenyl group or alkenyloxy group in which a —$CH_2$— group is substituted with an oxygen atom (hereinafter, abbreviated as an alkenyloxyalkyl group and an alkenyloxyalkoxyl group),
(5) a linear or branched alkyl group or alkoxyl group in which a —$CH_2$— group is substituted with an oxygen atom and a hydrogen atom is substituted with a halogen atom (hereinafter, abbreviated as a haloalkoxyalkyl group and a haloalkoxyalkoxyl group),
(6) a linear or branched alkyl group or alkoxyl group in which a —$CH_2$— group is substituted with a sulfur atom (hereinafter, abbreviated as an alkylthioalkyl group and an alkylthioalkoxyl group),
(7) a linear or branched alkyl group or alkoxyl group in which a —$CH_2$— group is substituted with a —CO— group (hereinafter, abbreviated as an alkylcarbonylalkyl group and an alkylcarbonylalkoxyl group),
(8) a linear or branched alkyl group or alkoxyl group in which a —$CH_2$— group is substituted with a —COO— group (hereinafter, abbreviated as an alkylcarbonyloxyalkyl group and an alkylcarbonyloxyalkoxyl group),
(9) a linear or branched alkyl group or alkoxyl group in which a —$CH_2$— group is substituted with a —OCO— group (hereinafter, abbreviated as an alkoxycarbonylalkyl group and an alkoxycarbonylalkoxyl group), and
(10) a linear or branched alkenyl group or alkenyloxy group (hereinafter, abbreviated as an alkenyl group and an alkenyloxy group).

$R_1$ and $R_2$ each have preferably 4 to 22 carbon atoms, more preferably 5 to 20 carbon atoms. $R_1$ and $R_2$ each are preferably an alkyl group, an alkoxyl group, an alkoxyalkyl group, an alkoxyalkoxyl group, an alkylthioalkyl group, an alkylthioalkoxyl group, an alkylcarbonylalkyl group, an alkylcarbonylalkoxyl group, an alkylcarbonyloxyalkyl group, an alkylcarbonyloxyalkoxyl group, an alkoxycarbonylalkyl group, an alkoxycarbonylalkoxyl group, an alkenyl group or an alkenyloxy group, more preferably an alkyl group, an alkoxyl group, an alkoxyalkyl group, an alkoxyalkoxyl group, an alkylcarbonyloxyalkyl group, an alkylcarbonyloxyalkoxyl group, an alkoxycarbonylalkyl group, an alkoxycarbonylalkoxyl group, an alkenyl group, or an alkenyloxy group.

The concrete examples of the groups represented by $R_1$ and $R_2$ include, for example, alkyl groups such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicocyl, n-heneicocyl, n-dococyl, n-tricocyl, n-tetracocyl, 1-methylethyl, 1,1-dimethylethyl, 1-methylpropyl, 1-methylbutyl, 1-methylpentyl, 1-methylhexyl, 1-methylheptyl, 1-methyloctyl, 1-methylnonyl, 1-methyldecyl, 2-methylpropyl, 2-methylbutyl, 2-ethylbutyl, 2-methylpentyl, 2-methylhexyl, 2-methylheptyl, 2-ethylhexyl, 2-methyloctyl, 2-methylnonyl, 2-methyldecyl, 2,3-dimethylbutyl, 2,3,3-trimethylbutyl, 3-methylbutyl, 3-methylpentyl, 3-ethylpentyl, 4-methylpentyl, 4-ethylhexyl, 2,3-dimethylpentyl, 2,4-dimethylpentyl, 2,4,4-trimethylpentyl, 2,3,4,4-tetramethylpentyl, 3-methylhexyl, 2,5-dimethylhexyl, 3-ethylhexyl, 3,5,5-trimethylhexyl, 4-methylhexyl, 6-methylheptyl, 3,7-dimethyloctyl and 6-methyloctyl, and corresponding alkoxyl groups, haloalkyl groups such as 2-fluoroethyl, 1,2-difluoroethyl, 2-fluoro-n-propyl, 3-fluoro-n-propyl, 1,3-difluoro-n-propyl, 2,3-difluoro-n-propyl, 2-fluoro-n-butyl, 3-fluoro-n-butyl, 4-fluoro-n-butyl, 3-fluoro-2-methylpropyl, 2,3-difluoro-n-butyl, 2,4-difluoro-n-butyl, 3,4-difluoro-n-butyl, 2-fluoro-n-pentyl, 3-fluoro-n-pentyl, 5-fluoro-n-pentyl, 2,4-difluoro-n-pentyl, 2,5-difluoro-n-pentyl, 2-fluoro-3-methylbutyl, 2-fluoro-n-hexyl, 3-fluoro-n-hexyl, 4-fluoro-n-hexyl, 5-fluoro-n-hexyl, 6-fluoro-n-hexyl, 2-fluoro-n-heptyl, 4-fluoro-n-heptyl, 5-fluoro-n-heptyl, 2-fluoro-n-octyl, 3-fluoro-n-octyl, 6-fluoro-n-octyl, 4-fluoro-n-nonyl, 7-fluoro-n-nonyl, 3-fluoro-n-decyl, 6-fluoro-n-decyl, 4-fluoro-n-dodecyl, 8-fluoro-n-dodecyl, 5-fluoro-n-tetradecyl, 9-fluoro-n-tetradecyl, 2-chloroethyl, 3-chloro-n-propyl, 2-chloro-n-butyl, 4-chloro-n-butyl, 2-chloro-n-pentyl, 5-chloro-n-pentyl, 5-chloro-n-hexyl, 4-chloro-n-heptyl, 6-chloro-n-octyl, 7-chloro-n-nonyl, 3-chloro-n-decyl, 8-chloro-n-dodecyl, trifluoromethyl, perfluoroethyl, perfluoro-n-propyl, perfluoro-n-butyl, perfluoro-n-pentyl, perfluoro-n-hexyl, perfluoro-n-heptyl, perfluoro-n-octyl, perfluoro-n-nonyl, perfluoro-n-decyl, perfluoro-n-undecyl, perfluoro-n-dodecyl, perfluoro-n-tetradecyl, 1-hydroperfluoro-ethyl, 1-hydroperfluoro-n-propyl, 1-hydroperfluoro-n-butyl, 1-hydroperfluoro-n-pentyl, 1-hydroperfluoro-n-hexyl, 1-hydroperfluoro-n-heptyl, 1-hydroperfluoro-n-octyl, 1-hydroperfluoro-n-nonyl, 1-hydroperfluoro-n-decyl, 1-hydroperfluoro-n-undecyl, 1-hydroperfluoro-n-dodecyl, 1-hydroperfluoro-n-tetradecyl, 1,1-dihydroperfluoroethyl, 1,1-dihydroperfluoro-n-propyl, 1,1-dihydroperfluoro-n-butyl, 1,1-dihydroperfluoro-n-pentyl, 1,1-dihydroperfluoro-n-hexyl, 1,1-dihydroperfluoro-n-heptyl, 1,1-dihydroperfluoro-n-octyl, 1,1-dihydroperfluoro-n-nonyl, 1,1-dihydroperfluoro-n-decyl, 1,1-dihydroperfluoro-n-undecyl, 1,1-dihydroperfluoro-n-dodecyl, 1,1-dihydroperfluoro-n-tetradecyl, 1,1-dihydroperfluoro-n-pentadecyl, 1,1-dihydroperfluoro-n-hexadecyl, 1,1,2-trihydroperfluoroethyl, 1,1,3-trihydroperfluoro-n-propyl, 1,1,3-trihydroperfluoro-n-butyl, 1,1,4-trihydroperfluoro-nbutyl, 1,1,4-trihydroperfluoro-n-pentyl, 1,1,5-trihydroperfluoro-n-pentyl, 1,1,3-trihydroperfluoro-n-hexyl, 1,1,6-trihydroperfluoro-n-hexyl, 1,1,5-trihydroperfluoro-nheptyl, 1,1,7-trihydroperfluoro-n-heptyl, 1,1,8-trihydroperfluoro-n-octyl, 1,1,9-trihydroperfluoro-n-nonyl, 1,1,11-trihydroperfluoro-n-undecyl, 2-(perfluoroethyl)ethyl, 2-(perfluoro-n-propyl)ethyl, 2-(perfluoro-n-butyl)ethyl, 2-(perfluoro-n-pentyl)ethyl, 2-(perfluoro-n-hexyl)ethyl, 2-(perfluoro-n-heptyl)ethyl, 2-(perfluoro-n-octyl)ethyl, 2-(perfluoro-n-decyl)ethyl, 2-(perfluoro-n-nonyl)ethyl, 2-(perfluoro-n-dodecyl)ethyl, 2-trifluoromethylpropyl, 3-(perfluoro-n-propyl)propyl, 3-(perfluoro-n-butyl)propyl, 3-(perfluoro-n-hexyl)propyl, 3-(perfluoro-n-heptyl)propyl, 3-(perfluoro-n-octyl)propyl, 3-(perfluoro-n-decyl)propyl, 3-(perfluoro-n-dodecyl)propyl, 4-(perfluoroethyl)butyl, 4-(perfluoro-n-propyl)butyl, 4-(perfluoro-n-butyl)butyl, 4-(perfluoro-n-pentyl)butyl, 4-(perfluoro-n-hexyl)butyl, 4-(perfluoro-n-heptyl)butyl, 4-(perfluoro-n-octyl)butyl, 4-(perfluoro-n-decyl)butyl, 5-(perfluoro-n-propyl)pentyl, 5-(perfluoro-n-butyl)pentyl, 5-(perfluoro-n-pentyl)pentyl, 5-(perfluoro-n-hexyl)pentyl, 5-(perfluoro-n-heptyl)pentyl, 5-(perfluoro-n-octyl)pentyl, 6-(perfluoroethyl)hexyl, 6-(perfluoro-n-propyl)hexyl, 6-(perfluoro-n-butyl)hexyl, 6-(perfluoro-n-hexyl)hexyl, 6-(perfluoro-n-heptyl)hexyl, 6-(perfluoro-n-octyl)hexyl, 7-(perfluoroethyl)heptyl, 7-(perfluoro-n-propyl)heptyl, 7-(perfluoro-n-butyl)heptyl and 7-(perfluoro-n-pentyl)heptyl, and corresponding haloalkoxyl groups, alkoxyalkyl groups such as methoxymethyl, 2-methoxyethyl, 3-methoxypropyl, 4-methoxybutyl, 5-methoxypentyl, 6-methoxyhexyl, 7-methoxyheptyl, 8-methoxyoctyl, 9-methoxynonyl, 10-methoxydecyl, ethoxymethyl, 2-ethoxyethyl, 3-ethoxypropyl, 4-ethoxybutyl, 5-ethoxypentyl, 6-ethoxyhexyl, 7-ethoxyheptyl, 8-ethoxyoctyl, 9-ethoxynonyl, 10-ethoxydecyl, n-propoxymethyl, 2-n-propoxyethyl, 3-n-propoxypropyl, 4-n-propoxybutyl, 5-n-propoxypentyl, 6-n-propoxyhexyl, 7-n-propoxyheptyl, 8-n-propoxyoctyl, 9-n-propoxynonyl, 10-n-propoxydecyl, n-butoxymethyl, 2-n-butoxyethyl, 3-n-butoxypropyl, 4-n-butoxybutyl, 5-n-butoxypentyl, 6-n-butoxyhexyl, 7-n-butoxyheptyl, 8-n-butoxyoctyl, 9-n-butoxynonyl, 10-n-butoxydecyl, n-pentyloxymethyl, 2-n-pentyloxyethyl, 3-n-pentyloxypropyl, 4-n-pentyloxybutyl, 5-n-pentyloxypentyl, 6-n-pentyloxyhexyl, 7-n-pentyloxyheptyl, 8-n-pentyloxy-octyl, 9-n-pentyloxynonyl, 10-n-pentyloxydecyl, n-hexyloxymethyl, 2-n-hexyloxyethyl, 3-n-hexyloxypropyl, 4-n-hexyloxybutyl, 5-n-hexyloxypentyl, 6-n-hexyloxyhexyl, 7-n-hexyloxyheptyl, 8-n-hexyloxyoctyl, 9-n-hexyloxynonyl, 10-n-hexyloxydecyl, n-heptyloxymethyl, 2-n-heptyloxyethyl, 3-n-heptyloxypropyl, 4-n-heptyloxybutyl, 5-n-heptyloxypentyl, 6-n-heptyloxyhexyl, 7-n-heptyloxyheptyl, 8-n-heptyloxyoctyl, 9-n-heptyloxynonyl, 10-n-heptyloxydecyl, n-octyloxymethyl, 2-n-octyloxyethyl, 3-n-octyloxypropyl, 4-n-octyloxybutyl, 5-n-octyloxypentyl, 6-n-octyloxyhexyl, 7-n-octyloxyheptyl, 8-n-octyloxyoctyl, 9-n-octyloxynonyl, 10-n-octyloxydecyl, n-nonyloxymethyl, 2-n-nonyloxyethyl, 3-n-nonyloxypropyl, 4-n-nonyloxybutyl, 5-n-nonyloxypentyl, 6-n-nonyloxyhexyl, 7-n-nonyloxyheptyl, 8-n-nonyloxyoctyl, 9-n-nonyloxynonyl, 10-n-nonyloxydecyl, n-decyloxymethyl, 2-n-decyloxyethyl, 3-n-decyloxypropyl, 4-n-decyloxybutyl, 5-n-decyloxypentyl, 6-n-decyloxyhexyl, 7-n-decyloxyheptyl, 8-n-decyloxyoctyl, 9-n-decyloxynonyl, 10-n-decyloxydecyl, n-undecyloxymethyl, 2-n-undecyloxyethyl, 3-n-undecyloxypropyl, 4-n-undecyloxybutyl, 6-n-undecyloxyhexyl, 7-n-undecyloxyheptyl, 8-n-undecyloxyoctyl, 9-n-undecyloxynonyl, 10-n-undecyloxydecyl, 2-ndodecyloxyethyl, 4-n-dodecyloxybutyl, 6-n-dodecyloxyhexyl, 8-n-dodecyloxyoctyl, 10-n-dodecyloxydecyl, 1-methyl-2-methoxyethyl, 1-methyl-2-ethoxyethyl, 1-methyl-2-n-propoxyethyl, 1-methyl-2-n-butoxyethyl, 1-methyl-2-n-pentyloxyethyl, 1-methyl-2-n-hexyloxyethyl, 1-methyl-2-n-heptyloxyethyl, 1-methyl-2-n-octyloxyethyl, 1-methyl-2-n-nonyloxyethyl, 1-methyl-2-n-decyloxyethyl, 1-methyl-2-n-undecyloxyethyl, 1-methyl-2-n-dodecyloxyethyl, 2-methoxypropyl, 2-ethoxypropyl, 2-n-propoxypropyl, 2-n-butoxypropyl, 2-n-pentyloxypropyl, 2-n-hexyloxypropyl, 2-n-heptyloxypropyl, 2-n-octyloxypropyl, 2-n-nonyloxypropyl, 2-n-decyloxypropyl, 2-n-undecyloxypropyl, 2-n-dodecyloxypropyl, 1-methyl-3-methoxypropyl, 1-methyl-3-ethoxypropyl, 1-methyl-3-n-propoxypropyl, 1-methyl-3-n-butoxypropyl, 1-methyl-3-n-pentyloxypropyl, 1-methyl-3-n-hexyloxypropyl, 1-methyl-3-n-heptyloxypropyl, 1-methyl-3-n-octyloxypropyl, 1-methyl-3-n-nonyloxypropyl, 1-methyl-3-n-decyloxypropyl, 1-methyl-3-n-undecyloxypropyl, 1-methyl-3-n-dodecyloxypropyl, 3-methoxybutyl, 3-ethoxybutyl, 3-n-propoxybutyl, 3-n-butoxybutyl, 3-n-pentyloxybutyl, 3-n-hexyloxybutyl, 3-n-heptyloxybutyl, 3-n-octyloxybutyl, 3-n-nonyloxybutyl, 3-n-decyloxybutyl, 3-n-undecyloxybutyl, 3-n-dodecyloxybutyl, isopropoxymethyl, 2-isopropoxyethyl, 3-isopropoxypropyl, 4-isopropoxybutyl, 5-isopropoxypentyl, 6-isopropoxyhexyl, 7-isopropoxyheptyl, 8-isopropoxyoctyl, 9-isopropoxynonyl, 10-isopropoxydecyl, isobutoxymethyl, 2-isobutoxyethyl, 3-isobutoxypropyl, 4-isobutoxybutyl, 5-isobutoxypentyl, 6-isobuyoxyhexyl, 7-isobutoxyheptyl, 8-isobutoxyoctyl, 9-isobutoxynonyl, 10-isobutoxydecyl, tert-butoxymethyl, 2-tert-butoxyethyl, 3-tert-butoxypropyl, 4-tert-butoxybutyl, 5-tert-butoxypentyl, 6-tert-butoxyhexyl, 7-tert-butoxyheptyl, 8-tert-butoxyoctyl, 9-tert-butoxynonyl, 10-tert-butoxydecyl, (2-ethylbutoxy)methyl, 2-(2'-ethylbutoxy)ethyl, 3-(2'-ethylbutoxy)propyl, 4-(2'-ethylbutoxy)butyl, 5-(2'-ethylbutoxy)pentyl, 6-(2'-ethylbutoxy) hexyl, 7-(2'-ethylbutoxy)heptyl, 8-(2'-ethylbutoxy)octyl, 9-(2'-ethylbutoxy)nonyl, 10-(2'-ethylbutoxy)decyl, (3-ethylpentyloxy)methyl, 2-(3'-ethylpentyloxy)ethyl, 3-(3'-ethylpentyloxy)propyl, 4-(3'-ethylpentyloxy)butyl, 5-(3'-ethylpentyloxy)pentyl, 6-(3'-ethylpentyloxy)hexyl, 7-(3'-ethylpentyloxy)heptyl, 8-(3'-ethylpentyloxy)octyl, 9-(3'-ethyl-pentyloxy)nonyl, 10-(3'-ethylpentyloxy)decyl, 6-(1'-methyl-n-heptyloxy)hexyl, 4-(1'-methyl-n-heptyloxy)-butyl, 2-(2'-methoxyethoxy) ethyl, 2-(2'-ethoxyethoxy)ethyl, 2-(2'-n-propoxyethoxy) ethyl, 2-(2'-isopropoxyethoxy)ethyl, 2-(2'-n-butoxyethoxy) ethyl, 2-(2'-isobutoxyethoxy)ethyl, 2-(2'-tert-butoxyethoxy) ethyl, 2-(2'-n-pentyloxyethoxy)ethyl, 2-[2'-(2"-ethylbutoxy) ethoxy]ethyl, 2-(2'-n-hexyloxyethoxy) ethyl, 2-[2'-(3"-ethylpentyloxy)ethoxy]ethyl, 2-(2'-n-heptyloxyethoxy) ethyl, 2-(2'-n-octyloxyethoxy)ethyl, 2-(2'-n-nonyloxyethoxy)ethyl, 2-(2'-n-decyloxyethoxy)ethyl, 2-(2'-n-undecyloxyethoxy)ethyl, 2-(2'-n-dodecyloxyethoxy)ethyl, 2-[2'-(2"-methoxyethoxy)ethoxy]ethyl, 2-[2'-(2"-ethoxyethoxy)ethoxy]ethyl, 2-[2'-(2"-n-propoxyethoxy) ethoxy]ethyl, 2-[2'-(2"-isopropoxyethoxy)ethoxy]ethyl, 2-[2'-(2"-n-butoxyethoxy)ethoxy]ethyl, 2-[2'-(2"-isobutoxyethoxy)ethoxy]ethyl, 2-[2'-(2"-tertbutoxyethoxy) ethoxy]ethyl, 2-{2'-[2"-(2'"-ethylbutoxy)ethoxy] ethoxy}ethyl, 2-[2'-(2"-n-pentyloxyethoxy)ethoxy]ethyl, 2-[2'-(2"-n-hexyloxyethoxy)ethoxy]ethyl, 2-{2'-[2"-(3'"-ethylpentyloxy)-ethoxy]ethoxy}ethyl, 2-[2'-(2"-n-heptyloxyethoxy)-ethoxy]ethyl, 2-[2'-(2"-n-octyloxyethoxy)ethoxy]ethyl, 2-[2'-(2"-n-nonyloxyethoxy) ethoxy]ethyl, 2-[2'-(2"-n-decyloxyethoxy)ethoxy]ethyl, 2-[2'-(2"-n-undecyloxyethoxy)ethoxy]ethyl, 2-[2'-(2"-n-dodecyloxyethoxy)-ethoxy]ethyl, 2-{2'-[2"-(2'"-methoxyethoxy)ethoxy]-ethoxy}ethyl, 2-{2'-[2"-(2'"-n-dodecyloxyethoxy)-ethoxy]ethoxy}ethyl, 2-{2'-{2"-[2'"-(2-methoxyethoxy) ethoxy]ethoxy}ethoxy}ethyl, 2-{2'-{2"-[2'"-(2-n-dodecyloxyethoxy) ethoxy]ethoxy}ethoxy}ethyl, 2-{2'-{2"-{2'"-[-2-( 2-methoxyethoxy)ethoxy]-ethoxy}ethoxy}-ethoxy}ethyl, 2-(2'-methoxypropoxy) propyl, 2-(2'-ethoxypropoxy)propyl, 2-(2'-n-propoxypropoxy)propyl, 2-(2'-isopropoxypropoxy)-propyl, 2-(2'-n-butoxypropoxy)propyl, 2-(2'-isobutoxypropoxy) propyl, 2-(2'-tert-butoxypropoxy)propyl, 2-(2'-n-pentyloxypropoxy)propyl, 2-(2'-n-hexyloxypropoxy)-propyl, 2-(2'-n-heptyloxypropoxy)propyl, 2-(2'-n-octyloxypropoxy)propyl, 2-(2'-n-nonyloxypropoxy)propyl, 2-(2'-n-decyloxypropoxy)propyl,2-(2'-n-undecyloxypropoxy)-propyl, 2-(2'-n-dodecyloxypropoxy) propyl, 2-[2'-(2"-methoxypropoxy) propoxy]propyl, 2-[2'-(2"-ethoxypropoxy)-propoxy]propyl, 2-[2'-(2"-n-propoxypropoxy)propoxy]propyl, 2-[2'-(2"-isopropoxypropoxy)propoxy]propyl, 2-[2'-(2"-n-butoxypropoxy)propoxy]propyl, 2-[2'-(2"-isobutoxypropoxy) propoxy]propyl, 2-[2'-(2"-tert-butoxypropoxy)propoxy]propyl, 2-[2'-(2"-n-pentyloxypropoxy)propoxy]propyl, 2-[2'-(2"-n-hexyloxypropoxy)propoxy]propyl, 2-[2'-(2"-n-heptyloxypropoxy)propoxy]propyl, 2-[2'-(2"-n-octyloxypropoxy)propoxy]propyl, 2-[2'-(2"-n-nonyloxypropoxy) propoxy]propyl, 2-[2'-(2"-n-decyloxypropoxy)propoxy]propyl, 2-[2'-(2"-n-undecyloxypropoxy)propoxy]propyl, 2-[2'-(2"-n-dodecyloxypropoxy)propoxy]propyl, 2-(2'-pentyloxyethylthio)ethyl, 2-ethoxyethoxymethyl, 2-n-butoxyethoxymethyl, 2-n-hexyloxyethoxymethyl, 3-ethoxypropoxymethyl, 3-n-propoxypropoxymethyl, 3-n-pentyloxypropoxymethyl, 3-n-hexyloxypropoxymethyl, 2-methoxy-1-methylethoxymethyl, 2-ethoxy-1-methylethoxymethyl, 2-n-butoxy-1-methylethoxymethyl, 4-methoxybutoxymethyl, 4-ethoxybutoxymethyl, 4-n-butoxybutoxymethyl, 2-(3'-methoxypropoxy)ethyl, 2-(3'-ethoxypropoxy)ethyl, 2-(2'-methoxy-1'-methyl-ethoxy) ethyl, 2-(2'-ethoxy-1'-methylethoxy)ethyl, 2-(2'-n-butoxy-1'-methylethoxy)ethyl, 2-(4-'methoxybutoxy)ethyl, 2-(4'-ethoxybutoxy)ethyl, 2-['4-(2"-ethylbutoxy)butoxy]ethyl, 2-[4'-(3"-ethylpentyloxy) butoxy]ethyl, 3-(2'-methoxyethoxy)propyl, 3-(2'-ethoxyethoxy)propyl, 3-(2'-n-pentyloxyethoxy)propyl, 3-(2'-n-hexyloxyethoxy)propyl, 3-(3'-ethoxypropoxy)propyl, 3-(3'-n-propoxypropoxy) propyl, 3-(3'-n-butoxypropoxy)propyl, 3-(4'-ethoxybutoxy) propyl, 3-(5'-ethoxypentyloxy)propyl, 4-(2'-methoxyethoxy)butyl, 4-(2'-ethoxyethoxy)butyl, 4-(2'-isopropoxyethoxy)butyl, 4-(2'-isobutoxyethoxy)butyl, 4-(2'-n-butoxyethoxy)butyl, 4-(2'-n-hexyloxyethoxy)butyl, 4-(3'-n-propoxypropoxy)butyl, 4-(2'-n-propoxy-1'-methylethoxy) butyl, 4-[2'-(2"-methoxyethoxy)-ethoxy]butyl, 4-[2'-(2-n-butoxyethoxy)ethoxy]butyl, 4-[2'-(2"-n-hexyloxyethoxy) ethoxy]butyl, 5-(2'-n-hexyloxyethoxy)pentyl, 2-[2'-(2"-n-butoxyethoxy)ethoxy]ethyl, (2-ethylhexyloxy)methyl, (3,5, 5-trimethylhexyloxy)methyl, (3,7-dimethyloctyloxy) methyl, 2-(2'-ethylhexyloxy)ethyl, 2-(3',5',5'-trimethylhexyloxy)-ethyl, 2-(3',7-dimethyloctyloxy)ethyl, 3-(2'-ethylhexyloxy)propyl, 3-(3',5',5'-trimethylhexyloxy) propyl, 3-(3',7'-dimethyloctyloxy)propyl, 4-(2'-ethylhexyloxy)butyl, 4-(3',5',5'-trimethylhexyloxy) butyl, 4-(3',7'-dimethyloctyloxy)butyl, 5-(2'-ethylhexyloxy)pentyl, 5-(3',5',5'-trimethylhexyloxy)pentyl, 5-(3',7'-dimethyloctyloxy)pentyl, 6-(2'-ethylhexyloxy)hexyl, 6-(3',5',5'-trimethylhexyloxy)hexyl and 6-(3',7'-dimethyloctyloxy)hexyl, and corresponding alkoxyalkoxyl groups, alkenyloxyalkyl groups such as 2-propenyloxymethyl, 2-(2'propenyloxy)ethyl, 2-[2'-(2"-propenyloxy)ethoxy]ethyl, 3-(2'propenyloxy)propyl, 4-(2'-propenyloxy)butyl, 5-(2'-propenyloxy)pentyl, 6-(2'-propenyloxy)hexyl, 7-(2'-propenyloxy)heptyl, 8-(2'-propenyloxy)octyl, 9-(2'-propenyloxy)nonyl and 10-(2'-propenyloxy)decyl, and corresponding alkenyloxyalkoxyl groups, haloalkoxyalkyl groups such as 2-(2'-trifluoromethylpropoxy)ethyl, 4-(2'-trifluoromethylpropoxy)butyl, 6-(2'-trifluoromethylpropoxy)-hexyl, 8-(2'-trifluoromethylpropoxy)octyl, 2-(2'-trifluoromethylbutoxy)ethyl, 4-(2'-trifluoromethyl-butoxy) butyl, 6-(2'-trifluoromethylbutoxy)hexyl, 8-(2'-trifluoromethylbutoxy)octyl, 2-(2'-trifluoromethylheptyloxy)ethyl, 4-(2'-trifluoromethylheptyloxy) butyl, 6-(2'-trifluoromethylheptyloxy)hexyl, 8-(2'-trifluoromethylheptyloxy)octyl, 2-(2'-fluoroethoxy)ethyl, 4-(2'-fluoroethoxy)butyl, 6-(2'-fluoroethoxy)hexyl, 8-(2'-fluoroethoxy)octyl, 2-(2'-fluoro-n-propoxy)ethyl, 4-(2'-fluoro-n-propoxy)butyl, 6-(2'-fluoro-n-propoxy)hexyl, 8-(2'-fluoro-n-propoxy)octyl, 2-(3'-fluoro-n-propoxy)ethyl, 4-(3'-fluoro-n-propoxy)butyl, 6-(3'-fluoro-n-propoxy)hexyl, 8-(3'-fluoro-n-propoxy)octyl, 2-(3'-fluoro-2'-methylpropoxy) ethyl, 4-(3'-fluoro-2'-methylpropoxy)butyl, 6-(3'-fluoro-2'-methylpropoxy)hexyl, 8-(3'-fluoro-2'-methylpropoxy)octyl, 2-(2',3'-difluoro-n-propoxy)ethyl, 4-(2',3'-difluoro-n-propoxy)butyl, 6-(2',3'-difluoro-n-propoxy)hexyl, 8-(2',3'-difluoro-n-propoxy)octyl, 2-(2'-fluoro-n-butoxy)ethyl, 4-(2'-fluoro-n-butoxy)butyl, 6-(2'-fluoro-n-butoxy)hexyl, 8-(2'- fluoro-n-butoxy)octyl, 2-(3'-fluoro-n-butoxy)ethyl, 4-(3'-fluoro-n-butoxy)butyl, 6-(3'-fluoro-n-butoxy)hexyl, 8-(3'-fluoro-n-butyloxy)octyl,2-(4'-fluoro-n-butoxy)ethyl, 4-(4'-fluoro-n-butoxy)butyl, 6-(4'-fluoro-n-butoxy)hexyl, 8-(4'-fluoro-n-butoxy)octyl, 2-(2',3'-difluoro-n-butoxy)ethyl, 4-(2',3'-difluoro-n-butoxy)butyl, 6-(2',3'-difluoro-n-butoxy)hexyl, 8-(2',3'-difluoro-n-butoxy)octyl, 2-(2'-trichloromethylpropoxy)ethyl, 4-(2'-trichloromethylpropoxy)butyl, 6-(2'-trichloromethylpropoxy)hexyl, 8-(2'-trichloromethylpropoxy)octyl, 2-(2'-trichloromethylbutoxy)ethyl, 4-(2'-trichloromethylbutoxy)butyl, 6-(2'-trichloromethylbutoxy)hexyl, 8-(2'-trichloromethylbutoxy)octyl, 2-(2'-trichloromethylheptyloxy)ethyl, 4-(2'-trichloromethylheptyloxy)butyl, 6-(2'-trichloromethylheptyloxy)hexyl, 8-(2'-trichloromethylheptyloxy)octyl, 2-(2'-chloroethoxy)ethyl, 4-(2'-chloroethoxy)butyl, 6-(2'-chloroethoxy)hexyl, 8-(2'-chloroethoxy)octyl, 2-(2'-chloro-n-propoxy)ethyl, 4-(2'-chloro-n-propoxy)butyl, 6-(2'-chloro-n-propoxy)hexyl, 8-(2'-chloro-n-propoxy)octyl, 2-(3'-chloro-n-propoxy)ethyl, 4-(3'-chloro-n-propoxy)butyl, 6-(3'-chloro-n-propoxy)hexyl, 8-(3'-chloro-n-propoxy)octyl, 2-(3'-chloro-2'-methylpropoxy)ethyl, 4-(3'-chloro-2'-methylpropoxy)butyl, 6-(3'-chloro-2'-methylpropoxy)hexyl, 8-(3'-chloro-2'-methylpropoxy)octyl, 2-(2',3'-dichloro-n-propoxy)ethyl, 4-(2',3'-dichloro-npropoxy)butyl, 6-(2',3'-dichloro-n-propoxy)hexyl, 8-(2',3'-dichloro-n-propoxy)octyl, 2-(2'-chloro-n-butoxy)ethyl, 4-(2'-chloro-n-butoxy)butyl, 6-(2'-chloro-n-butoxy)hexyl, 8-(2'-chloro-n-butoxy)octyl, 2-(3'-chloro-n-butoxy)ethyl, 4-(3'-chloro-n-butoxy)butyl, 6-(3'-chloro-n-butoxy)hexyl, 8-(3'-chloro-n-butoxy)octyl, 2-(4'-chloro-n-butoxy)ethyl, 4-(4'-chloro-n-butoxy)butyl, 6-(4'-chloro-n-butoxy)hexyl, 8-(4'-chloro-n-butoxy)octyl, 2-(2',3'-dichloro-n-butoxy)ethyl, 4-(2',3'-dichloro-n-butoxy)butyl, 6-(2',3'-dichloro-n-butoxy)hexyl and 8-(2',3'-dichloro-n-butoxy)octyl, and corresponding haloalkoxyalkoxyl groups, alkylthioalkyl groups such as methylthiomethyl, 2-methylthioethyl, 3-methylthiopropyl, 4-methylthiobutyl, 5-methylthiopentyl, 6-methylthiohexyl, 7-methylthioheptyl, 8-methylthiooctyl, 9-methylthiononyl, 10-methylthiodecyl, ethylthiomethyl, 2-ethylthioethyl, 3-ethylthiopropyl, 4-ethylthiobutyl, 5-ethylthiopentyl, 6-ethylthiohexyl, 7-ethylthioheptyl, 8-ethylthiooctyl, 9-ethylthiononyl, 10-ethylthiodecyl, n-propylthiomethyl, 2-n-propylthioethyl, 3-n-propylthiopropyl, 4-n-propylthiobutyl, 5-n-propylthiopentyl, 6-n-propylthiohexyl, 7-n-propylthioheptyl, 8-n-propylthiooctyl, 9-n-propylthiononyl, 10-n-propylthiodecyl, n-butylthiomethyl, 2-n-butylthioethyl, 3-n-butylthiopropyl, 4-n-butylthiobutyl, 5-n-butylthiopentyl, 6-n-butylthiohexyl, 7-n-butylthioheptyl, 8-n-butylthiooctyl, 9-n-butylthiononyl, 10-n-butylthiodecyl, n-pentylthiomethyl, 2-n-pentylthioethyl, 3-n-pentylthiopropyl, 4-n-pentylthiobutyl, 5-n-pentylthiopentyl, 6-n-pentylthiohexyl, 7-n-pentylthioheptyl, 8-n-pentylthiooctyl, 9-n-pentylthiononyl, 10-n-pentylthiodecyl, n-hexylthiomethyl, 2-n-hexylthioethyl, 3-n-hexylthiopropyl, 4-n-hexylthiobutyl, 5-n-hexylthiopentyl, 6-n-hexylthiohexyl, 7-n-hexylthioheptyl, 8-n-hexylthiooctyl, 9-n-hexylthiononyl, 10-n-hexylthiodecyl, n-heptylthiomethyl, 2-n-heptylthioethyl, 3-n-heptylthiopropyl, 4-n-heptylthiobutyl, 5-n-heptylthiopentyl, 6-n-heptylthiohexyl, 7-n-heptylthioheptyl, 8-n-heptylthiooctyl, 9-n-heptylthiononyl, 10-n-heptylthiodecyl, n-octylthiomethyl, 2-n-octylthioethyl, 3-n-octylthiopropyl, 4-n-octylthiobutyl, 5-n-octylthiopentyl, 6-n-octylthiohexyl, 7-n-octylthioheptyl, 8-n-octylthiooctyl, 9-n-octylthiononyl, 10-n-octylthiodecyl, n-nonylthiomethyl, 2-n-nonylthioethyl, 3-n-nonylthiopropyl, 4-n-nonylthiobutyl, 5-n-nonylthiopentyl, 6-n-nonylthiohexyl, 7-n-nonylthioheptyl, 8-n-nonylthiooctyl, 9-n-nonylthiononyl, 10-n-nonylthiodecyl, n-decylthiomethyl, 2-n-decylthioethyl, 3-n-decylthiopropyl, 4-n-decylthiobutyl, 5-n-decylthiopentyl, 6-n-decylthiohexyl, 7-n-decylthioheptyl, 8-n-decylthiooctyl, 9-n-decylthiononyl, 10-n-decylthiodecyl, 2-(2'-ethylhexylthio)ethyl, 2-(3',5',5'-trimethylhexylthio)ethyl, 2-(3',7'-dimethyloctylthio)ethyl, 4-(2'-ethylhexylthio) butyl, 4-(3',5',5'-trimethylhexylthio) butyl, 4-(3',7'-dimethyloctyl-thio)butyl, 6-(2'-ethylhexylthio)hexyl, 6-(3',5',5'-trimethylhexylthio)hexyl and 6-(3',7'-dimethyloctylthio)hexyl, and corresponding alkylthioalkoxyl groups, alkylcarbonylalkyl groups such as ethylcarbonylmethyl, 2-ethylcarbonylethyl, 3-ethylcarbonylpropyl, 4-ethylcarbonylbutyl, 5-ethylcarbonylpentyl, 6-ethylcarbonylhexyl, 7-ethylcarbonylheptyl, 8-ethylcarbonyloctyl, 9-ethylcarbonylnonyl, n-propylcarbonylmethyl, 2-n-propylcarbonylethyl, 3-n-propylcarbonylpropyl, 4-n-propylcarbonylbutyl, 5-n-propylcarbonylpentyl, 6-n-propylcarbonylhexyl, 7-n-propylcarbonylheptyl, 8-n-propylcarbonyloctyl, 9-n-propylcarbonylnonyl, n-butylcarbonylmethyl, 2-n-butylcarbonylethyl, 3-n-butylcarbonylpropyl, 4-n-butylcarbonylbutyl, 5-n-butylcarbonylpentyl, 6-n-butylcarbonylhexyl, 7-n-butylcarbonylheptyl, 8-n-butylcarbonyloctyl, 9-n-butylcarbonylnonyl, n-pentylcarbonylmethyl, 2-n-pentylcarbonylethyl, 3-n-pentylcarbonylpropyl, 4-n-pentylcarbonylbutyl, 5-n-pentylcarbonylpentyl, 6-n-pentylcarbonylhexyl, 7-n-pentylcarbonylheptyl, 8-n-pentylcarbonyloctyl, 9-n-pentylcarbonylnonyl, n-hexylcarbonylmethyl, 2-n-hexylcarbonylethyl, 3-n-hexylcarbonylpropyl, 4-n-hexylcarbonylbutyl, 5-n-hexylcarbonylpentyl, 6-n-hexylcarbonylhexyl, 7-n-hexylcarbonylheptyl, 8-n-hexylcarbonyloctyl and 9-n-hexylcarbonylnonyl, and corresponding alkylcarbonylalkoxyl groups, alkylcarbonyloxyalkyl groups such as methylcarbonyloxymethyl, 2-methylcarbonyloxyethyl, 3-methylcarbonyloxypropyl, 4-methylcarbonyloxybutyl, 5-methylcarbonyloxypentyl, 6-methylcarbonyloxyhexyl, 7-methylcarbonyloxyheptyl, 8-methylcarbonyloxyoctyl, 9-methylcarbonyloxynonyl, ethylcarbonyloxymethyl, 2-ethylcarbonyloxyethyl, 3-ethylcarbonyloxypropyl, 4-ethylcarbonyloxybutyl, 5-ethylcarbonyloxypentyl, 6-ethylcarbonyloxyhexyl, 7-ethylcarbonyloxyheptyl, 8-ethylcarbonyloxyoctyl, 9-ethylcarbonyloxynonyl, n-propylcarbonyloxymethyl, 2-n-propylcarbonyloxyethyl, 3-n-propylcarbonyloxypropyl, 4-n-propylcarbonyloxybutyl, 5-n-propylcarbonyloxypentyl, 6-n-propylcarbonyloxyhexyl, 7-n-propylcarbonyloxyheptyl, 8-n-propylcarbonyloxyoctyl, 9-n-propylcarbonyloxynonyl, n-butylcarbonyloxymethyl, 2-n-butylcarbonyloxyethyl, 3-n-butylcarbonyloxypropyl, 4-n-butylcarbonyloxybutyl, 5-n-butylcarbonyloxypentyl, 6-n-butylcarbonyloxyhexyl, 7-n-butylcarbonyloxyheptyl, 8-n-butylcarbonyloxyoctyl, 9-n-butylcarbonyloxynonyl, n-pentylcarbonyloxymethyl, 2-n-pentylcarbonyloxyethyl, 3-n-pentylcarbonyloxypropyl, 4-n-pentylcarbonyloxybutyl, 5-n-pentylcarbonyloxypentyl, 6-n-pentylcarbonyloxyhexyl, 7-n-pentylcarbonyloxyheptyl, 8-n-pentylcarbonyloxyoctyl, 9-n-pentylcarbonyloxynonyl, n-hexylcarbonyloxymethyl, 2-n-hexylcarbonyloxyethyl, 3-n-hexylcarbonyloxypropyl, 4-n-hexylcarbonyloxybutyl, 5-n-hexylcarbonyloxypentyl, 6-n-hexylcarbonyloxyhexyl, 7-n-hexylcarbonyloxyheptyl, 8-n-hexylcarbonyloxyoctyl, 9-n-hexylcarbonyloxynonyl, n-heptylcarbonyloxymethyl, 2-n-heptylcarbonyloxyethyl, 3-n-heptylcarbonyloxypropyl, 4-n-heptylcarbonyloxybutyl, 5-n-heptylcarbonyloxypentyl, 6-n-heptylcarbonyloxyhexyl, 7-n-heptylcarbonyloxyheptyl, 8-n-heptylcarbonyloxyoctyl, 9-n-heptylcarbonyloxynonyl, n-octylcarbonyloxymethyl, 2-n-octylcarbonyloxyethyl, 3-n-octylcarbonyloxypropyl, 4-n-octylcarbonyloxybutyl, 5-n-octylcarbonyloxypentyl, 6-n-octylcarbonyloxyhexyl, 7-n-octylcarbonyloxyheptyl, 8-n-octylcarbonyloxyoctyl, 9-n-octylcarbonyloxynonyl, n-nonylcarbonyloxymethyl, 2-n-nonylcarbonyloxyethyl, 3-n-nonylcarbonyloxypropyl, 4-n-nonylcarbonyloxybutyl, 5-n-nonylcarbonyloxypentyl, 6-n-nonylcarbonyloxyhexyl, 7-n-nonylcarbonyloxyheptyl, 8-n-nonylcarbonyloxyoctyl and 9-n-nonylcarbonyloxynonyl, and corresponding alkylcarbonyloxyalkoxyl groups, alkoxycarbonyl alkyl groups such as methoxycarbonylmethyl, 2-methoxycarbonylethyl, 3-methoxycarbonylpropyl, 4-methoxycarbonylbutyl, 5-methoxycarbonylpentyl, 6-methoxycarbonylhexyl, 7-methoxycarbonylheptyl, 8-methoxycarbonyloctyl, 9-methoxycarbonylnonyl, ethoxycarbonylmethyl, 2-ethoxycarbonylethyl, 3-ethoxycarbonylpropyl, 4-ethoxycarbonylbutyl, 5-ethoxycarbonylpentyl, 6-ethoxycarbonylhexyl, 7-ethoxycarbonylheptyl, 8-ethoxycarbonyloctyl, 9-ethoxycarbonylnonyl, n-propoxycarbonylmethyl, 2-n-propoxycarbonylethyl, 3-n-propoxyarbonylpropyl, 4-n-propoxycarbonylbutyl, 5-n-propoxycarbonylpentyl, 6-n-propoxycarbonylhexyl, 7-n-propoxycarbonylheptyl, 8-n-propoxycarbonyloctyl, 9-n-propoxycarbonylnonyl, n-butoxycarbonylmethyl, 2-n-butoxycarbonylethyl, 3-n-butoxycarbonylpropyl, 4-n-butoxycarbonylbutyl, 5-n-butoxycarbonylpentyl, 6-n-butoxycarbonylhexyl, 7-n-butoxycarbonylheptyl, 8-n-butoxycarbonyloctyl, 9-n-butoxycarbonylnonyl, n-pentyloxycarbonylmethyl, 2-n-pentyloxycarbonylethyl, 3-n-pentyloxycarbonylpropyl, 4-n-pentyloxycarbonylbutyl, 5-n-pentyloxycarbonylpentyl, 6-n-pentyloxycarbonylhexyl, 7-n-pentyloxycarbonylheptyl, 8-n-pentyloxycarbonyloctyl, 9-n-pentyloxycarbonylnonyl, n-hexyloxycarbonylmethyl, 2-n-hexyloxycarbonylethyl, 3-n-hexyloxycarbonylpropyl, 4-n-hexyloxycarbonylbutyl, 5-n-hexyloxycarbonylpentyl, 6-n-hexyloxycarbonylhexyl, 7-n-hexyloxycarbonylheptyl, 8-n-hexyloxycarbonyloctyl, 9-n-hexyloxycarbonylnonyl, n-heptyloxycarbonylmethyl, 2-n-heptyloxycarbonylethyl, 3-n-heptyloxycarbonylpropyl, 4-n-heptyloxycarbonylbutyl, 5-heptyloxycarbonylpentyl, 6-n-heptyloxycarbonylhexyl, 7-n-heptyloxycarbonylheptyl, 8-n-heptyloxycarbonyloctyl, 9-n-heptyloxycarbonylnonyl, n-octyloxycarbonylmethyl, 2-n-octyloxycarbonylethyl, 3-n-octyloxycarbonylpropyl, 4-n-octyloxycarbonylbutyl, 5-n-octyloxycarbonylpentyl, 6-n-octyloxycarbonylhexyl, 7-n-octyloxycarbonylheptyl, 8-n-octyloxycarbonyloctyl, 9-n-octyloxycarbonylnonyl, n-nonyloxycarbonylmethyl, 2-n-nonyloxycarbonylethyl, 3-n-nonyloxycarbonylpropyl, 4-n-nonyloxycarbonylbutyl, 5-n-nonyloxycarbonylpentyl, 6-n-nonyloxycarbonylhexyl, 7-n-nonyloxycarbonylheptyl, 8-n-nonyloxycarbonyloctyl and 9-n-nonyloxycarbonylnonyl, and corresponding alkoxycarbonyl-alkoxyl groups, alkenyl group such as 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl, 2-octenyl, 3-octenyl, 4-octenyl, 5-octenyl, 6-octenyl, 7-octenyl, 2-nonenyl, 3-nonenyl, 4-nonenyl, 5-nonenyl, 6-nonenyl, 7-nonenyl, 8-nonenyl, 2-decenyl, 3-decenyl, 4-decenyl, 5-decenyl, 6-decenyl, 7-decenyl, 8-decenyl, 9-decenyl, 2-butynyl, 3-hexynyl, 3-heptynyl, 4-heptynyl, 5-heptynyl, 7-octynyl and 3,7-dimethyl-6-octenyl, and corresponding alkenyloxy groups.

In the pyrimidine compound of the present invention represented by Formula (1), $A_1$ and $A_2$ each represent a substituted or unsubstituted 1,4-phenylene group, a pyridine-2,5-diyl group or a trans-1,4-cyclohexylene group, and the substituents therefor include a halogen atom such as a fluorine atom, a chlorine atom and a bromine atom, a cyano group, a nitro group, a methyl group, a trifluoromethyl group, and a hydroxyl group. $A_1$ and $A_2$ each are preferably a 1,4-phenylene group, a pyridine-2,5-diyl group or a trans-1,4-cyclohexylene group each of which is substituted with a fluorine atom, a cyano group, a methyl group, a trifluoromethyl group or a hydroxyl group, or an unsubstituted 1,4-phenylene group, a pyridine-2,5-diyl group or a trans-1,4-cyclohexylene group, more preferably a 1,4-phenylene group substituted with a fluorine atom or a hydroxyl group, or an unsubstituted 1,4-phenylene group, a pyridine-2,5-diyl group or a trans-1,4-cyclohexylene group.

$X_1$ and $X_2$ each represent a connecting group selected from a single bond, a —COO— group, a —OCO— group, a —OCH$_2$— group and a —CH$_2$O— group.

$Y_1$ and $Y_2$ each represent a —COO— group or a —OCO group.

When $Y_1$ is a —COO— group, $R_1$ is not a linear or branched alkoxyl group or alkenyloxy group, and when $Y_2$ is a —COO— group, $R_2$ is not a linear or branched alkoxyl group or alkenyloxy group.

a, b, p and q each represent 0 or 1, and a+b+p+q is not 0, preferably 1, 2 or 3, and more preferably 1 or 2.

In the pyrimidine compound represented by Formula (1), the combinations of a, b, p, q, $Y_1$, $Y_2$, $A_1$, $A_2$, $X_1$ and $X_2$ comprise preferably the following combinations 1 to 18:

1. a is 1; b, p and q are 0; and $Y_1$ is a —COO— group,
2. a is 1; b, p and q are 0; and $Y_1$ is a —COO— group,
3. b is 1; a, p and q are 0; and $Y_2$ is a —COO— group,
4. p is 1; a, b and q are 0; $A_1$ is a 1,4-phenylene group; and $X_1$ is a single bond,
5. p is 1; a, b and q are 0; $A_1$ is a 1,4-phenylene group; and $X_1$ is a —COO— group,
6. p is 1; a, b and q are 0; $A_1$ is a 1,4-phenylene group; and $X_1$ is a —CH$_2$O— group,
7. p is 1; a, b and q are 0; $A_1$ is a 1,4-phenylene group; and $X_1$ is a —OCH$_2$— group,
8. p is 1; a, b and q are 0; $A_1$ is a pyridine-2,5-diyl group; and $X_1$ is a —COO— group,
9. q is 1; a, b and p are 0; $A_2$ is a 1,4-phenylene group; and $X_2$ is a —COO— group,
10. q is 1; a, b and p are 0; $A_2$ is a pyridine-2,5-diyl group; and $X_2$ is a —COO— group,
11. q is 1; a, b and p are 0; $A_2$ is a trans-1,4-cyclohexylene group; and $X_2$ is a —COO— group,
12. q is 1; a, b and p are 0; $A_2$ is a 1,4-phenylene group; and $X_2$ is a —OCH$_2$— group,
13. a and b are 1; p and q are 0; $Y_1$ is a —COO— group; $Y_2$ is a —COO— group,
14. a and b are 1; p and q are 0; $Y_1$ is a —COO— group; $Y_2$ is a —COO— group,
15. p and b are 1; a and q are 0; $A_1$ is a 1,4-phenylene group; $X_1$ is a single bond; and $Y_2$ is a —COO— group,
16. p and b are 1; a and q are 0; $A_1$ is a 1,4-phenylene group; $X_1$ is a —COO— group; and $Y_2$ is a —COO— group,
17. p and b are 1; a and q are 0; $A_1$ is a pyridine-2,5-diyl group; $X_1$ is a —COO— group; and $Y_2$ is a —COO— group, and
18. a and q are 1; p and b are 0; $Y_1$ is a —COO— group; $A_2$ is a 1,4-phenylene group; and $X_2$ is a —COO— group.

The following compounds can be given as the concrete examples of the pyrimidine compound represented by Formula (1) of the present invention:

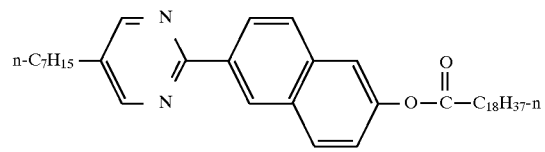

Exemplified compound 1

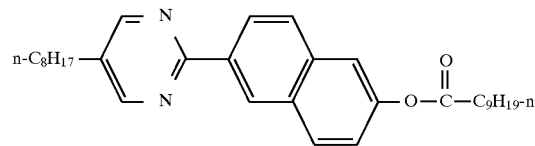

Exemplified compound 2

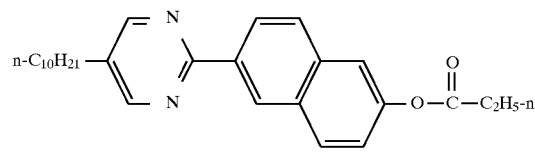

Exemplified compound 3

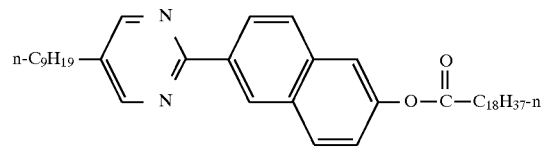

Exemplified compound 4

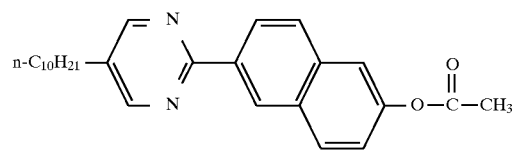

Exemplified compound 5

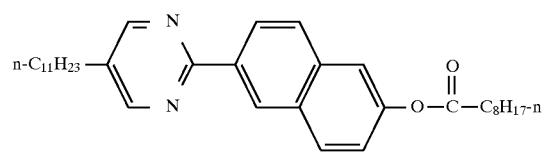

Exemplified compound 6

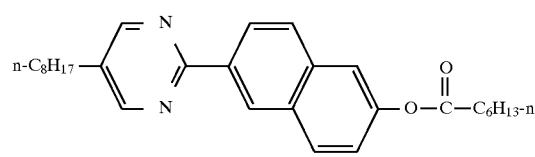

Exemplified compound 7

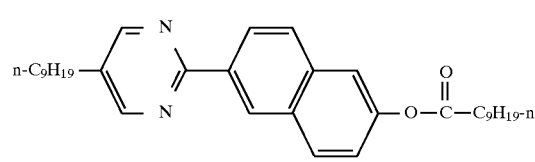

Exemplified compound 8

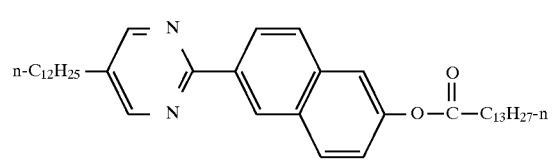

Exemplified compound 9

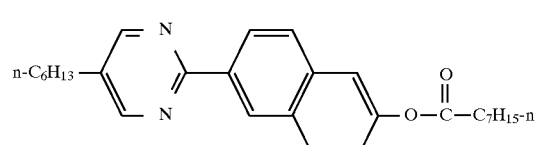

Exemplified compound 10

-continued
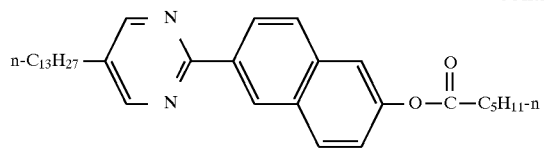
Exemplified compound 11
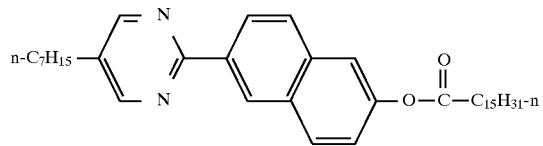
Exemplified compound 12
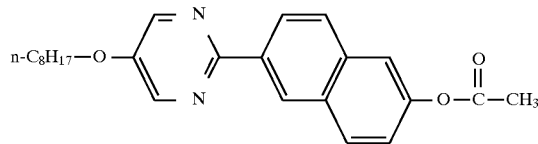
Exemplified compound 13
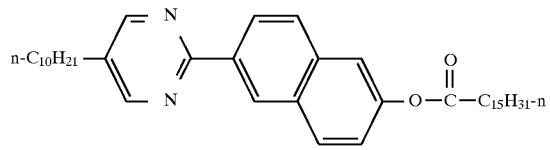
Exemplified compound 14
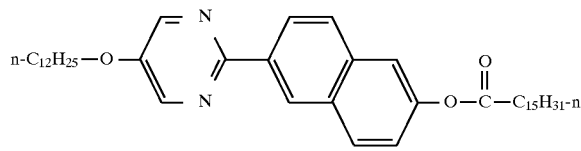
Exemplified compound 15
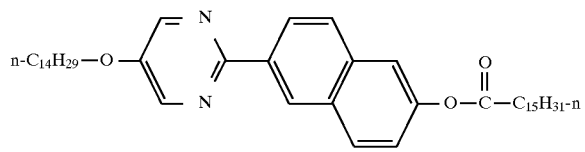
Exemplified compound 16
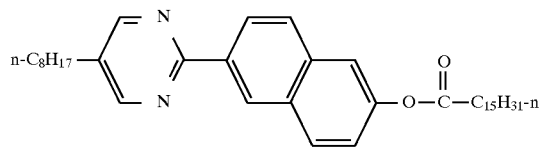
Exemplified compound 17
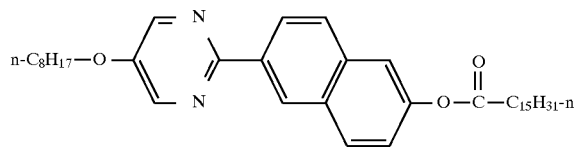
Exemplified compound 18
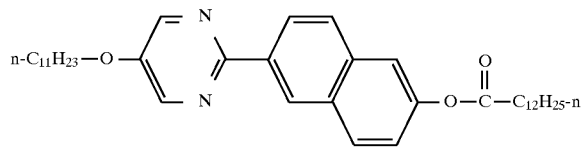
Exemplified compound 19
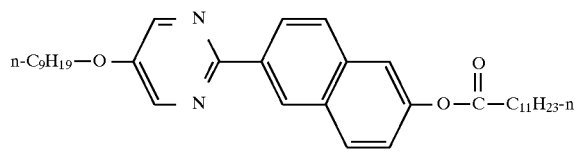
Exemplified compound 20

-continued
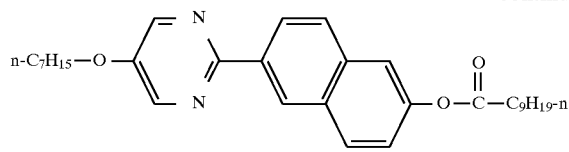
Exemplified compound 21
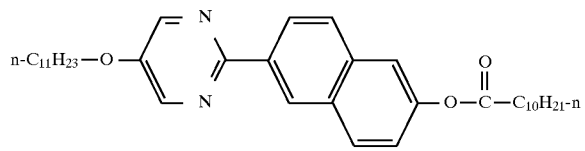
Exemplified compound 22
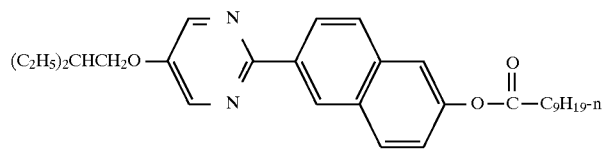
Exemplified compound 23
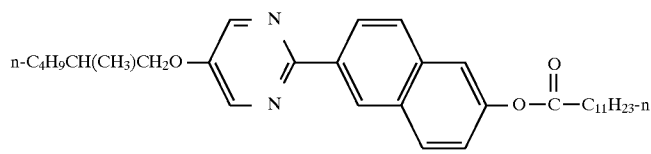
Exemplified compound 24
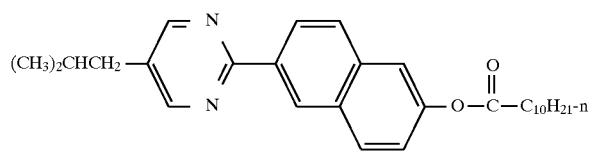
Exemplified compound 25
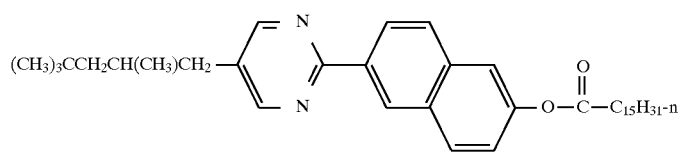
Exemplified compound 26
Exemplified compound 27
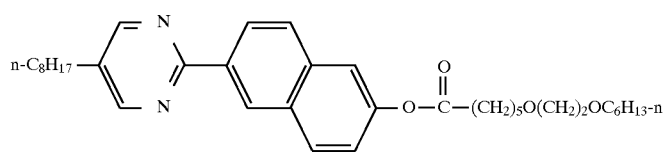
Exemplified compound 28
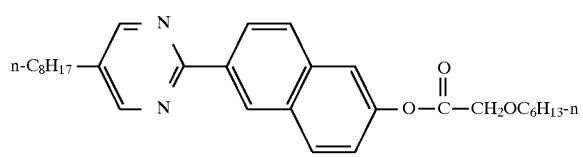
Exemplified compound 29
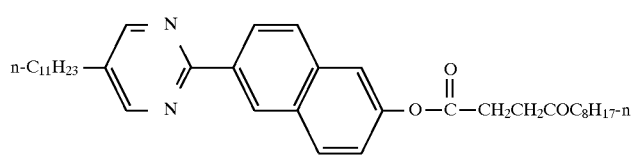
Exemplified compound 30

-continued
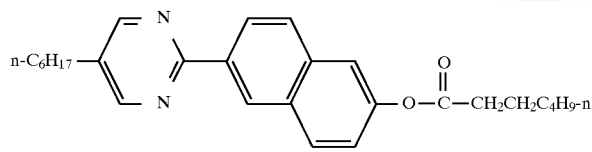 Exemplified compound 31
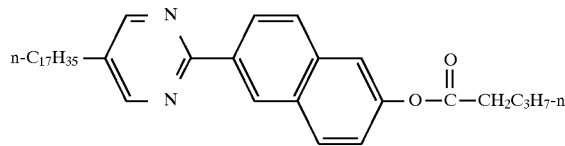 Exemplified compound 32
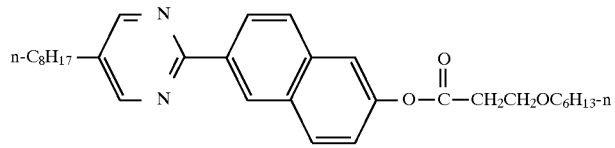 Exemplified compound 33
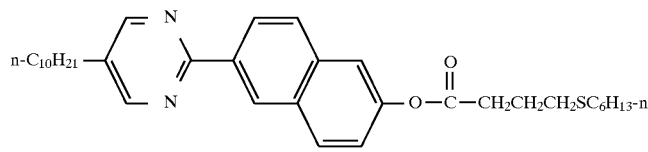 Exemplified compound 34
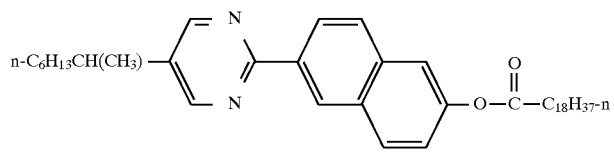 Exemplified compound 35
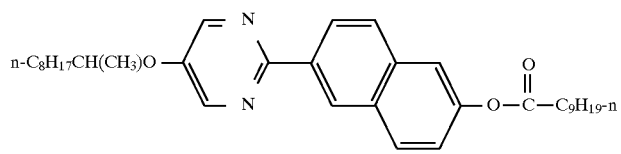 Exemplified compound 36
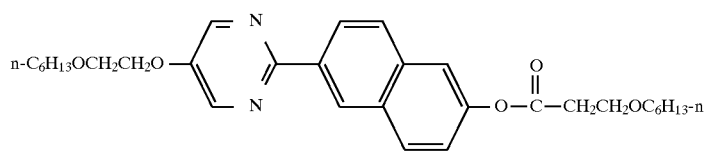 Exemplified compound 37
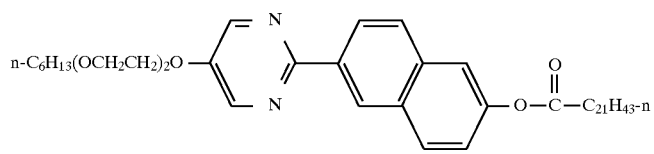 Exemplified compound 38
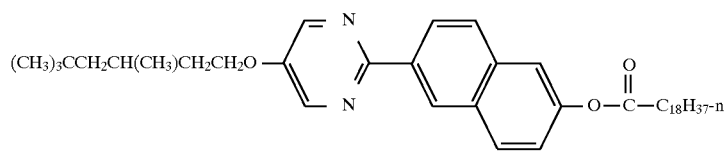 Exemplified compound 39
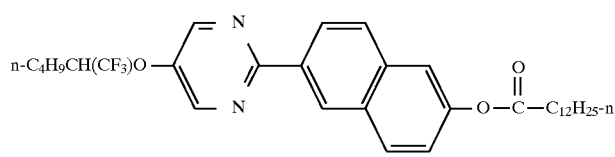 Exemplified compound 40

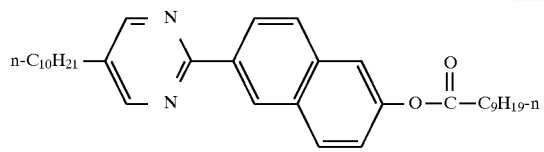
Exemplified compound 41
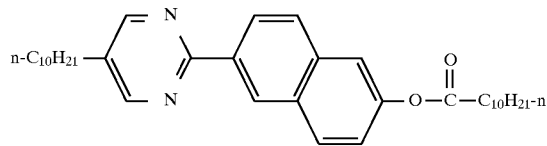
Exemplified compound 42
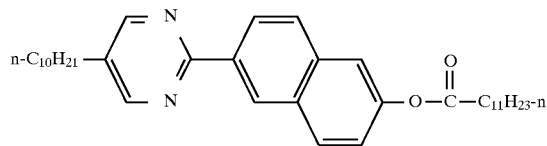
Exemplified compound 43
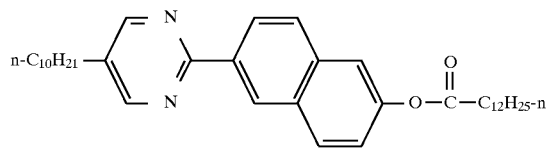
Exemplified compound 44
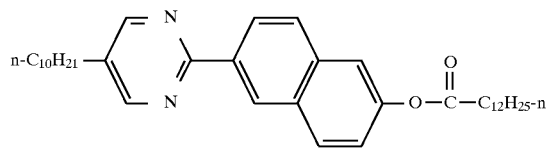
Exemplified compound 45
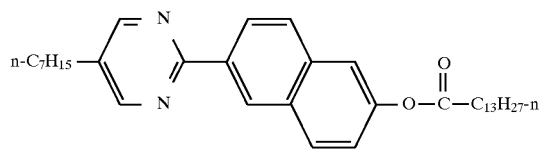
Exemplified compound 46
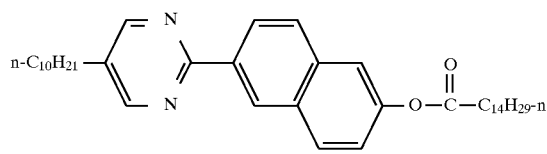
Exemplified compound 47
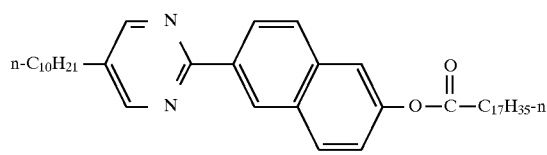
Exemplified compound 48
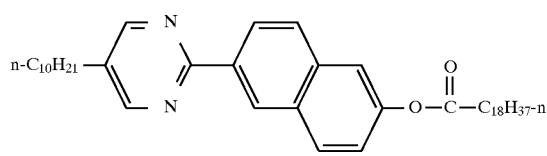
Exemplified compound 49
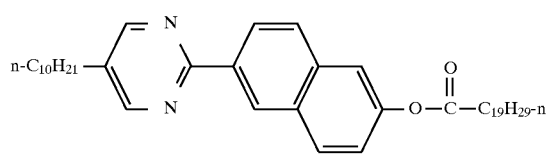
Exemplified compound 50
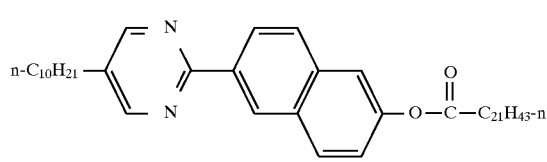

-continued
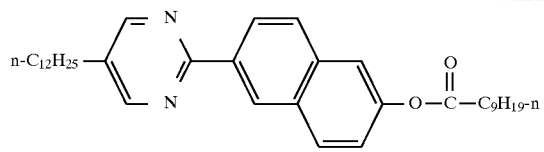
Exemplified compound 51
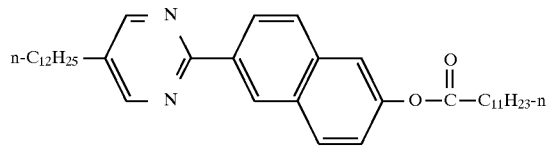
Exemplified compound 52
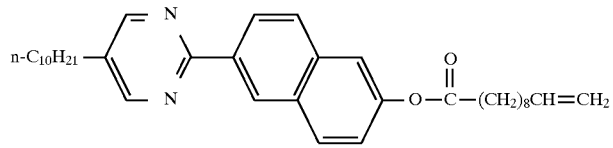
Exemplified compound 53
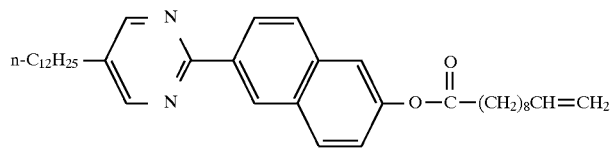
Exemplified compound 54
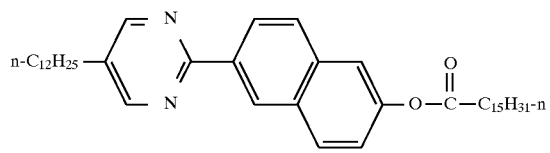
Exemplified compound 55
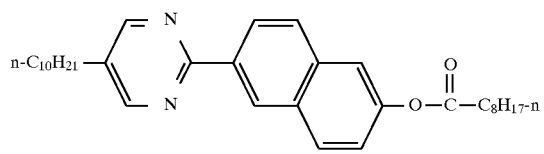
Exemplified compound 56
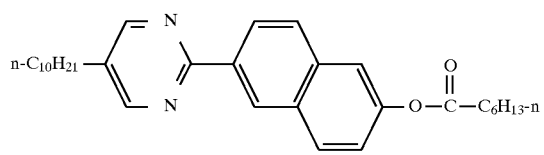
Exemplified compound 57
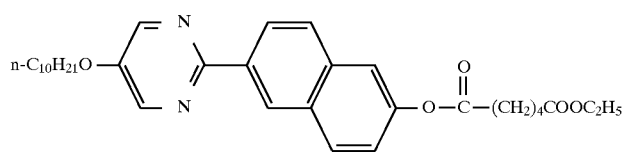
Exemplified compound 58
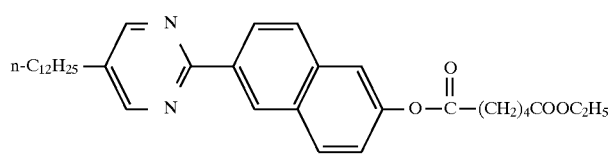
Exemplified compound 59
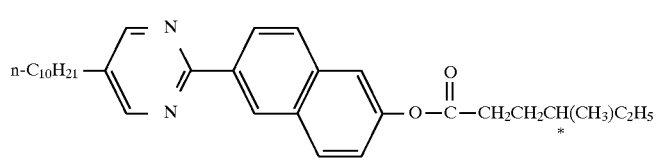
Exemplified compound 60

-continued
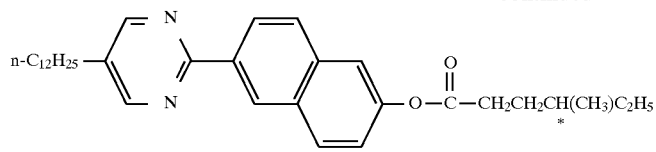
Exemplified compound 61
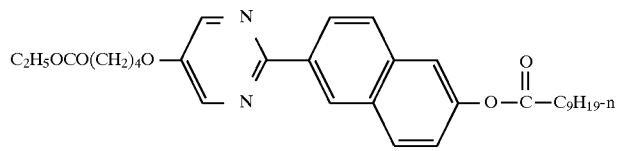
Exemplified compound 62
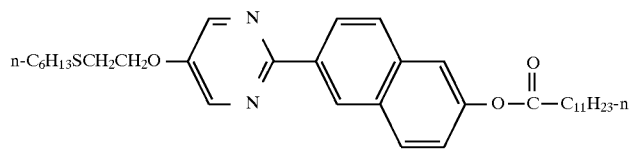
Exemplified compound 63
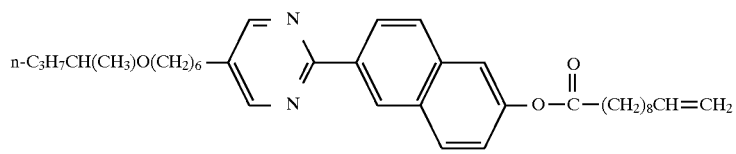
Exemplified compound 64
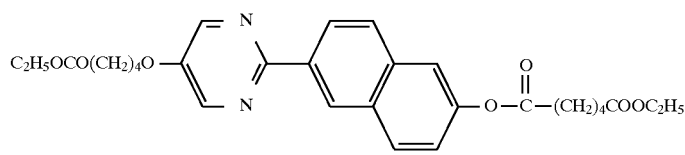
Exemplified compound 65
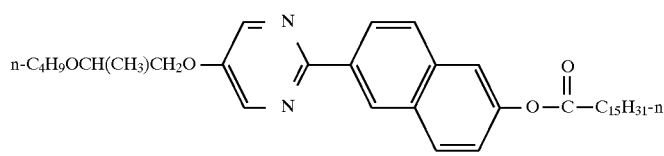
Exemplified compound 66
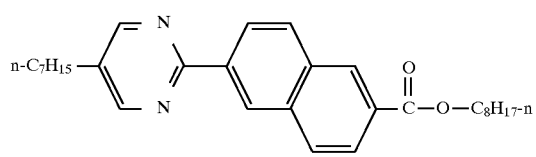
Exemplified compound 67
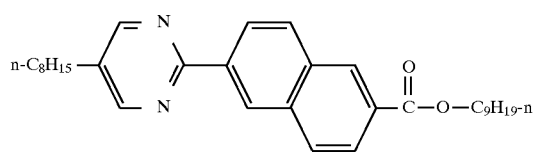
Exemplified compound 68
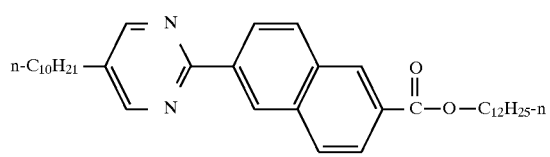
Exemplified compound 69
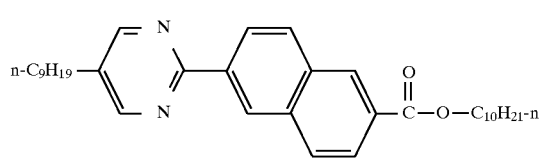
Exemplified compound 70

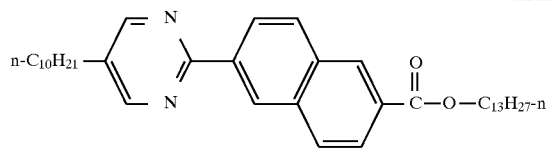
Exemplified compound 71
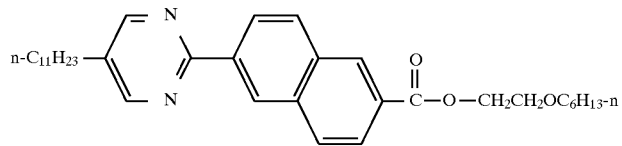
Exemplified compound 72
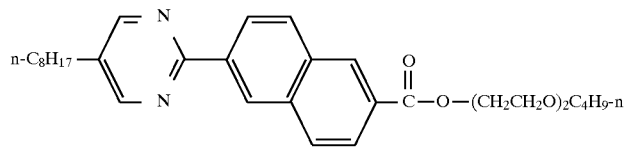
Exemplified compound 73
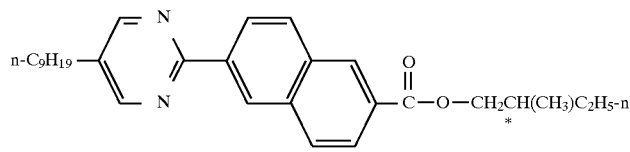
Exemplified compound 74
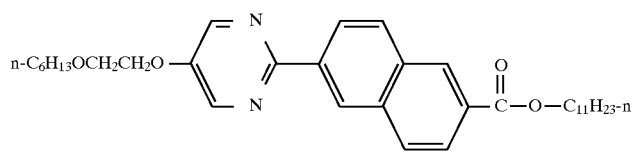
Exemplified compound 75
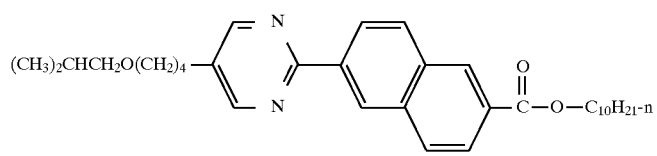
Exemplified compound 76
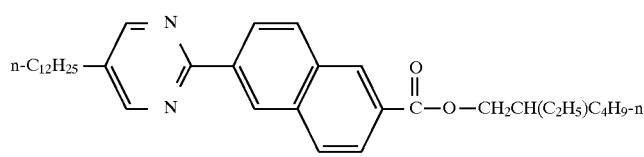
Exemplified compound 77
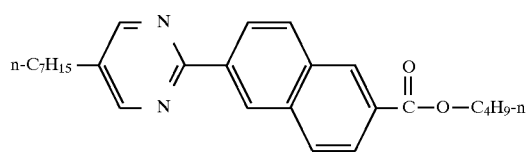
Exemplified compound 78
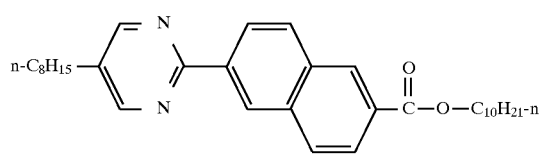
Exemplified compound 79
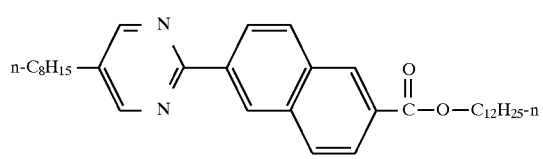
Exemplified compound 80

-continued
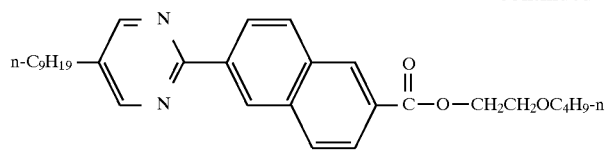
Exemplified compound 81
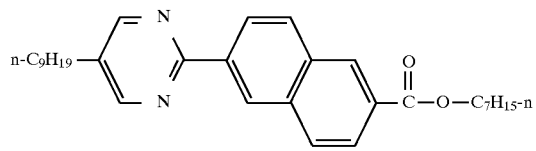
Exemplified compound 82
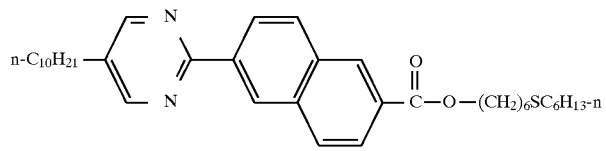
Exemplified compound 83
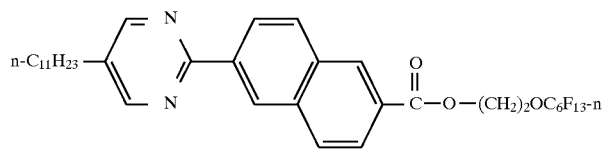
Exemplified compound 84
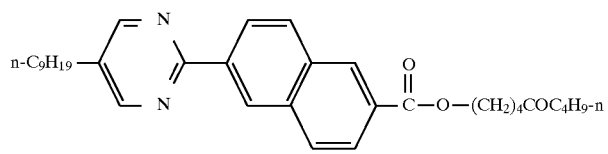
Exemplified compound 85
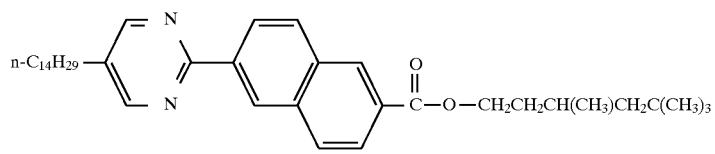
Exemplified compound 86
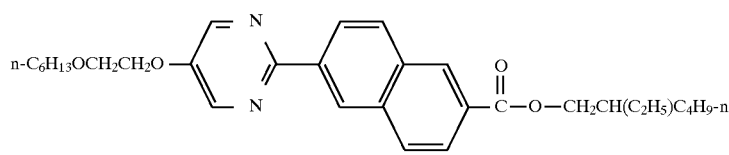
Exemplified compound 87
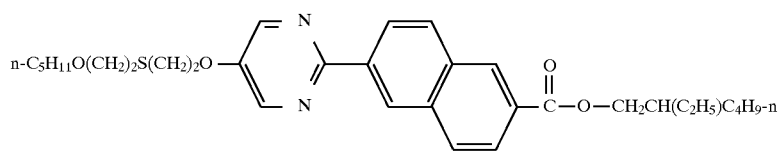
Exemplified compound 88
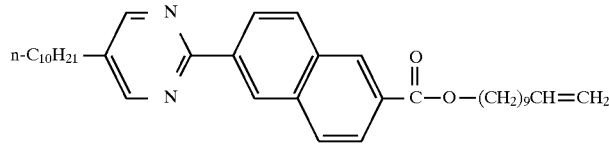
Exemplified compound 89
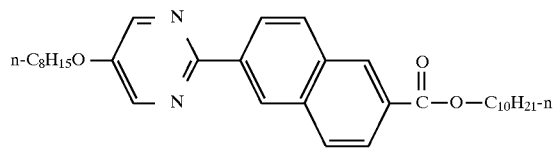
Exemplified compound 90

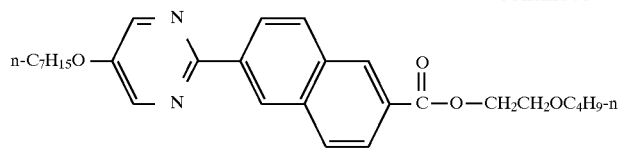
Exemplified compound 91
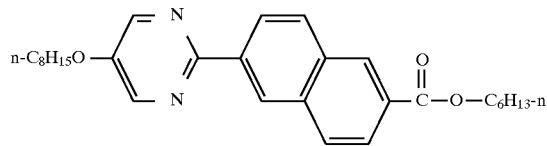
Exemplified compound 92
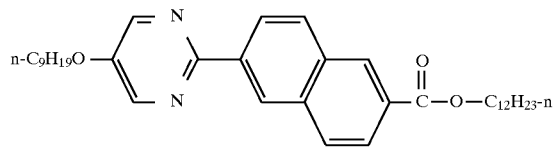
Exemplified compound 93
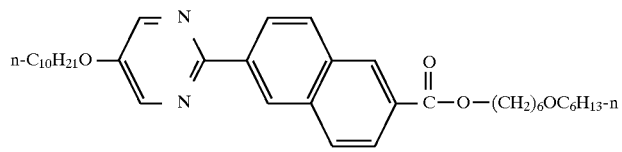
Exemplified compound 94
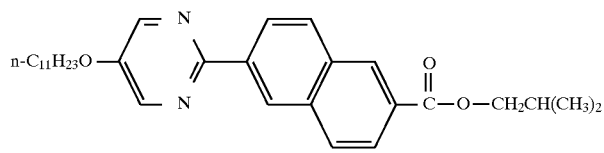
Exemplified compound 95
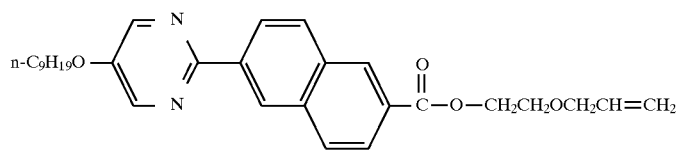
Exemplified compound 96
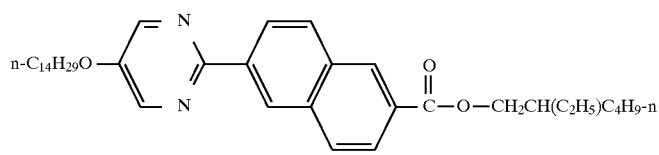
Exemplified compound 97
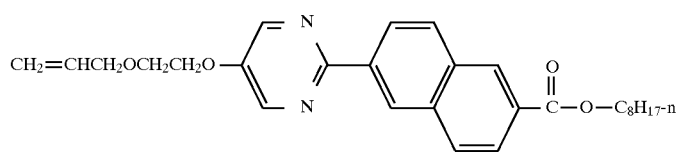
Exemplified compound 98
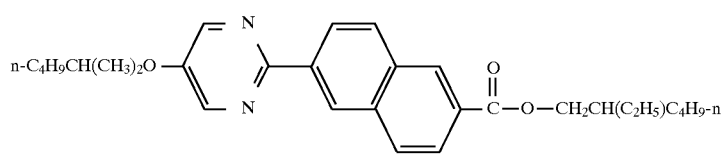
Exemplified compound 99
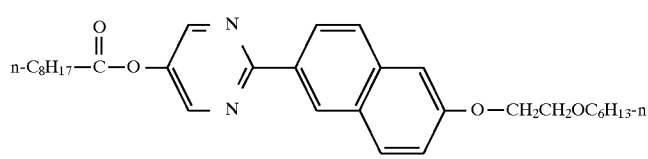
Exemplified compound 100

-continued
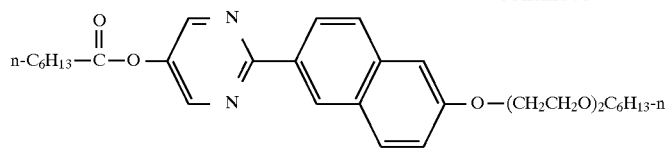
Exemplified compound 101
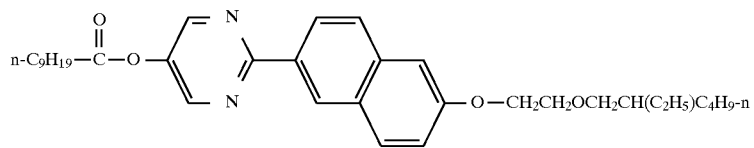
Exemplified compound 102
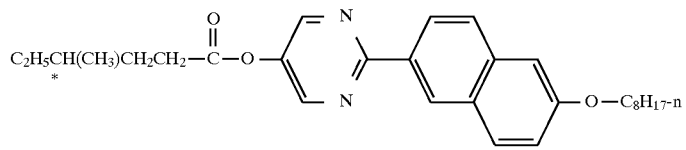
Exemplified compound 103
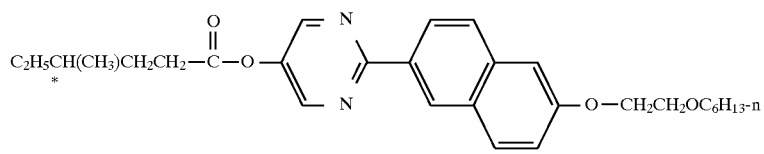
Exemplified compound 104
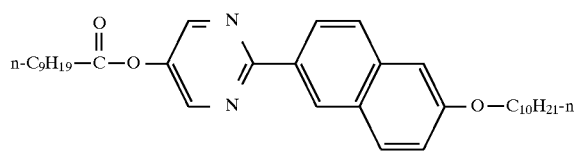
Exemplified compound 105
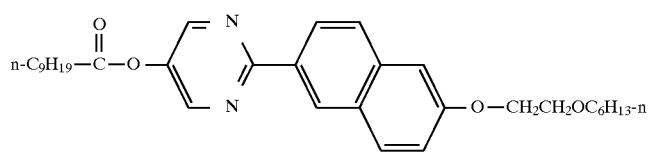
Exemplified compound 106
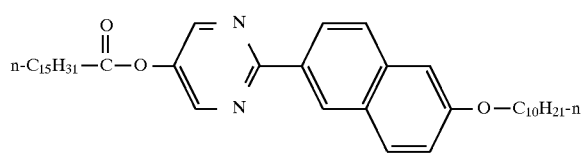
Exemplified compound 107
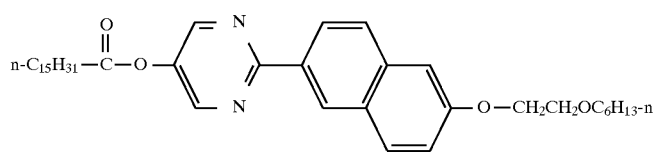
Exemplified compound 108
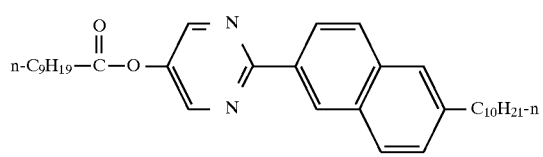
Exemplified compound 109
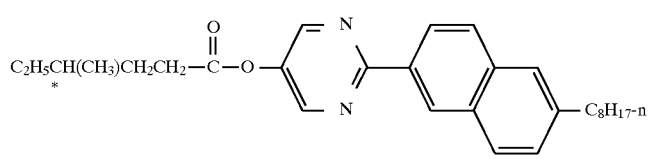
Exemplified compound 110

-continued
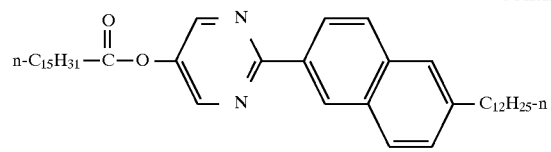
Exemplified compound 111
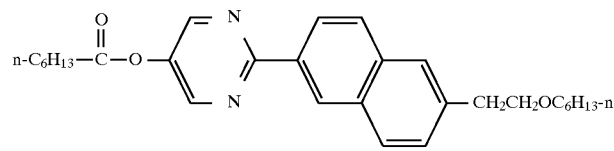
Exemplified compound 112
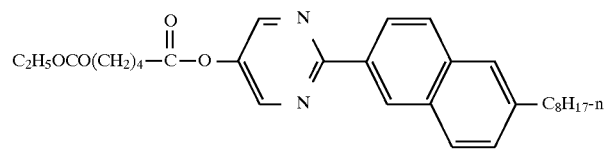
Exemplified compound 113
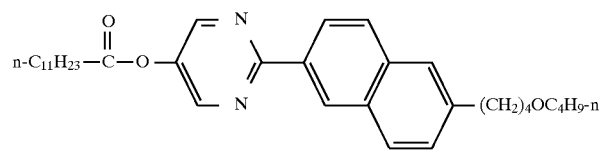
Exemplified compound 114
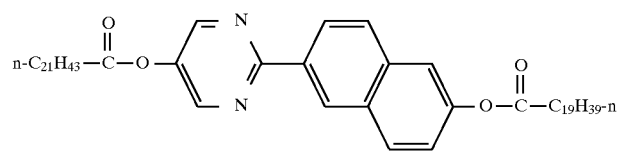
Exemplified compound 115
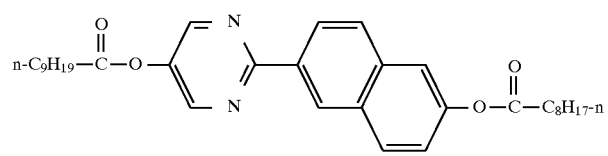
Exemplified compound 116
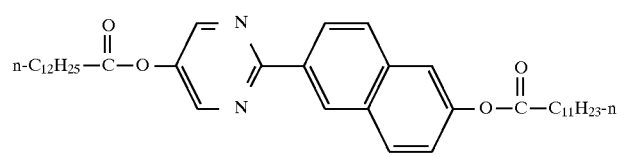
Exemplified compound 117
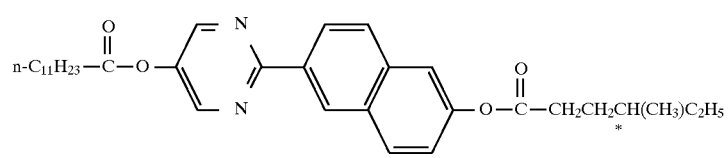
Exemplified compound 118
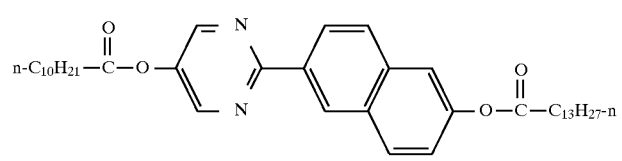
Exemplified compound 119
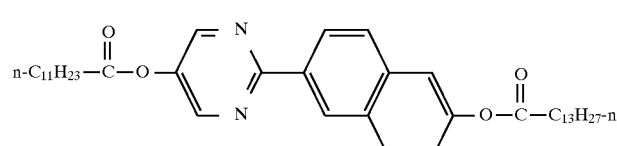
Exemplified compound 120

-continued
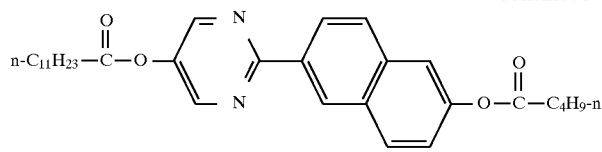
Exemplified compound 121
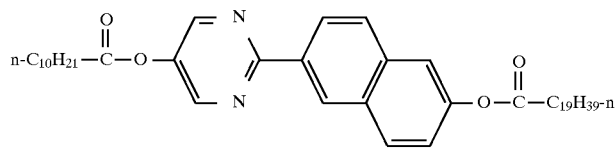
Exemplified compound 122
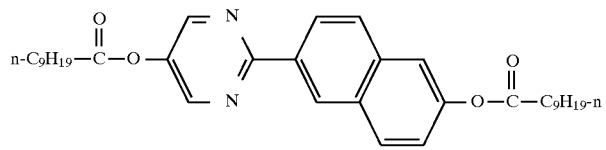
Exemplified compound 123
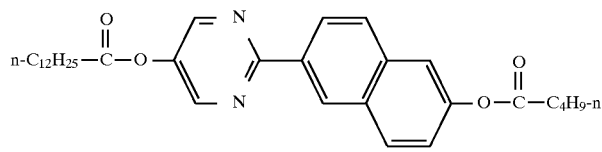
Exemplified compound 124
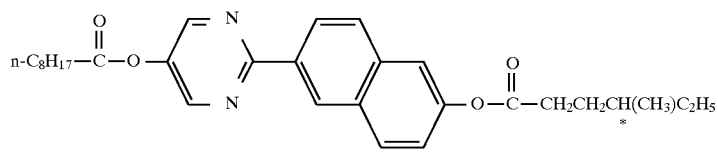
Exemplified compound 125
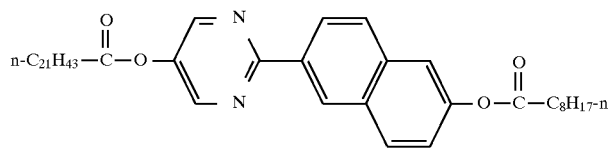
Exemplified compound 126
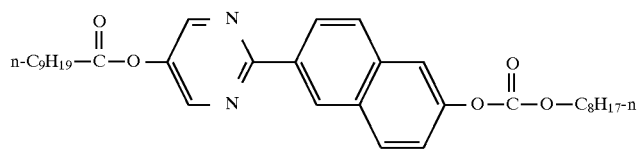
Exemplified compound 127
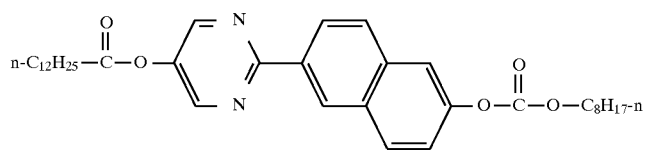
Exemplified compound 128
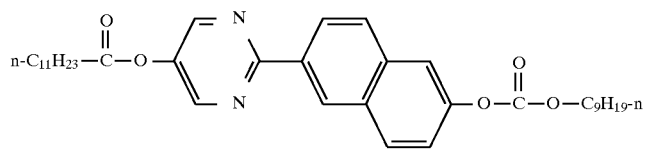
Exemplified compound 129
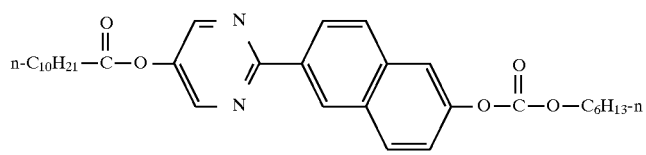
Exemplified compound 130

-continued
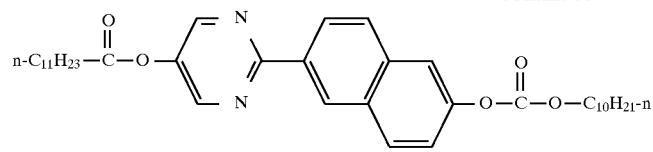
Exemplified compound 131
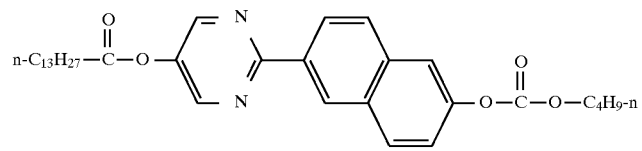
Exemplified compound 132
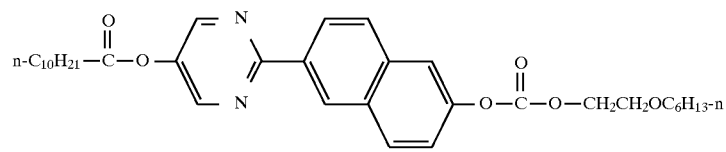
Exemplified compound 133
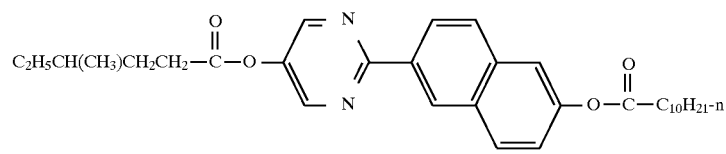
Exemplified compound 134
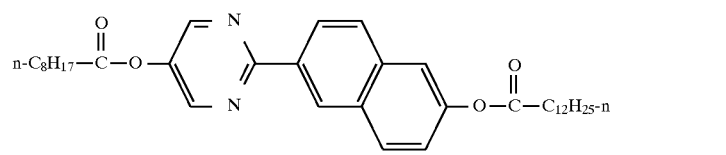
Exemplified compound 135
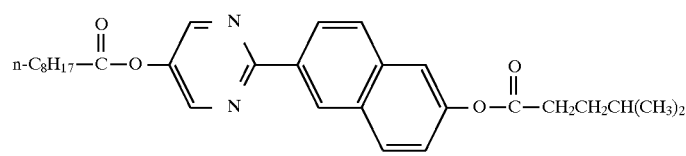
Exemplified compound 136
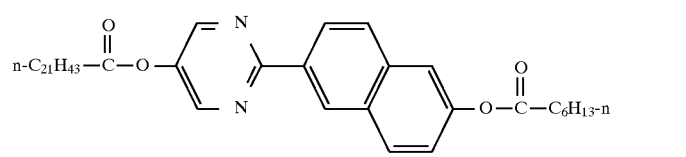
Exemplified compound 137
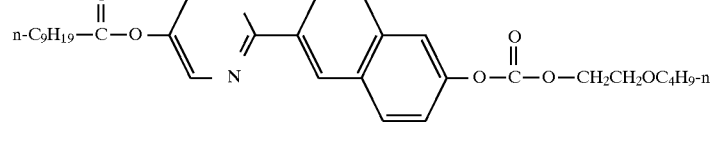
Exemplified compound 138
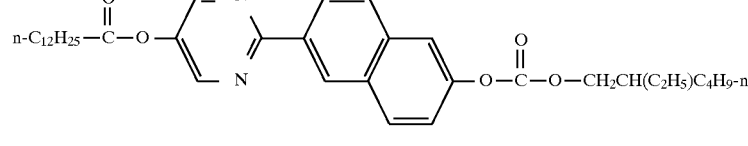
Exemplified compound 139
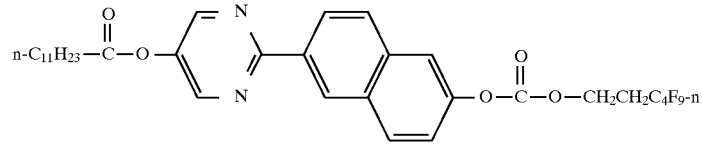
Exemplified compound 140

-continued
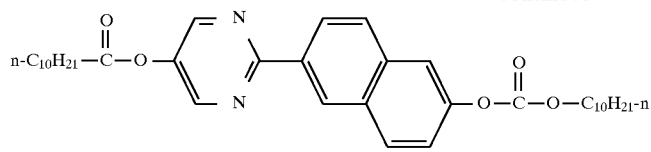
Exemplified compound 141
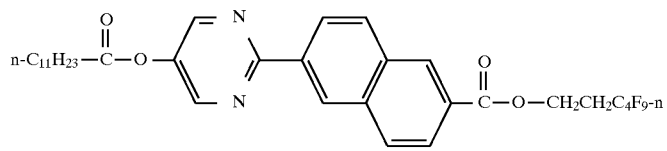
Exemplified compound 142
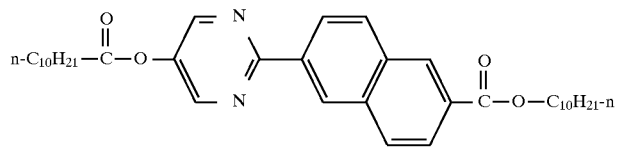
Exemplified compound 143
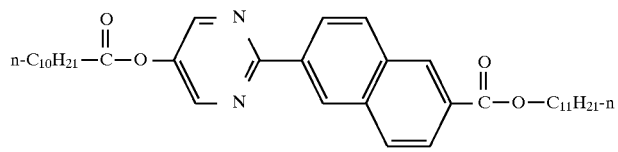
Exemplified compound 144
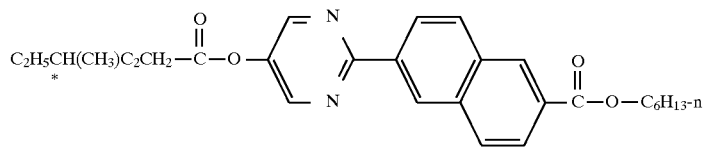
Exemplified compound 145
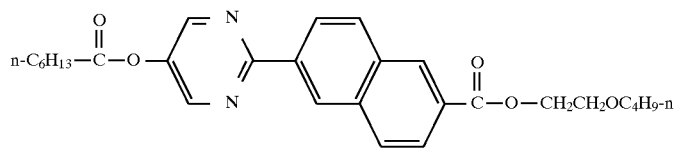
Exemplified compound 146
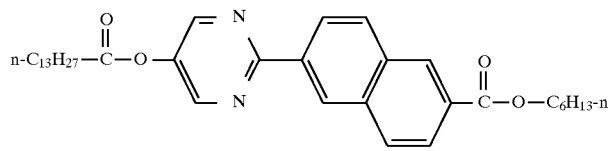
Exemplified compound 147
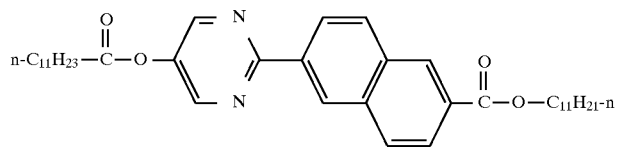
Exemplified compound 148
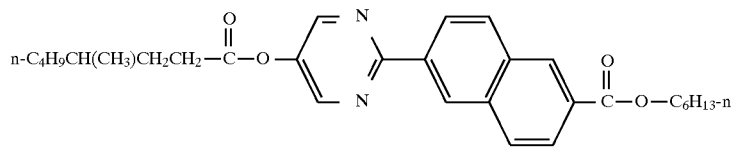
Exemplified compound 149
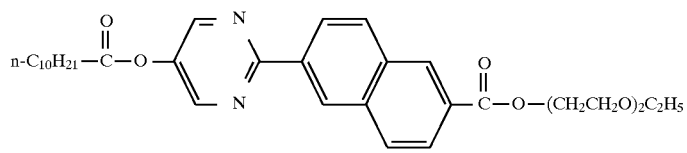
Exemplified compound 150

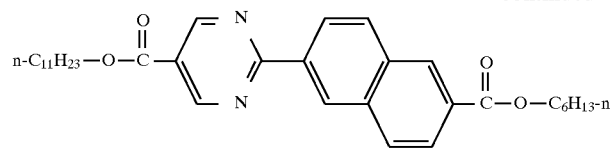
Exemplified compound 151
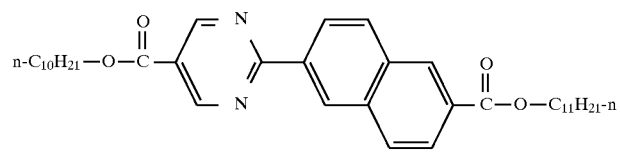
Exemplified compound 152
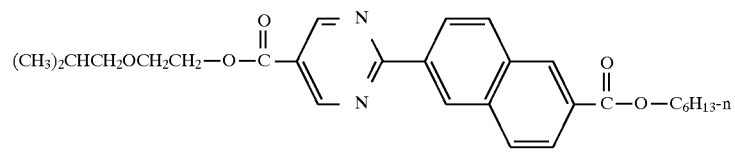
Exemplified compound 153
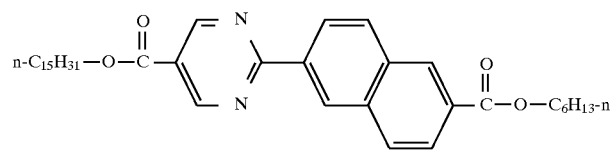
Exemplified compound 154
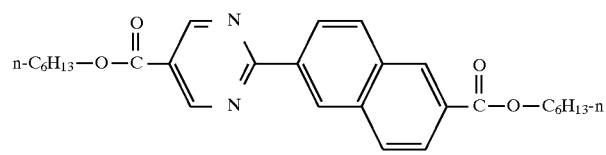
Exemplified compound 155
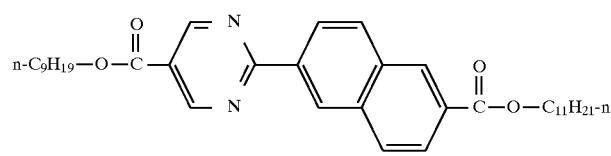
Exemplified compound 156
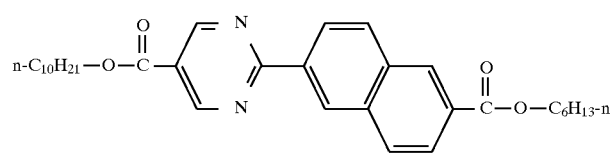
Exemplified compound 157
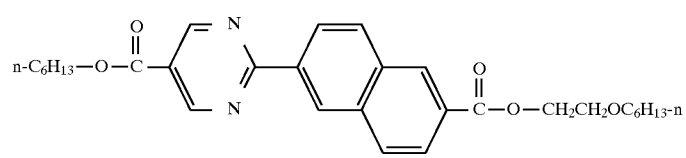
Exemplified compound 158
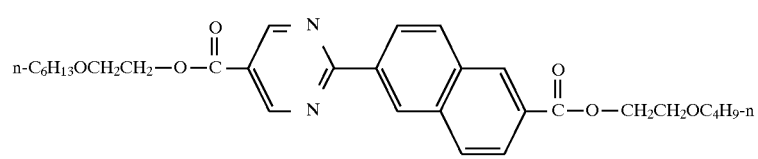
Exemplified compound 159
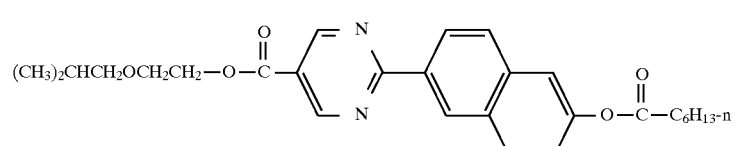
Exemplified compound 160

-continued
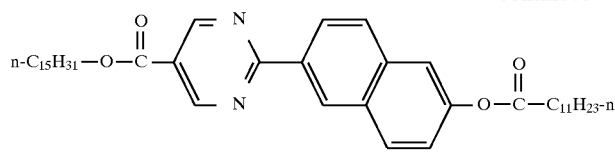
Exemplified compound 161
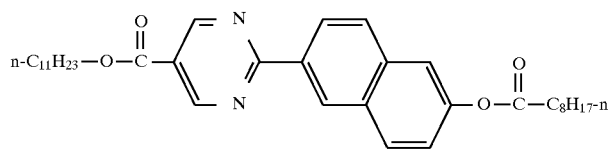
Exemplified compound 162
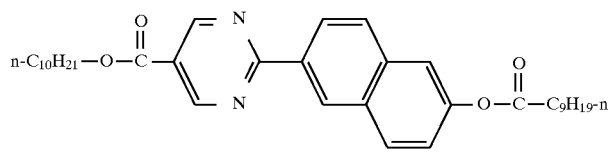
Exemplified compound 163
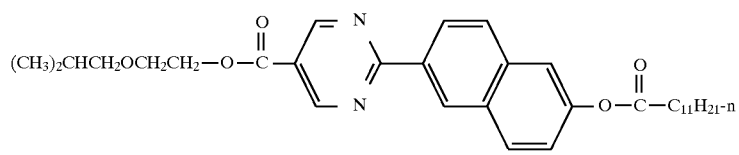
Exemplified compound 164
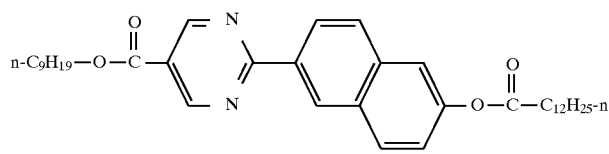
Exemplified compound 165
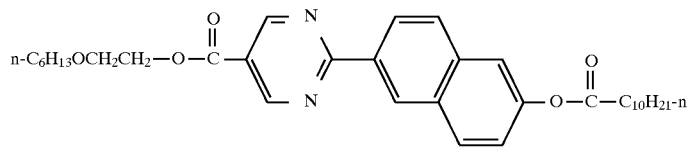
Exemplified compound 166
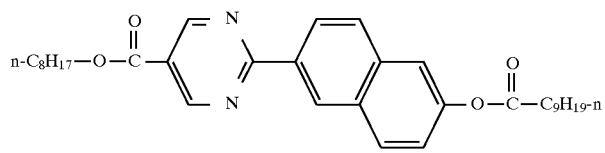
Exemplified compound 167
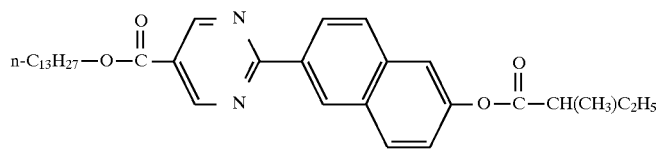
Exemplified compound 168
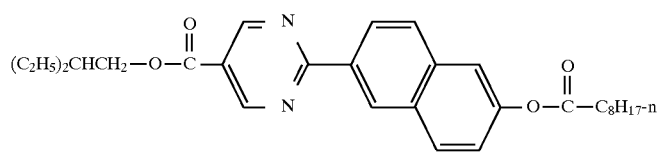
Exemplified compound 169
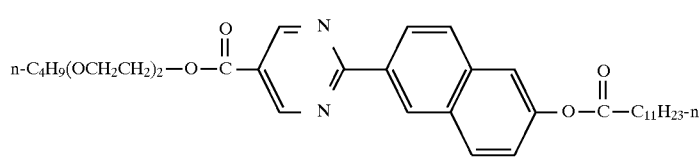
Exemplified compound 170

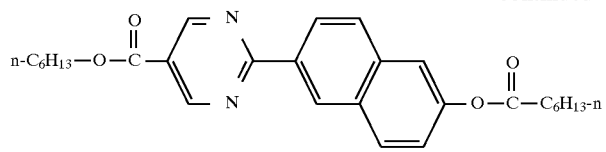
Exemplified compound 171
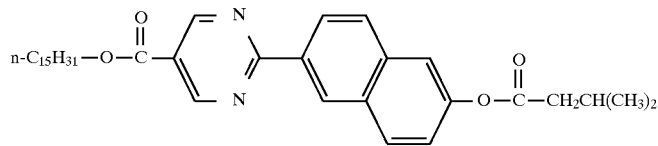
Exemplified compound 172
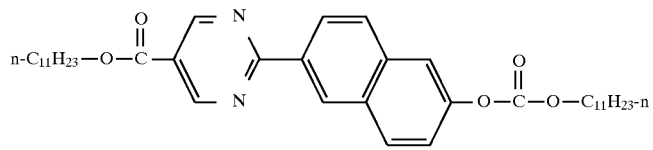
Exemplified compound 173
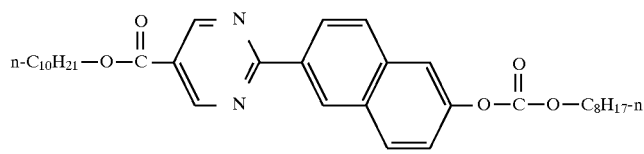
Exemplified compound 174
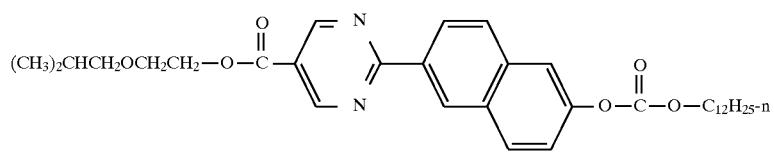
Exemplified compound 175
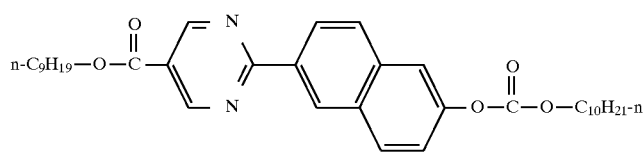
Exemplified compound 176
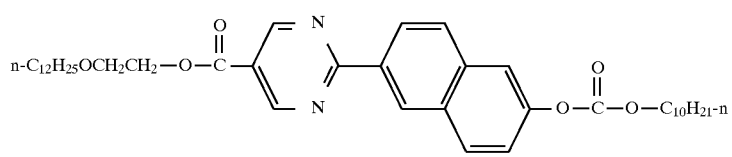
Exemplified compound 177
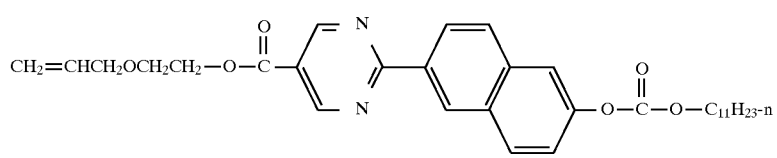
Exemplified compound 178
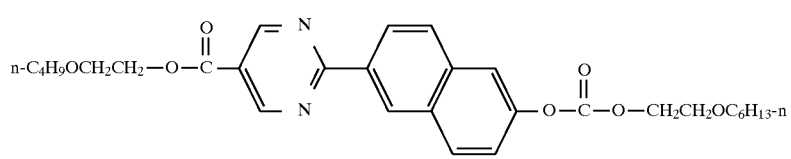
Exemplified compound 179
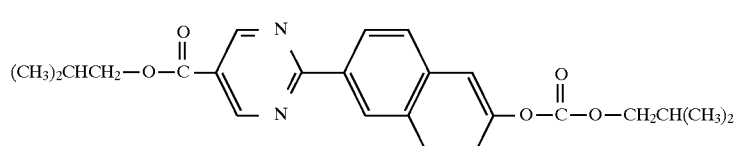
Exemplified compound 180

-continued
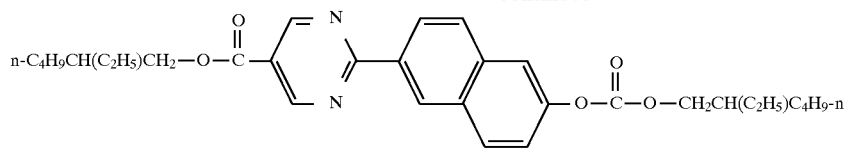
Exemplified compound 181
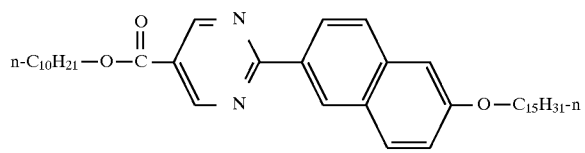
Exemplified compound 182
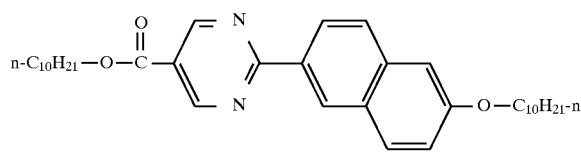
Exemplified compound 183
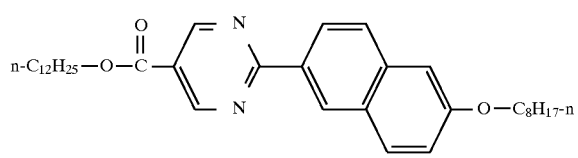
Exemplified compound 184
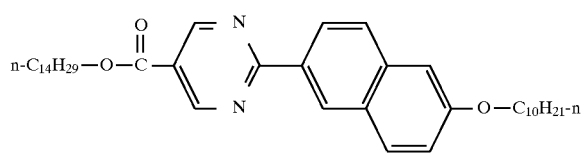
Exemplified compound 185
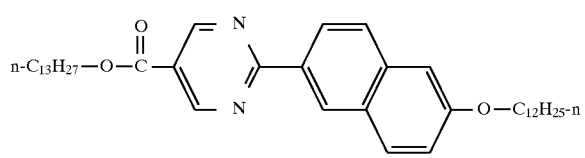
Exemplified compound 186
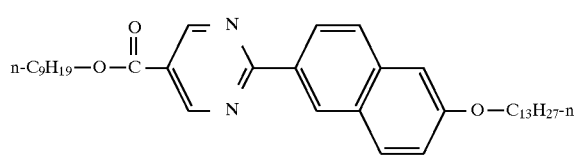
Exemplified compound 187
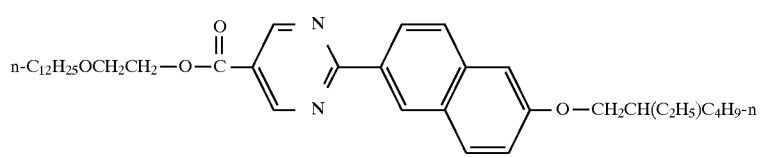
Exemplified compound 188
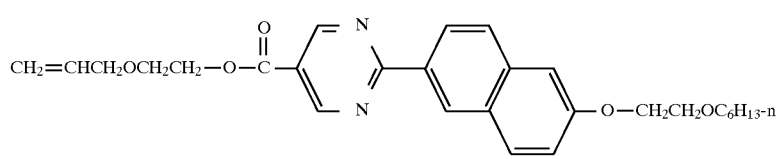
Exemplified compound 189
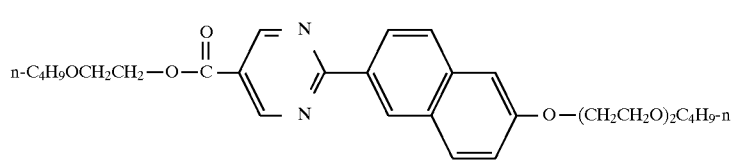
Exemplified compound 190

-continued
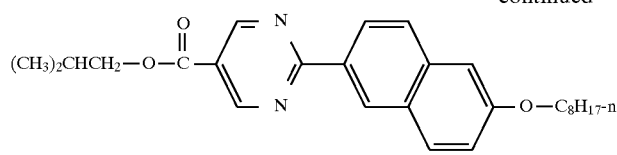
Exemplified compound 191
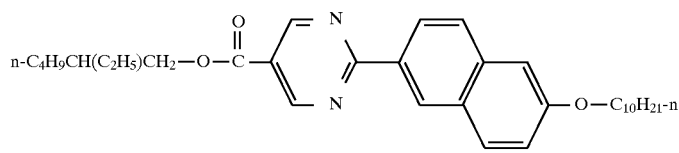
Exemplified compound 192
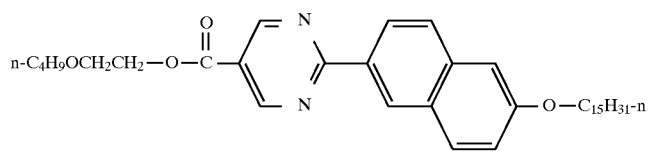
Exemplified compound 193
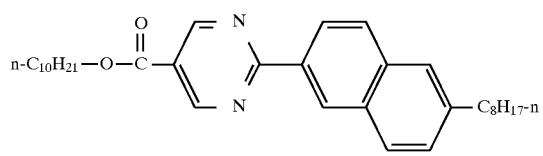
Exemplified compound 194
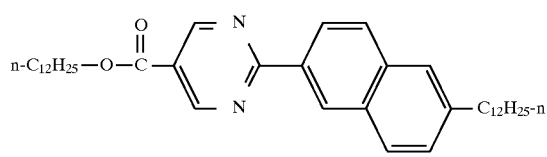
Exemplified compound 195
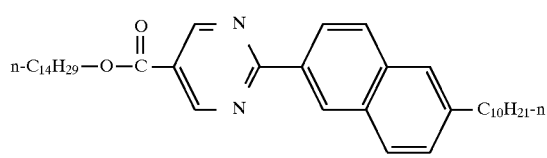
Exemplified compound 196
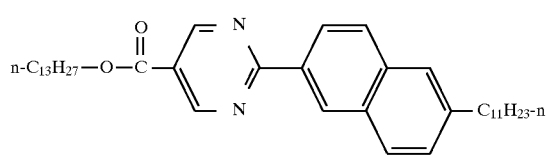
Exemplified compound 197
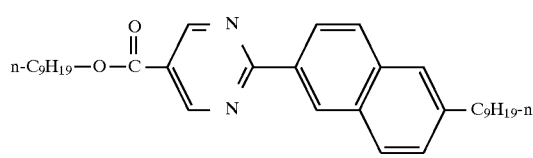
Exemplified compound 198
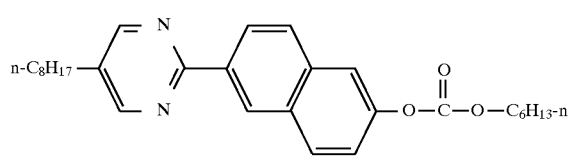
Exemplified compound 199
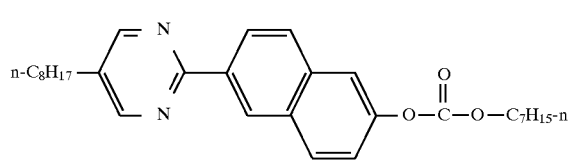
Exemplified compound 200

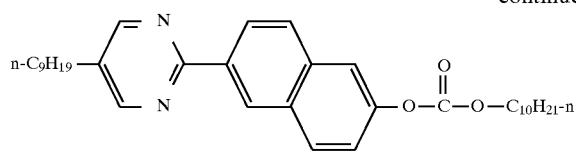
Exemplified compound 201
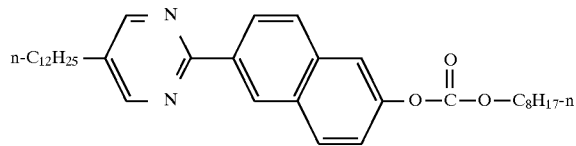
Exemplified compound 202
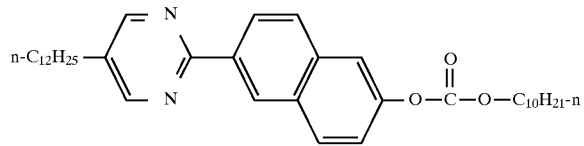
Exemplified compound 203
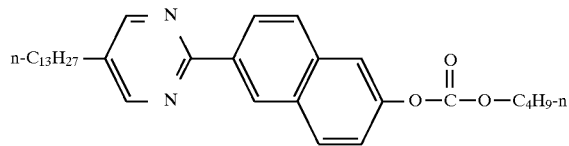
Exemplified compound 204
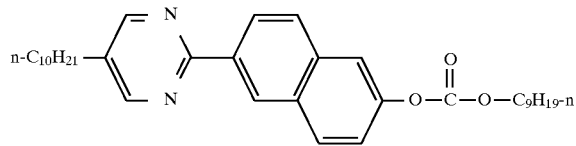
Exemplified compound 205
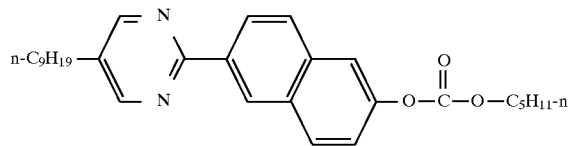
Exemplified compound 206
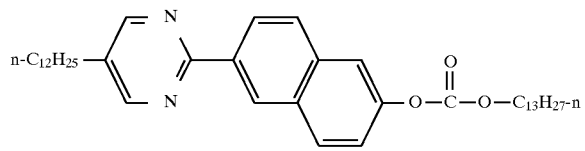
Exemplified compound 207
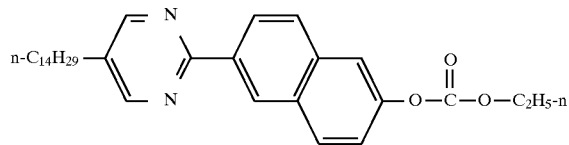
Exemplified compound 208
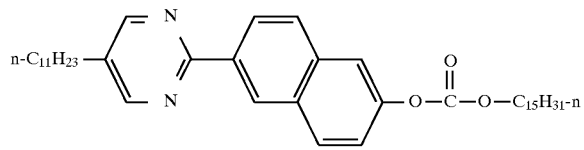
Exemplified compound 209
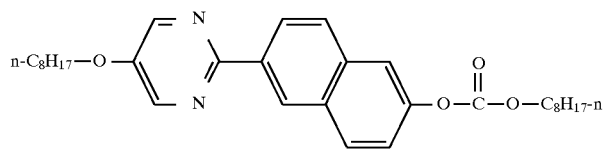
Exemplified compound 210

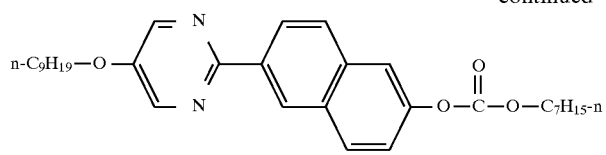
Exemplified compound 211
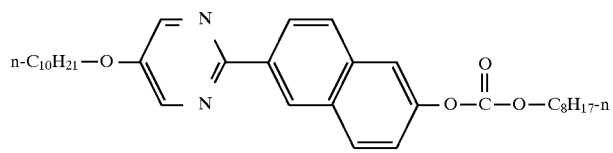
Exemplified compound 212
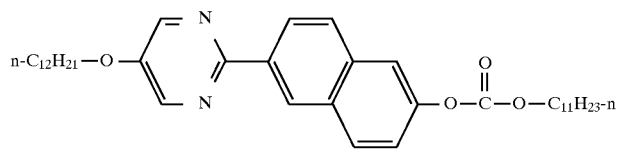
Exemplified compound 213
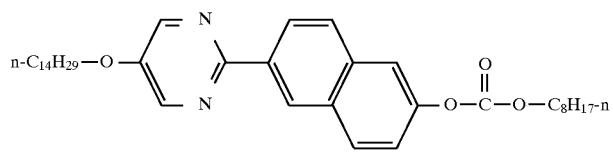
Exemplified compound 214
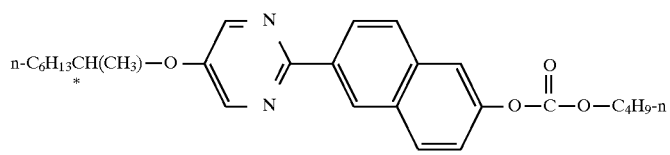
Exemplified compound 215
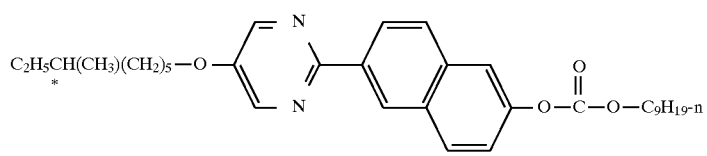
Exemplified compound 216
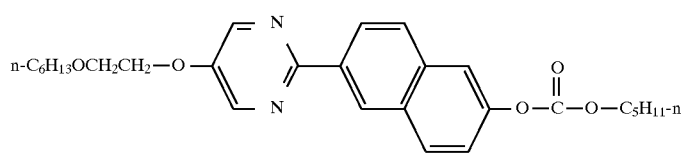
Exemplified compound 217
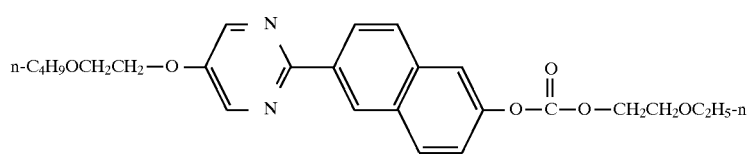
Exemplified compound 218
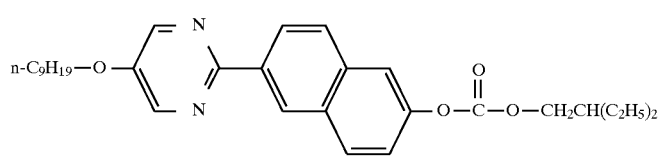
Exemplified compound 219
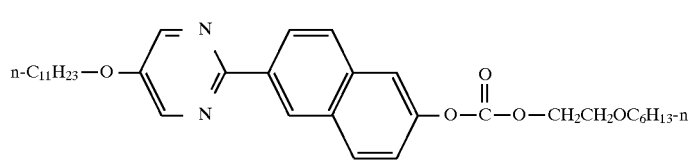
Exemplified compound 220

-continued
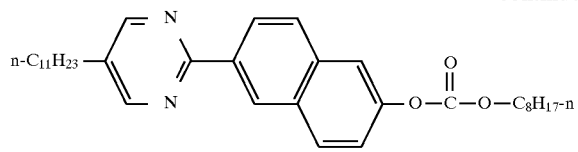
Exemplified compound 221
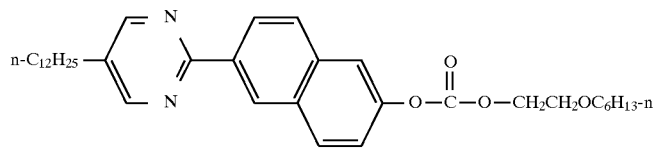
Exemplified compound 222
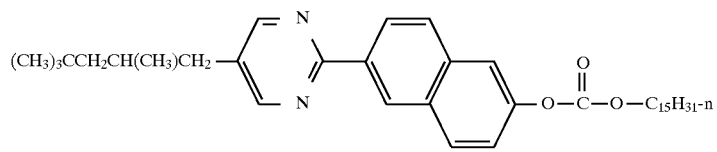
Exemplified compound 223
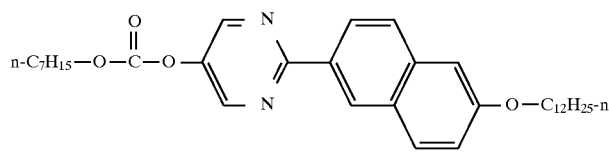
Exemplified compound 224
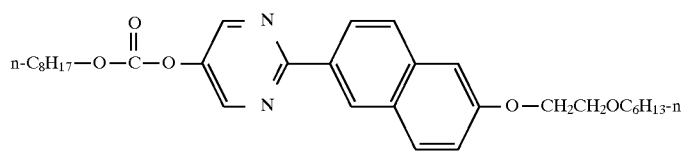
Exemplified compound 225
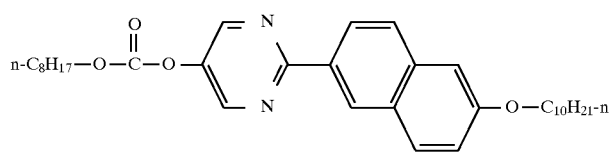
Exemplified compound 226
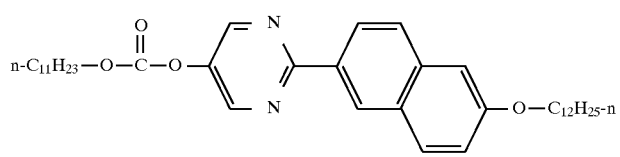
Exemplified compound 227
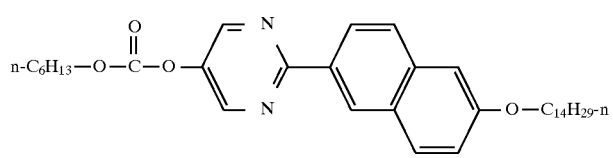
Exemplified compound 228
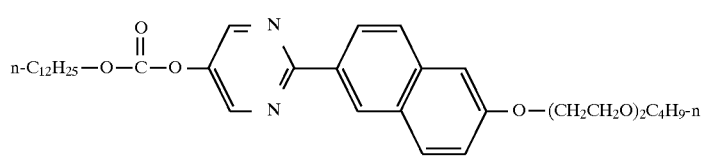
Exemplified compound 229
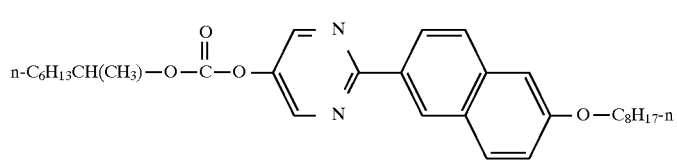
Exemplified compound 230

-continued
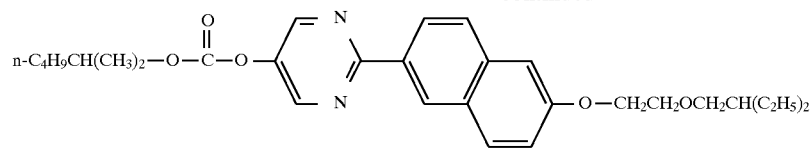
Exemplified compound 231
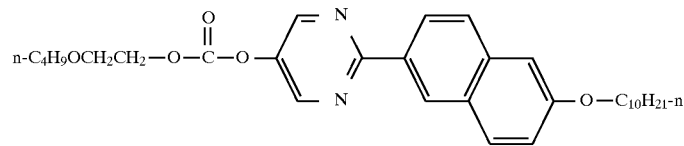
Exemplified compound 232
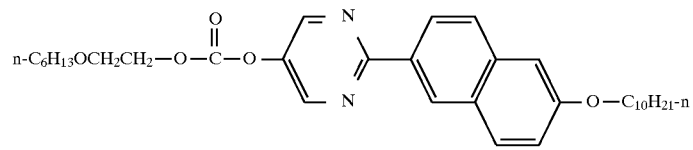
Exemplified compound 233
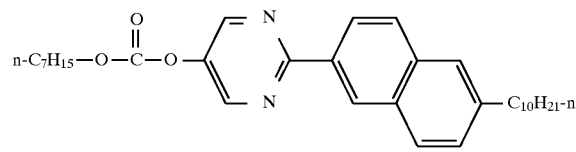
Exemplified compound 234
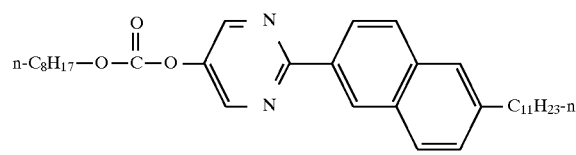
Exemplified compound 235
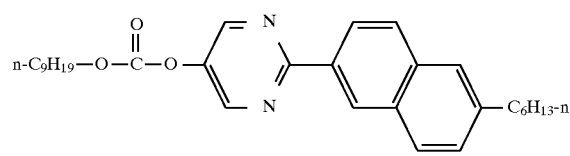
Exemplified compound 236
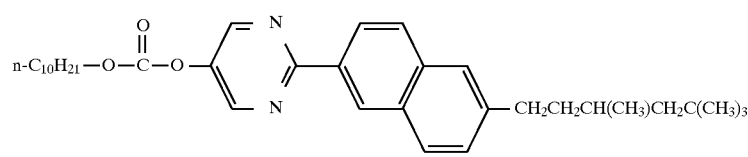
Exemplified compound 237
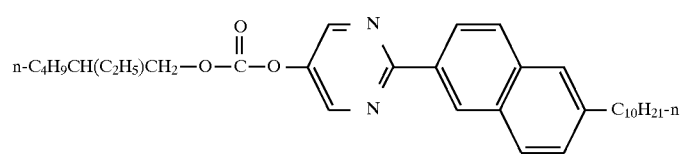
Exemplified compound 238
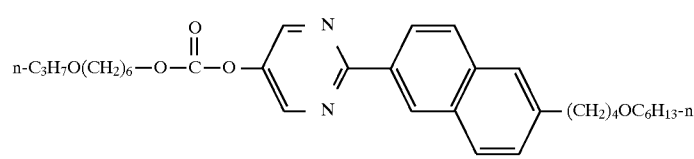
Exemplified compound 239
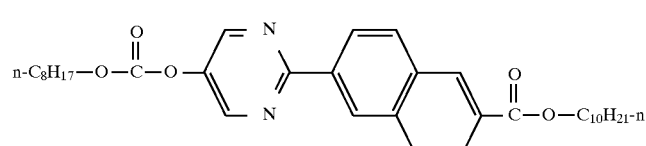
Exemplified compound 240

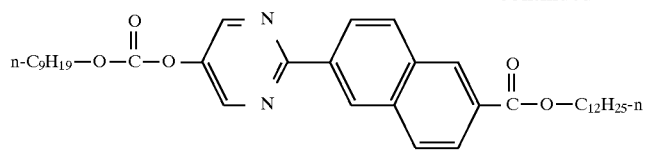
Exemplified compound 241
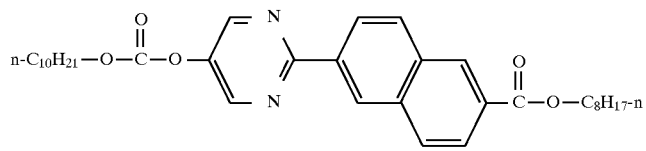
Exemplified compound 242
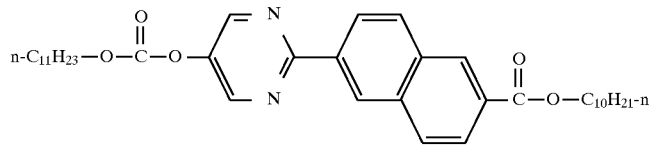
Exemplified compound 243
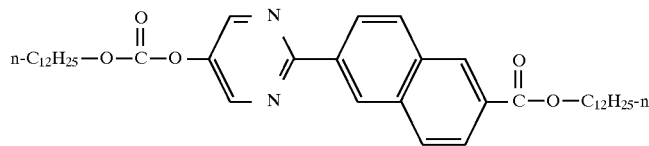
Exemplified compound 244
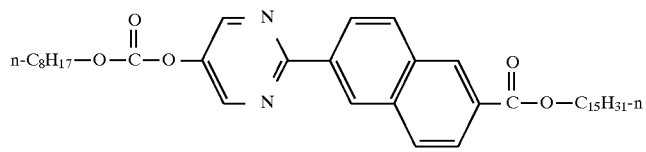
Exemplified compound 245
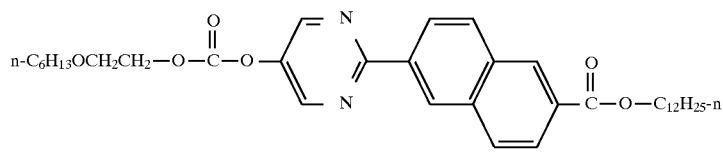
Exemplified compound 246
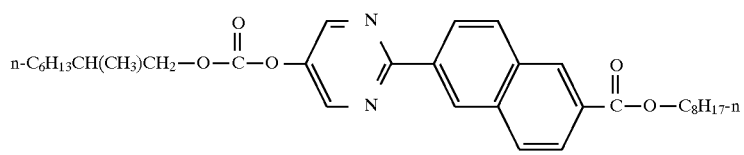
Exemplified compound 247
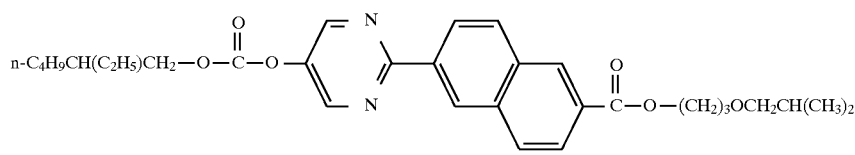
Exemplified compound 248
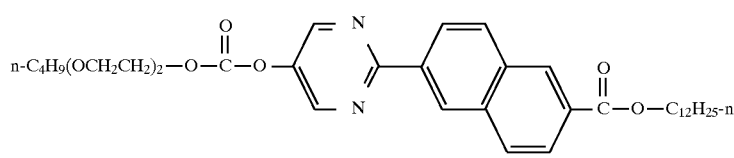
Exemplified compound 249
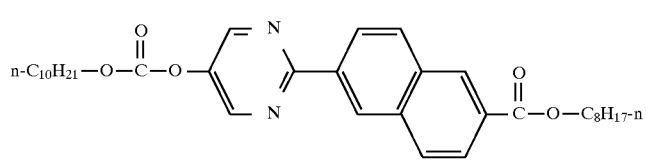
Exemplified compound 250

-continued
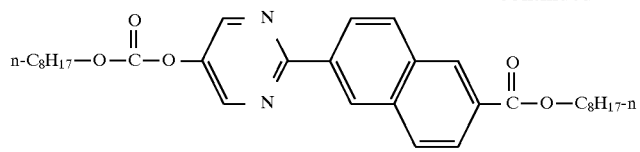
Exemplified compound 251
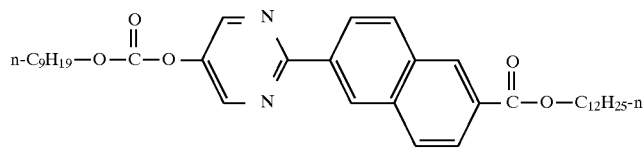
Exemplified compound 252
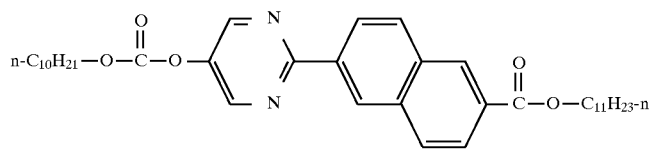
Exemplified compound 253
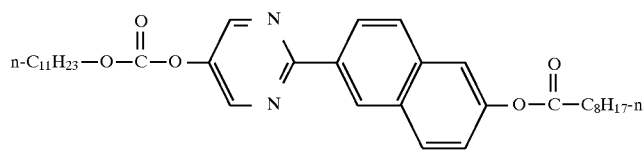
Exemplified compound 254
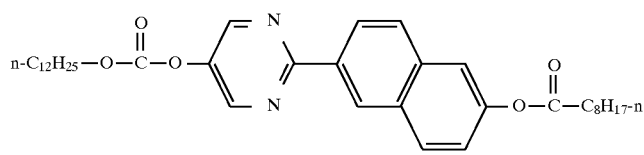
Exemplified compound 255
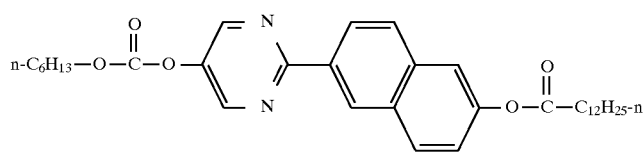
Exemplified compound 256
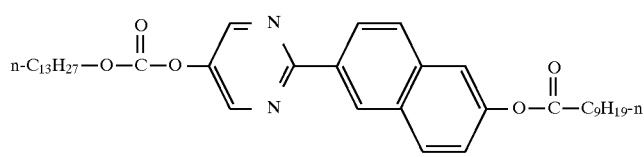
Exemplified compound 257
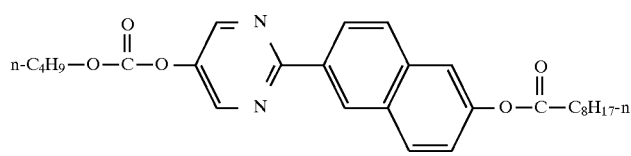
Exemplified compound 258
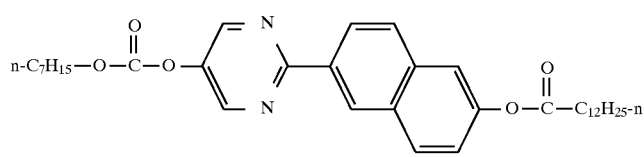
Exemplified compound 259
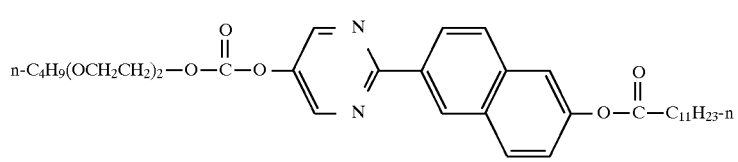
Exemplified compound 260

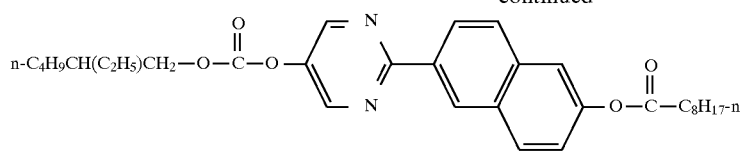
Exemplified compound 261
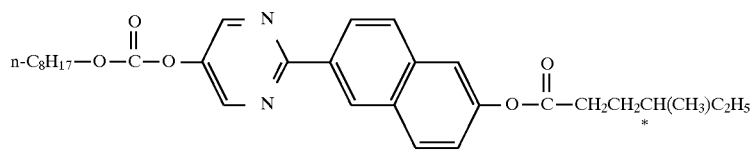
Exemplified compound 262
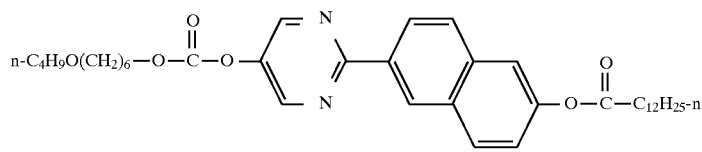
Exemplified compound 263
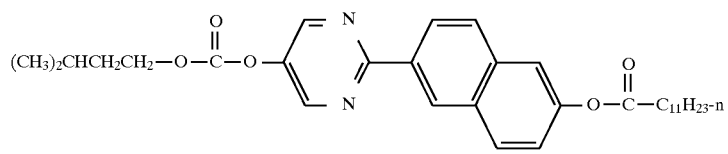
Exemplified compound 264
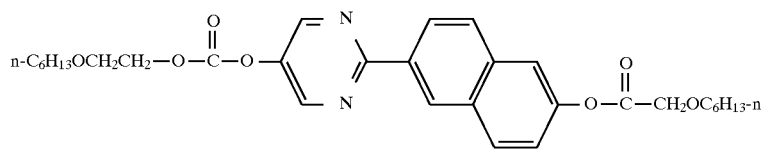
Exemplified compound 265
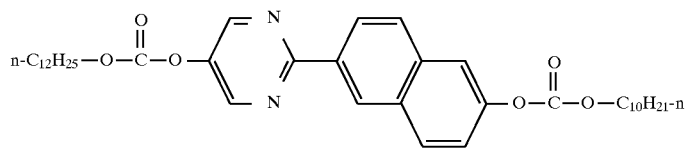
Exemplified compound 266
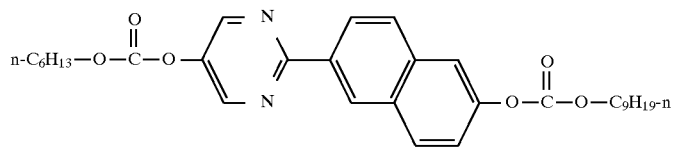
Exemplified compound 267
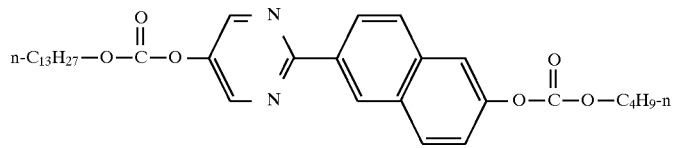
Exemplified compound 268
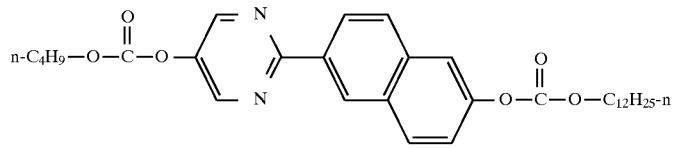
Exemplified compound 269
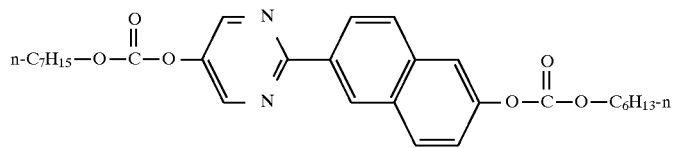
Exemplified compound 270

-continued
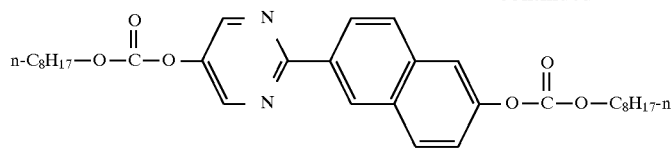
Exemplified compound 271
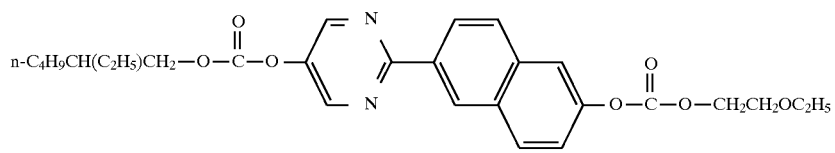
Exemplified compound 272
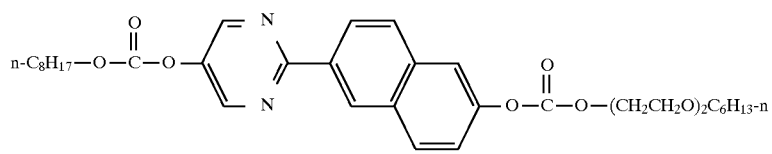
Exemplified compound 273
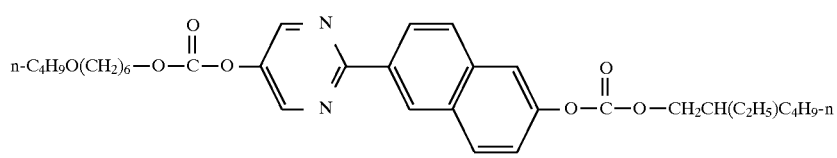
Exemplified compound 274
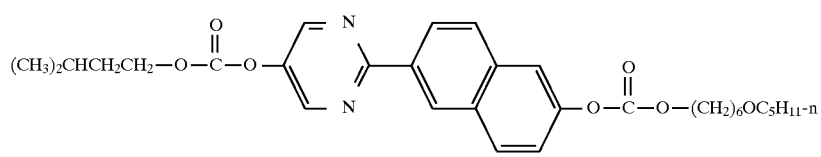
Exemplified compound 275
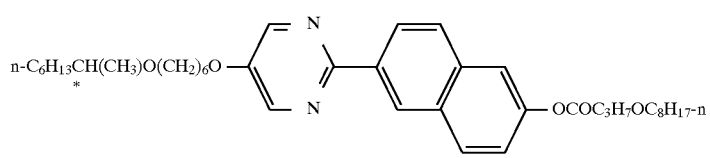
Exemplified compound 276
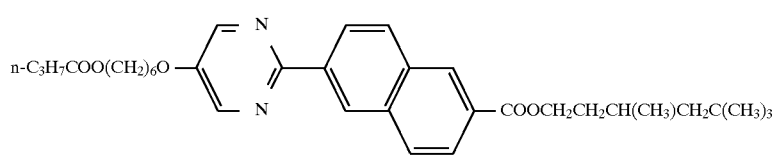
Exemplified compound 277
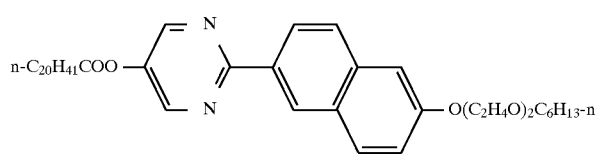
Exemplified compound 278
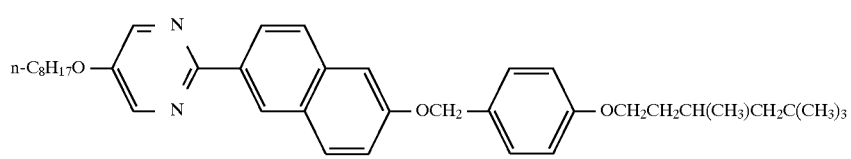
Exemplified compound 279
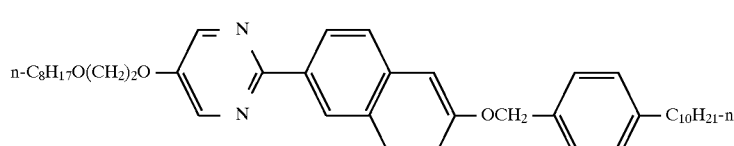
Exemplified compound 280

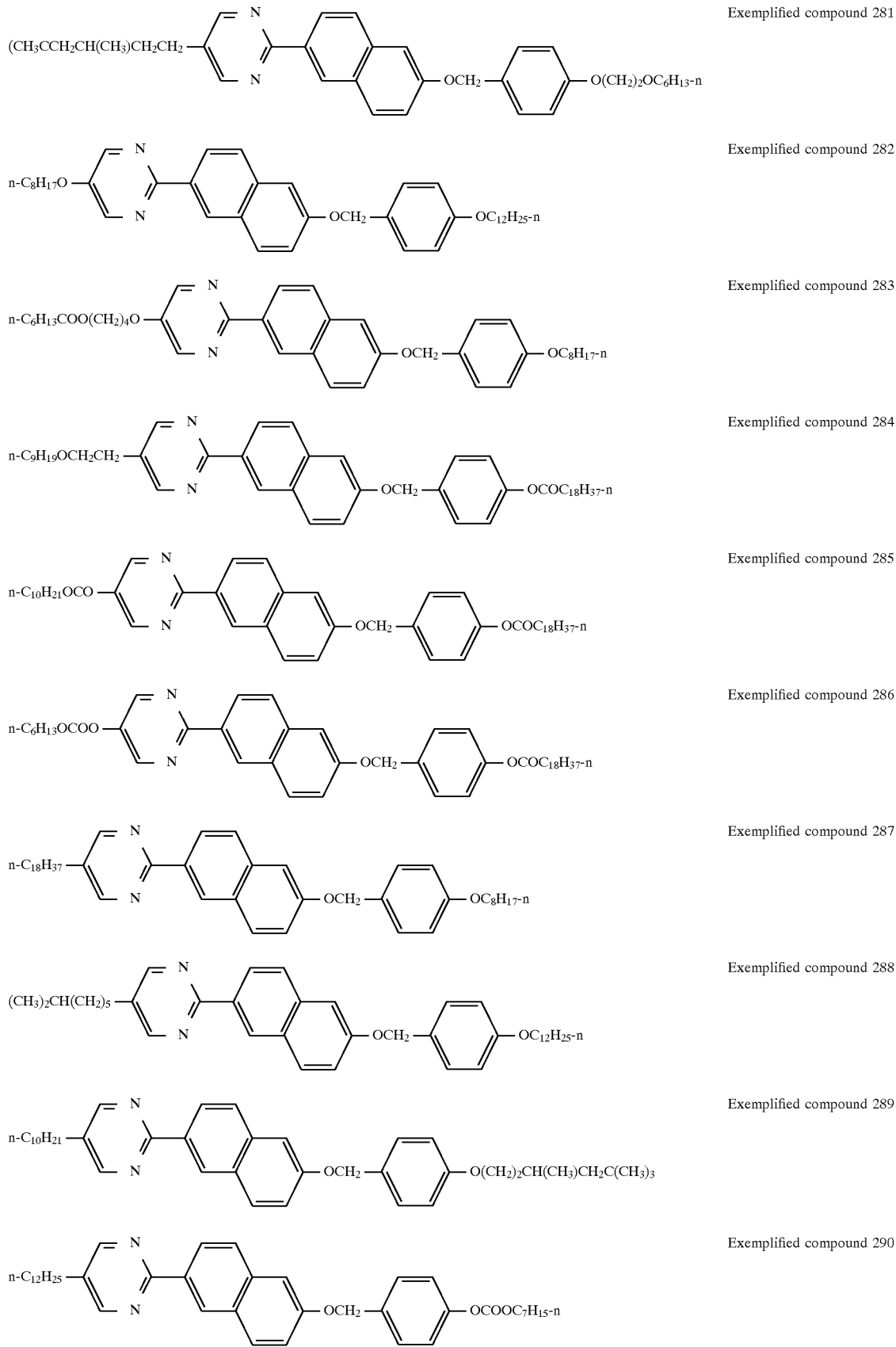

-continued
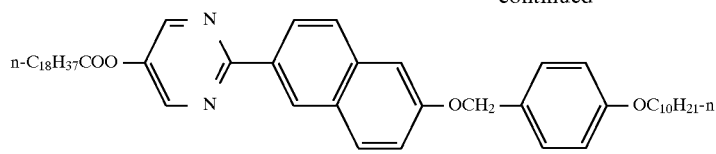
Exemplified compound 291
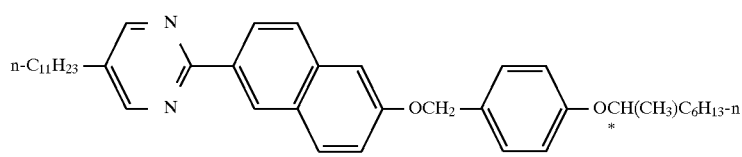
Exemplified compound 292
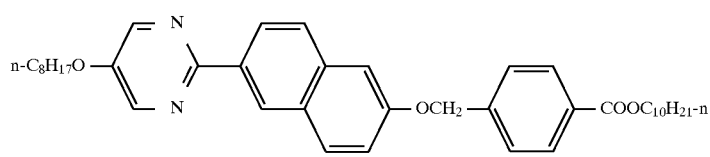
Exemplified compound 293
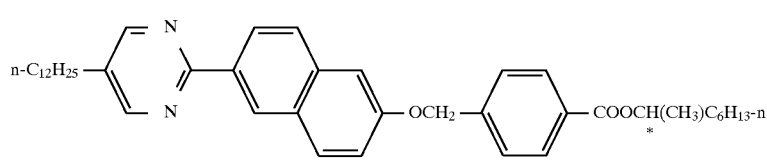
Exemplified compound 294
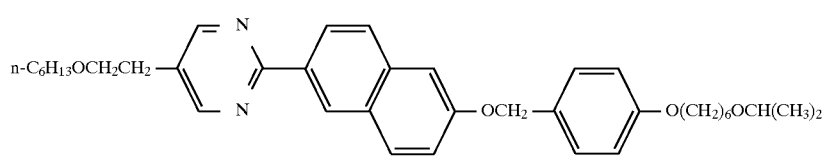
Exemplified compound 295
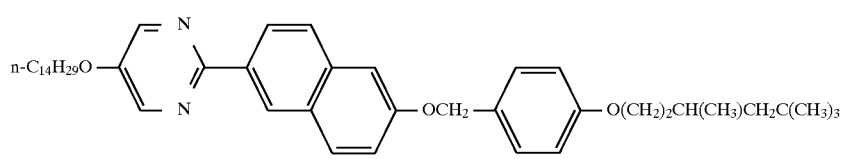
Exemplified compound 296
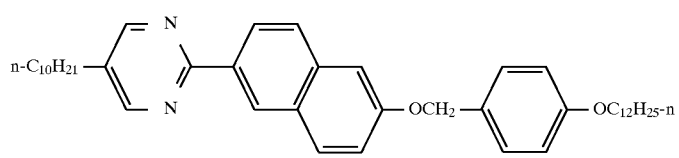
Exemplified compound 297
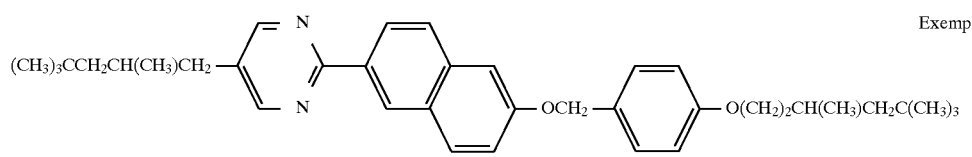
Exemplified compound 298
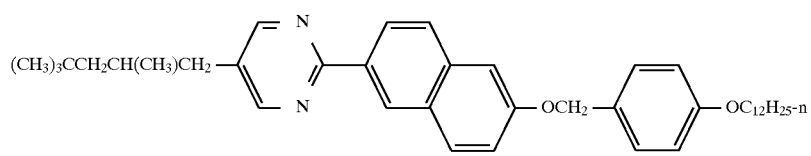
Exemplified compound 299
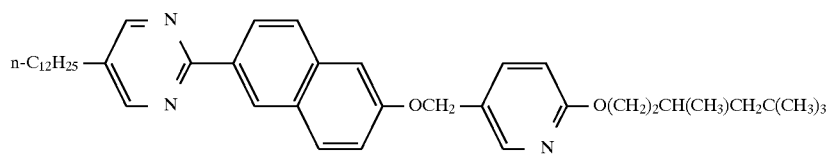
Exemplified compound 300

-continued
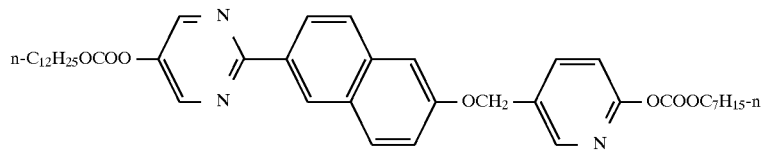
Exemplified compound 301
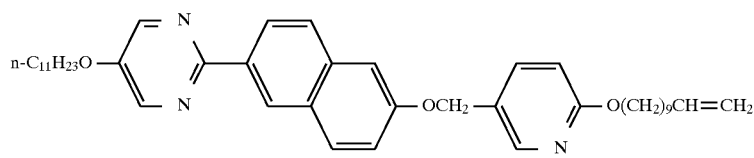
Exemplified compound 302
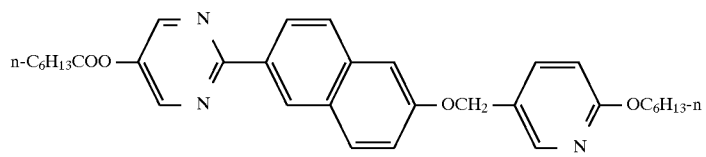
Exemplified compound 303
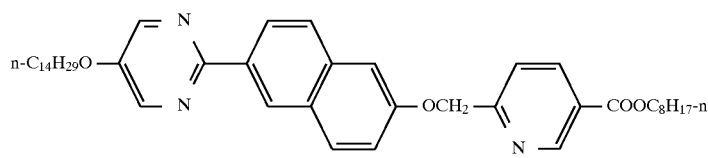
Exemplified compound 304
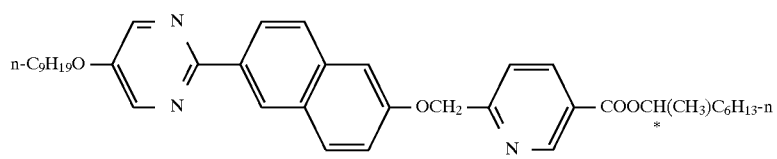
Exemplified compound 305
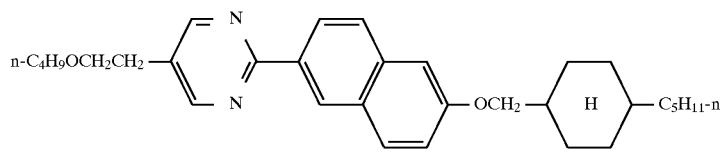
Exemplified compound 306
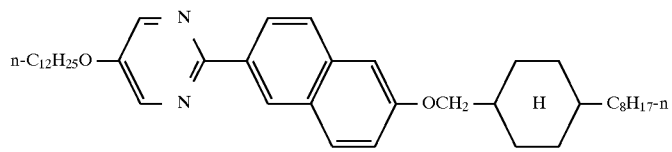
Exemplified compound 307
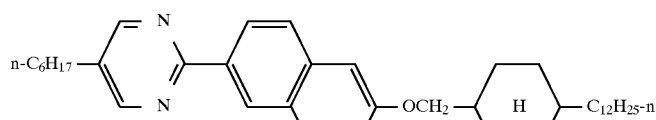
Exemplified compound 308
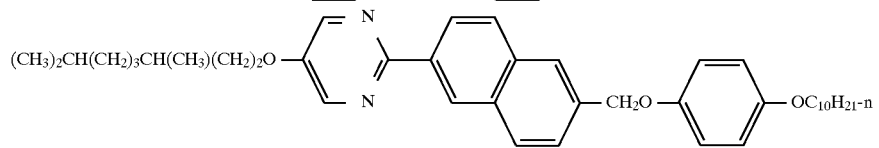
Exemplified compound 309
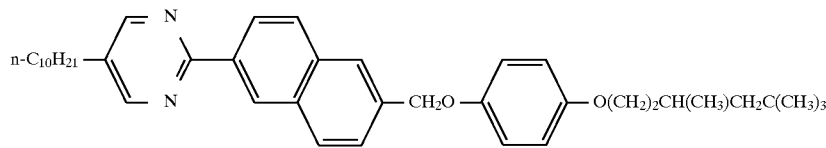
Exemplified compound 310

-continued
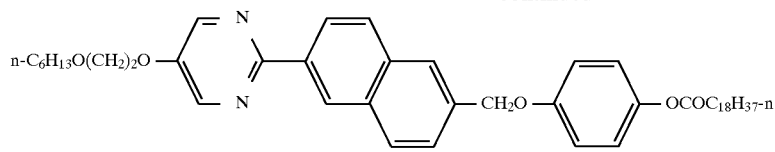
Exemplified compound 311
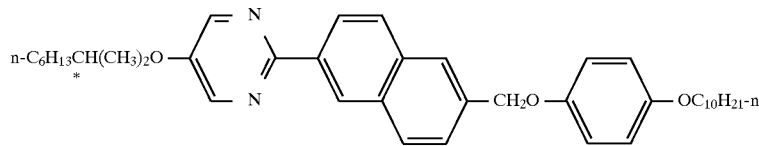
Exemplified compound 312
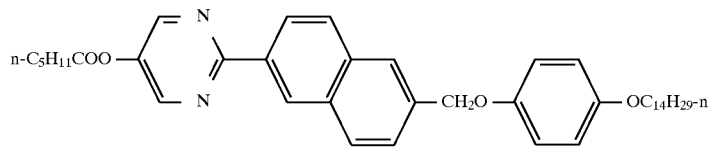
Exemplified compound 313
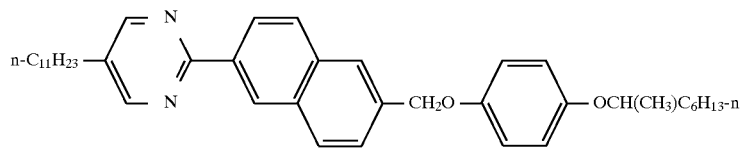
Exemplified compound 314
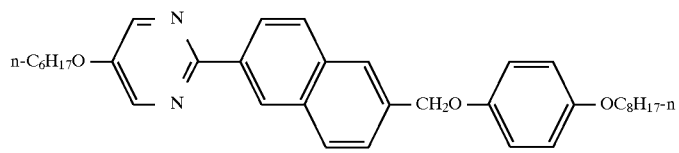
Exemplified compound 315
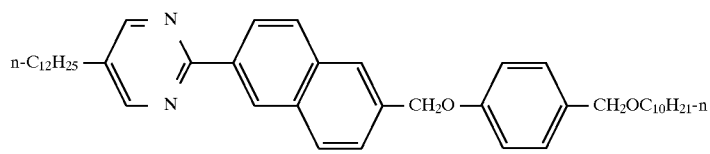
Exemplified compound 316
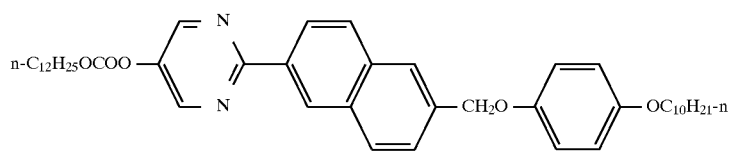
Exemplified compound 317
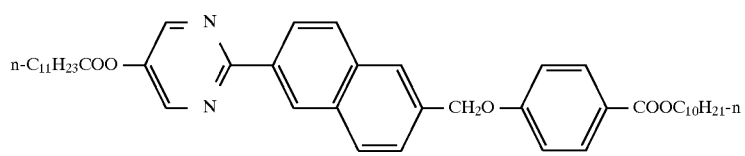
Exemplified compound 318
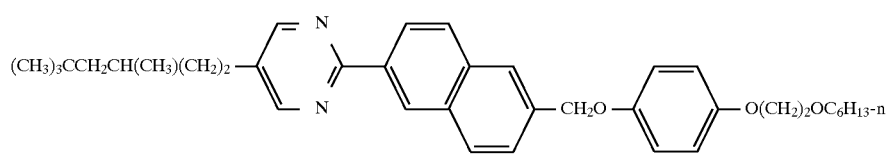
Exemplified compound 319
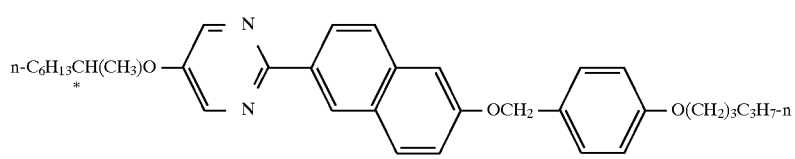
Exemplified compound 320

-continued
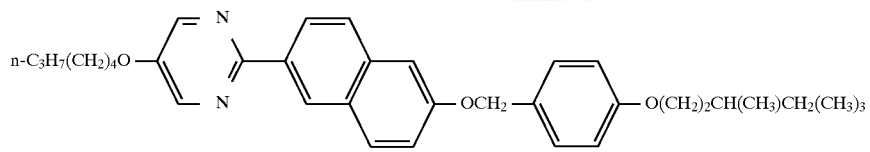
Exemplified compound 321
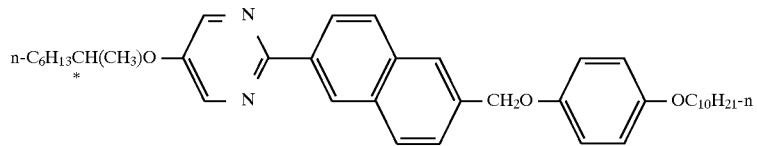
Exemplified compound 322
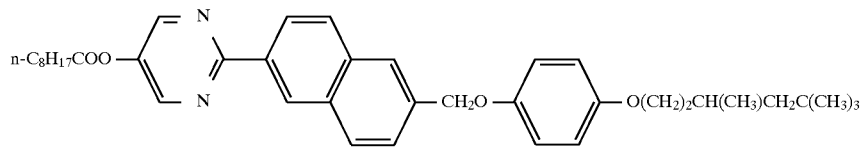
Exemplified compound 323
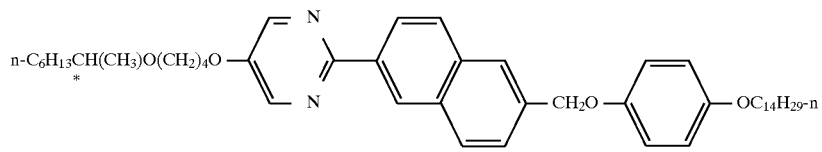
Exemplified compound 324
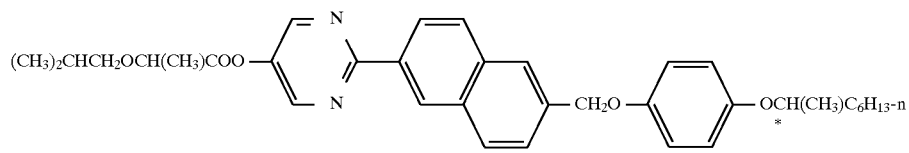
Exemplified compound 325
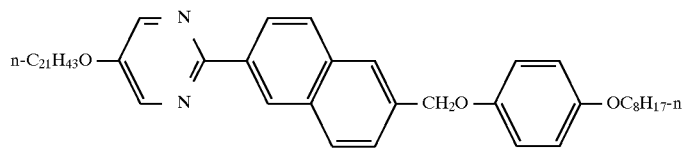
Exemplified compound 326
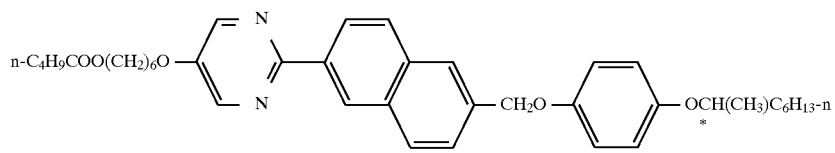
Exemplified compound 327
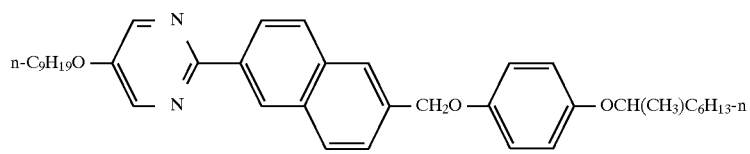
Exemplified compound 328
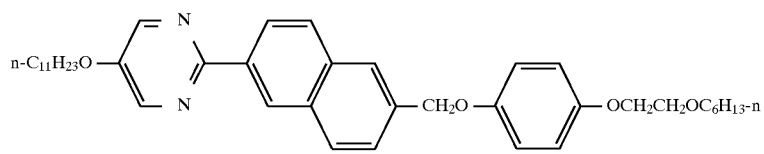
Exemplified compound 329
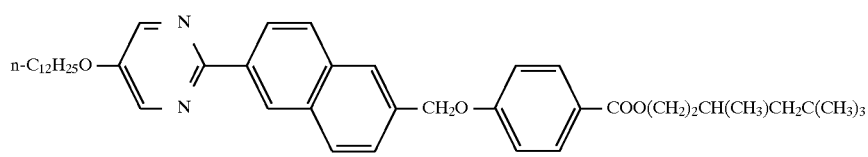
Exemplified compound 330

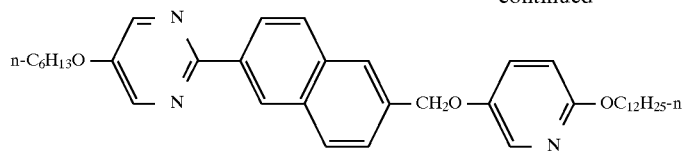
Exemplified compound 331
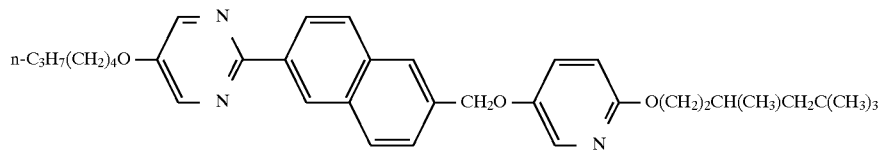
Exemplified compound 332
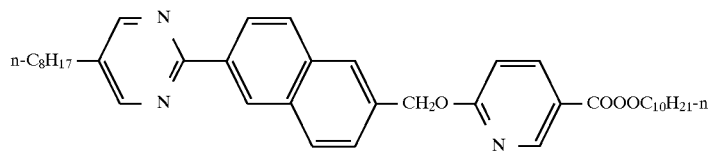
Exemplified compound 333
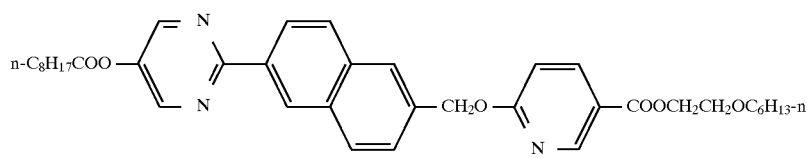
Exemplified compound 334
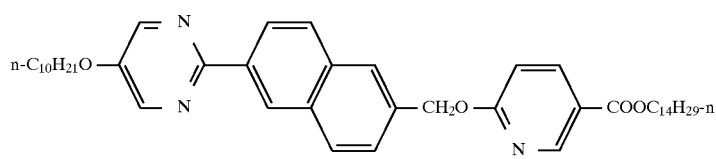
Exemplified compound 335
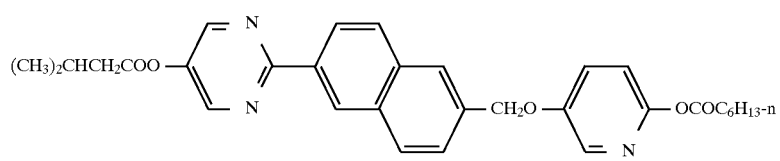
Exemplified compound 336
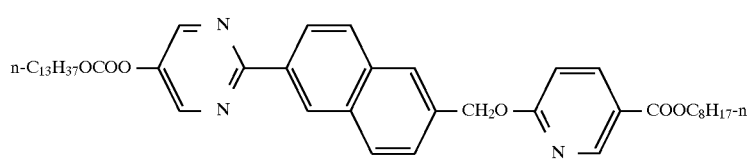
Exemplified compound 337
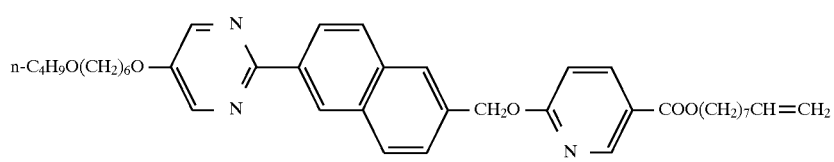
Exemplified compound 338
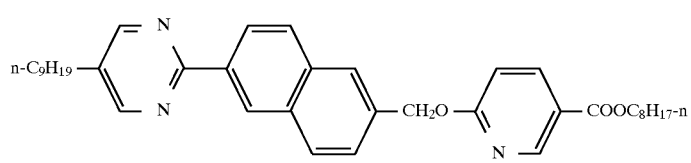
Exemplified compound 339
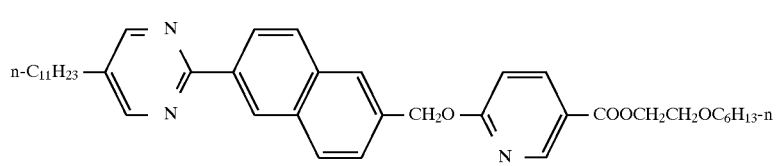
Exemplified compound 340

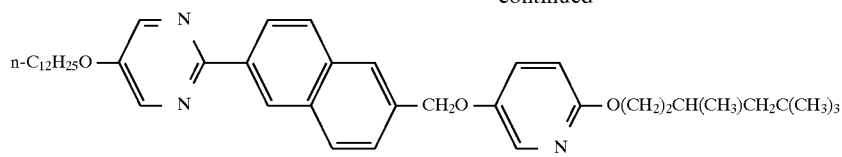
Exemplified compound 341
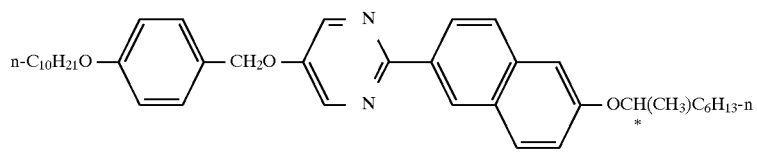
Exemplified compound 342
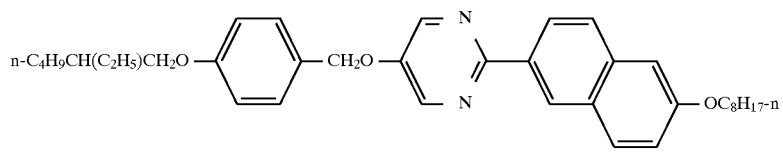
Exemplified compound 343
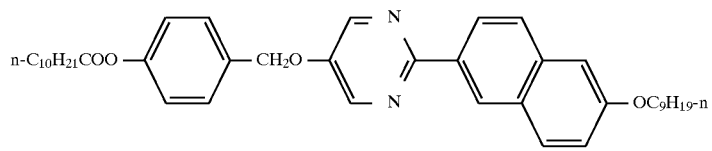
Exemplified compound 344
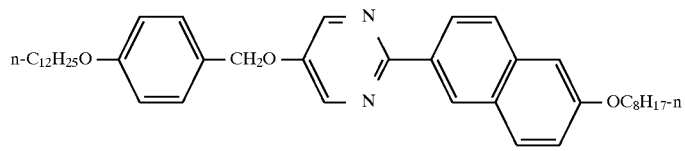
Exemplified compound 345
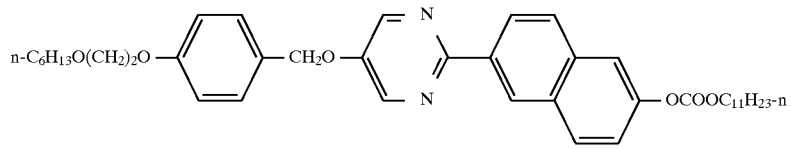
Exemplified compound 346
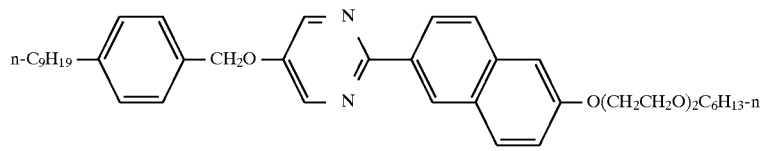
Exemplified compound 347
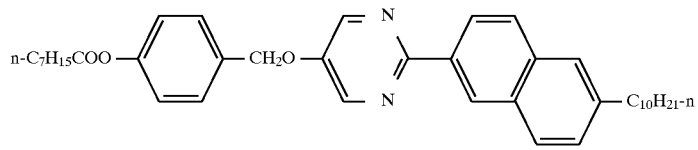
Exemplified compound 348
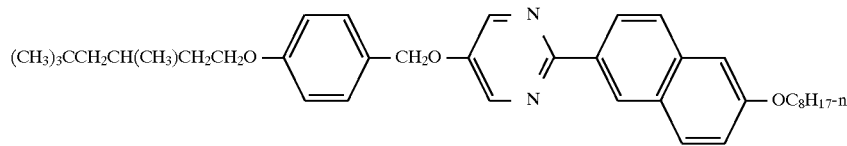
Exemplified compound 349
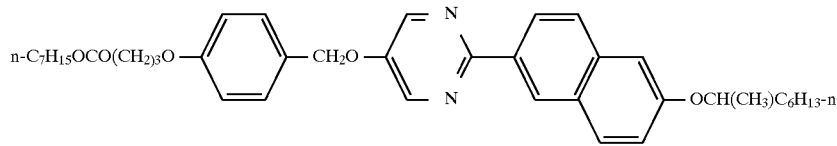
Exemplified compound 350

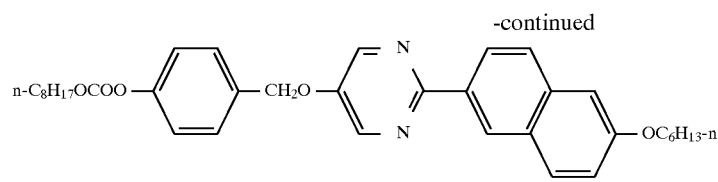
Exemplified compound 351
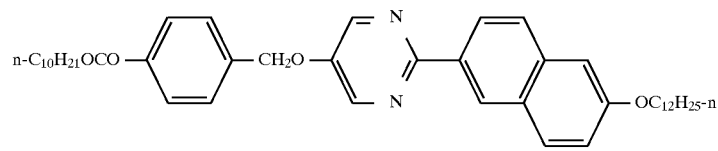
Exemplified compound 352
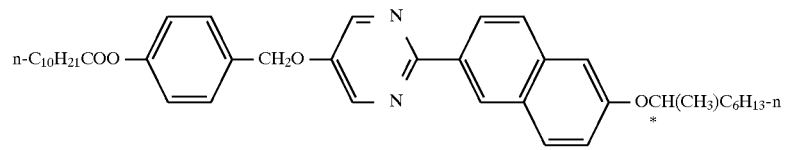
Exemplified compound 353
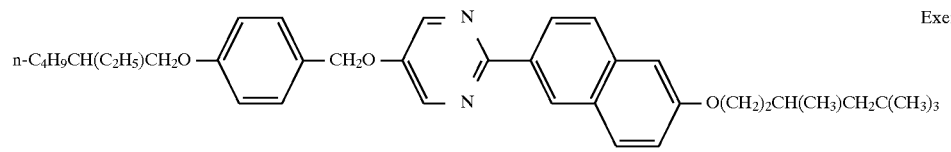
Exemplified compound 354
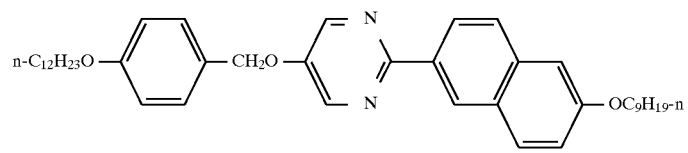
Exemplified compound 355
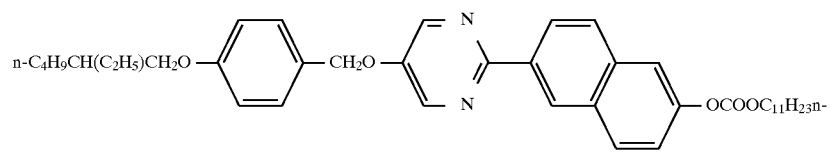
Exemplified compound 356
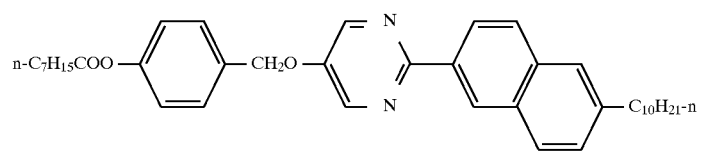
Exemplified compound 357
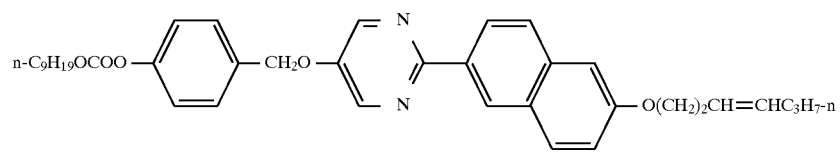
Exemplified compound 358
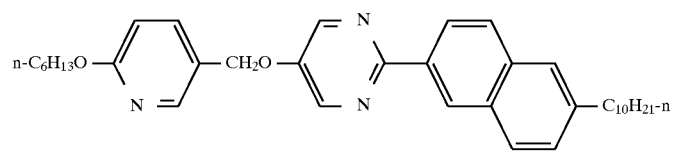
Exemplified compound 359
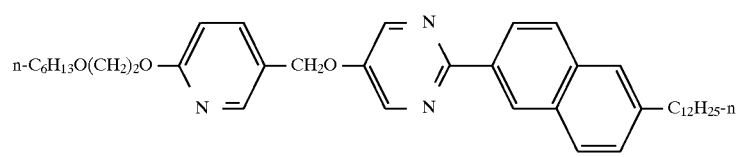
Exemplified compound 360

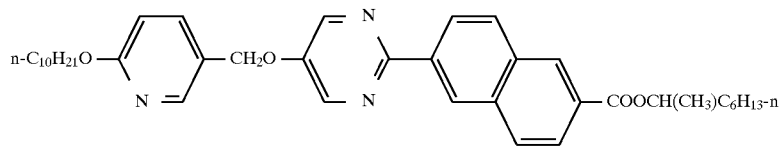
Exemplified compound 361
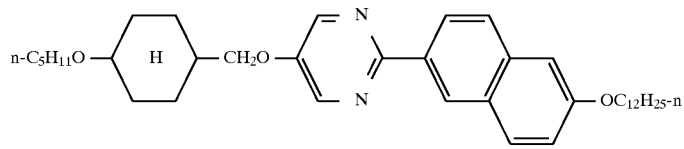
Exemplified compound 362
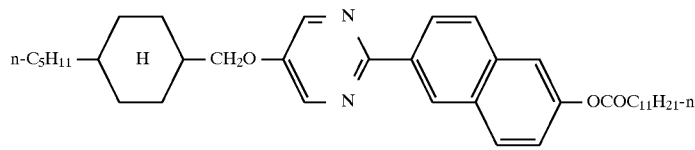
Exemplified compound 363
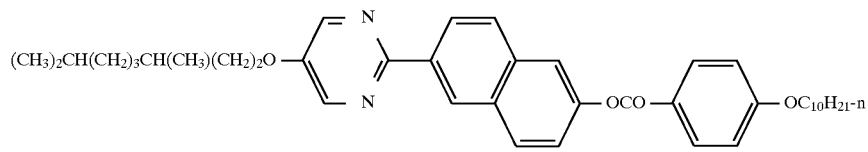
Exemplified compound 364
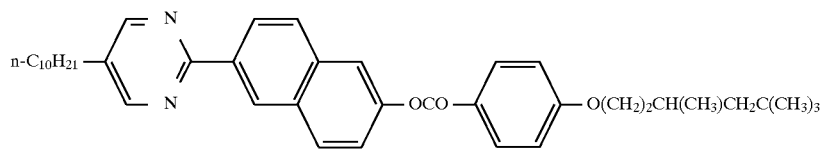
Exemplified compound 365
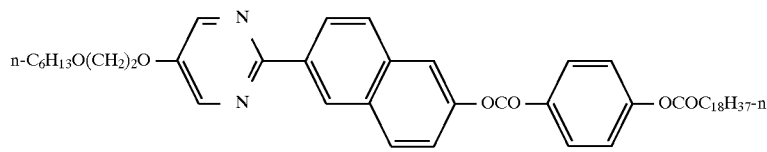
Exemplified compound 366
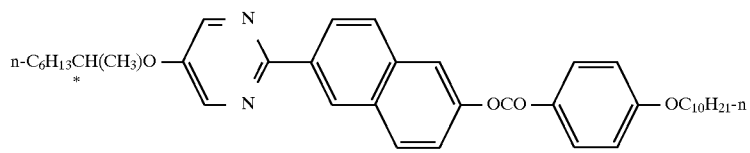
Exemplified compound 367
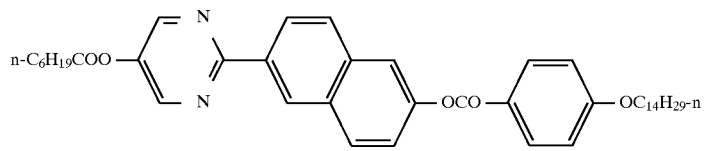
Exemplified compound 368
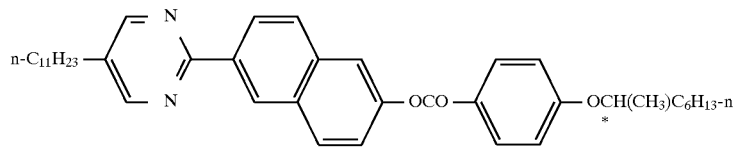
Exemplified compound 369
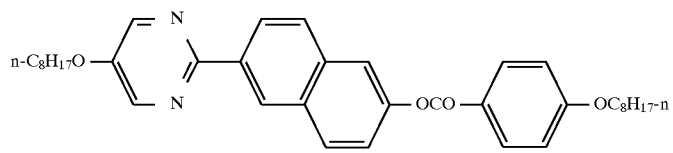
Exemplified compound 370

-continued
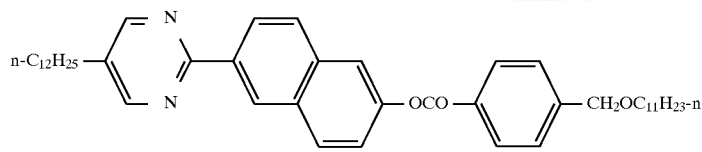 Exemplified compound 371
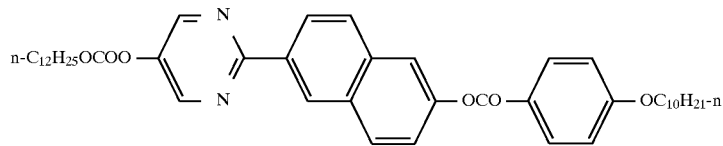 Exemplified compound 372
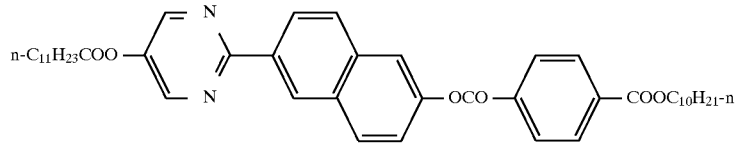 Exemplified compound 373
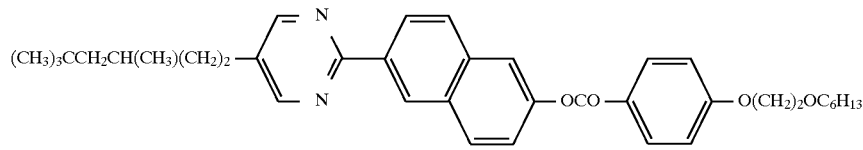 Exemplified compound 374
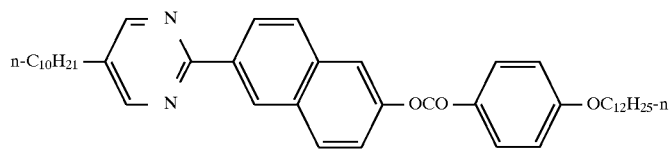 Exemplified compound 375
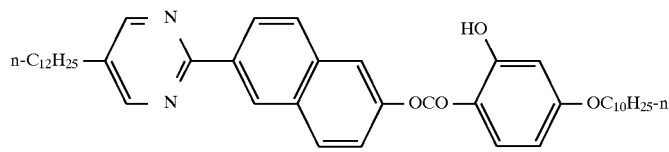 Exemplified compound 376
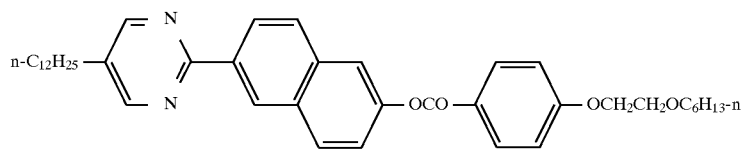 Exemplified compound 377
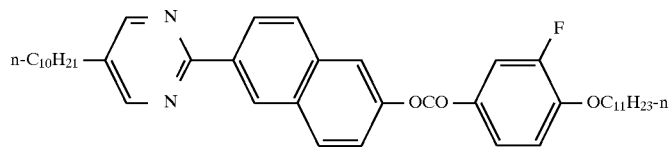 Exemplified compound 378
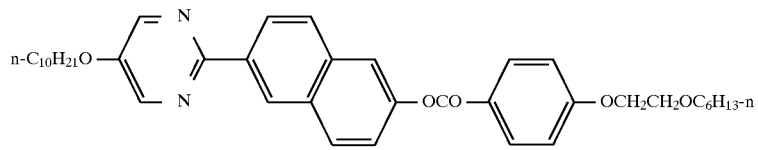 Exemplified compound 379
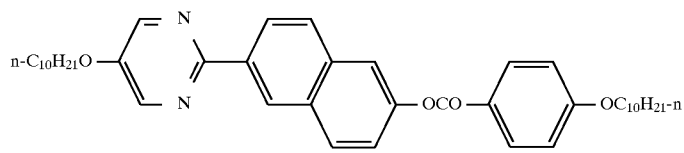 Exemplified compound 380

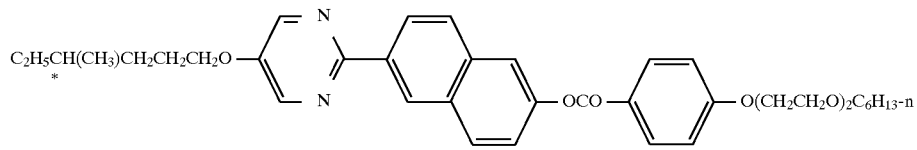
Exemplified compound 381
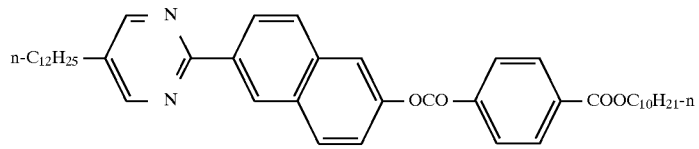
Exemplified compound 382
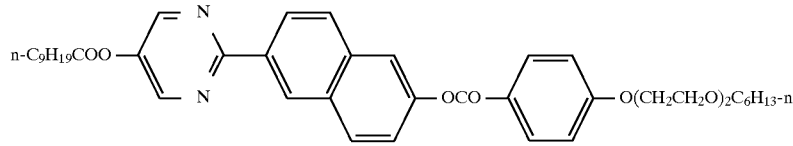
Exemplified compound 383
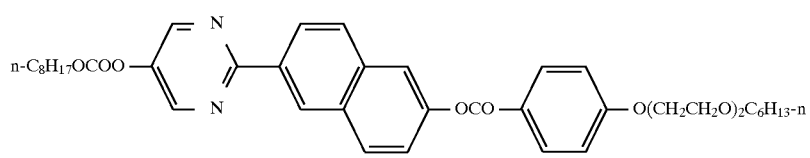
Exemplified compound 384
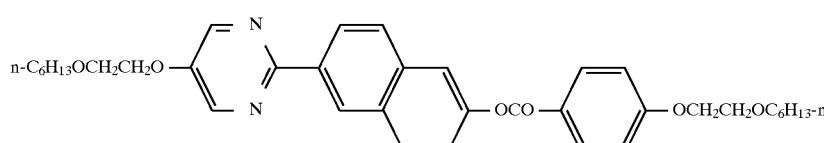
Exemplified compound 385
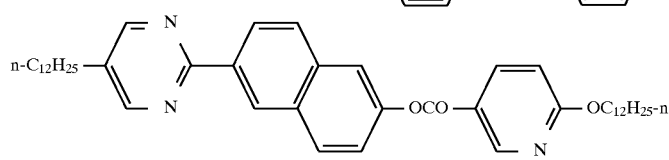
Exemplified compound 386
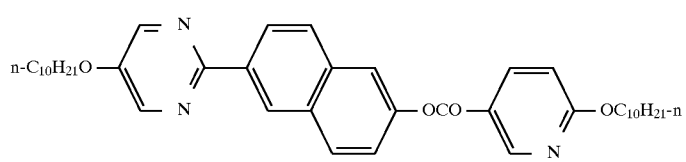
Exemplified compound 387
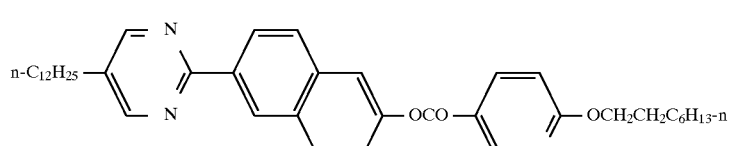
Exemplified compound 388
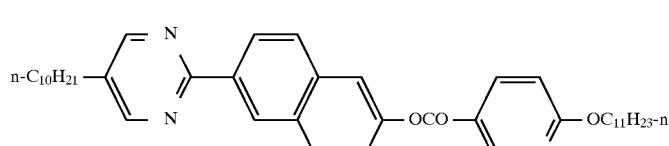
Exemplified compound 389
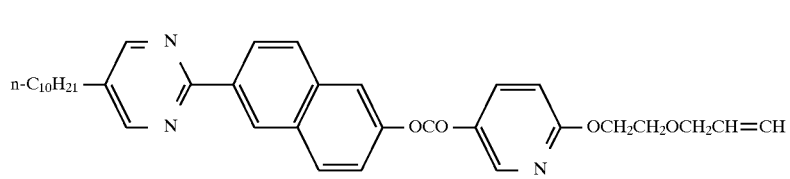
Exemplified compound 390

-continued
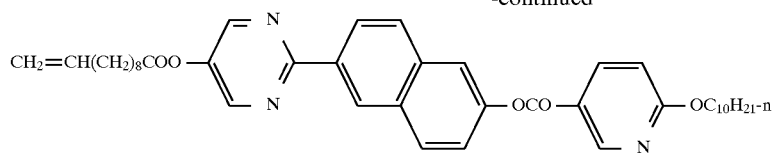
Exemplified compound 391
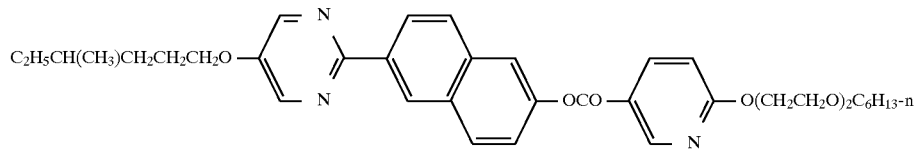
Exemplified compound 392
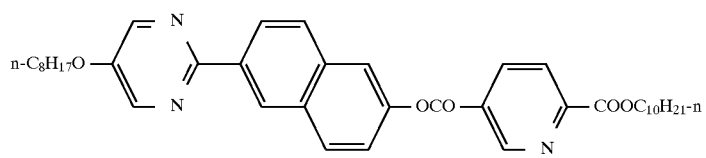
Exemplified compound 393
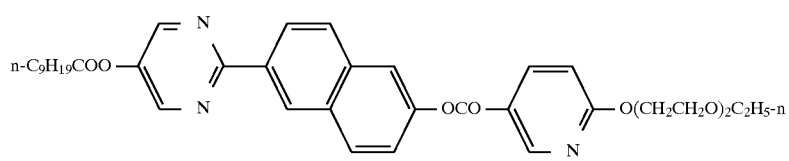
Exemplified compound 394
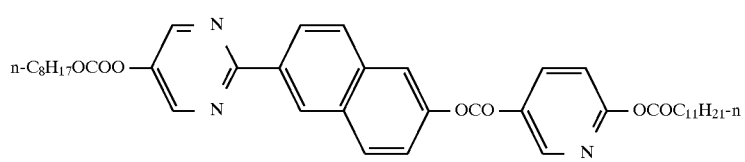
Exemplified compound 395
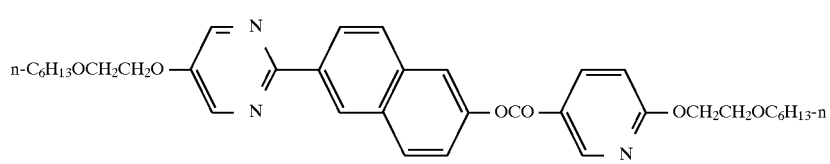
Exemplified compound 396
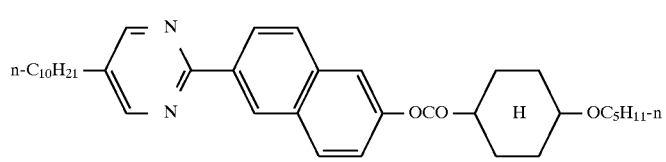
Exemplified compound 397
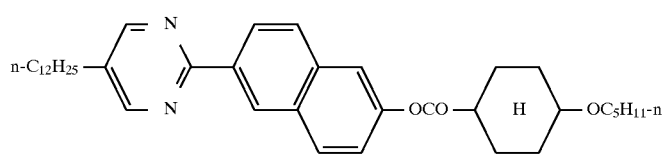
Exemplified compound 398
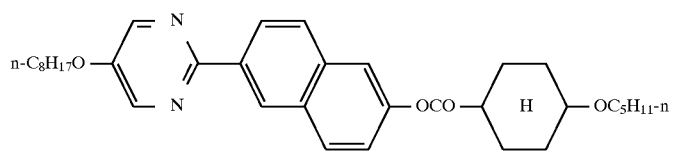
Exemplified compound 399
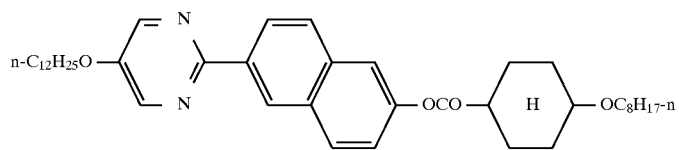
Exemplified compound 400

-continued
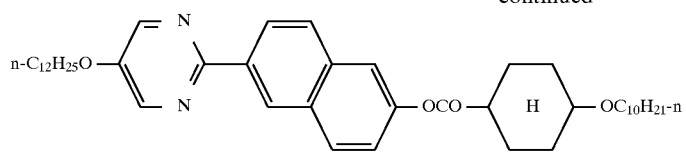 Exemplified compound 401
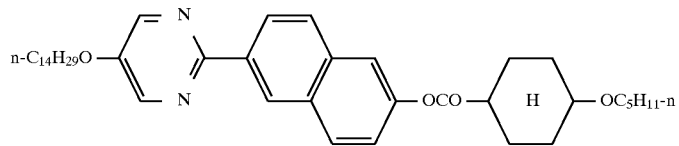 Exemplified compound 402
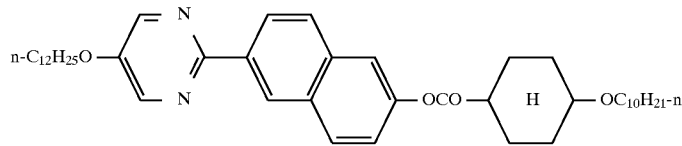 Exemplified compound 403
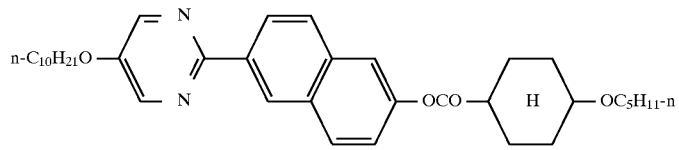 Exemplified compound 404
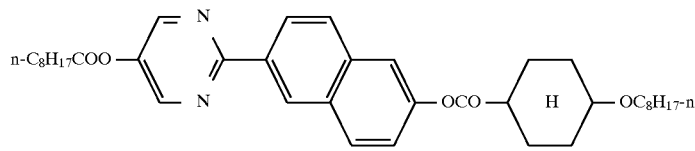 Exemplified compound 405
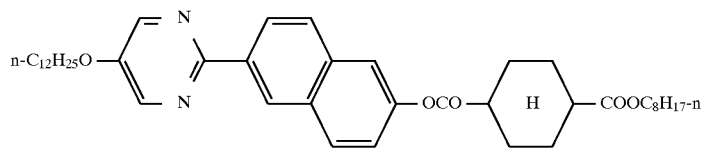 Exemplified compound 406
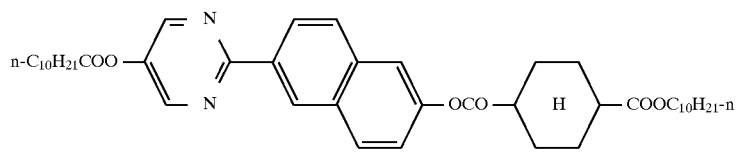 Exemplified compound 407
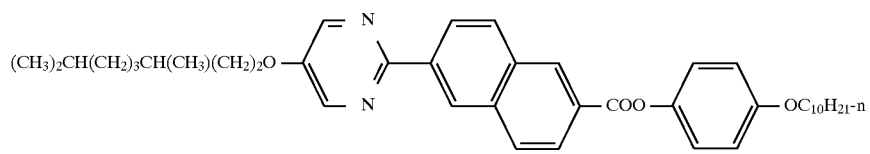 Exemplified compound 408
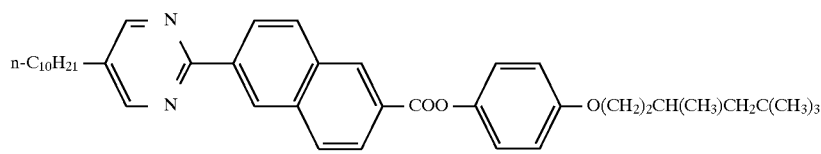 Exemplified compound 409
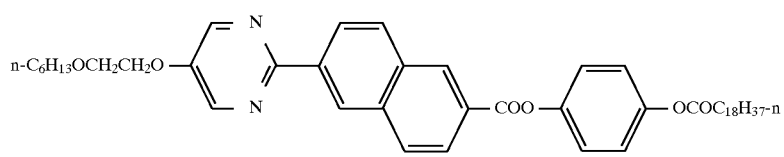 Exemplified compound 410

-continued
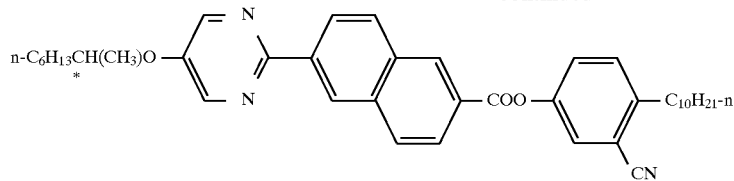
Exemplified compound 411
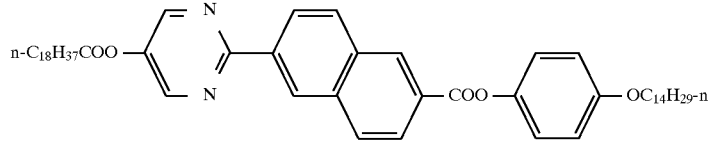
Exemplified compound 412
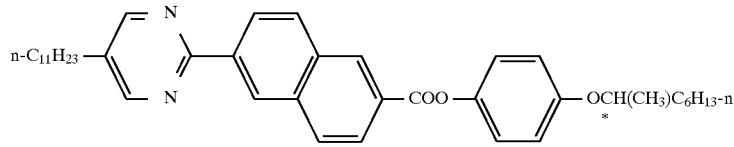
Exemplified compound 413
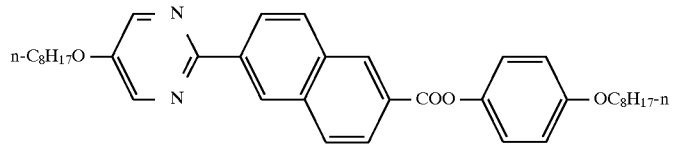
Exemplified compound 414
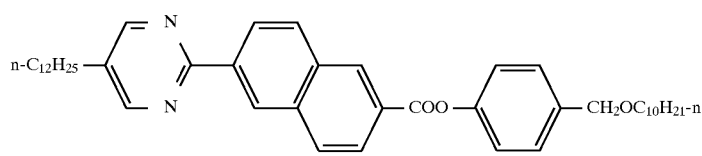
Exemplified compound 415
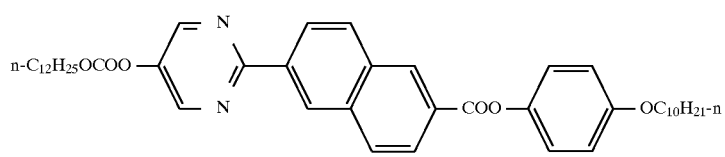
Exemplified compound 416
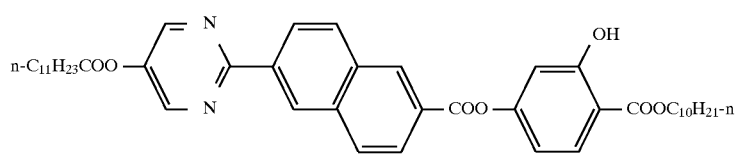
Exemplified compound 417
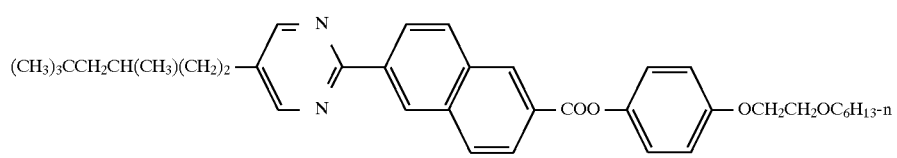
Exemplified compound 418
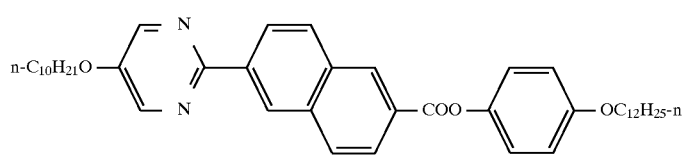
Exemplified compound 419
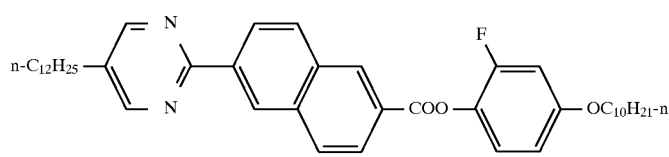
Exemplified compound 420

-continued
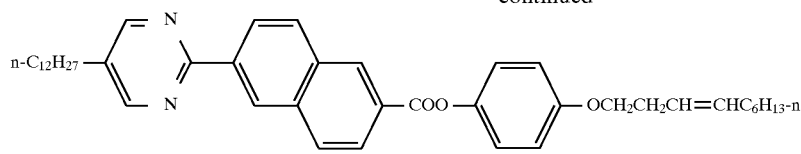
Exemplified compound 421
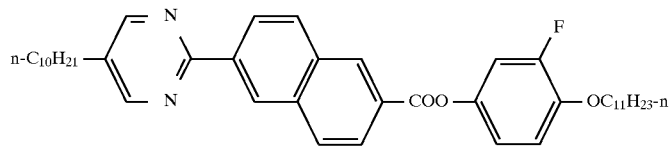
Exemplified compound 422
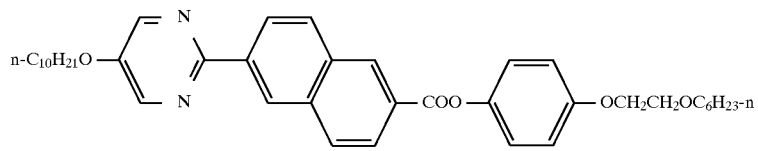
Exemplified compound 423
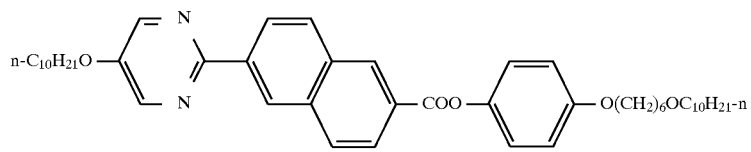
Exemplified compound 424
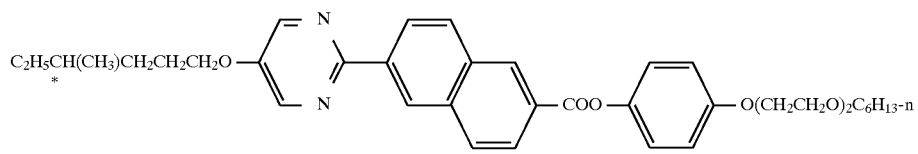
Exemplified compound 425
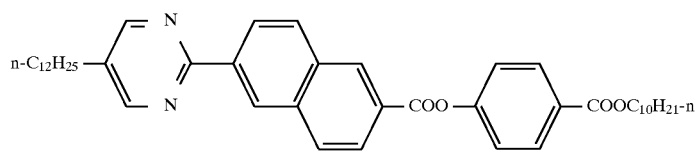
Exemplified compound 426
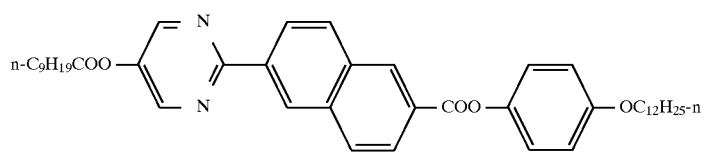
Exemplified compound 427
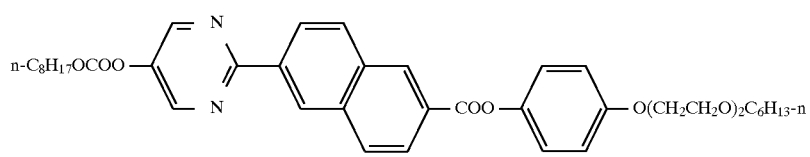
Exemplified compound 428
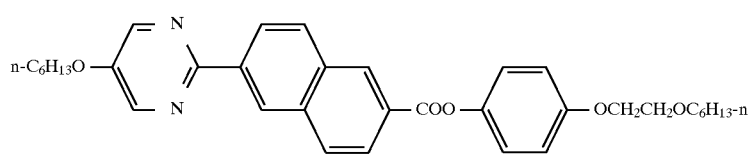
Exemplified compound 429
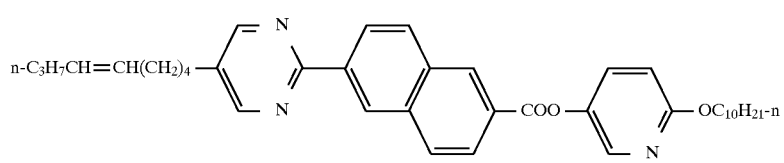
Exemplified compound 430

-continued
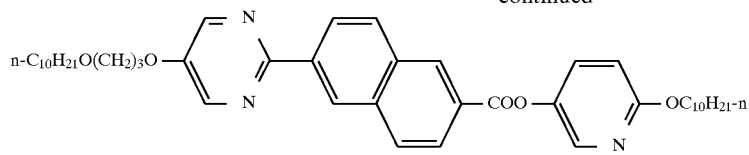
Exemplified compound 431
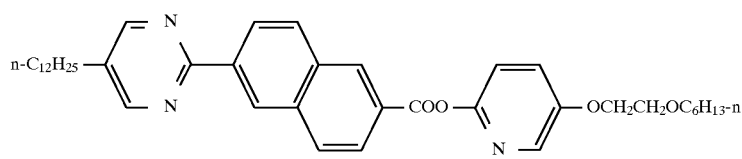
Exemplified compound 432
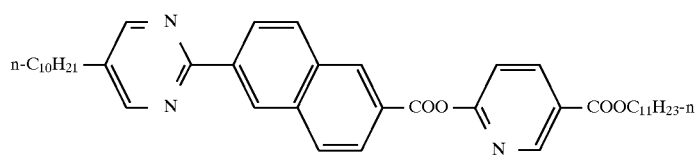
Exemplified compound 433
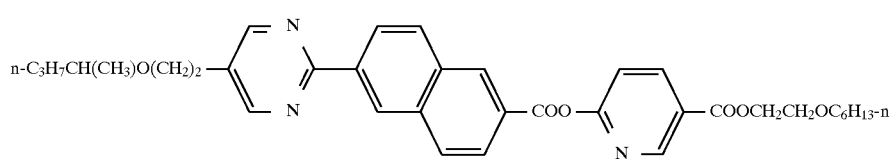
Exemplified compound 434
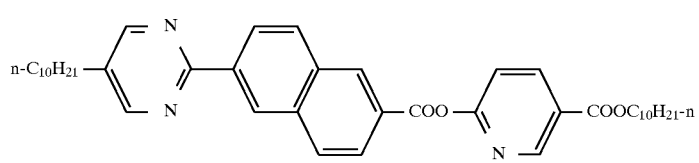
Exemplified compound 435
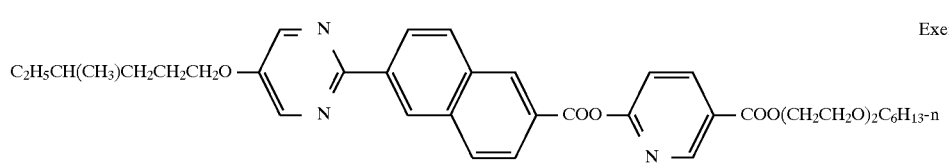
Exemplified compound 436
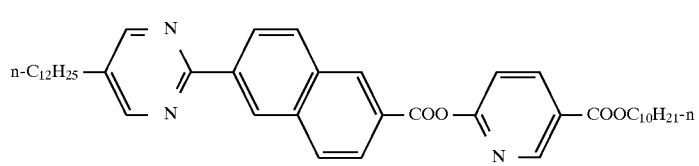
Exemplified compound 437
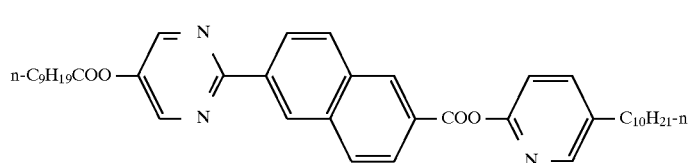
Exemplified compound 438
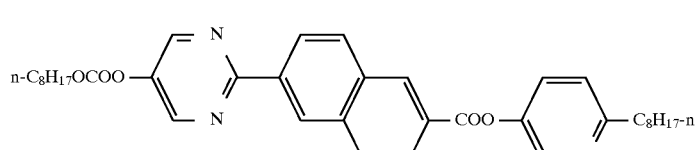
Exemplified compound 439
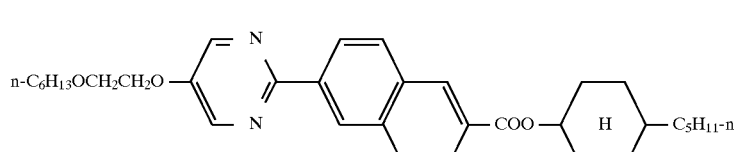
Exemplified compound 440

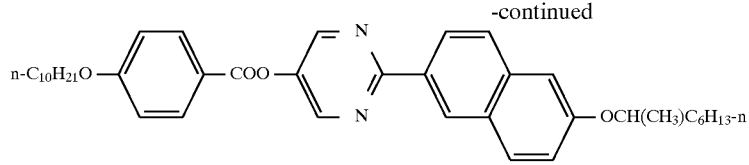 Exemplified compound 441
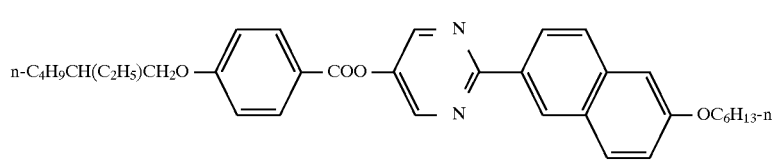 Exemplified compound 442
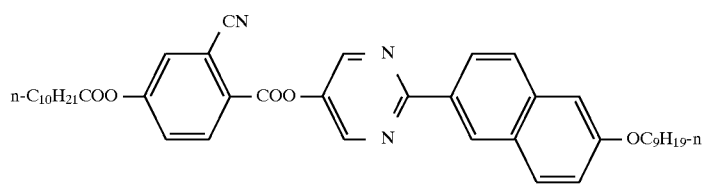 Exemplified compound 443
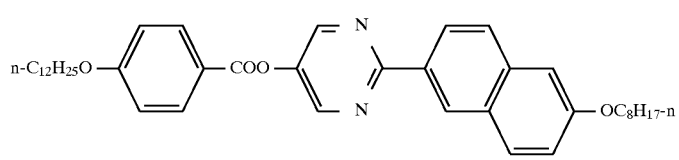 Exemplified compound 444
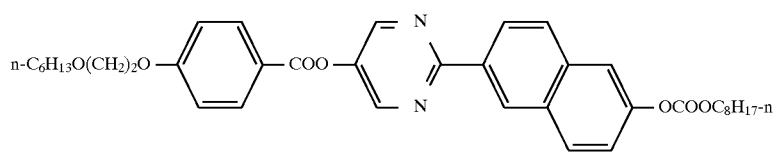 Exemplified compound 445
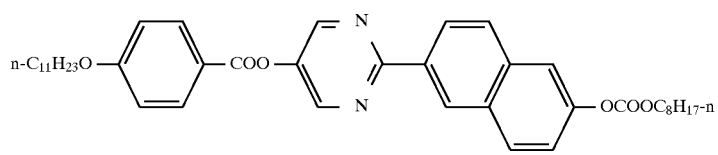 Exemplified compound 446
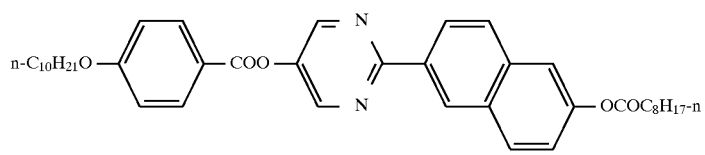 Exemplified compound 447
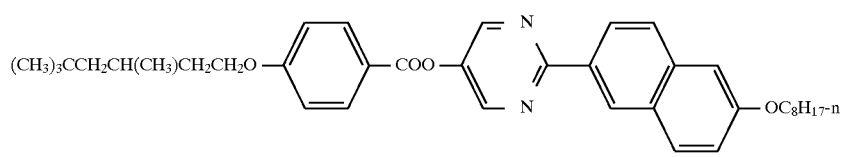 Exemplified compound 448
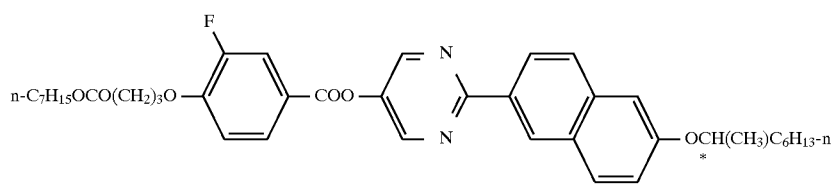 Exemplified compound 449
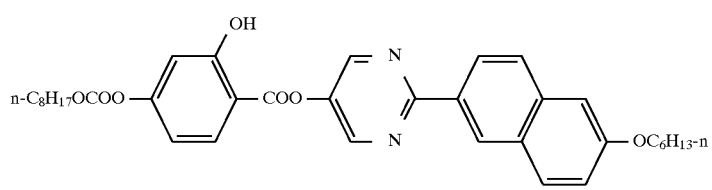 Exemplified compound 450

-continued
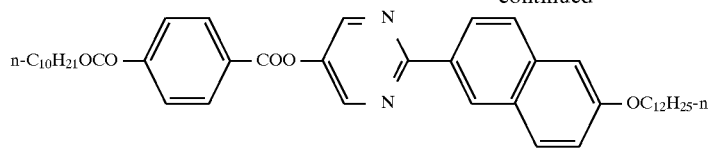
Exemplified compound 451
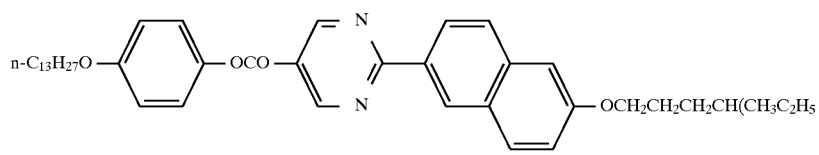
Exemplified compound 452
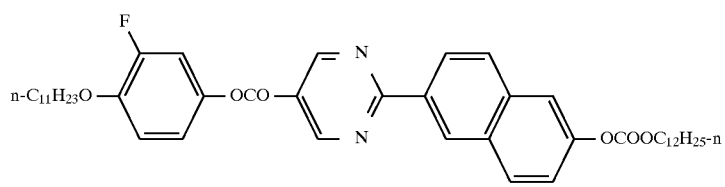
Exemplified compound 453
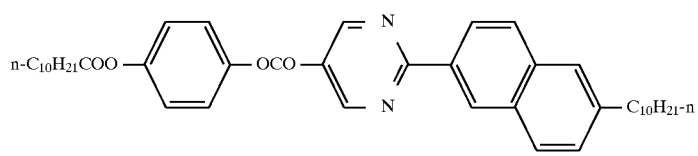
Exemplified compound 454
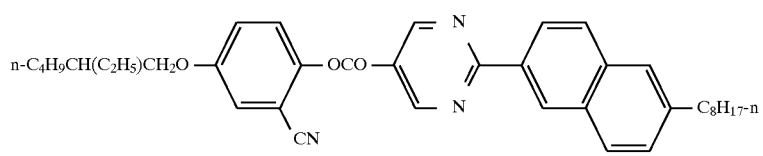
Exemplified compound 455
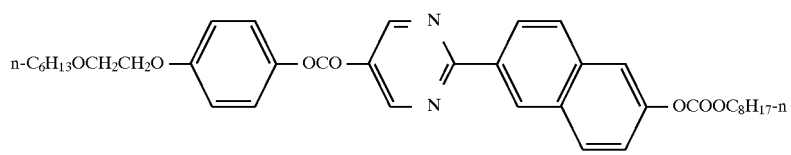
Exemplified compound 456
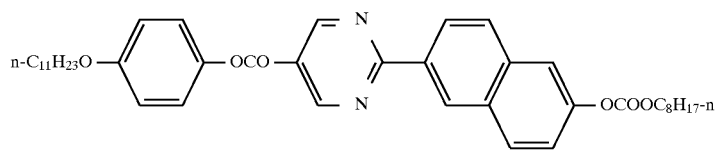
Exemplified compound 457
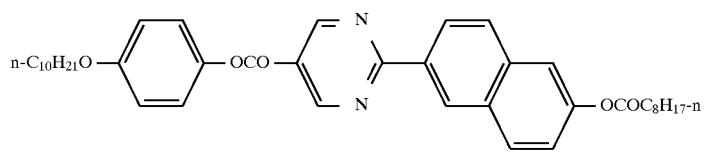
Exemplified compound 458
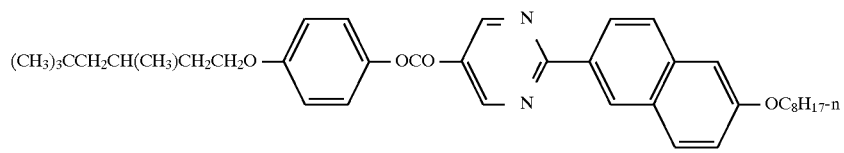
Exemplified compound 459
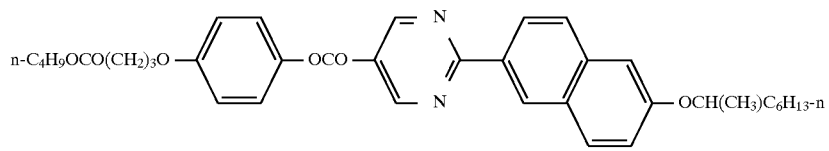
Exemplified compound 460

-continued
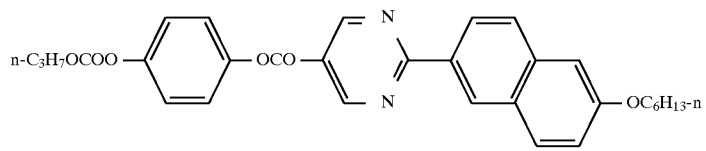 Exemplified compound 461
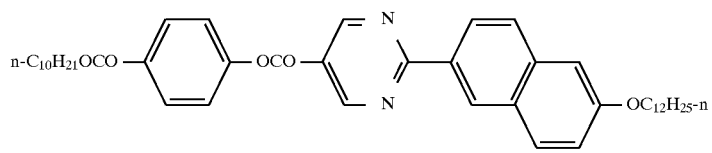 Exemplified compound 462
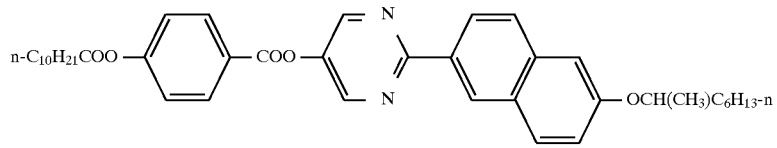 Exemplified compound 463
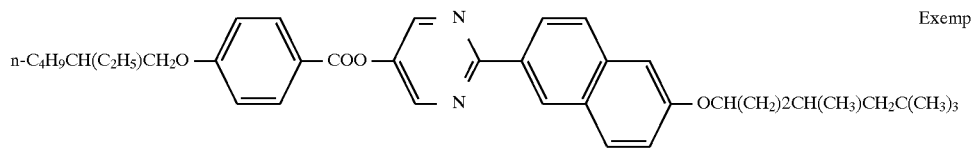 Exemplified compound 464
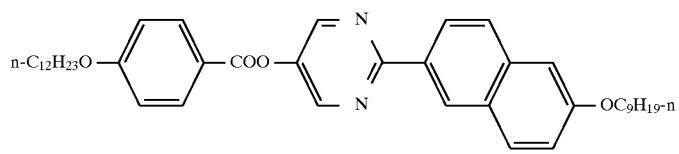 Exemplified compound 465
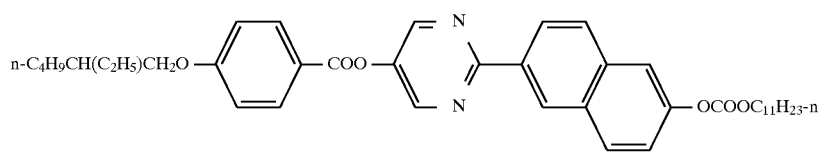 Exemplified compound 466
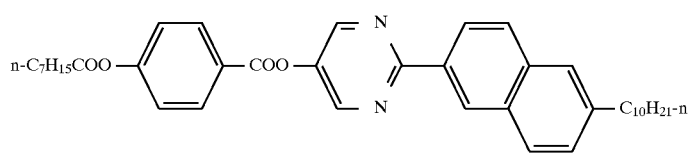 Exemplified compound 467
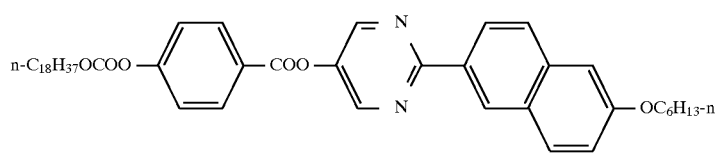 Exemplified compound 468
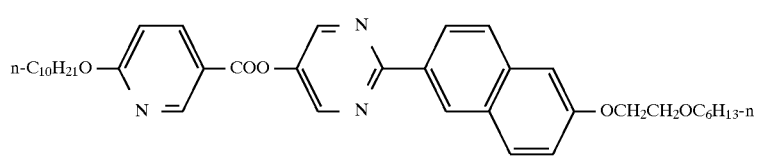 Exemplified compound 469
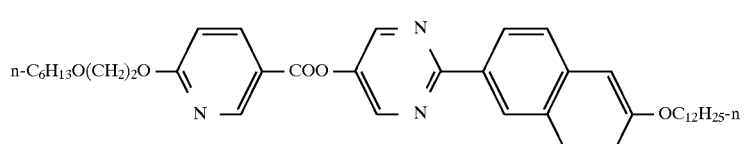 Exemplified compound 470

-continued
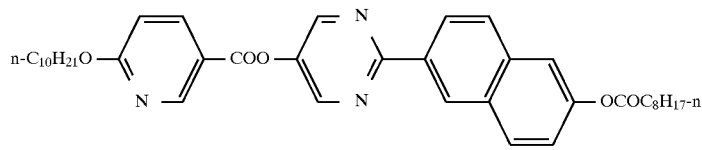
Exemplified compound 471
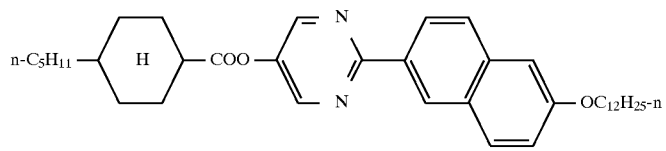
Exemplified compound 472
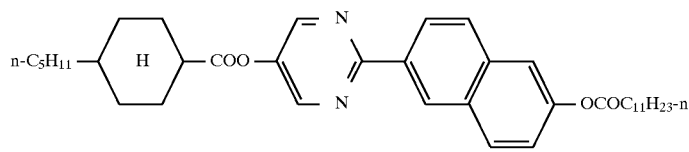
Exemplified compound 473
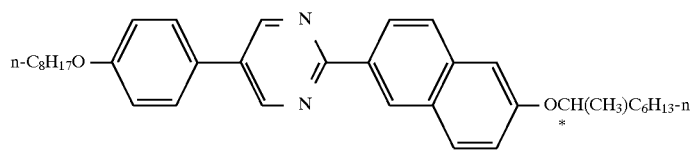
Exemplified compound 474
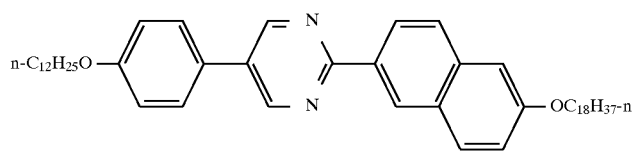
Exemplified compound 475
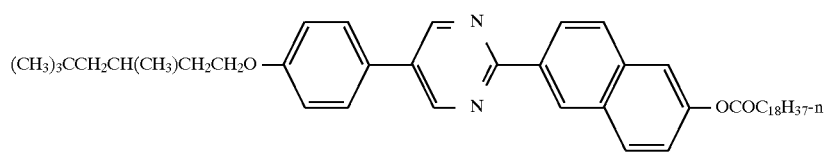
Exemplified compound 476
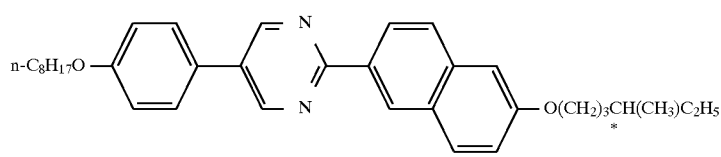
Exemplified compound 477
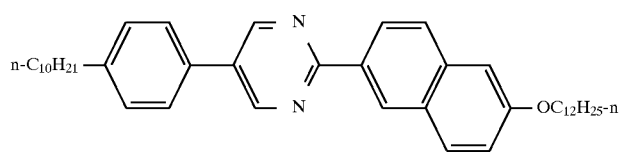
Exemplified compound 478
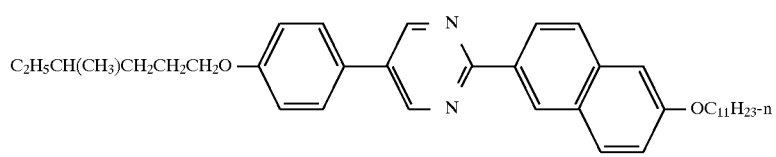
Exemplified compound 479
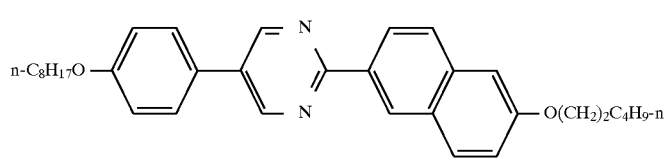
Exemplified compound 480

-continued
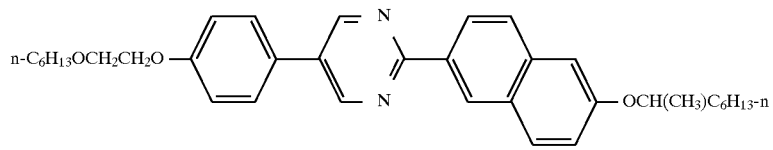
Exemplified compound 481
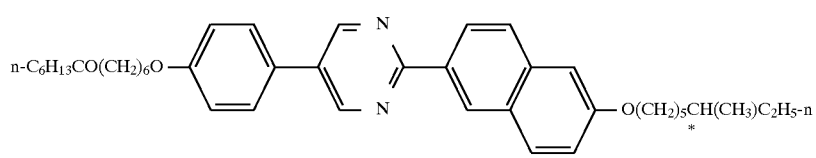
Exemplified compound 482
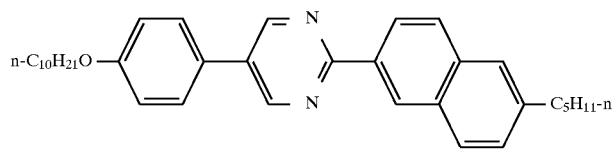
Exemplified compound 483
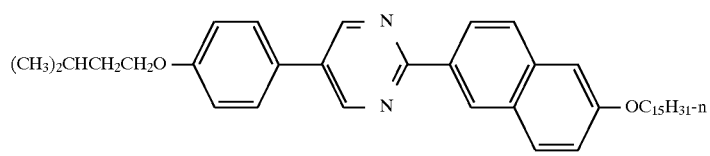
Exemplified compound 484
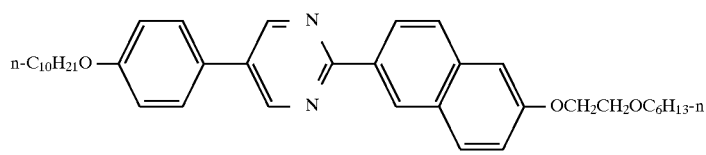
Exemplified compound 485
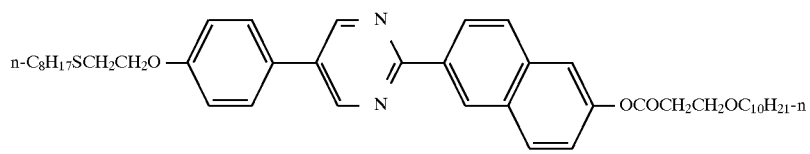
Exemplified compound 486
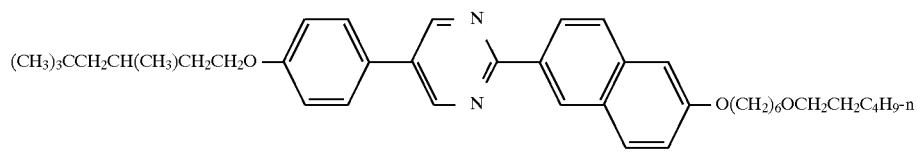
Exemplified compound 487
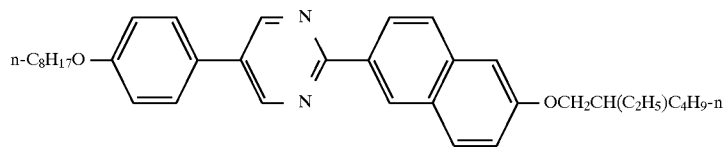
Exemplified compound 488
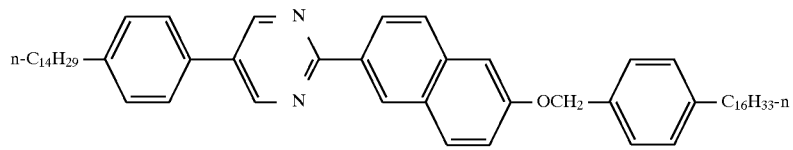
Exemplified compound 489
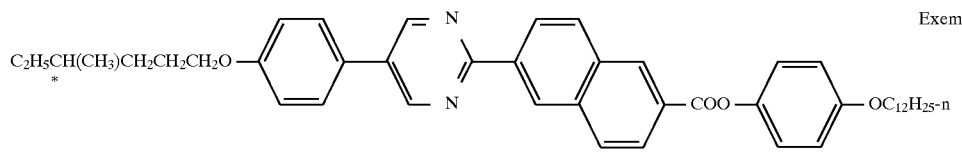
Exemplified compound 490

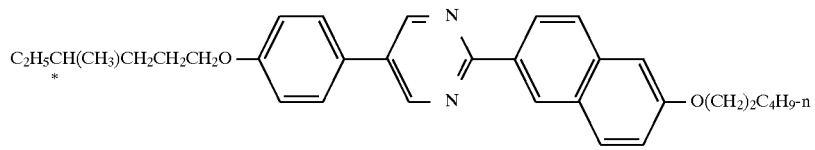 Exemplified compound 491
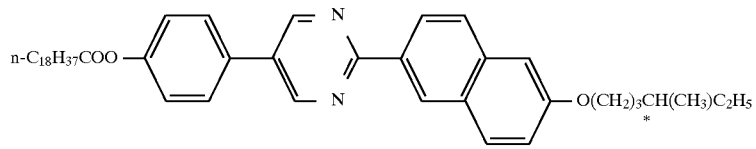 Exemplified compound 492
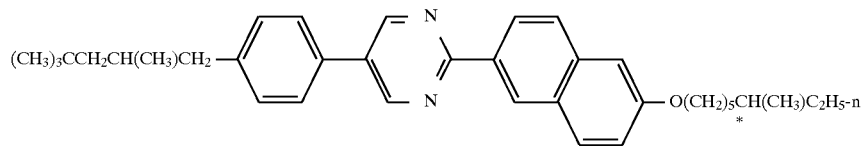 Exemplified compound 493
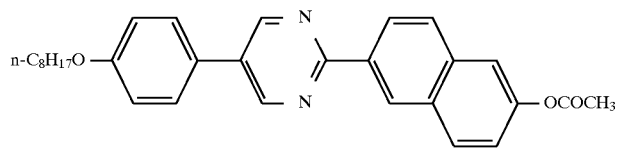 Exemplified compound 494
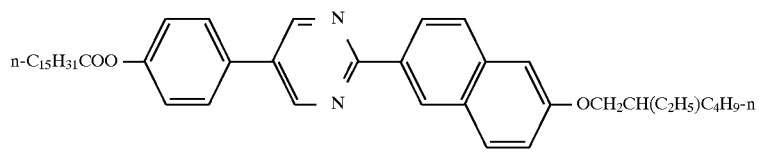 Exemplified compound 495
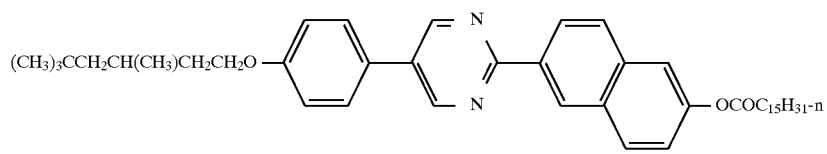 Exemplified compound 496
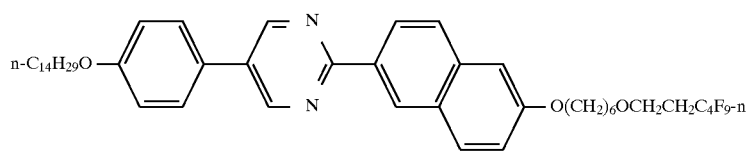 Exemplified compound 497
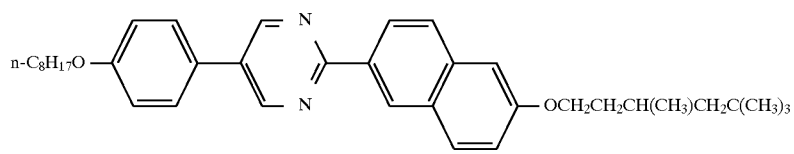 Exemplified compound 498
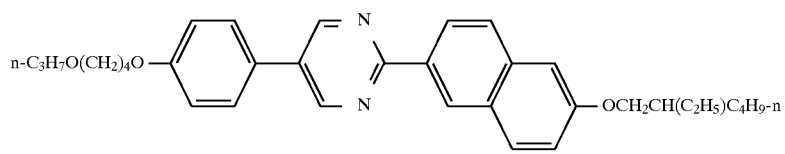 Exemplified compound 499
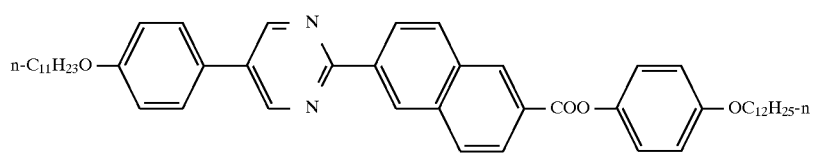 Exemplified compound 500

-continued
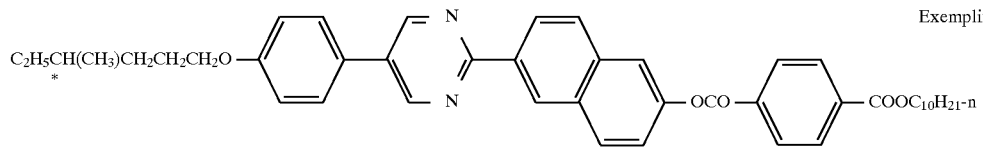 Exemplified compound 501
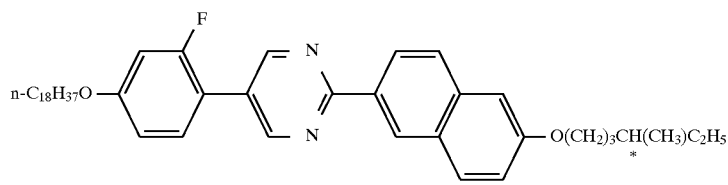 Exemplified compound 502
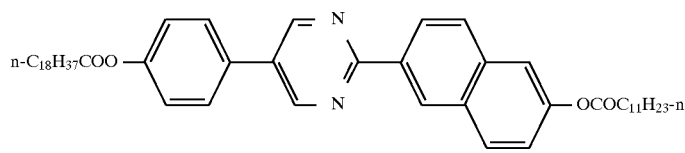 Exemplified compound 503
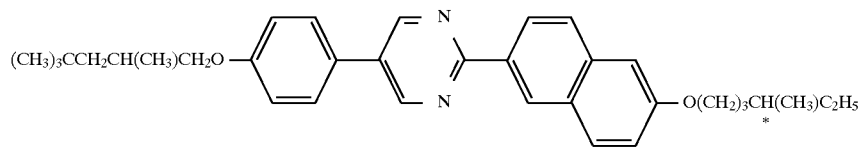 Exemplified compound 504
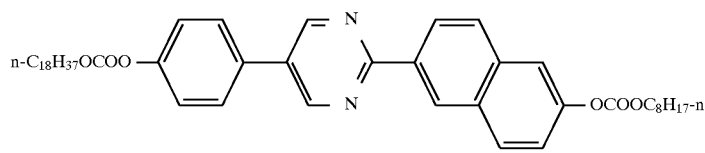 Exemplified compound 505
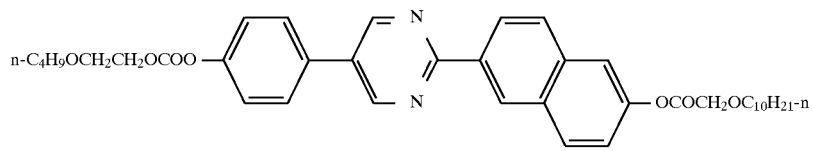 Exemplified compound 506
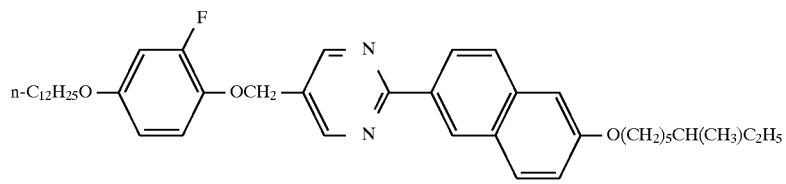 Exemplified compound 507
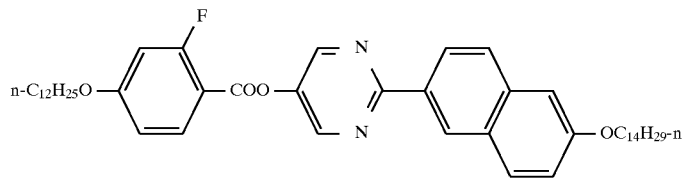 Exemplified compound 508
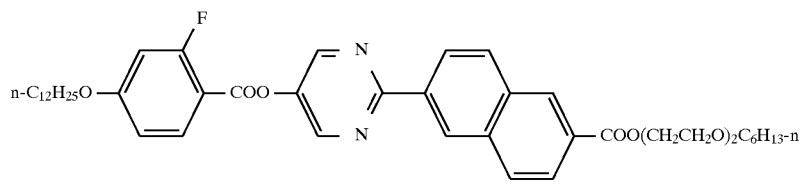 Exemplified compound 509

-continued
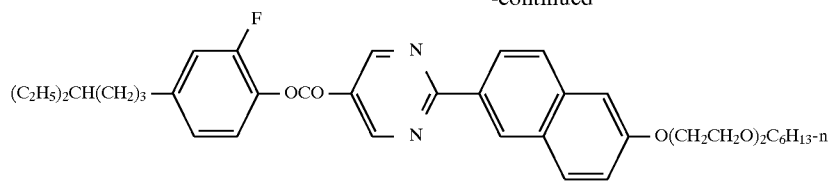
Exemplified compound 510
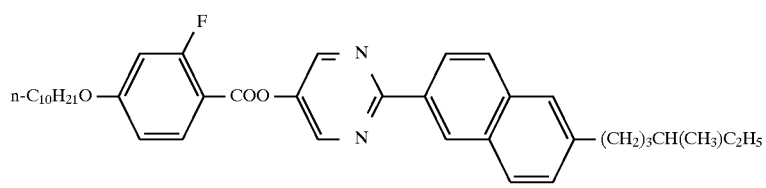
Exemplified compound 511
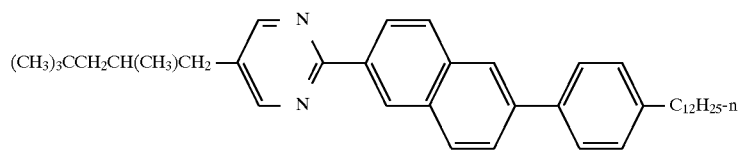
Exemplified compound 512
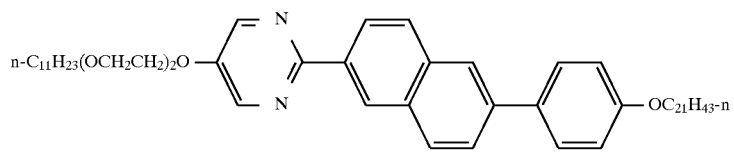
Exemplified compound 513
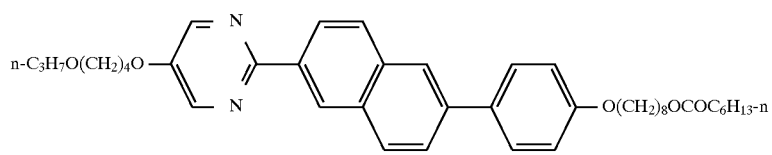
Exemplified compound 514
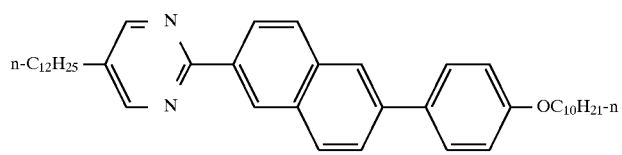
Exemplified compound 515
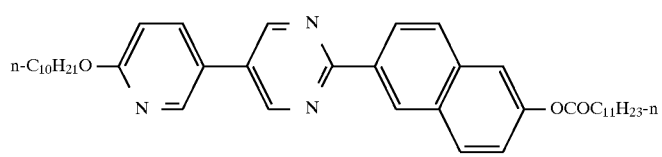
Exemplified compound 516
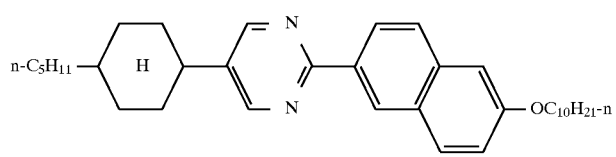
Exemplified compound 517
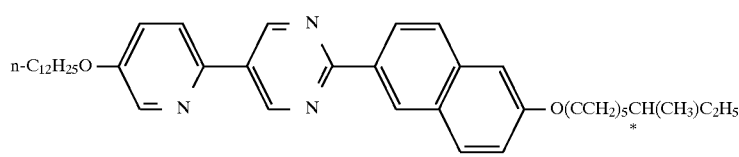
Exemplified compound 518
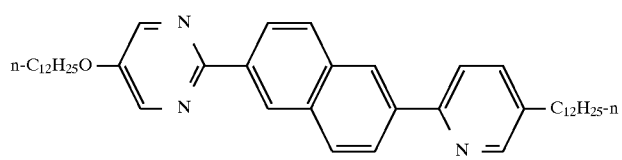
Exemplified compound 519

-continued

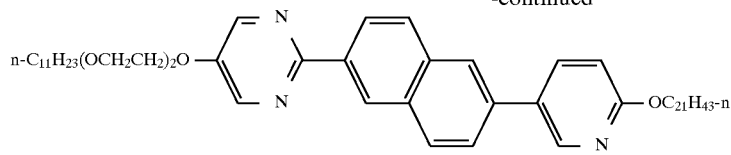

Exemplified compound 520

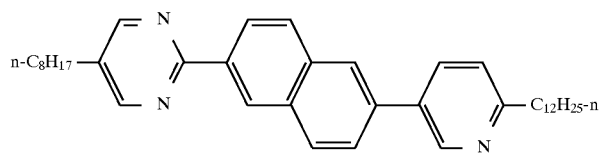

Exemplified compound 521

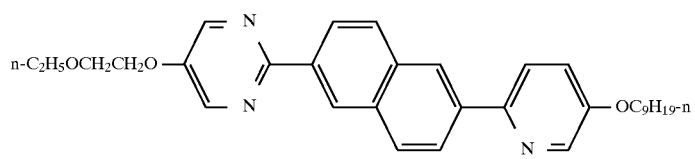

Exemplified compound 522

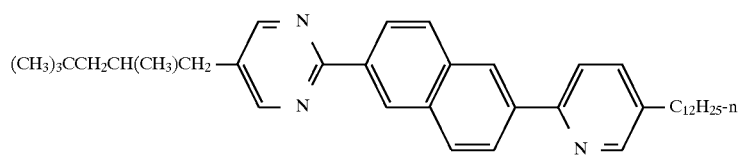

Exemplified compound 523

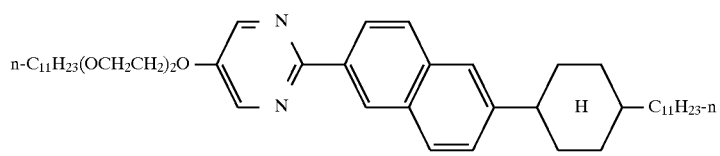

Exemplified compound 524

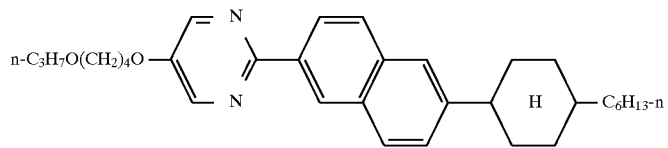

Exemplified compound 525

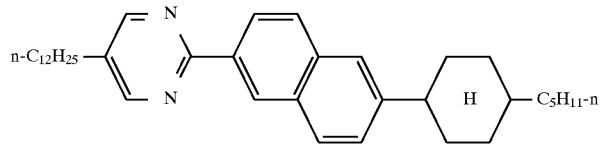

Exemplified compound 526

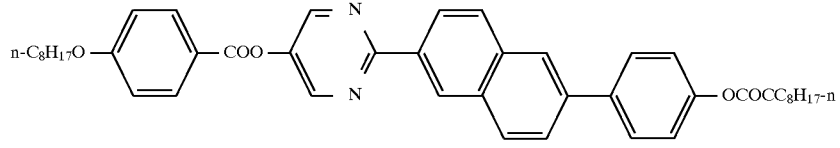

Exemplified compound 527

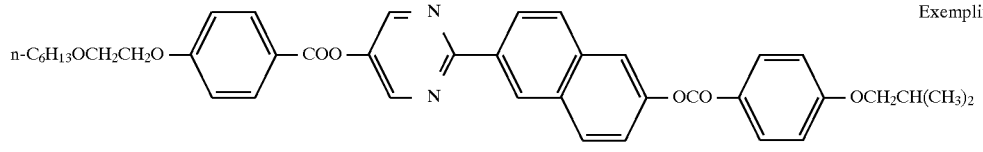

Exemplified compound 528

The compound of the present invention can be produced through the steps shown below.

Production steps of the pyrimidine compound represented by Formula (1-A2):

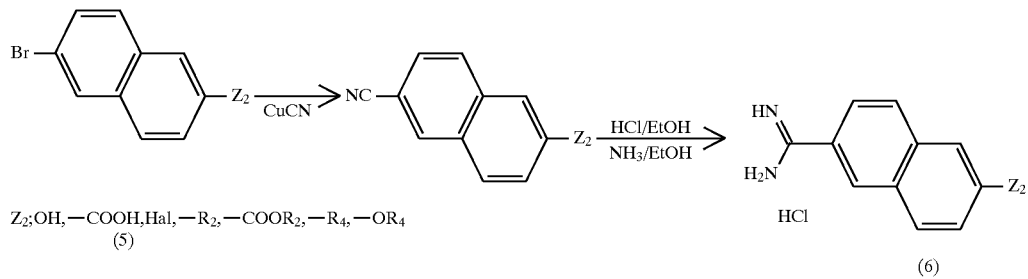

$Z_2$; OH, —COOH, Hal, —$R_2$, —COOR$_2$, —$R_4$, —OR$_4$
(5)

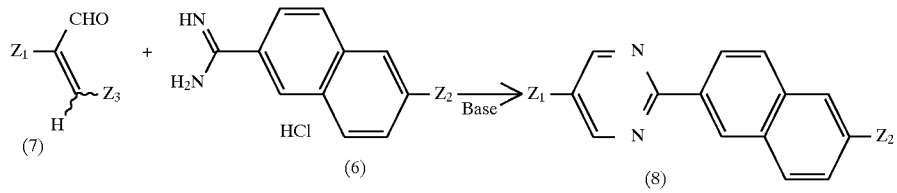

$Z_1$; $R_1$—, $R_3$—, $R_3$O—, BzO—, $R_1$—Ar—, $R_1$OCO—, $R_1$COO—
$Z_2$; OH, —COOH, —COOR$_2$, —OCOR$_2$, —Hal, —$R_2$, —$R_4$, —OR$_4$
$Z_3$; —NMe$_2$, —OEt

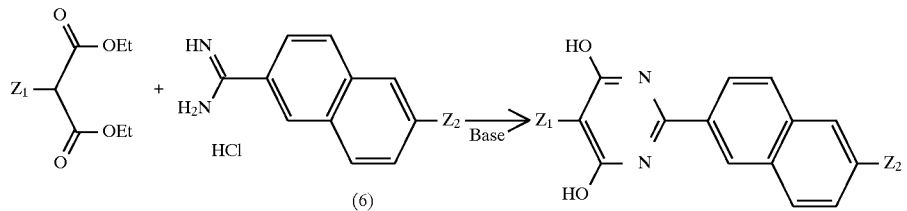

$Z_1$; $R_1$—, $R_3$—, $R_3$O—, BzO—, $R_1$—Ar—, $R_1$OCO—, $R_1$COO—
$Z_2$; OH, —COOH, —COOR$_2$, —OCOR$_2$, —Hal, —$R_2$, —$R_4$, —OR$_4$

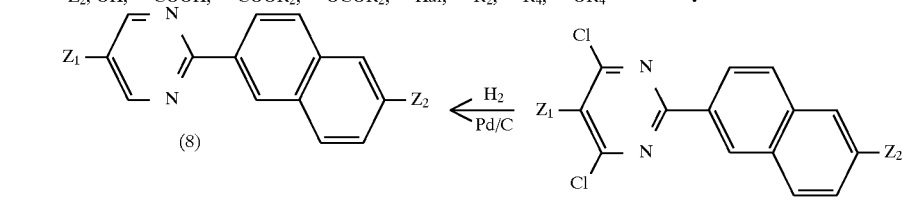

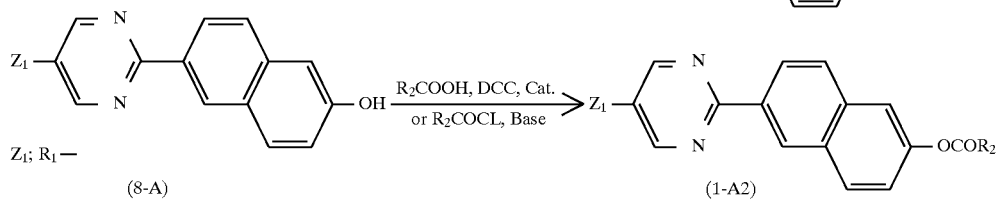

$Z_1$; $R_1$—
(8-A)

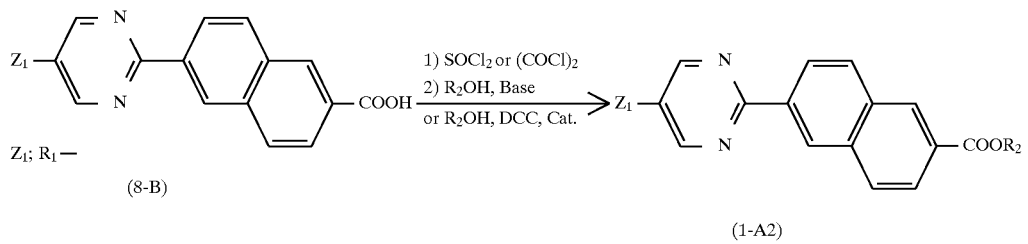

$Z_1$; $R_1$—
(8-B)

A 2-cyanophthalene derivative obtained by reacting copper (I) cyanide with a 2-bromonaphthalene represented by Formula (5) is reacted in anhydrous ethanol with hydrogen chloride, and then with ammonia, whereby amidine hydrochloride represented by Formula (6) can be obtained.

This amidine hydrochloride is reacted with an acrolein derivative represented by Formula (7) in ethanol in the presence of a base (for example, sodium methoxide and sodium ethoxide), whereby there can be produced a compound represented by Formula (8), wherein $Z_1$ represents an $R_1$— group, an $R_3$— group, an $R_3$O— group, a BzO— group (Bz represents a benzyl group), an $R_1$—Ar— group (Ar represents a 1,4-phenylene group, a pyridine-2,5-diyl group or a trans-1,4-cyclohexylene group) or an $R_1$OOC— group; and $Z_2$ represents a —OH group, a —COOH group, a —COOR$_2$ group, a—OCOR$_2$ group, a —Hal group (Hal represents a halogen atom), a —R₂ group, a —R₄ group or a —OR₄ group.

Alternatively, a diethyl malonate derivative is reacted with the amidine hydrochloride represented by Formula (6) in the presence of a base and then halogenated with a halogenation reagent such as phosphorous oxychloride, followed by reduction-dehalogenating this, whereby a compound represented by Formula (8) can be produced.

The pyrimidine compound represented by Formula (1-A2) can be produced by a method in which a compound [Formula (8A)] in which $Z_2$ in Formula (8) is an OH group is reacted with carboxylic chloride in the presence of a base (for example, pyridine, triethylamine, sodium hydroxide and potassium carbonate), or a method in which the compound of Formula (8-A) is reacted with carboxylic acid in the presence of N,N'-dicyclohexylcarbodiimide (hereinafter abbreviated as DCC) and a base catalyst (for example, 4-pyrrolidinopyridine and 4-dimethylaminopyridine).

Further, the pyrimidine compound represented by Formula (1-A2) can be produced by a method in which a compound [Formula (8-B)] in which $Z_2$ in Formula (8) is a COOH group is chlorinated with a chlorinating agent such as thionyl chloride and oxalyl chloride and then reacted with alcohol in the presence of a base, or a method in which the compound of Formula (8-B) is reacted with alcohol in the presence of DCC and a base catalyst.

Production steps of an acrolein derivative represented by Formula (7):

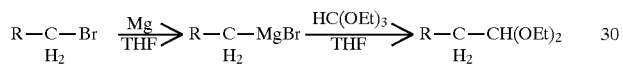

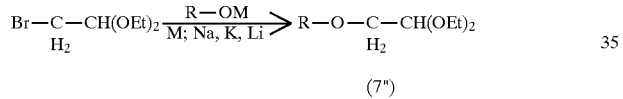

(7")

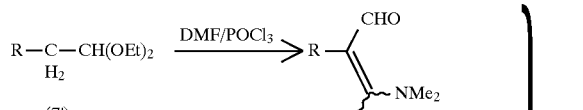

(7)

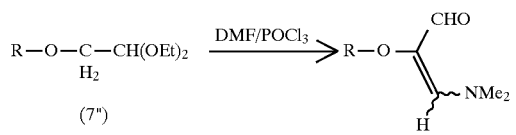

Some of the acrolein compounds represented by Formula (7) are available as a commercial product and can be produced as well through the following steps. That is, diethyl acetal (7') is produced by reacting a Grignard reagent prepared from alkyl halide and magnesium metal with triethyl orthoformate, or alkoxyacetaldehyde diethyl acetal (7") is produced by a method in which bromoacetaldehyde diethylacetal is reacted with alkoxide. Then, the acrolein derivative represented by Formula (7) can be produced by a method in which these acetals are reacted with a Vilsmyer reagent.

Production steps of a pyrimidine compound represented by Formula (1-A1):

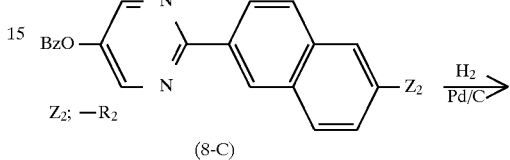

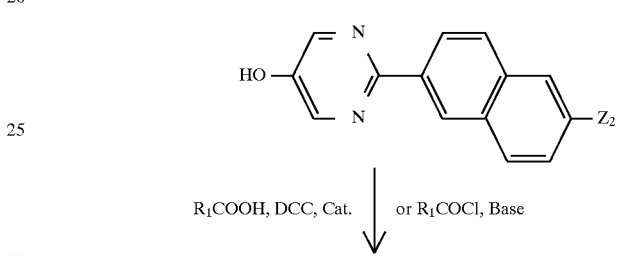

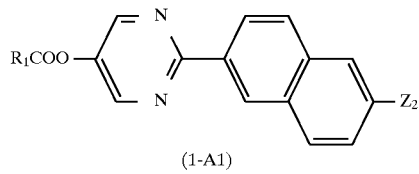

The pyrimidine compound represented by Formula (1-A1) can be produced by a method in which the protective group of a compound [Formula (8-C)] in which $Z_1$ in Formula (8) is a protective group for an OH group such as a benzyloxy group (BzO group) is liberated, and then the non-protected compound is reacted with carboxylic chloride in the presence of a base (for example, pyridine, triethylamine, sodium hydroxide, and potassium carbonate), or a method in which the non-protected compound is reacted with carboxylic acid in the presence of DCC and a base catalyst (for example, 4-pyrrolidinopyridine and 4-dimethylaminopyridine).

Production steps of a pyrimidine compound represented by Formula (1-A3):

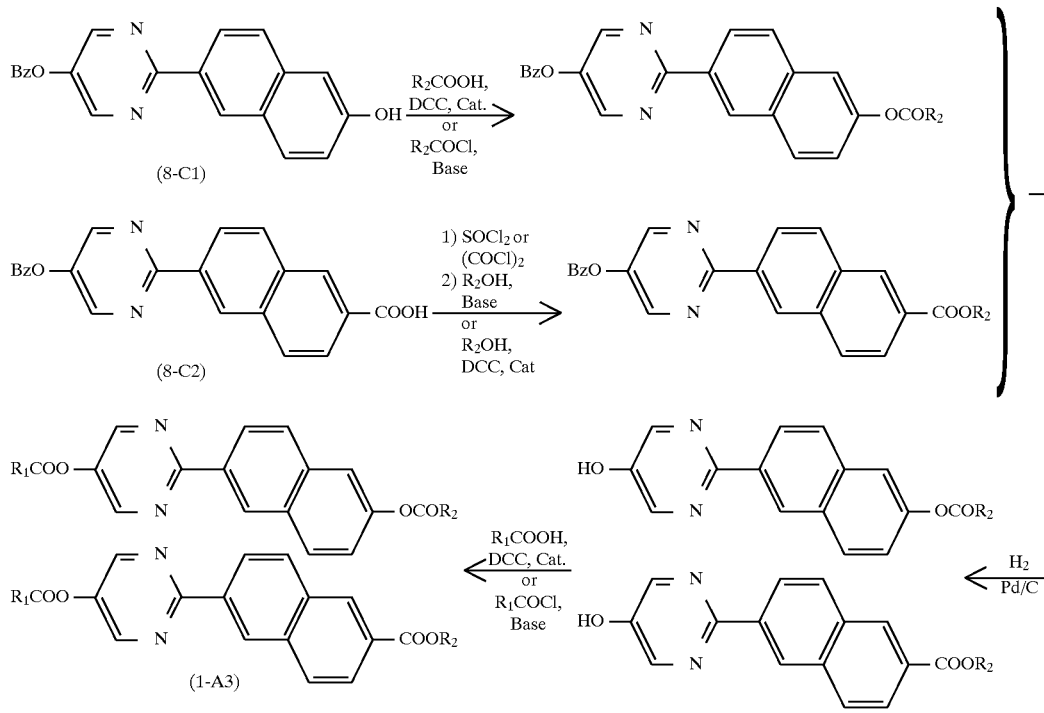

The ester derivative is prepared by (1) a method in which a compound [Formula (8-C1)] in which $Z_1$ in Formula (8) is a protective group for an OH group such as a benzyloxy group and $Z_2$ in Formula (8) is an OH group is reacted with carboxylic chloride in the presence of a base (for example, pyridine, triethylamine, sodium hydroxide, and potassium carbonate), or a method in which the compound [Formula (8-C1)] is reacted with carboxylic acid in the presence of DCC and a base catalyst [for example, 4-pyrrolidinopyridine and 4-dimethylaminopyridine, or (2) a method in which a compound [Formula (8-C2)] in which $Z_1$ in Formula (8) is a protective group for an OH group such as a benzyloxy group and $Z_2$ in Formula (8) is a COOH group is reacted with thionyl chloride or oxalyl chloride to turn into a carboxylic chloride, followed by reacting with alcohol, or a method in which the compound of Formula (8-C2) is reacted with alcohol in the presence of DCC and a base catalyst. Then, the pyrimidine compound represented by Formula (1-A3) can be produced by a method in which the protective group is liberated and then the non-protected compound is reacted with carboxylic chloride in the presence of a base (for example, pyridine, triethylamine, and potassium carbonate), or a method in which the non-protected compound is reacted with carboxylic acid in the presence of DCC and a base catalyst (for example, 4-pyrrolidinopyridine and 4-dimethylaminopyridine).

Production steps of a pyrimidine compound represented by Formula (1-B):

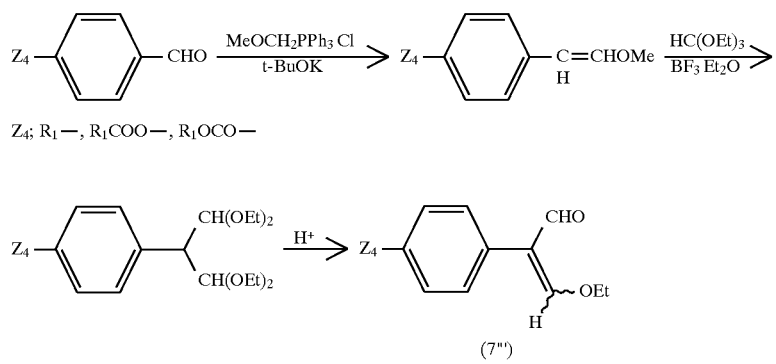

Production steps of a pyrimidine compound represented by Formula (1-B):
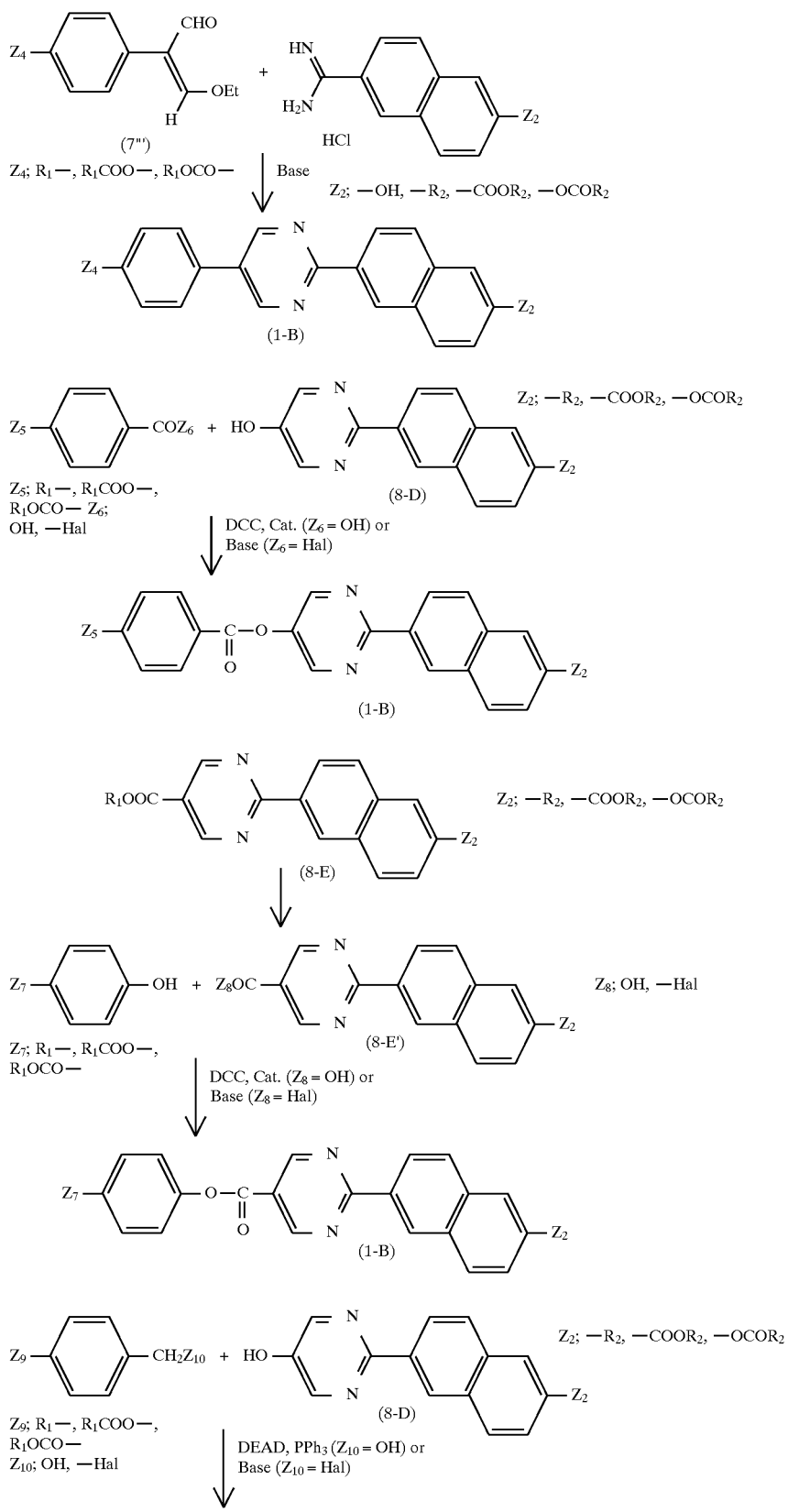

Production steps of a pyrimidine compound represented by Formula (1-B):

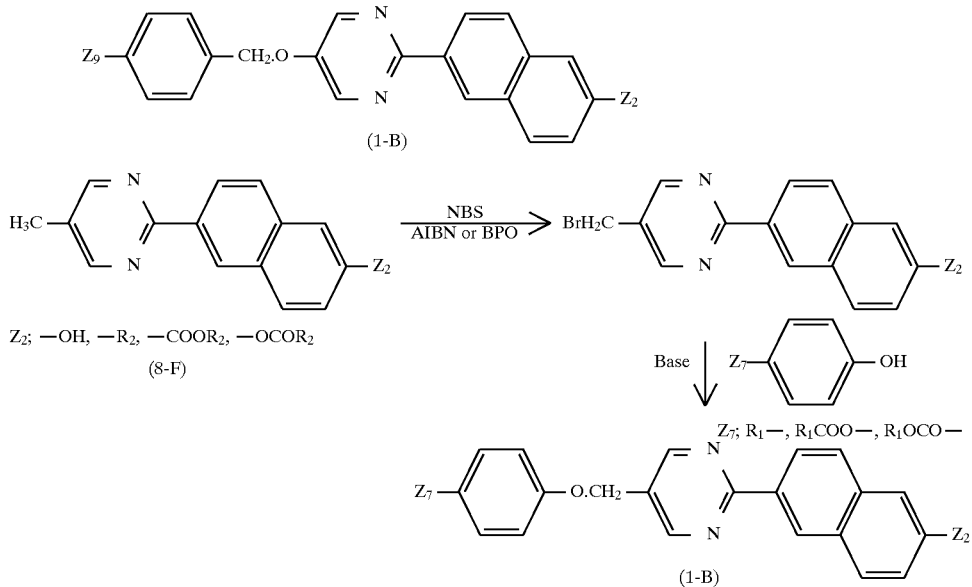

(1) A compound in which $X_1$ is a single bond can be produced by a method in which α-aryl-β-dimethylaminoacrolein or α-aryl-p-ethoxyacrolein (7''') is reacted with amidine hydrochloride (6) in the presence of a base (for example, sodium methoxide and sodium ethoxide).

(2) A compound in which $X_1$ is —COO— can be produced by a method in which a compound [Formula (8-D)] in which $Z_1$ in Formula (8) is OH group is reacted with an aromatic carboxylic acid derivative in the presence of DCC and a base catalyst (for example, 4-pyrrolidinopyridine and 4-dimethylaminopyridine), or a method in which the compound of Formula (8-D) is reacted with an aromatic carboxylic halide in the presence of a base (for example, triethylamine and sodium hydroxide).

(3) A compound in which $X_1$ is —COO— can be produced by a method in which a carboxylic acid or an acid halide derivative thereof [Formula (8-E')], is obtained by hydrolyzing a compound [Formula (8-E)] in which $Z_1$ in Formula (8) is $R_1OOC$, and then the carboxylic acid ($Z_8$ in Formula (8-E) is OH group) is reacted with a phenol derivative in the presence of DCC and a base catalyst (for example, 4-pyrrolidinopyridine and 4-dimethylaminopyridine), or a method in which the acid halide derivative in which $Z_8$ in Formula (8-E') is a halogen atom (Hal) is reacted with a phenol derivative in the presence of a base (for example, pyridine, triehylamine, sodium hydroxide and potassium carbonate).

(4) A compound in which $X_1$ is —$CH_2O$— can be produced by a method in which the compound represented by Formula (8-D) is reacted with a benzyl halide derivative. Further, the above compound can be produced as well by a method in which the compound represented by Formula (8-D) is reacted with a benzyl alcohol derivative in the presence of diethylazodicarboxylic acid (hereinafter abbreviated as DEAD) and triphenylphosphine.

(5) A compound in which $X_1$ is —$OCH_2$— can be produced by obtaining a bromomethylpyrimidine derivative by reacting a compound [Formula (8-F)] in which $Z_1$ in Formula (8) is methyl group with a brominating agent such as N-bromosuccinimide (hereinafter abbreviated as NBS) in the presence of azobisisobutyronitrile (hereinafter abbreviated as AIBN) or benzoyl peroxide and then reacting the bromomethylpyrimidine derivative with a phenol derivative.

Production steps of a pyrimidine compound represented by Formula (1C):

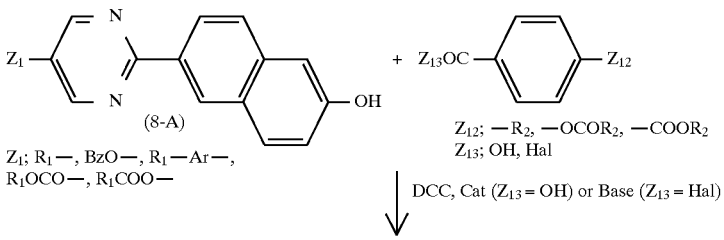

Production steps of a pyrimidine compound represented by Formula (1C):
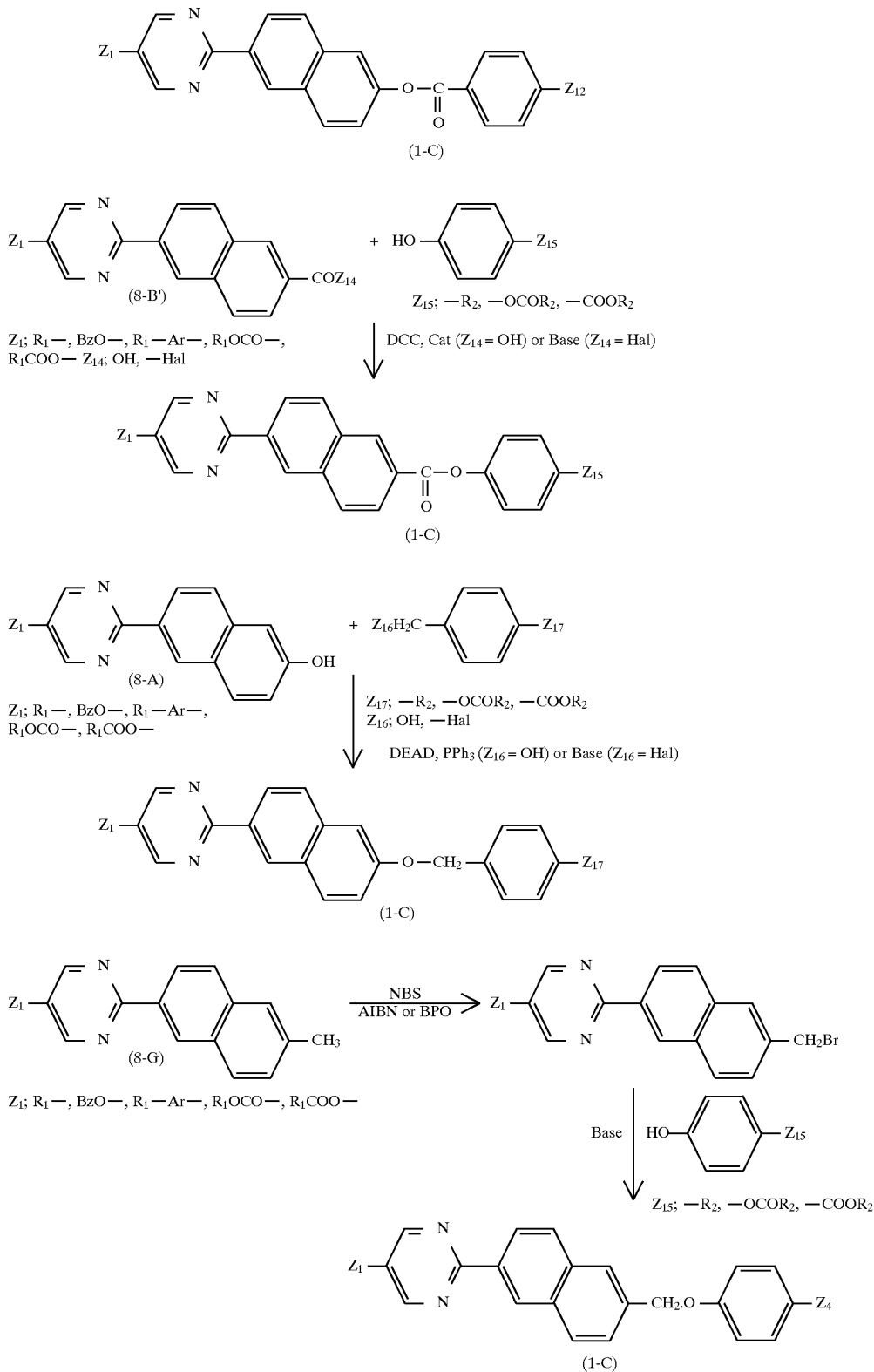

Production steps of a pyrimidine compound represented by Formula (1C):

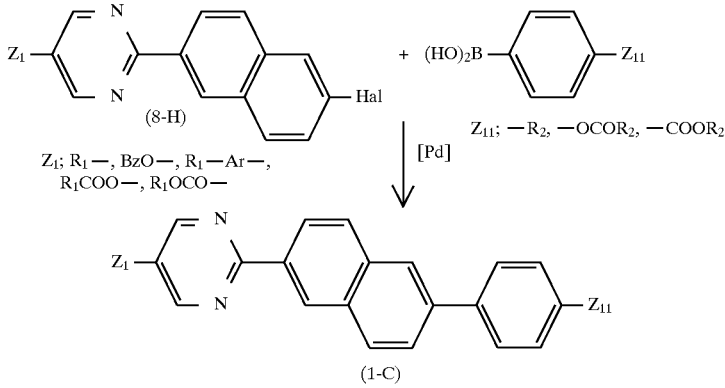

(1) A compound in which $X_2$ is —COO— can be produced by reacting a compound [Formula (8-A)] in which $Z_2$ in Formula (8) is OH group with an aromatic carboxylic acid derivative.

(2) A compound in which $X_2$ is —COO— can be produced by a method in which a compound [Formula (8-B')] in which $Z_2$ in Formula (8) is $COZ_{14}$ [$Z_{14}$ is OH or a halogen atom (Hal)] is reacted with phenol derivative.

(3) A compound in which $X_2$ is —OCH$_2$— can be produced by reacting the compound [Formula (8-A)] in which $Z_2$ in Formula (8) is an OH group with a benzyl halide derivative in the presence of a base such as potassium carbonate. Further, the above compound can be produced as well by a method in which the compound represented by Formula (8-A) is reacted with a benzyl alcohol derivative in the presence of DEAD and triphenylphosphine.

(4) A compound in which $X_2$ is -CH$_2$O— can be produced by obtaining a bromomethylnaphthalene derivative by reacting a compound [Formula (8-G)] in which $Z_2$ in Formula (8) is methyl group with a brominating agent such as NBS in the presence of AIBN or benzoyl peroxide and then reacting the bromomethylnaphthalene derivative with a phenol derivative.

(5) A compound in which X2 is a single bond can be produced by reacting a compound [Formula (8-H)] in which $Z_2$ in Formula (8) is halogen with boric acid ester (this is obtained by reacting a Grignard reagent prepared from a halogenated benzene derivative with trimethyl borate and then hydrolyzing the resulting compound) in the presence of a palladium catalyst.

Next, the pyrimidine compound represented by Formula (2) of the present invention will be explained in detail.

In the pyrimidine compound represented by Formula (2) of the present invention, $R_3$ and $R_4$ each represent a linear or branched alkyl or alkenyl group having 3 to 24 carbon atoms; at least one —CH$_2$— group (provided that adjacent —CH$_2$— groups and —CH$_2$— groups bonded to oxygen atoms or aromatic rings are excluded) present in the alkyl group or alkenyl group of at least one of $R_3$ and $R_4$ is substituted with an oxygen atom; $R_3$ and $R_4$ may be substituted with halogen atoms such as fluorine, chlorine and bromine; the branched alkyl or alkenyl group may have asymmetric carbon atoms, and the asymmetric carbon atoms may be optically active; and m and n each represent 0 or 1.

The pyrimidine compound represented by Formula (2) of the present invention has any of the following four structures of (2-A), (2-B), (2-C) and (2-D) when m and n each represent 0 or 1:

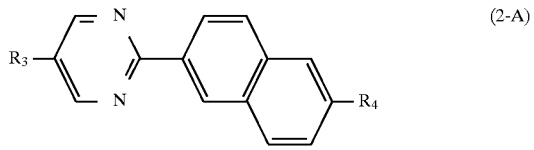 (2-A)

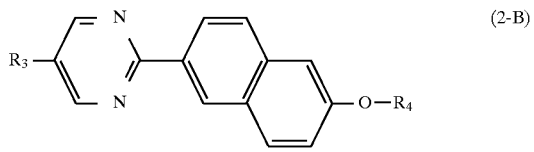 (2-B)

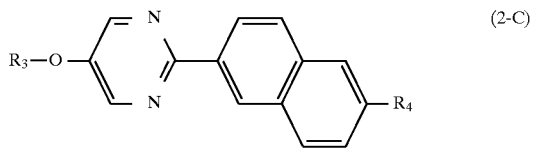 (2-C)

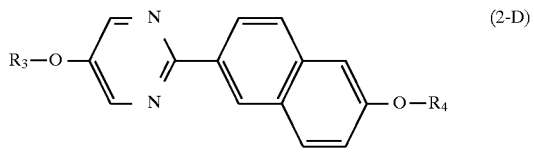 (2-D)

Among them, preferred are the structures of (2-B), (2-C) and (2-D) in which m+n is 1 or 2.

Further, an alkyl group and alkenyl group in which the —CH$_2$— groups which are not adjacent in at least one of $R_3$ and $R_4$ are substituted with oxygen atoms shall be designated as $Q_1$ and $Q_2$, respectively, and an alkyl group and alkenyl group containing no oxygen atoms shall be designated as $R_5$ and $R_6$, respectively. Then, the pyrimidine compound represented by Formula (2) has any of the following structures of (2-A1 to 2-A3), (2-B1 to 2-B3), (2-C1 to 2-C3), and (2-D1 to 2-D3):

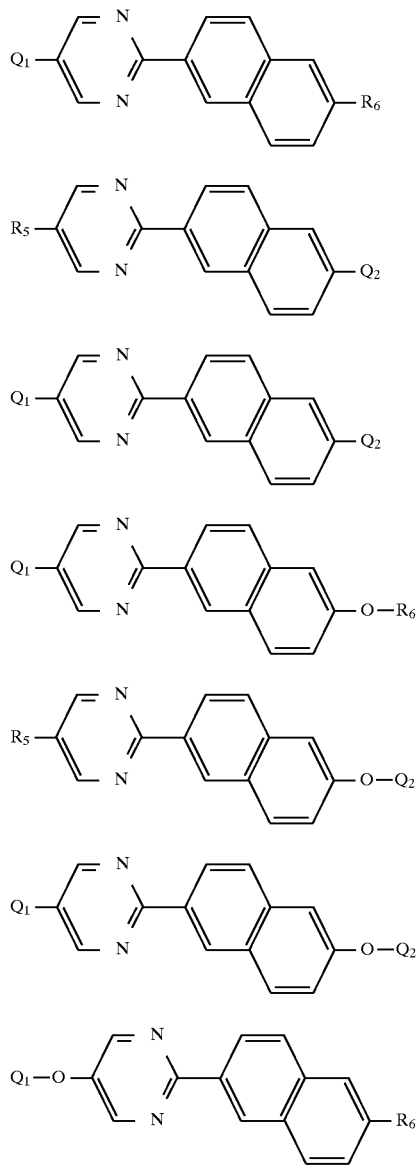
(2-A1)
(2-A2)
(2-A3)
(2-B1)
(2-B2)
(2-B3)
(2-C1)
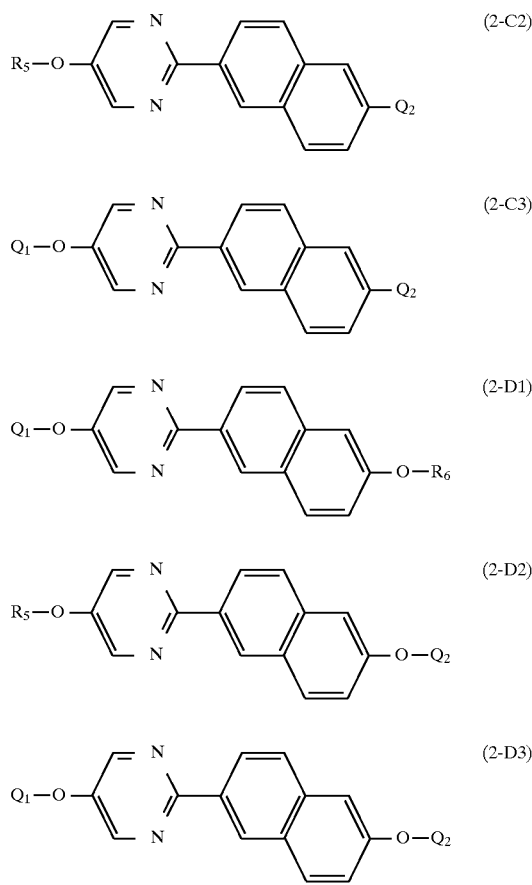
(2-C2)
(2-C3)
(2-D1)
(2-D2)
(2-D3)
The groups represented by $Q_1$ and $Q_2$ are represented preferably by the following Formula (9):
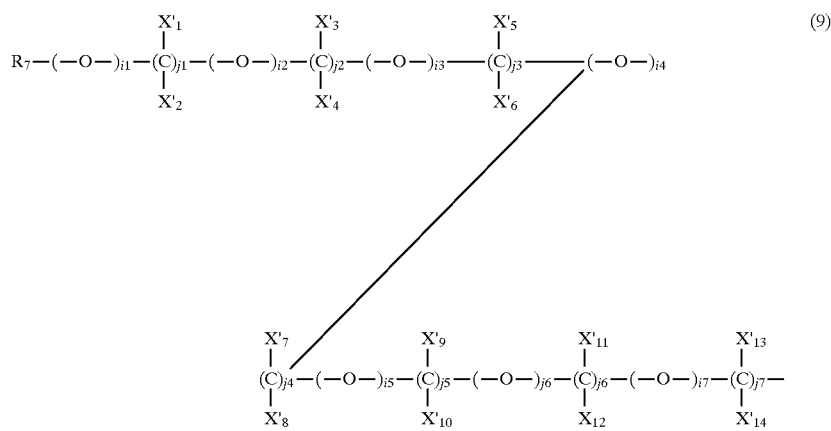

In Formula (9), $R_7$ represents a linear or branched alkyl group having 1 to 15 carbon atoms and may be substituted with a halogen atom; $X'_1$ to $X'_{14}$ each are groups selected from a halogen atom, a hydrogen atom, methyl group, ethyl group, and n-propyl group; $i_1$, $i_2$, $i_3$, $i_4$, $i_5$, $i_6$, and $i_7$ each represent 0 or 1, provided that all of $i_1$, to $i_7$ do not represent 0 at the same time; $j_1$, $j_2$, $j_3$, $j_4$, $j_5$, $j_6$, and $j_7$ each represent an integer of 0 to 10, and the total number of the carbon atoms in Formula (9) is 2 to 23.

There can be given as concrete examples of the groups represented by $Q_1$ and $Q_2$, for example, the alkoxyalkyl groups, alkenyloxyalkyl groups and haloalkoxyalkyl groups given in the concrete examples of $R_1$ and $R_2$ in Formula (1). Preferred are the alkoxyalkyl groups and the alkenyloxyalkyl groups.

There can be given as concrete examples of the groups represented by $R_5$ and $R_6$, for example, the alkyl groups, haloalkyl groups and alkenyl groups given in the concrete examples of $R_1$ and $R_2$ in Formula (1). Preferred are the alkyl groups and the alkenyl groups, and more preferred are the alkyl groups.

In the groups represented by $Q_1$, $Q_2$, $R_5$ and $R_6$, the groups having branched chains may have asymmetric carbons. These carbons may be either optically active or inactive. Preferred are the groups having no optically active asymmetric carbons.

The following compounds can be given as concrete examples of the pyrimidine compound represented by Formula (2):

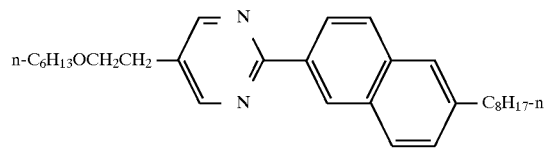

Exemplified compound 529

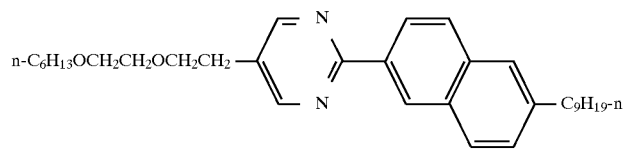

Exemplified compound 530

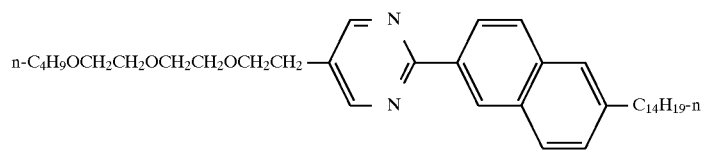

Exemplified compound 531

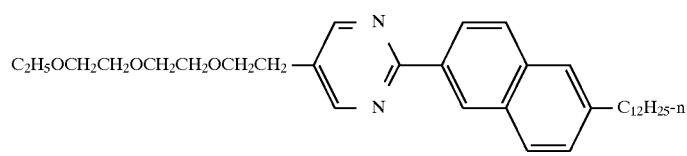

Exemplified compound 532

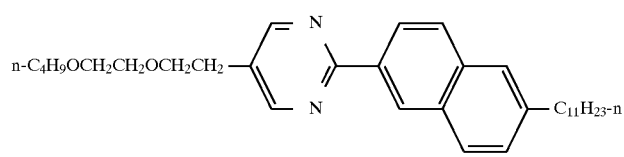

Exemplified compound 533

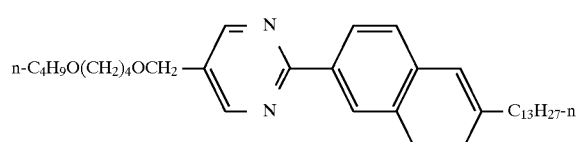

Exemplified compound 534

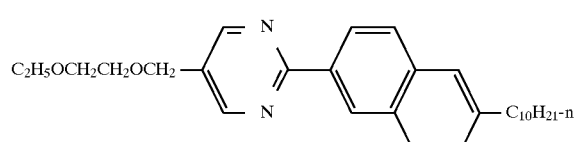

Exemplified compound 535

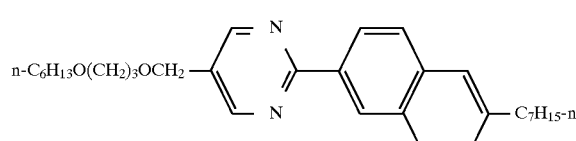

Exemplified compound 536

-continued
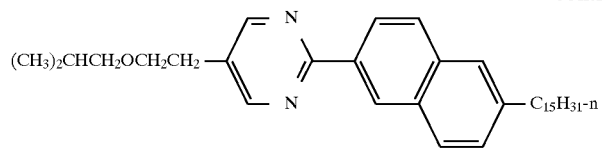 Exemplified compound 537
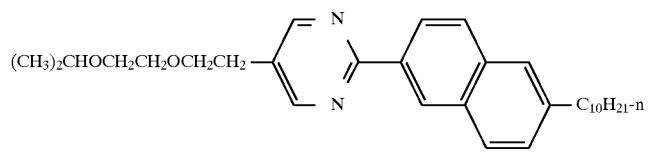 Exemplified compound 538
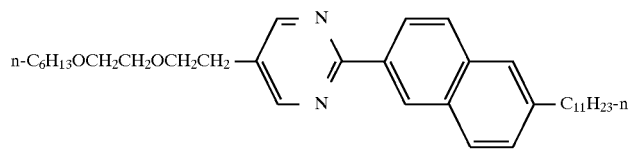 Exemplified compound 539
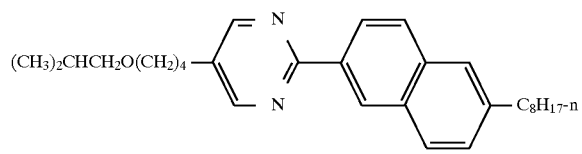 Exemplified compound 540
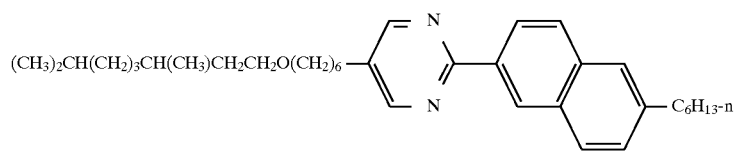 Exemplified compound 541
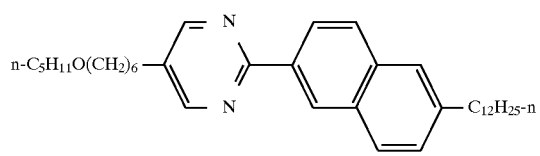 Exemplified compound 542
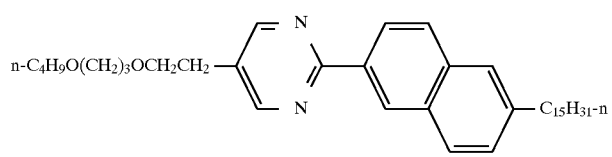 Exemplified compound 543
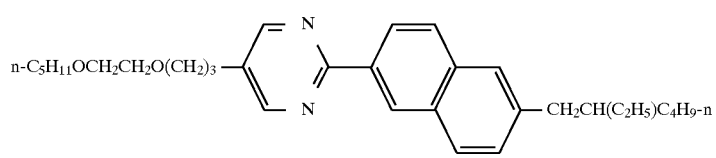 Exemplified compound 544
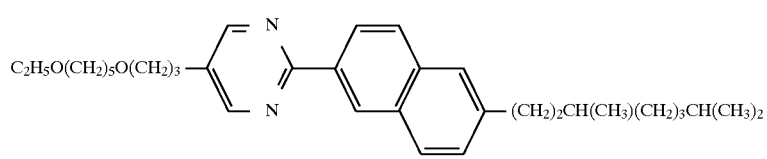 Exemplified compound 545
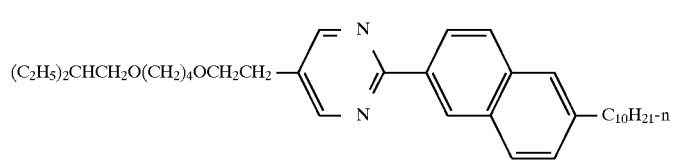 Exemplified compound 546

-continued
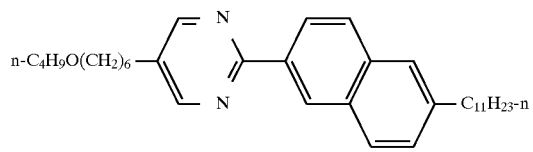
Exemplified compound 547
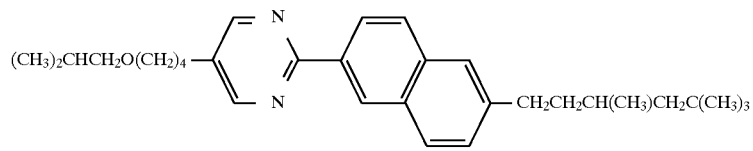
Exemplified compound 548
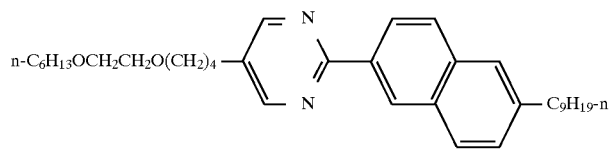
Exemplified compound 549
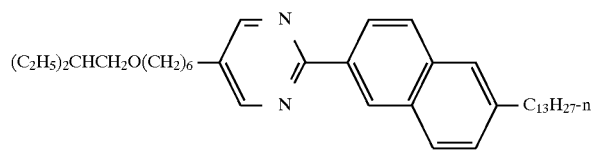
Exemplified compound 550
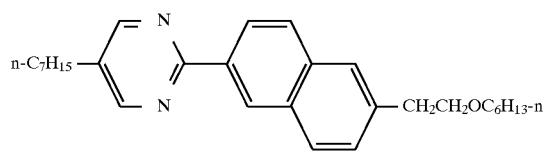
Exemplified compound 551
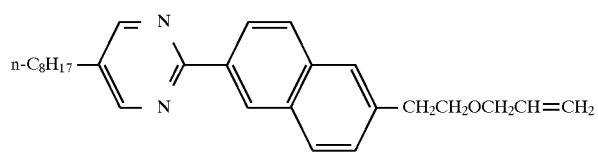
Exemplified compound 552
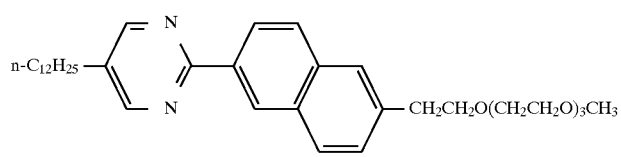
Exemplified compound 553
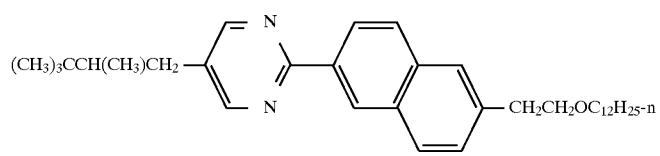
Exemplified compound 554
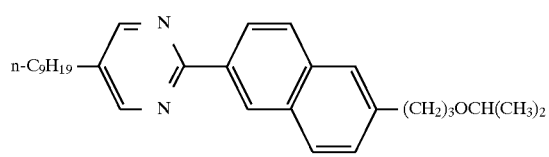
Exemplified compound 555
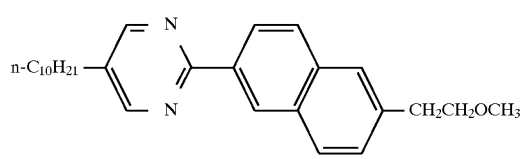
Exemplified compound 556

-continued
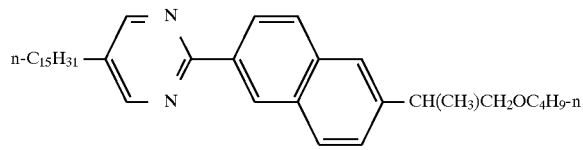
Exemplified compound 557
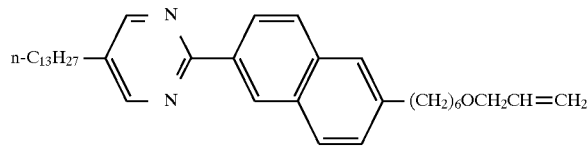
Exemplified compound 558
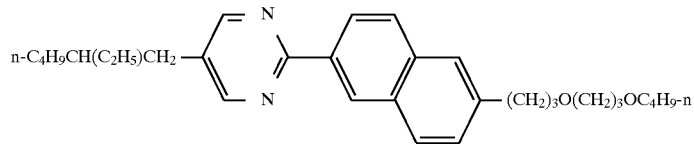
Exemplified compound 559
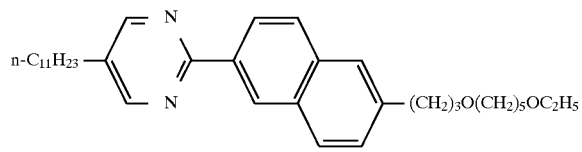
Exemplified compound 560
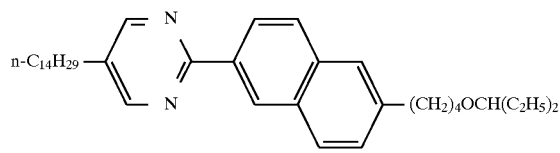
Exemplified compound 561
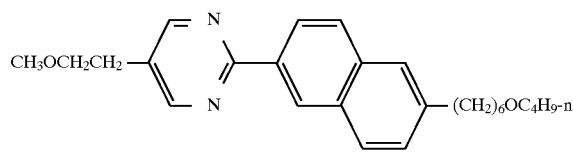
Exemplified compound 562
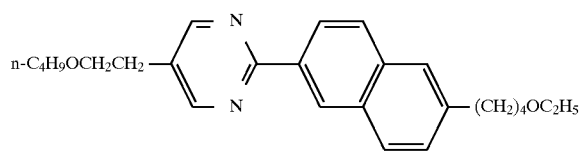
Exemplified compound 563
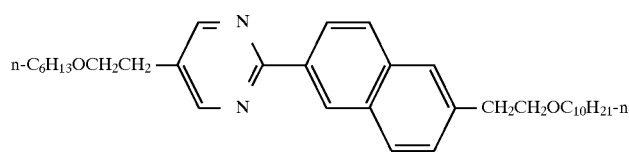
Exemplified compound 564
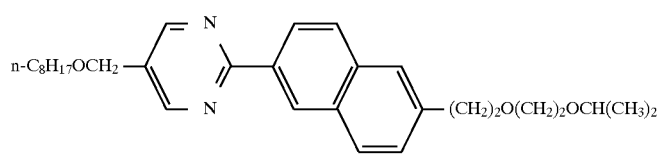
Exemplified compound 565
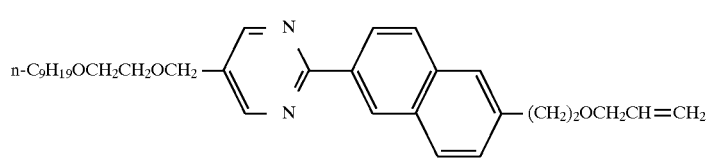
Exemplified compound 566

-continued
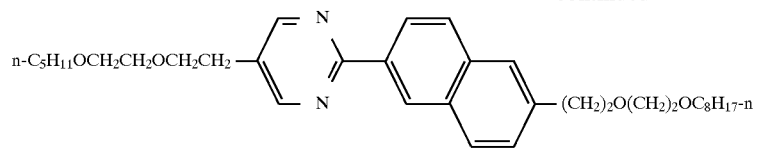
Exemplified compound 567
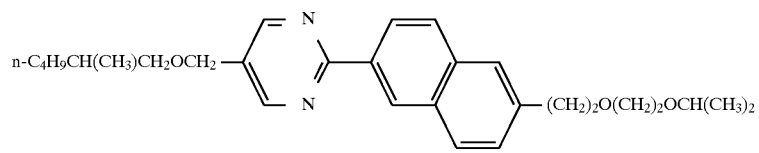
Exemplified compound 568
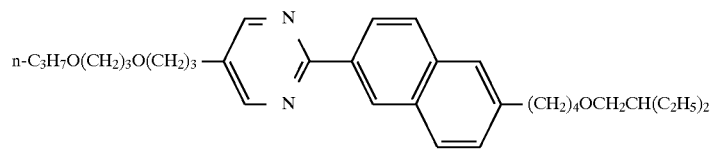
Exemplified compound 569
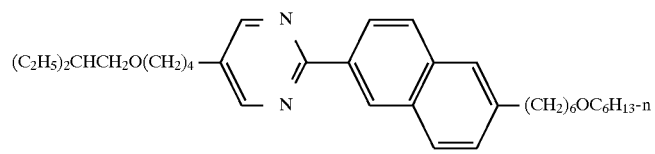
Exemplified compound 570
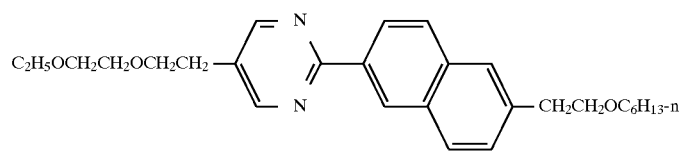
Exemplified compound 571
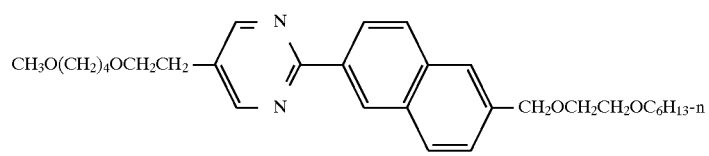
Exemplified compound 572
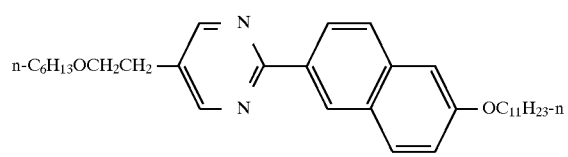
Exemplified compound 573
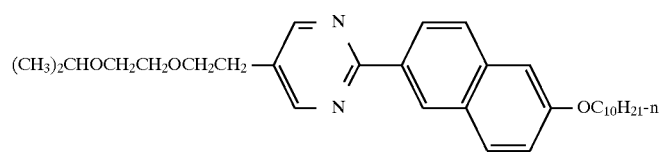
Exemplified compound 574
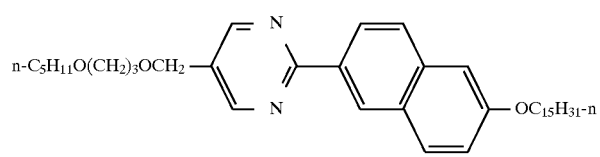
Exemplified compound 575
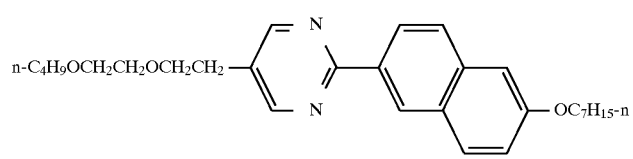
Exemplified compound 576

-continued
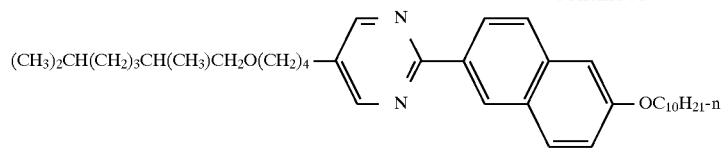
Exemplified compound 577
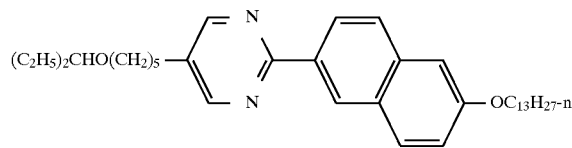
Exemplified compound 578
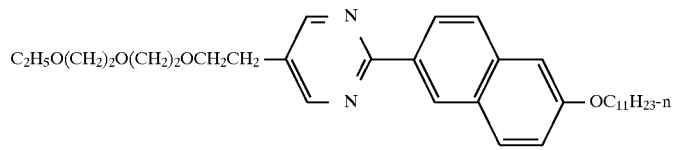
Exemplified compound 579
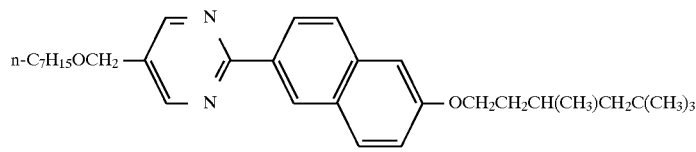
Exemplified compound 580
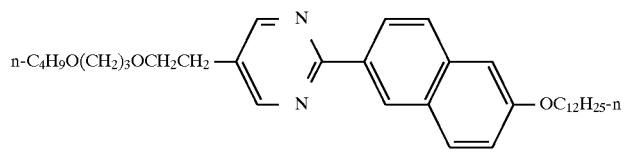
Exemplified compound 581
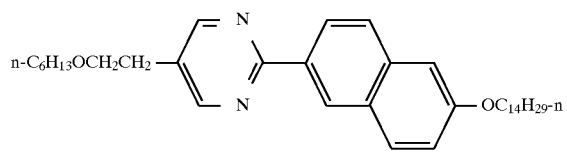
Exemplified compound 582
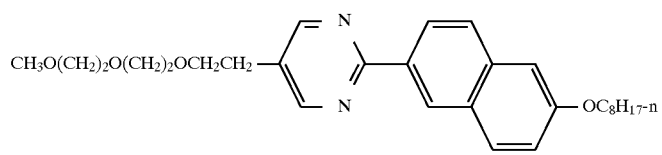
Exemplified compound 583
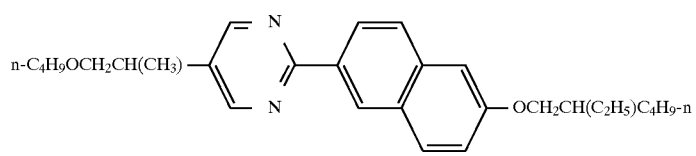
Exemplified compound 584
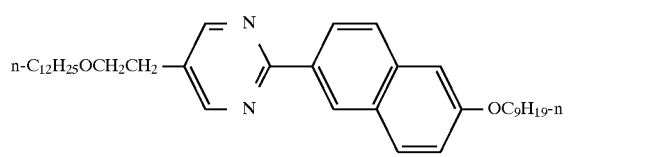
Exemplified compound 585
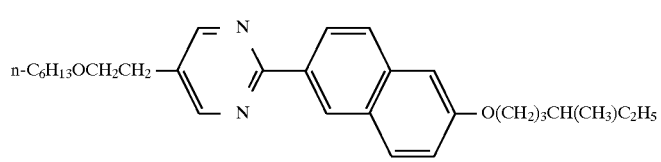
Exemplified compound 586

-continued
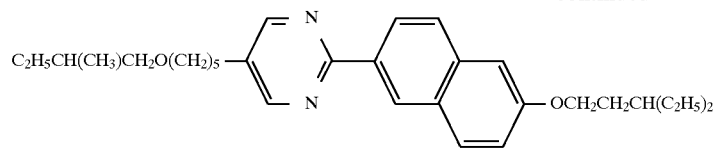
Exemplified compound 587
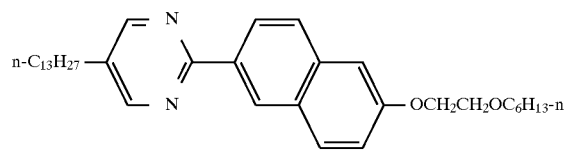
Exemplified compound 588
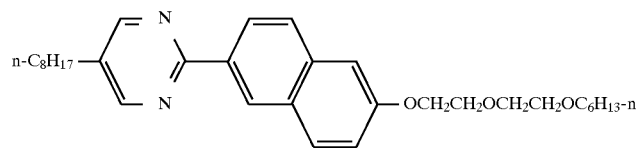
Exemplified compound 589
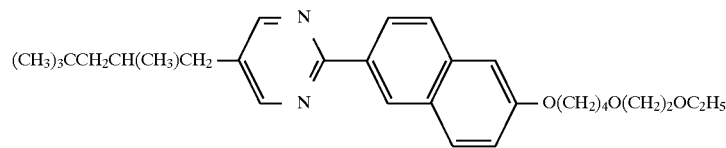
Exemplified compound 590
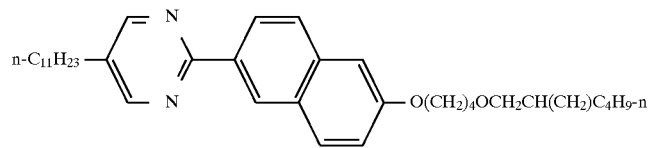
Exemplified compound 591
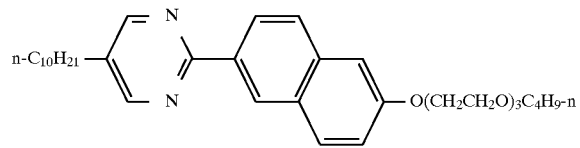
Exemplified compound 592
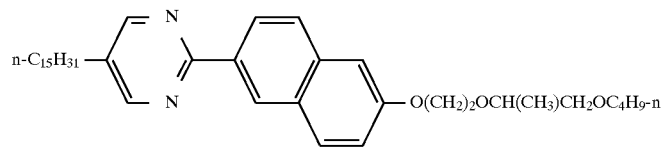
Exemplified compound 593
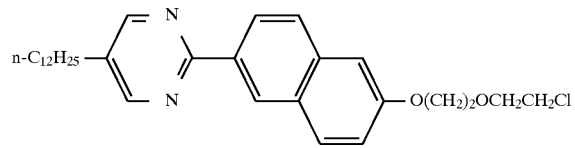
Exemplified compound 594
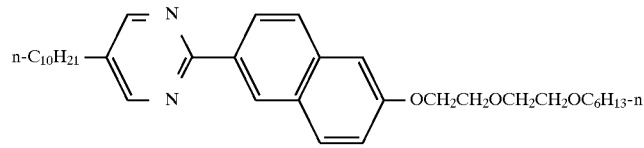
Exemplified compound 595
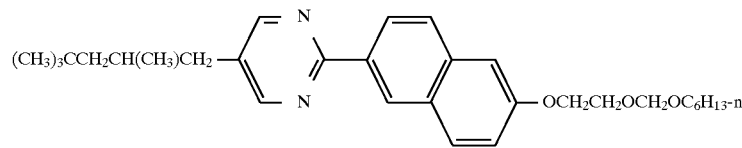
Exemplified compound 596

-continued
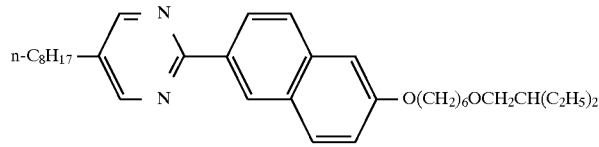
Exemplified compound 597
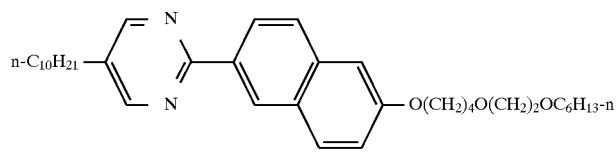
Exemplified compound 598
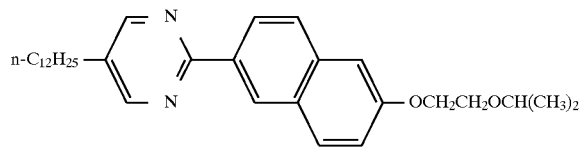
Exemplified compound 599
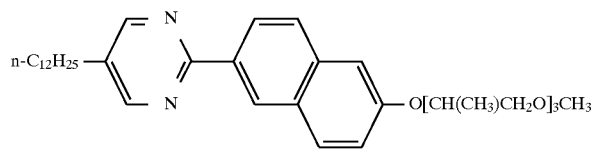
Exemplified compound 600
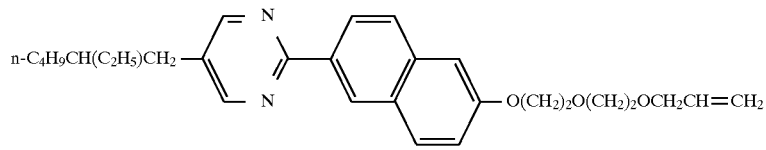
Exemplified compound 601
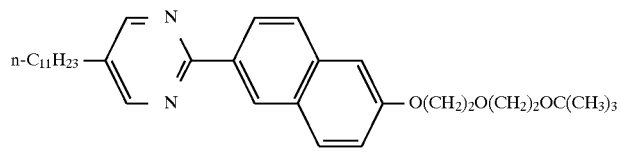
Exemplified compound 602
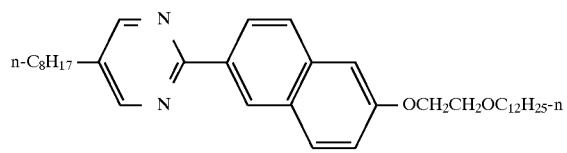
Exemplified compound 603
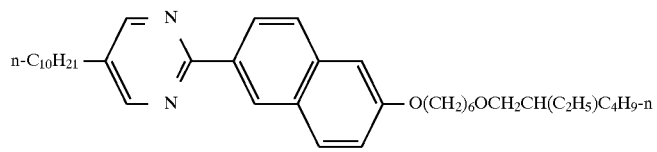
Exemplified compound 604
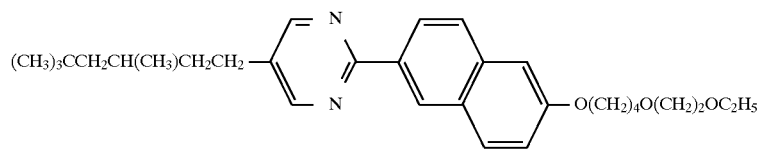
Exemplified compound 605
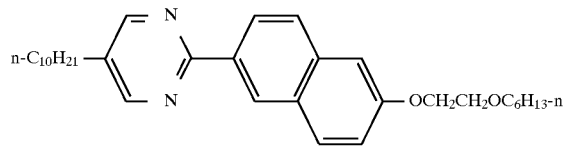
Exemplified compound 606

-continued
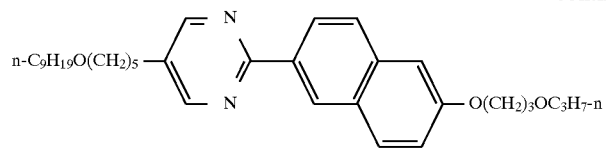
Exemplified compound 607
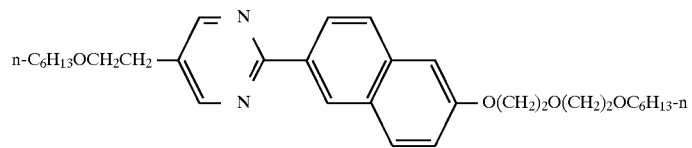
Exemplified compound 608
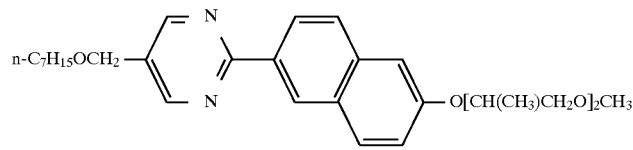
Exemplified compound 609
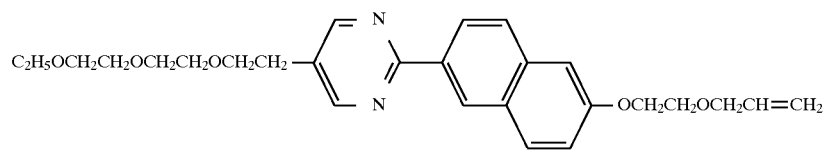
Exemplified compound 610
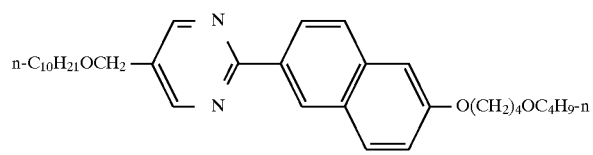
Exemplified compound 611
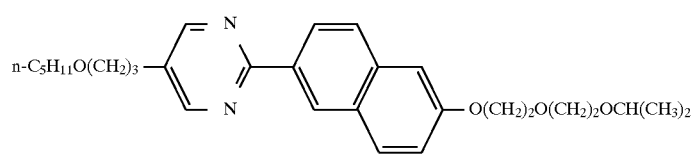
Exemplified compound 612
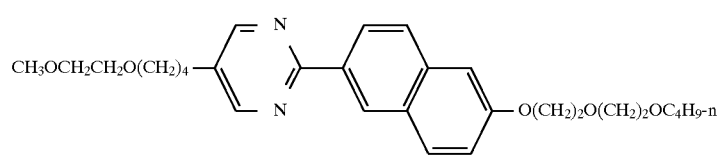
Exemplified compound 613
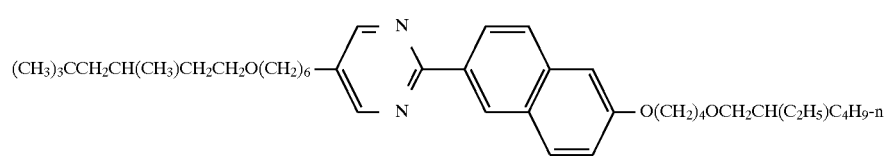
Exemplified compound 614
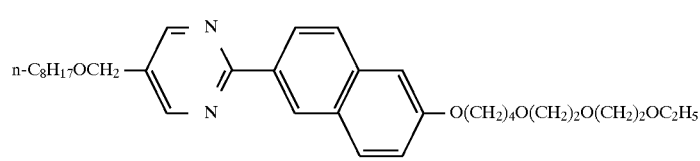
Exemplified compound 615
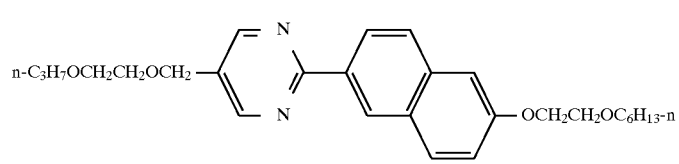
Exemplified compound 616

-continued
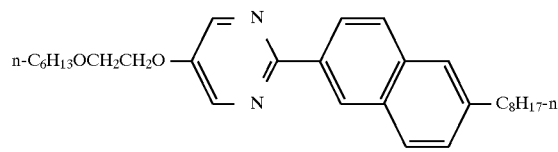 Exemplified compound 617
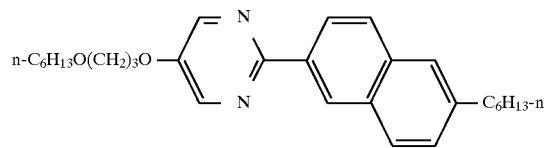 Exemplified compound 618
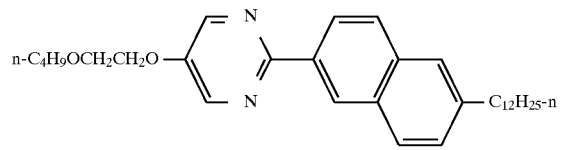 Exemplified compound 619
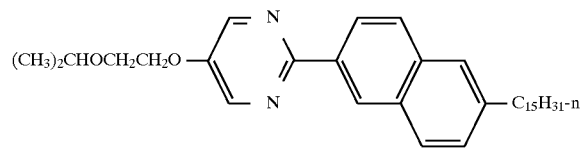 Exemplified compound 620
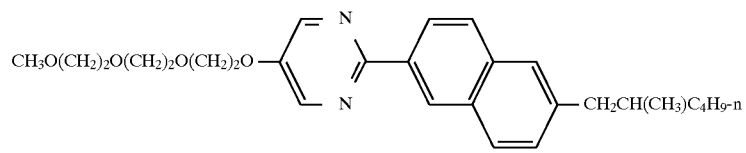 Exemplified compound 621
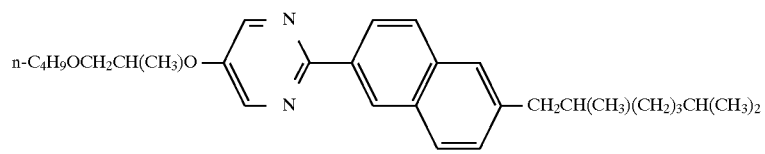 Exemplified compound 622
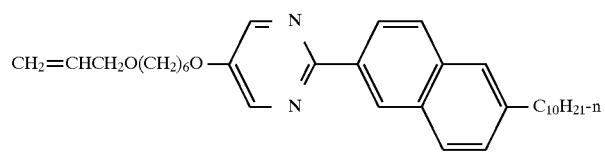 Exemplified compound 623
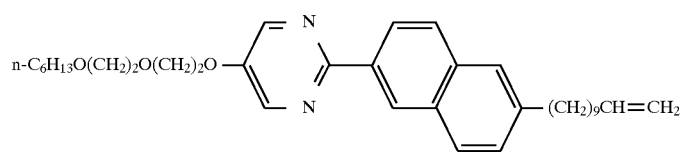 Exemplified compound 624
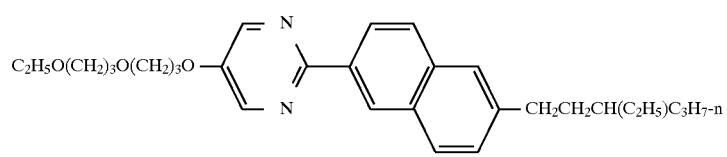 Exemplified compound 625
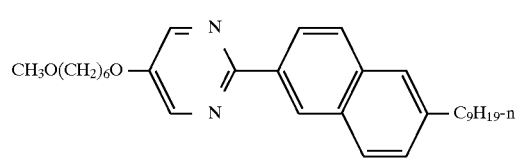 Exemplified compound 626

-continued
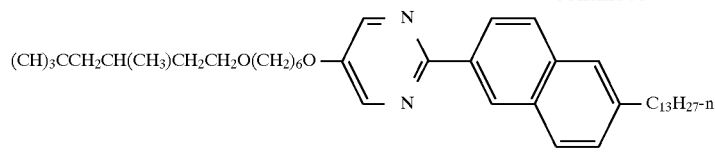
Exemplified compound 627
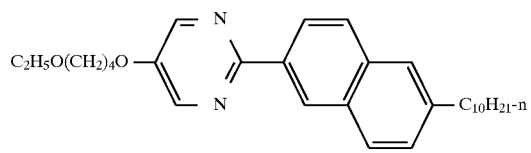
Exemplified compound 628
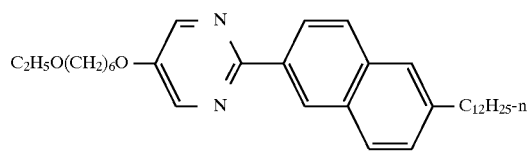
Exemplified compound 629
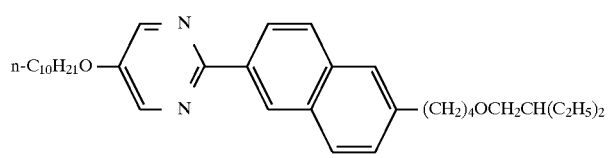
Exemplified compound 630
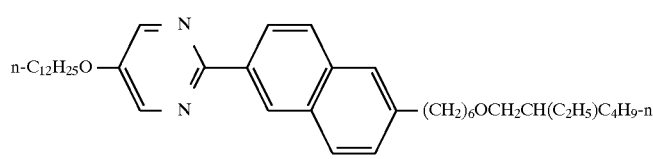
Exemplified compound 631
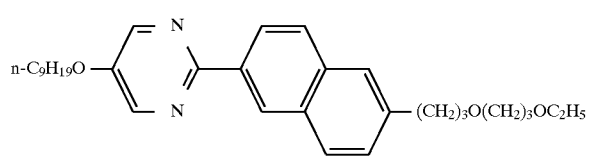
Exemplified compound 632
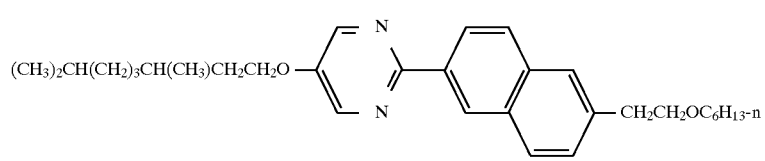
Exemplified compound 633
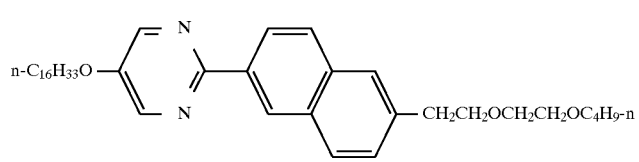
Exemplified compound 634
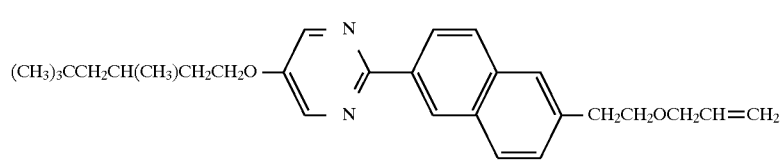
Exemplified compound 635
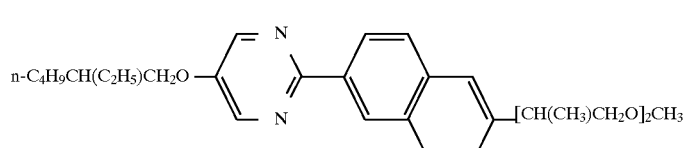
Exemplified compound 636

-continued
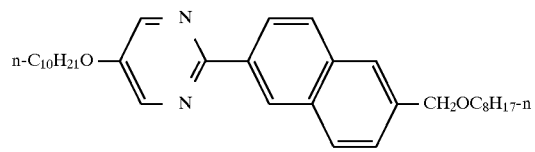
Exemplified compound 637
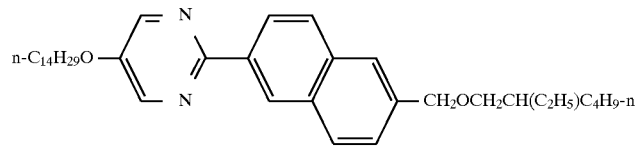
Exemplified compound 638
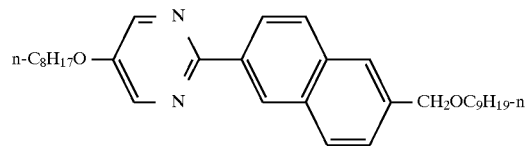
Exemplified compound 639
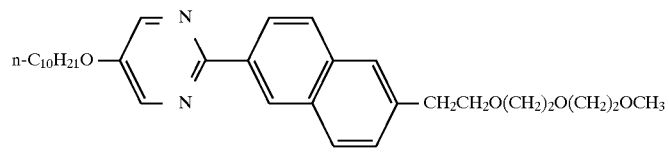
Exemplified compound 640
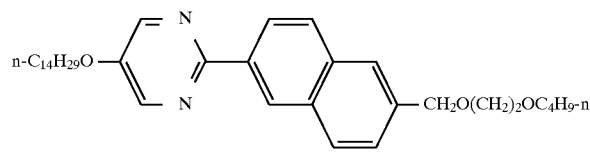
Exemplified compound 641
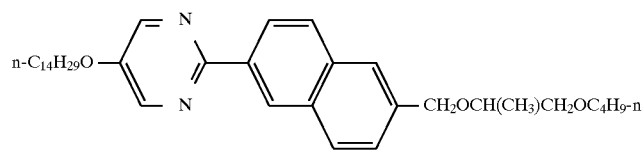
Exemplified compound 642
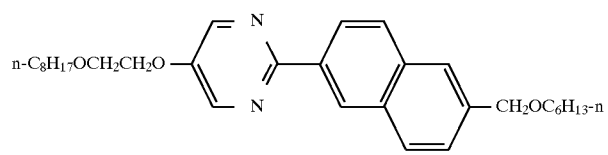
Exemplified compound 643
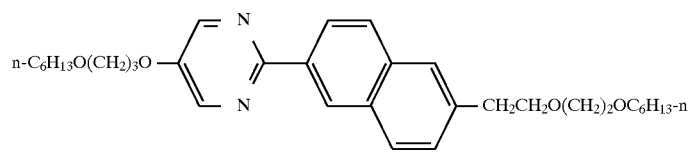
Exemplified compound 644
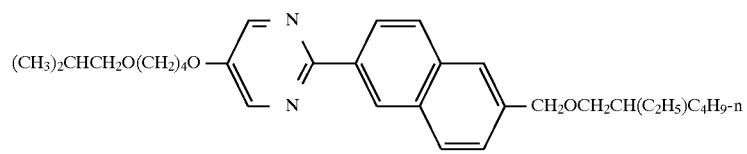
Exemplified compound 645
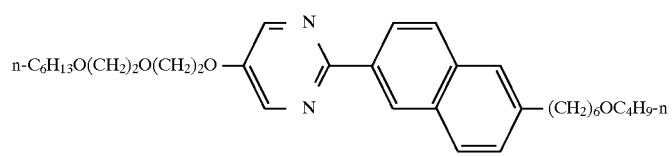
Exemplified compound 646

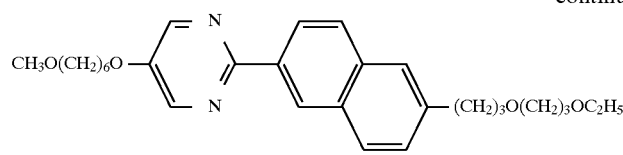
Exemplified compound 647
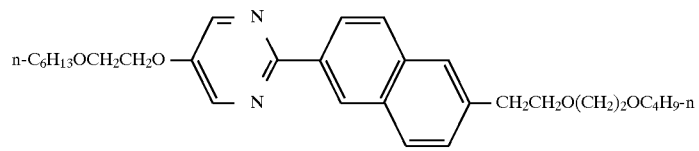
Exemplified compound 648
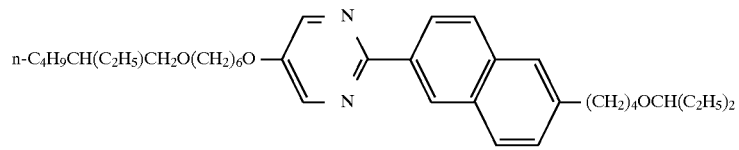
Exemplified compound 649
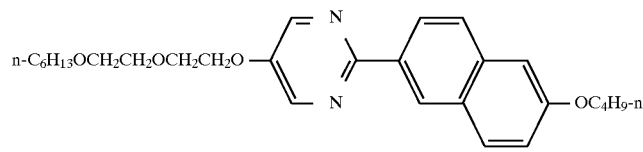
Exemplified compound 650
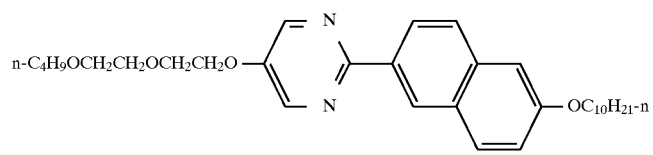
Exemplified compound 651
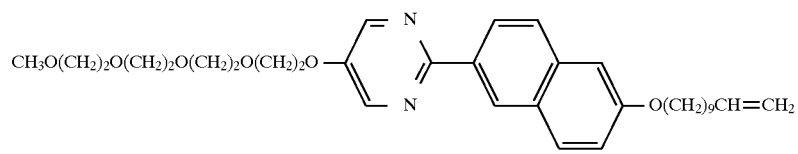
Exemplified compound 652
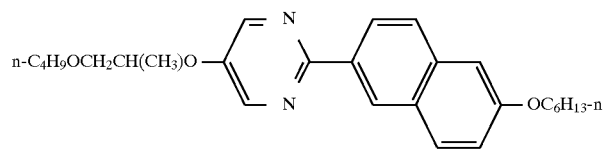
Exemplified compound 653
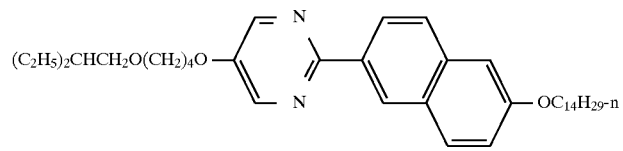
Exemplified compound 654
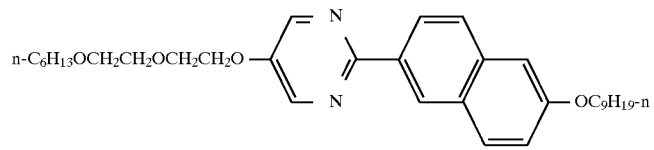
Exemplified compound 655
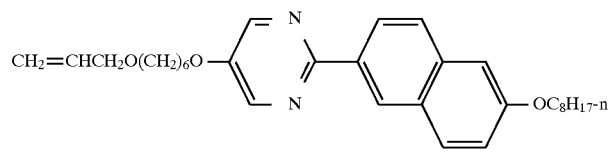
Exemplified compound 656

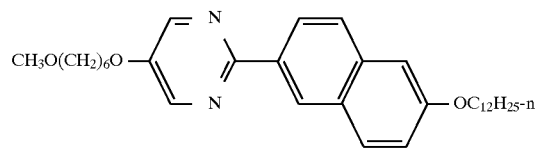
Exemplified compound 657
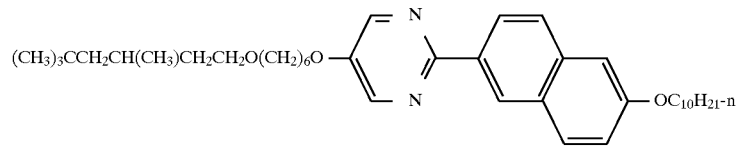
Exemplified compound 658
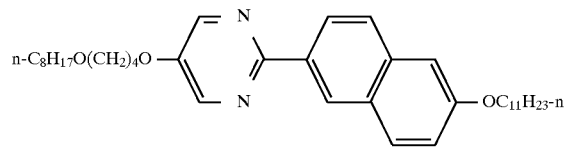
Exemplified compound 659
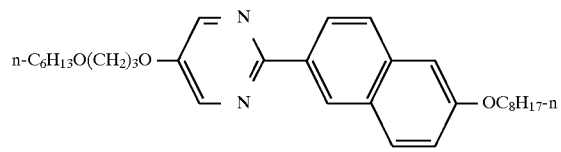
Exemplified compound 660
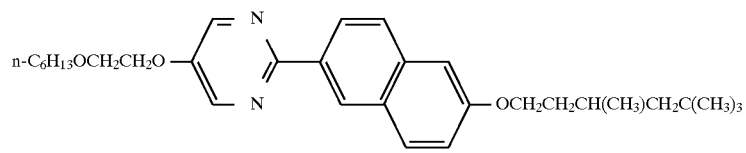
Exemplified compound 661
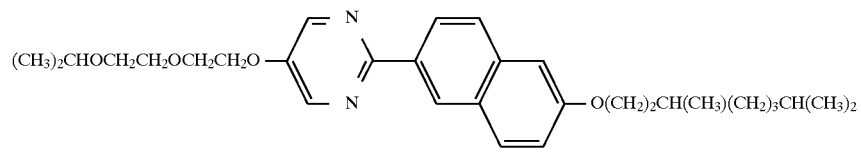
Exemplified compound 662
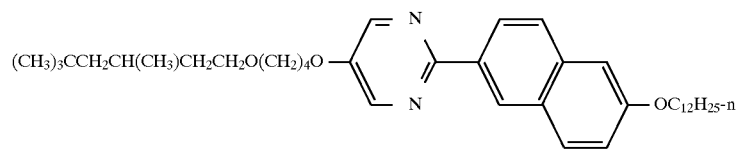
Exemplified compound 663
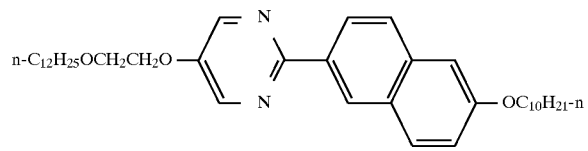
Exemplified compound 664
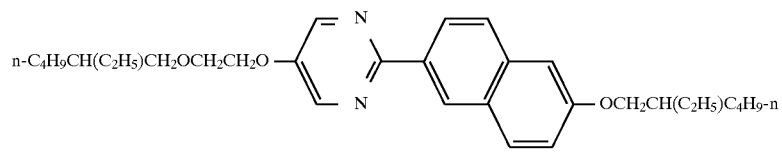
Exemplified compound 665
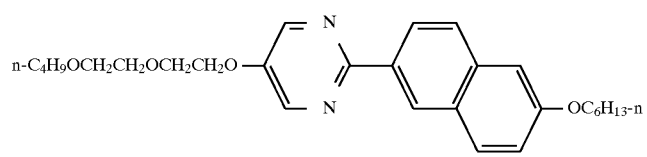
Exemplified compound 666

-continued
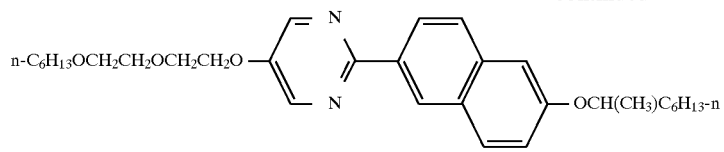
Exemplified compound 667
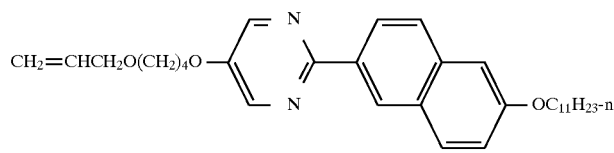
Exemplified compound 668
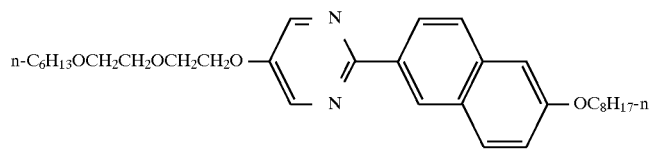
Exemplified compound 669
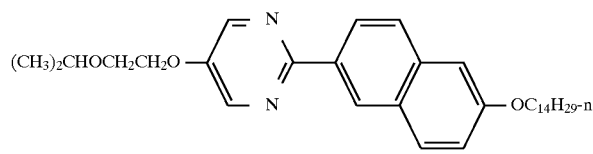
Exemplified compound 670
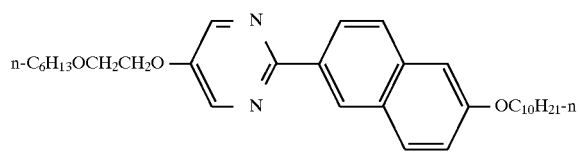
Exemplified compound 671
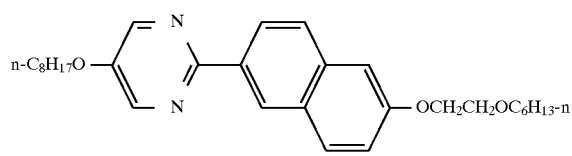
Exemplified compound 672
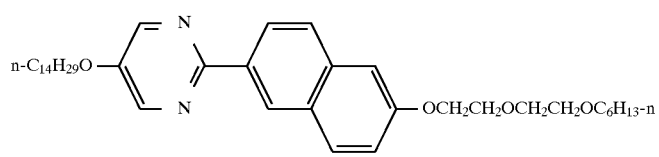
Exemplified compound 673
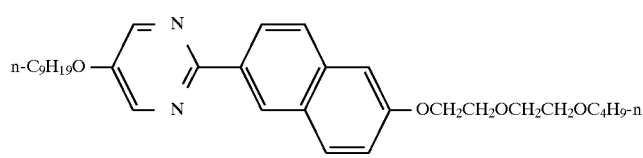
Exemplified compound 674
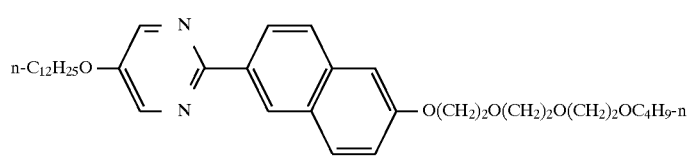
Exemplified compound 675
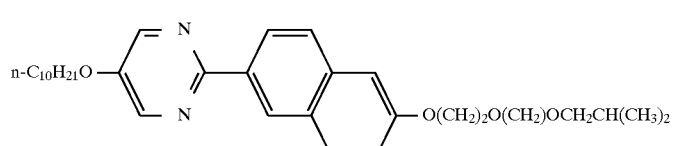
Exemplified compound 676

-continued
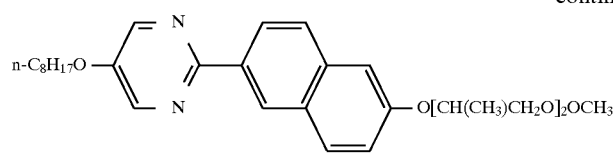
Exemplified compound 677
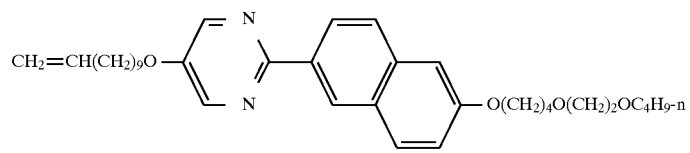
Exemplified compound 678
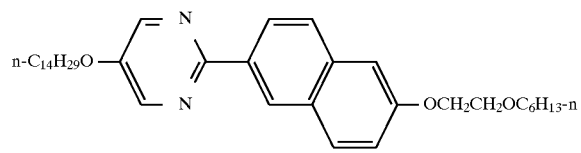
Exemplified compound 679
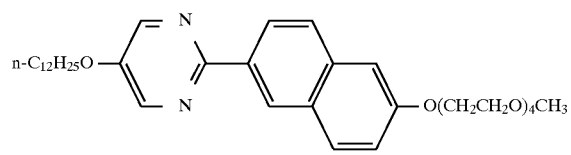
Exemplified compound 680
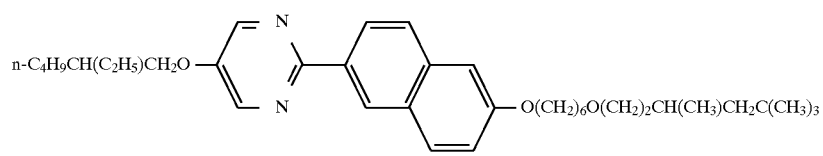
Exemplified compound 681
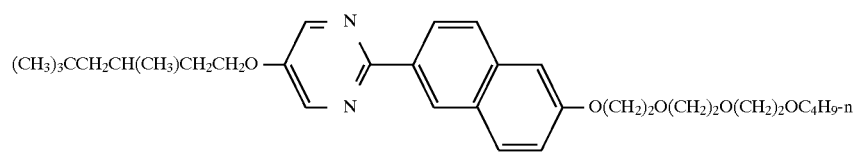
Exemplified compound 682
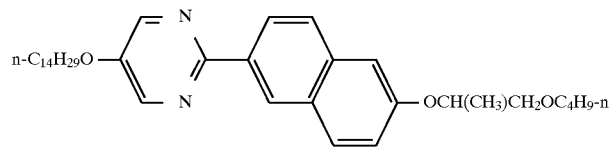
Exemplified compound 683
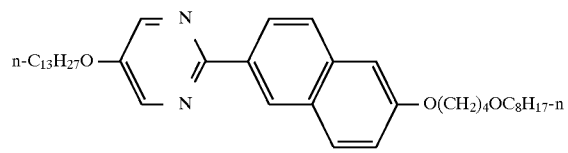
Exemplified compound 684
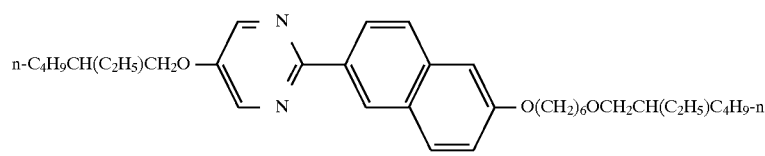
Exemplified compound 685
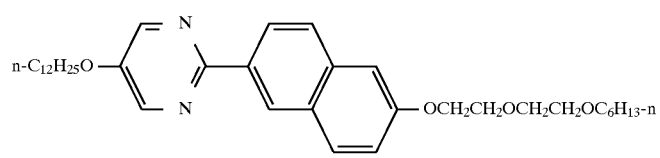
Exemplified compound 686

-continued
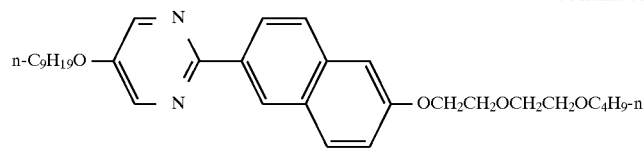
Exemplified compound 687
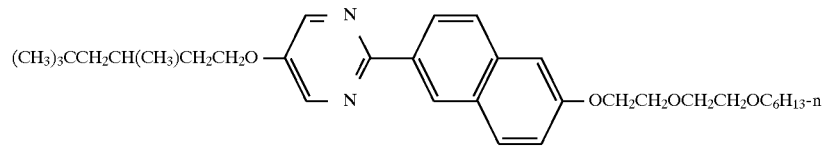
Exemplified compound 688
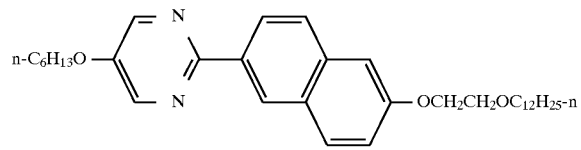
Exemplified compound 689
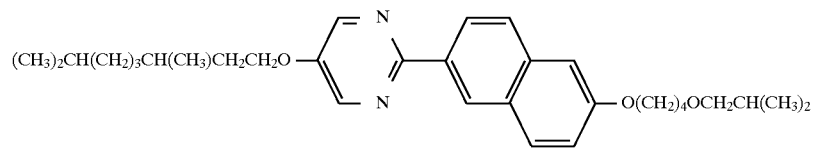
Exemplified compound 690
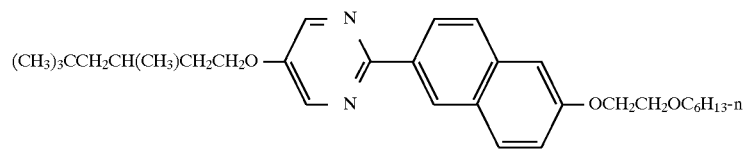
Exemplified compound 691
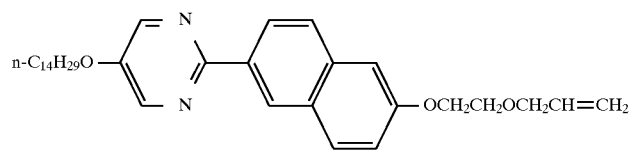
Exemplified compound 692
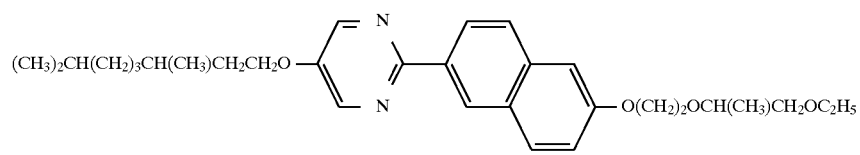
Exemplified compound 693
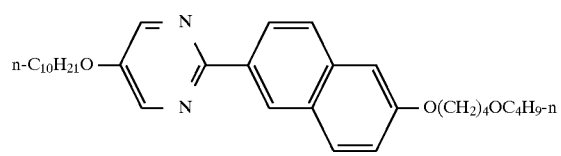
Exemplified compound 694
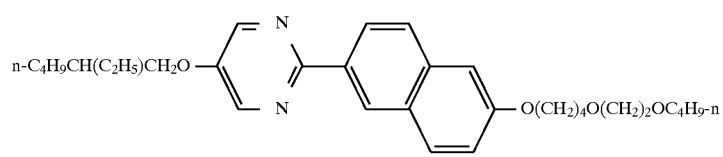
Exemplified compound 695
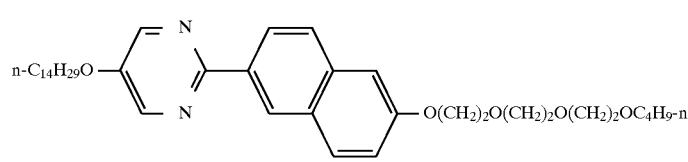
Exemplified compound 696

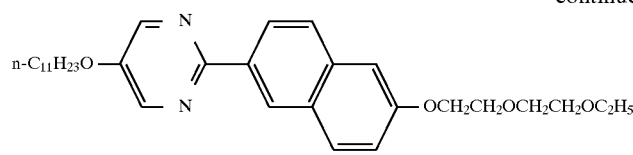
Exemplified compound 697
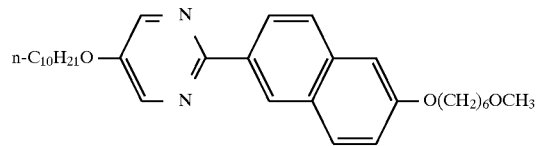
Exemplified compound 698
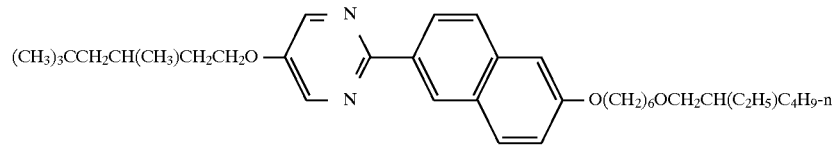
Exemplified compound 699
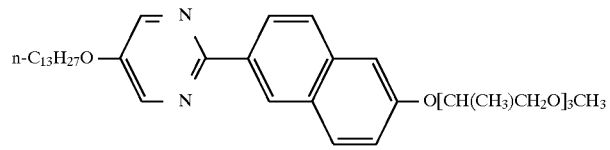
Exemplified compound 700
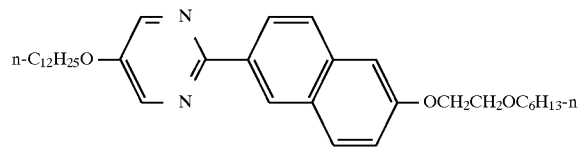
Exemplified compound 701
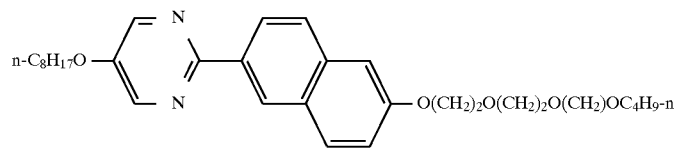
Exemplified compound 702
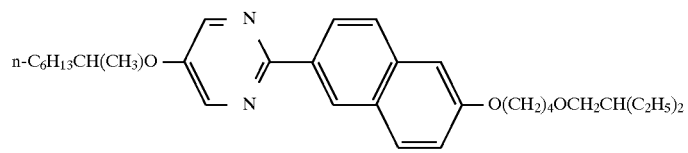
Exemplified compound 703
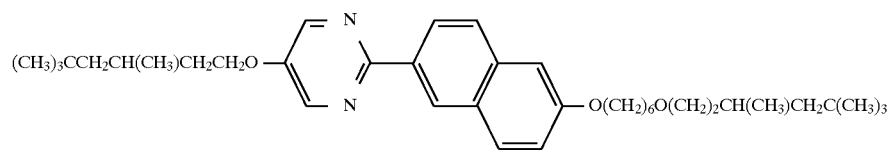
Exemplified compound 704
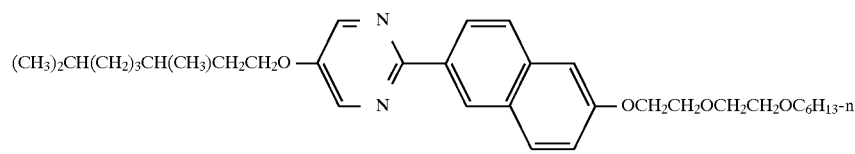
Exemplified compound 705
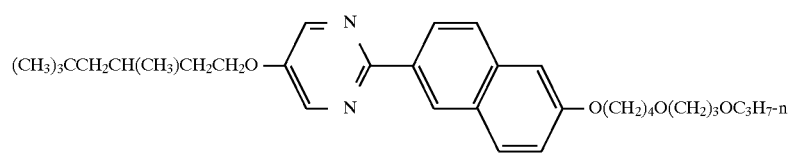
Exemplified compound 706

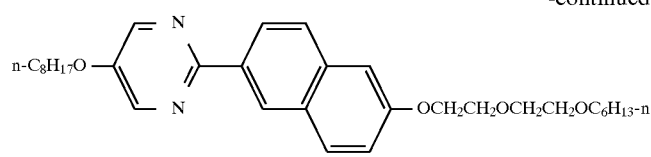
Exemplified compound 707
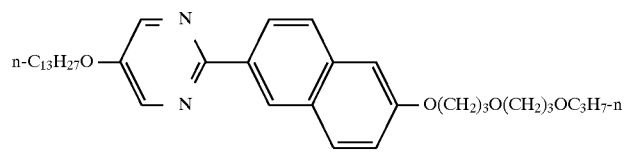
Exemplified compound 708
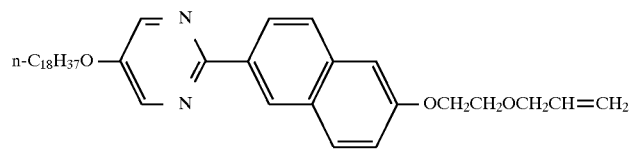
Exemplified compound 709
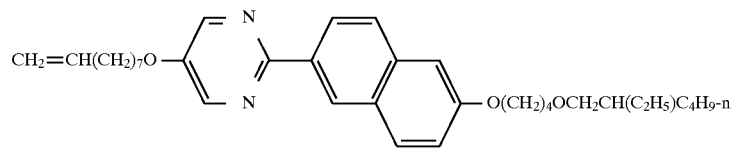
Exemplified compound 710
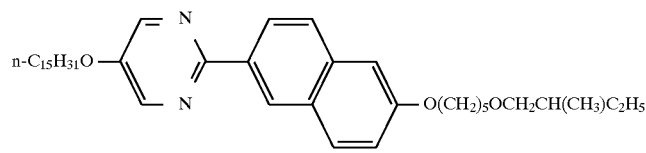
Exemplified compound 711
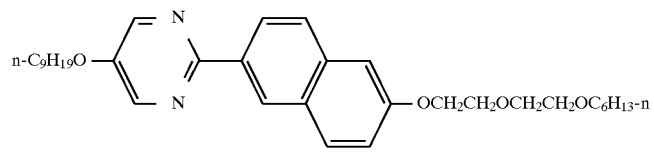
Exemplified compound 712
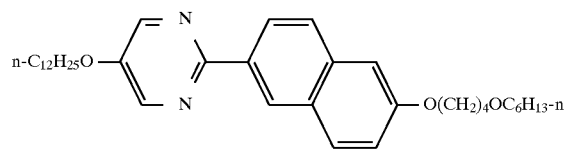
Exemplified compound 713
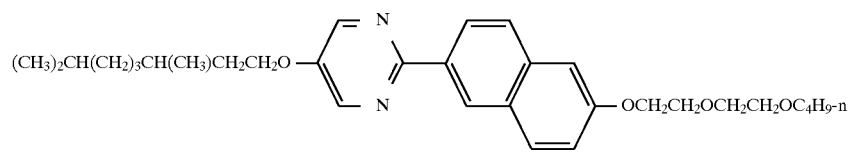
Exemplified compound 714
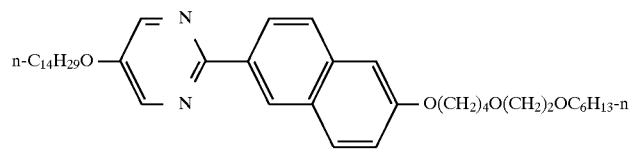
Exemplified compound 715
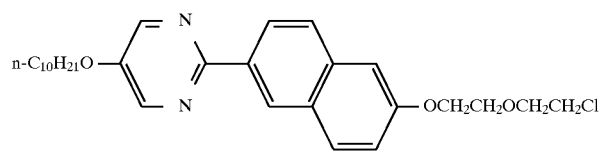
Exemplified compound 716

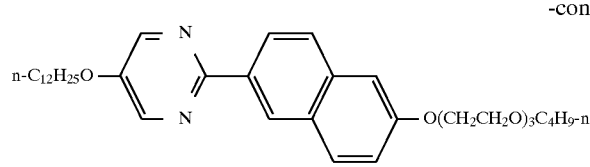
Exemplified compound 717
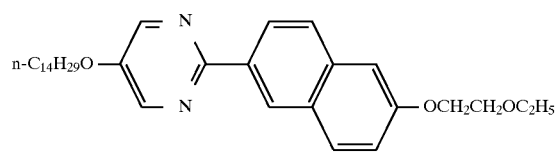
Exemplified compound 718
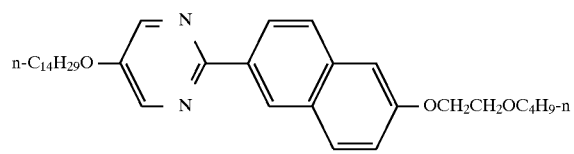
Exemplified compound 719
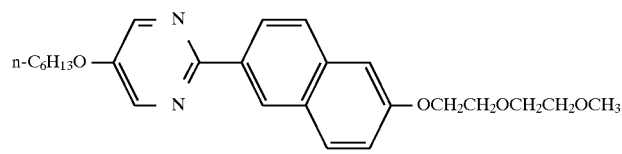
Exemplified compound 720
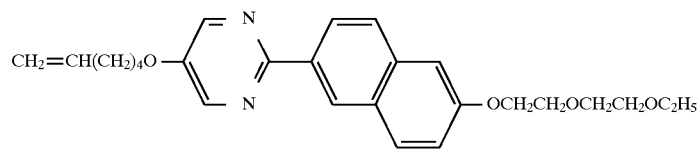
Exemplified compound 721
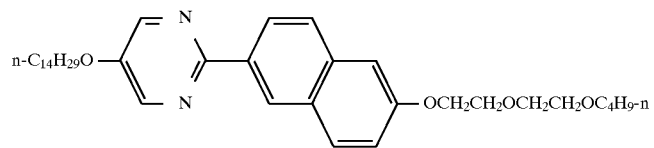
Exemplified compound 722
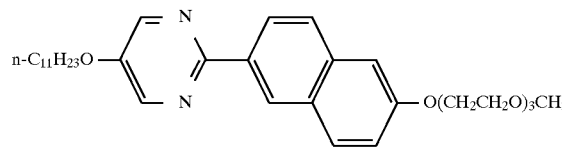
Exemplified compound 723
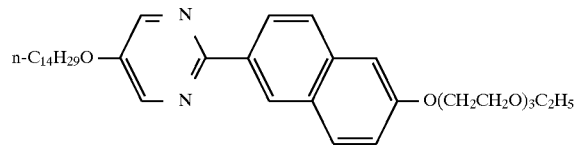
Exemplified compound 724
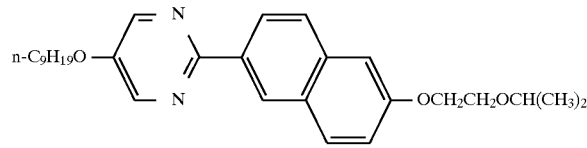
Exemplified compound 725
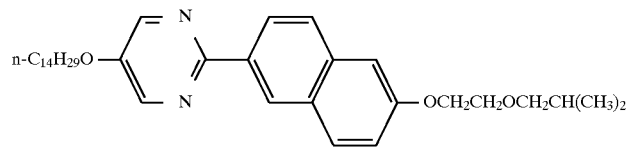
Exemplified compound 726

-continued
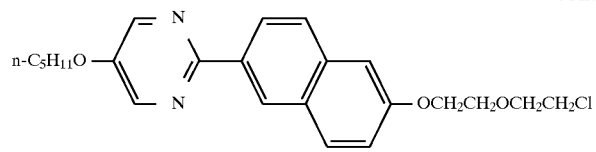
Exemplified compound 727
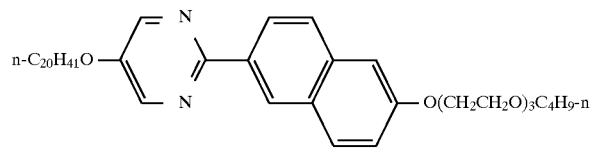
Exemplified compound 728
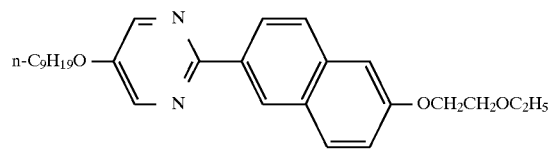
Exemplified compound 729
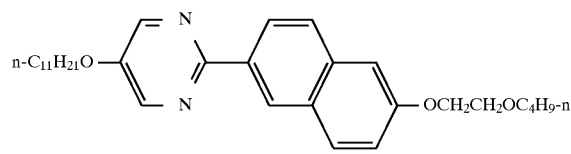
Exemplified compound 730
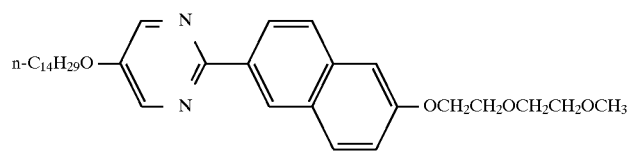
Exemplified compound 731
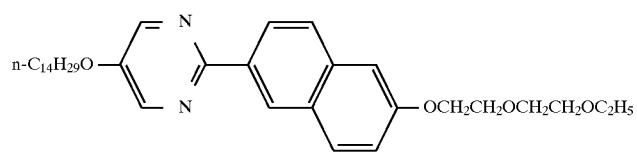
Exemplified compound 732
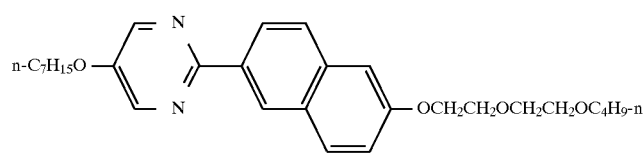
Exemplified compound 733
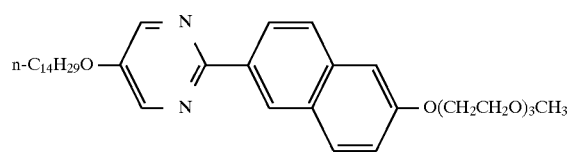
Exemplified compound 734
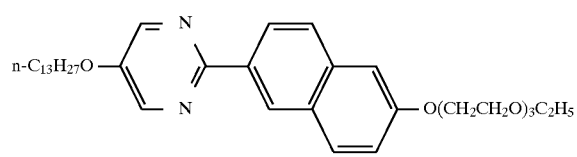
Exemplified compound 735
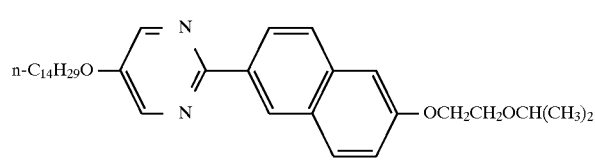
Exemplified compound 736

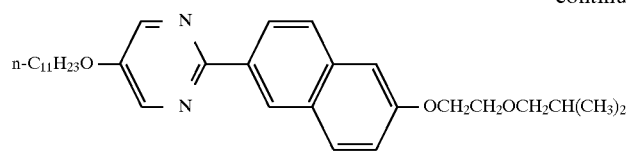
Exemplified compound 737
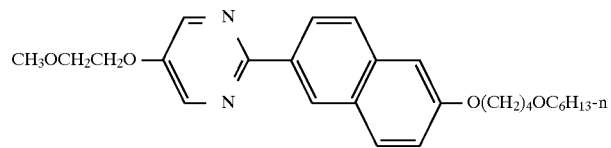
Exemplified compound 738
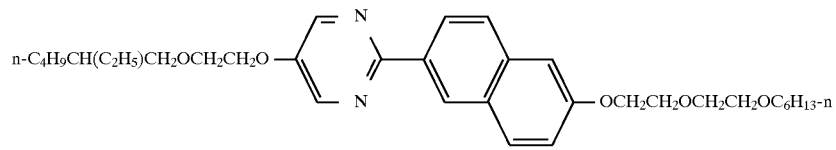
Exemplified compound 739
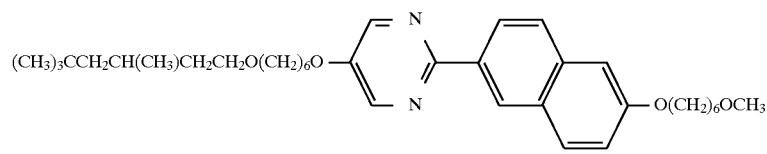
Exemplified compound 740
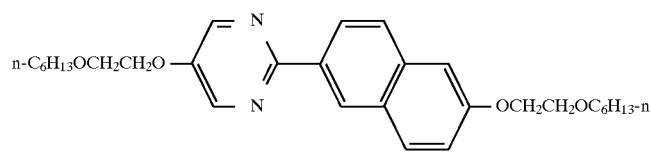
Exemplified compound 741
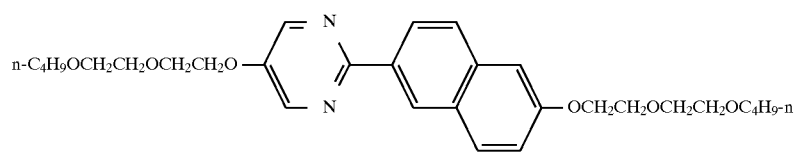
Exemplified compound 742
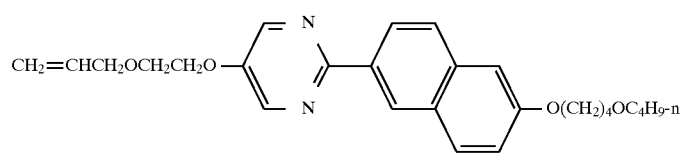
Exemplified compound 743
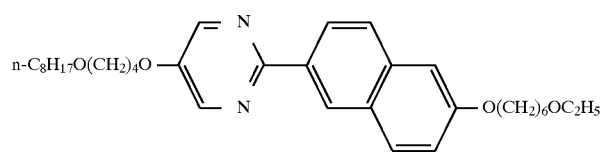
Exemplified compound 744
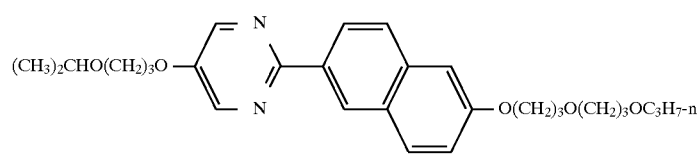
Exemplified compound 745
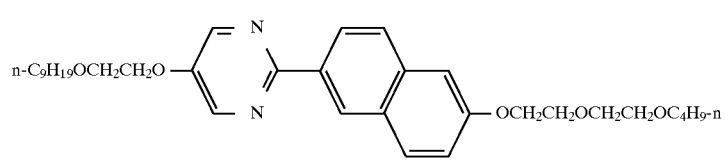
Exemplified compound 746

-continued

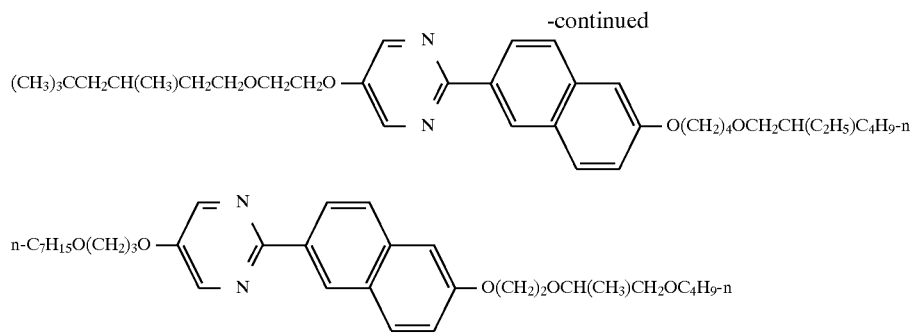

Exemplified compound 747

Exemplified compound 748

The compound represented by Formula (2) of the present invention can be produced through, for examples, the steps shown below.

Production steps of the pyrimidine compound represented by Formula (2):

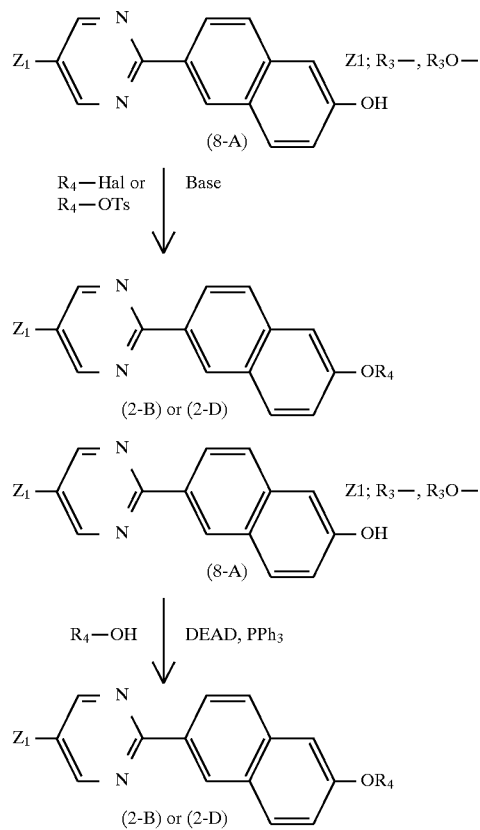

A compound in which $Z_2$ in Formula (8) is $R_4$ corresponds to the compound of Formula (2-A) or (2-C). A compound in which $Z_2$ in Formula (8) is —$OR_4$ corresponds to the compound of Formula (2-B) or (2-D). Further, the compound represented by Formula (2-B) or (2-D) can be produced by reacting the compound [Formula (8-A)] in which $Z_2$ in Formula (8) is an OH group with a reagent such as $R_4$—Hal or $R_4$—OTs (Hal represents a halogen atom, and Ts represents a tosyl group) in the presence of a base (for example, sodium hydroxide, potassium hydroxide, sodium carbonate and potassium carbonate). Further, the compound represented by Formula (2-B) or (2-D) can be produced as well by reacting the compound represented by Formula (8-A) with alcohol represented by $R_4$—OH in the presence of triphenylphosphine and DEAD.

Next, the compound represented by Formula (3) or (4) will be explained.

The compound represented by Formula (3) or (4) of the present invention is a compound which can be used as an intermediate for the pyrimidine compound represented by Formula (1) or (2) of the present invention.

The pyrimidine compounds of the present invention include compounds inherently showing liquid crystallinity and compounds showing no liquid crystallinity. Further, the compounds showing liquid crystallinity include compounds showing smectic C (hereinafter abbreviated as an Sc phase) or chiral smectic C (hereinafter abbreviated as a Sc* phase) and compounds showing liquid crystallinity but no Sc phase or Sc* phase. These compounds each can effectively be used as components for liquid crystal compositions.

Next, the liquid crystal composition of the present invention will be explained.

In general, a liquid crystal composition comprises two or more kinds of components. The liquid crystal composition of the present invention contains at least one pyrimidine compound of the present invention as an essential component.

The pyrimidine compound of the present invention used for the liquid crystal composition of the present invention includes a pyrimidine compound showing no liquid crystallinity, a compound showing an Sc phase, a compound showing an Sc* phase and a compound showing liquid crystallinity but no Sc phase or Sc* phase.

The liquid crystal composition of the present invention includes preferably liquid crystal compositions showing chiral smectic C, F, G, H and I phases, more preferably a liquid crystal composition showing an Sc* phase.

The liquid crystal composition of the present invention showing an Sc* phase is a composition prepared by combining the pyrimidine compound of the present invention with a plurality of compounds selected from liquid crystal compounds showing an Sc* phase other than the pyrimidine compound of the present invention, liquid crystal compounds showing an Sc phase other than the pyrimidine compound of the present invention and optically active compounds, and contains at least one pyrimidine compound of the present invention.

The liquid crystal compounds showing an Sc* phase other than the pyrimidine compound of the present invention are not specifically restricted and include, for example, optically active phenyl benzoate series liquid crystal compounds, optically active biphenyl benzoate series liquid crystal compounds, optically active naphthalene series liquid crystal compounds, optically active phenylnaphthalene series liquid crystal compounds, optically active tolan series liquid crystal compounds and optically active phenylpyrimidine series liquid crystal compounds.

The liquid crystal compounds showing an Sc phase other than the pyrimidine compound of the present invention are not specifically restricted and include, for example, phenyl benzoate series liquid crystal compounds, biphenyl benzoate series liquid crystal compounds, naphthalene series liquid crystal compounds, phenylnaphthalene series liquid crystal compounds, tolan series liquid crystal compounds and phenylpyrimidine series liquid crystal compounds.

An optically active compound means a compound showing inherently no liquid crystallinity but having ability to reveal an Sc* phase by blending with a liquid crystal compound or liquid crystal composition showing an Sc phase. The optically active compounds are not specifically restricted and include, for example, optically active phenyl benzoate series non-liquid crystal compounds, optically active biphenyl benzoate series non-liquid crystal compounds, optically active naphthalene series non-liquid crystal compounds, optically active phenylnaphthalene series non-liquid crystal compounds, optically active phenylpyrimidine series non-liquid crystal compounds and optically active tolan series non-liquid crystal compounds.

Further, in addition to the essential components described above, the liquid crystal composition of the present invention may contain, as optional components, smectic and nematic liquid crystal compounds showing no Sc phase, and compounds showing no liquid crystallinity other than the pyrimidine compound of the present invention (for example, dichromatic pigments such as anthraquinone pigments and azo pigments, electroconductivity-providing agents and life improving agents).

The content of the pyrimidine compound of the present invention contained in the liquid crystal composition of the present invention is not specifically restricted and is usually 5 to 99 weight %, preferably 10 to 90 weight %.

In the liquid crystal composition of the present invention, liquid crystal compositions showing chiral smectic C, F, G, H and I phases show ferroelectricity.

The liquid crystal compositions showing ferroelectricity cause a switching phenomenon by applying voltage, and liquid crystal elements having shorter response time can be prepared by making use of the phenomenon [for example, Japanese Patent Application Laid-Open No. 56-107216 (1981), Japanese Patent Application Laid-Open No. 59-118744 (1984) and Applied Physics Letter, 36 899 (1980)].

The liquid crystal composition containing at least one pyrimidine compound of the present invention is more excellent than conventional liquid crystal compositions in terms of response time, memory stability, layer structure in an Sc phase, tilt angle, orientation characteristics on a oriented film, and compatibility between liquid crystal compounds.

Next, the liquid crystal element of the present invention will be explained.

The liquid crystal element of the present invention comprises the liquid crystal composition of the present invention disposed between a pair of electrode substrates. FIG. 1 is a schematic cross-sectional drawing showing one example of a liquid crystal element having a chiral smectic phase for explaining the structure of a liquid crystal element making use of ferroelectricity.

The liquid crystal element comprises a pair of substrates 2 each of which are provided thereon with transparent electrodes 3 and insulating orientation-controlling layers 4, and a liquid crystal layer 1 showing a chiral smectic phase disposed between the substrates, wherein a space between the substrates is controlled by spacers 5, and a power source 7 is connected to a pair of the transparent electrodes 3 via lead wires 6 so that voltage can be applied between the transparent electrodes 3. Further, a pair of the substrates 2 are interposed between a pair of polarizing plates 8 disposed in a cross-nicol state, and a light source 9 is arranged on one outside thereof.

The materials for the substrate 2 include glasses such as soda lime glass and boron silicate glass, and transparent polymers such as polycarbonate, polyether sulfone and polyacrylate.

The transparent electrodes 3 disposed on two sheets of the substrates 2 include, for example, transparent electrodes comprising thin films of $In_2O_3$, $SnO_2$ and ITO (indium tin oxide).

The insulating orientation-controlling layers 4, which are prepared by rubbing a thin film of a polymer such as polyimide with gauze or acetate cloth, are for orienting liquid crystal. The materials for the insulating orientation-controlling layer 4 include, for example, inorganic materials such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide and magnesium fluoride, and organic materials such as polyvinyl alcohol, polyimide, polyamideimide, polyesterimide, polyetherimide, polyether ketone, polyether ether ketone, polyether sulfone, polyparaxylene, polyester, polycarbonate, polyvinylacetal, polyvinyl chloride, polyvinyl acetate, polyamide, polystyrene, cellulose resins, melamine resins, urea resins and acrylic resins. The insulating orientation-controlling layer 4 may be of a dual layer structure in which an organic insulating layer is formed on an inorganic insulating layer, or a structure comprising only the inorganic insulating layer or the organic insulating layer.

When the insulating orientation-controlling layer comprises an inorganic insulating layer, it can be formed by deposition. When it comprises an organic insulating layer, it can be formed by applying a precursor solution thereof by spinner coating, dip coating, screen printing, spray coating or roll coating, and then curing a resulting film on prescribed curing conditions (for example, heating). The insulating orientation-controlling layer 4 has usually a layer thickness of 1 nm to 1 $\mu$m, preferably 1 to 300 nm, more preferably 1 to 100 nm.

Two sheets of the substrates 2 are maintained at an optional space with the spacer 5. The substrates can be maintained at an optional space by interposing, for example, silica beads or alumina beads each having a prescribed diameter as the spacers between the substrates 2 and sealing the circumference of two sheets of the substrates 2 with a sealant (for example, epoxy adhesives). Further, polymer films and glass fibers may be used as the spacers. Liquid crystal showing a chiral smectic phase is charged between two sheets of the substrates. The liquid crystal layer 1 is controlled usually to a thickness of 0.5 to 20 $\mu$m, preferably 1 to 5 $\mu$m.

The transparent electrodes 3 are connected to the external power source 7 via lead wires.

Further, a pair of the polarizing plates 8 are disposed on the outsides of the substrates 2, wherein the respective polarizing axes are controlled in a cross-nicol state. An example shown in FIG. 1 is a transmitting type and has a light source 9.

The liquid crystal element using the liquid crystal composition of the present invention is applicable not only as an element of the transmitting type shown in FIG. 1 but also as an element of a reflecting type.

A display system of the liquid crystal element using the liquid crystal composition of the present invention is not specifically restricted, and there can be used, for example, display systems of (a) helical distortion type, (b) SSFLC (surface stabilized ferroelectric liquid crystal) type, (c) TSM (transient scattering mode) type, and (d) G-H (guest-host) type.

The pyrimidine compound of the present invention and the liquid crystal composition containing said compound are applicable to fields other than liquid crystal elements for display (for example, (1) non-linear photofunction element, (2) electronics materials such as a condenser material, (3) electronics elements such as limiter, memory, amplifier and modulator, (4) voltage sensing elements and sensors for heat, light, pressure and mechanical deformation, and (5) power generating elements such as thermoelectric generating element).

EXAMPLES

The present invention shall be explained in further detail with reference to examples but the present invention shall not be restricted to the following examples.

Signals I, N, N*, SA, Sc, Sc*, Sx and C shown in the respective examples and tables means the following:

I: isotropic liquid
N: nematic phase
N*: cholesteric phase
SA: smectic A phase
Sc: smectic C phase
Sc*: chiral smectic C phase
Sx: unidentified smectic phase
C: crystal phase In Table 4, the mark "•" means the presence of the liquid crystal phase, and the mark "-" means the absence of the liquid crystal phase. Numerals in parentheses in Table 4 mean temperatures in a descendent temperature step.

Production Example 1: production of 6-amidino-2-hydroxynaphthalene hydrochloride 6-Cyano-2-naphthol of 202.8 g (1.2 mole) was dissolved in anhydrous ethanol of 1500 ml and cooled down to 5° C. or lower on an ice bath. Hydrogen chloride of 438 g was blown at 15° C. or lower while stirring, and then stirring was continued for 2 hours on the ice bath. Stirring was further continued for 4 hours at room temperature, and then the solution was left for standing for 15 hours. Thereafter, ethanol was removed to obtain a yellow solid.

This solid was suspended in anhydrous ethanol of 500 ml. Anhydrous ethanol of 1300 ml in which ammonia was saturated was dropwise added to this suspension while cooling on ice, and stirring was continued at the same temperature as above for one hour. After further stirring at room temperature for 2 hours, the solution was left for standing for 15 hours. Ethanol was removed, and the resulting solid was washed with ether, whereby 6-amidino-2-hydroxynaphthalene hydrochloride of a brown solid of 262.3 g was obtained.

Production Example 2: production of 6-amidino-2-benzyloxynaphthalene hydrochloride The same procedure as described in Production Example 1 was repeated, except that 6-cyano-2-benzyloxynaphthalene was substituted for 6-cyano-2-naphthol in Production Example 1, whereby 6-amidino-2-benzyloxynaphthalene hydrochloride of 371.3 g was obtained.

Production Example 3: production of 6-(5'-substituted-2'-pyrimidyl)-2-hydroxynaphthalene (1) Production of 2-alkoxyacetaldehyde diethyl acetal:

Sodium hydride (60 weight %) of 12.7 g was suspended in toluene, and alcohol of 0.3 mole shown in Table 1 was added thereto. Then, the suspension was heated up to 100° C. and stirred until hydrogen stopped generating, thereby preparing sodium alkoxide. A solution prepared by dissolving 2-bromoacetaldehyde diethyl acetal of 60.9 g (0.309 mole) in N,N-dimethylacetamide of 68 g was dropwise added thereto. After heating at 80° C. for 20 hours, the solvent was distilled off, and the residue was extracted with toluene, followed by washing the extract with water. Then, 2-alkoxyacetaldehyde diethyl acetal was obtained by distillation under reduced pressure. The yield and the boiling point are shown in Table 1.

TABLE 1

| Alcohol | Product | Yield (%) | Boiling point |
|---|---|---|---|
| $CH_3(CH_2)_9$—OH | $CH_3(CH_2)_9$—$OCH_2CH(OC_2H_5)_2$ | 75 | 128° C./3 mmHg |
| $CH_3(CH_2)_{13}$—OH | $CH_3(CH_2)_{13}$—$OCH_2CH(OC_2H_5)_2$ | 52 | 157° C./3.5 mmHg |
| $(CH_3)_3CCH_2CH(CH_3)CH_2CH_2$—OH | $(CH_3)_3CCH_2CH(CH_3)CH_2CH_2$—$OCH_2CH(OC_2H_5)_2$ | 70 | 99–100° C./4.5 mmHg |
| $CH_3(CH_2)_7$—OH | $CH_3(CH_2)_7$—$OCH_2CH(OC_2H_5)_2$ | 67 | 115° C./4 mmHg |
| $CH_3(CH_2)_{11}$—OH | $CH_3(CH_2)_{11}$—$OCH_2CH(OC_2H_5)_2$ | 68 | 148° C./2.5 mmHg |
| $C_6H_5$—$CH_2$—OH | $C_6H_5$—$CH_2$—$OCH_2CH(OC_2H_5)_2$ | 72 | 111–112° C./3 mmHg |

(2) Production of alkanal diethyl acetal:

A Grignard reagent was prepared from alkyl bromide of 0.275 mole shown in Table 2 and metal magnesium of 6.68 g in tetrahydrofuran of 250 ml. A solution prepared by dissolving triethyl orthoformate of 44.45 g (0.3 mole) in tetrahydrofuran of 50 ml was added thereto, and the solution was heated and refluxed for 40 hours. Then, tetrahydrofuran was distilled off, and ethyl acetate and an ammonium chloride aqueous solution were added to the residue to extract. An organic layer was separated and washed with water, and then alkanal diethyl acetal was obtained by distillation under reduced pressure. The yield and the boiling point are shown in Table 2.

TABLE 2

| Alkylbromide | Product | Yield (%) | Boiling point |
|---|---|---|---|
| $CH_3(CH_2)_8$—Br | $CH_3(CH_2)_8$—$CH(OC_2H_5)_2$ | 62 | 115–117° C./5 mmHg |
| $CH_3(CH_2)_{10}$—Br | $CH_3(CH_2)_{10}$—$CH(OC_2H_5)_2$ | 67 | 126–128° C./4 mmHg |
| $CH_3(CH_2)_{12}$—Br | $CH_3(CH_2)_{12}$—$CH(OC_2H_5)_2$ | 56 | 146° C./5 mmHg |
| $(CH_3)_3CCH_2CH(CH_3)CH_2CH_2$—Br | $(CH_3)_3CCH_2CH(CH_3)CH_2CH_2$—$CH(CC_2H_5)_2$ | 60 | 86° C./5 mmHg |

(3) Production of 6-(5'-substituted-2'-pyrimidyl)-2'-hydroxynaphthalene:

A mixed solution of N,N-dimethylformamide of 50.0 g and dichloroethane of 100 ml was cooled on ice, and a solution of phosphorus oxychloride 60.4 g and dichloroethane of 40 ml was dropwise added thereto. A solution of diethyl acetal of 0.2 mole shown in Table 1 and 2 and dichloroethane of 40 ml was dropwise added to this solution, and after finishing adding, the reaction was continued at 60° C. for 3 hours. After finishing the reaction, a saturated aqueous solution of potassium carbonate was added, and the mixed solution was subjected to extraction with toluene. Then, toluene was distilled off to obtain an α-substituted-β-dimethylaminoacrolein derivative.

Next, the α-substituted-β-dimethylaminoacrolein derivative and 6-amidino-2-hydroxynaphthalene hydrochloride of 44.3 g (0.2 mole) obtained in Production Example 1 were suspended in anhydrous ethanol of 200 ml, and sodium methoxide (28 weight %) methanol solution of 115.8 g was dropwise added thereto. After heating and refluxing for 10 hours, ethanol was distilled off, and the residue was subjected to extraction with ethyl acetate, followed by neutralizing the extract with hydrochloric acid and then washing with water. Ethyl acetate was distilled off to obtain 6-(5'-substituted-2'-pyrimidyl)-2-hydroxynaphthalene as shown in Table 3. The yield and the melting point are shown in Table 3.

TABLE 3

| Product | Yield (%) | Melting point (°C.) |
|---|---|---|
| n-$C_8H_{17}$O—[pyrimidyl-naphthyl-OH] | 67 | 95 |
| n-$C_{10}H_{21}$O—[pyrimidyl-naphthyl-OH] | 68 | 102–103 |
| n-$C_{12}H_{25}$O—[pyrimidyl-naphthyl-OH] | 72 | 77 |
| n-$C_{14}H_{29}$O—[pyrimidyl-naphthyl-OH] | 66 | 88 |
| n-$C_8H_{17}$—[pyrimidyl-naphthyl-OH] | 73 | 98 |
| n-$C_{10}H_{21}$—[pyrimidyl-naphthyl-OH] | 69 | 95 |

TABLE 3-continued

| Product | Yield (%) | Melting point (°C.) |
|---|---|---|
| 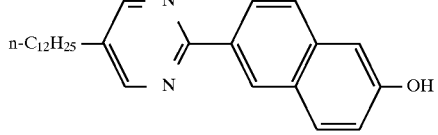 | 72 | 84–85 |
| 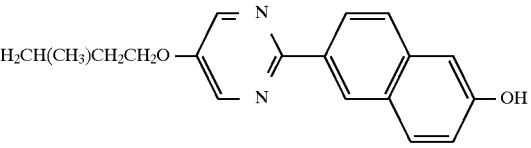 | 68 | 94 |
| 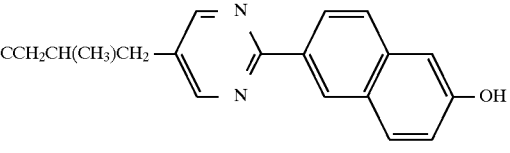 | 69 | 164 |
| 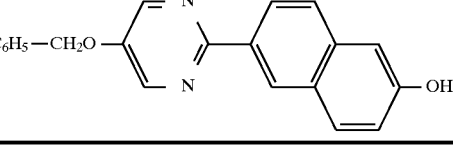 | 71 | 170–172 |

Production Example 4: production of 6-[5'-(4"-n-octyloxyphenyl)-2-pyrimidyl]-2-hydroxynaphthalene (1) Production of α-(4-n-octyloxyphenyl)-β-ethoxyacrolein:

Methoxymethyl triphenylphosphonium chloride of 34.28 g was suspended in anhydrous ether of 190 ml, and potassium t-butoxide of 11.22 g was added thereto. A solution prepared by dissolving 4-n-octyloxybenzaldehyde of 22.26 g in anhydrous ether of 110 ml was added thereto, and the solution was stirred at room temperature for 12 hours. Resulting triphenylphosphine oxide was removed by filtration, and the filtrate was poured into ice and water of 300 ml. An ether layer was separated and washed with water, followed by drying the ether layer with anhydrous sodium sulfate. Then, ether was distilled off to obtain crude (4'-n-octyloxyphenyl)-2-methoxyethylene. Further, the crude product was refined by distillation under reduced pressure to obtain (4'-n-octyloxyphenyl)-2-methoxyethylene of 25.4 g. Next, a mixed solution of triethyl orthoformate of 240 g and boron trifluoride ethyl ether complex salt of 6.53 g was cooled down to 0°C., and (4'-n-octyloxyphenyl)-2-methoxyethylene of 25.39 g was added thereto. Then, after stirring the solution at room temperature for 12 hours, toluene of 200 ml and a 10 weight % sodium hydrogencarbonate aqueous solution of 150 ml were added and mixed, and then a toluene layer was separated. The toluene layer was dried with anhydrous sodium sulfate, and then toluene was distilled off to obtain 4-n-octyloxyphenyl malonotetraethyl acetal. This 4-n-octyloxyphenyl malonotetraethyl acetal of 21.2 g was added to water of 12 ml and p-tolenesulfonic acid of 0.05 g, and the reaction was carried out at 80° C. for 3 hours. After cooling the solution down to room temperature, sodium carbonate of 0.52 g was added for neutralization, and then the product was extracted with toluene. The extract was washed with a 10 weight % sodium hydroxide aqueous solution and further washed with water. Then, a toluene layer was separated and dried with anhydrous sodium sulfate, and toluene was distilled off to obtain α-(4-n-octyloxyphenyl)-β-ethoxyacrolein of 16.62 g.

(2) Production of 6-[5'-( 4"-n-octyloxyphenyl)-2'-pyrimidyl]-2-hydroxynaphthalene:

Suspended in anhydrous ethanol of 113 ml were α-(4-n-octyloxyphenyl)-p-ethoxyacrolein of 14.57 g and 6-amidino-2-hydroxynaphthalene hydrochloride of 9.06 g obtained in Production Example 1, and sodium methoxide (28 weight %) methanol solution of 40.51 g was dropwise added thereto. The solution was heated to 60° C. and stirred for 10 hours. Then, ethanol was distilled off, and the remaining solution was neutralized with hydrochloric acid and subjected to extraction with ethyl acetate. Then, ethyl acetate was distilled off to obtain 6-[5'-(4"-n-octyloxyphenyl)-2'-pyrimidyl]-2-hydroxynaphthalene of 12.25 g (melting point: 148° C.).

Production Example 5: production of 6-(5'-n-decyloxycarbonyl-2'-pyrimidyl)-2-hydroxynaphthalene (1) Production of 6-(5-ethoxycarbonyl-2-pyrimidyl)2-benzyloxynaphthalene:

A mixed solution of N,N-dimethylformamide of 30.7 g and dichloroethane of 35 ml was cooled on ice, and a solution of phosphorus oxychloride 36.8 g and dichloroethane of 15 ml was dropwise added thereto. A solution of ethyl 3,3-diethoxypropionate of 19.0 g (0.1 mole) and dichloroethane of 15 ml was dropwise added to this solution, and after finishing adding, the reaction was continued at 70° C. for one hour. After finishing the reaction, a saturated aqueous solution of potassium carbonate was added, and the mixed solution was subjected to extraction with toluene. Then toluene was distilled off to obtain crude α-ethoxycarbonyl-β-dimethylaminoacrolein.

Next, 6-amidino-2-benzyloxynaphthalene hydrochloride of 31.2 g (0.1 mole) obtained in Production Example 2 and sodium ethoxide of 20.5 g were suspended in anhydrous ethanol of 100 ml, and a solution of α-ethoxycarbonyl-β-dimethylaminoacrolein and anhydrous ethanol of 20 ml was dropwise added thereto. After heating and refluxing for 10 hours, the solution was cooled down to room temperature and poured into 500 ml of an aqueous solution containing conc. hydrochloric acid of 25 ml. The resulting solid was filtrated to obtain 6-(5'-ethoxycarbonyl-2'-pyrimidyl)-2-benzyloxynaphthalene of 28.7 g (melting point: 181° C.).

(2) Production of 6-(5'-hydroxycarbonyl-2'-pyrimidyl)-2-benzyloxynaphthalene:

Suspended in 75 weight % hydrous ethanol were 6-(5'-ethoxycarbonyl-2'-pyrimidyl)-2-benzyloxynaphthalene of 28.7 g and sodium hydroxide of 3.2 g, and the reaction was carried out at 80° C. for 20 hours. Then, the solution was acidified with hydrochloric acid, and the resulting solid was filtered off and washed with toluene to obtain 6-(5'-hydroxycarbonyl-2'-pyrimidyl)-2-benzyloxynaphthalene of 23.9 g (melting point: 250° C. or higher).

(3) Production of 6-(5'-n-decyloxycarbonyl-2'-pyrimidyl)-2-benzyloxynaphthalene:

A suspension of 6-(5'-hydroxycarbonyl-2'-pyrimidyl)-2-benzyloxynaphthalene of 9.3 g, oxalyl chloride of 3.0 g and toluene of 50 ml was stirred at 60° C. for 5 hours. Then, toluene and excess oxalyl chloride were distilled off, and n-decyl alcohol of 4.2 g and toluene of 50 ml were added to the residue. Triethylamine of 5.05 g was dropwise added thereto while cooling on ice, and then the reaction was further continued at room temperature for 10 hours. After finishing the reaction, the reaction solution was neutralized with a hydrochloric acid aqueous solution, and an organic layer was separated and washed with water. Then, toluene was distilled off, and the residue was refined with silica gel column chromatography (eluent: chloroform), whereby 6-(5'-n-decyloxycarbonyl-2'-pyrimidyl)-2-benzyloxynaphthalene of 9.06 g was obtained (melting point: 144° C.).

(4) Production of 6-(5'-n-decyloxycarbonyl-2'-pyrimidyl)-2-hydroxynaphthalene:

Dissolved in ethyl acetate of 100 ml was 6-(5'-n-decyloxycarbonyl-2'-pyrimidyl)-2-benzyloxynaphthalene of 9.06 g, and 50 weight % hydrous Pd/C of 0.9 g was added thereto. The suspension was stirred for 20 hours under a hydrogen atmosphere, and then Pd/C was removed by filtration. Ethyl acetate was distilled off from the filtrate to obtain 6-(5'-n-decyloxycarbonyl-2'-pyrimidyl)-2-hydroxynaphthalene of 7.3 g (melting point: 123° C.).

Production Example 6: production of 6-(5'-benzyloxy-2'-pyrimidyl)-2-n-octyloxynaphthalene Suspended in N,N-dimethylformamide of 10 ml were 6-(5'-benzyloxy-2'-pyrimidyl)-2-hydroxynaphthalene of 3.28 g (10 mmole), n-octyl bromide of 2.32 g (12 mmole) and potassium carbonate of 0.96 g, and they were reacted at 60° C. for 5 hours. After finishing the reaction, water was added, and the mixed solution was subjected to extraction with chloroform. Then, chloroform was distilled off, and the residue was refined with silica gel column chromatography (eluent: chloroform), whereby 6-(5'-benzyloxy-2'-pyrimidyl)-2-n-octyloxynaphthalene of 3.74 g was obtained. The phase transition temperatures (° C.) of this compound are shown below:

Production Example 7: production of 6-(5'-benzyloxy-2'-pyrimidyl)-2-n-decyloxynaphthalene The same procedure as described in Production Example 6 was repeated, except that n-decyl bromide was substituted for n-octyl bromide in Production Example 6, whereby 6-(5'-benzyloxy-2'-pyrimidyl)-2-n-decyloxynaphthalene of 4.12 g was obtained. The phase transition temperatures (° C.) of this compound are shown below:

Production Example 8: production of 6-(5'-hydroxy-2'-pyrimidyl)-2-n-octyloxynaphthalene:

Dissolved in ethyl acetate of 100 ml was 6-(5'-benzyloxy-2'-pyrimidyl)-2-n-octyloxynaphthalene of 3.56 g (8 mmole), and 50 weight % hydrous Pd/C of 0.35 g was added thereto. The suspension was stirred for 20 hours under a hydrogen atmosphere, and then Pd/C was removed by filtration. Ethyl acetate was distilled off from the filtrate to obtain 6-(5'-hydroxy-2'-pyrimidyl)-2-n-octyloxynaphthalene of 2.79 g (melting point: 161° C.).

Production Example 9: production of 6-(5'-hydroxy-2'-pyrimidyl)-2-n-decyloxynaphthalene The same procedure as described in Production Example 8 was repeated, except that 6-(5'-benzyloxy-2'-pyrimidyl)2-n-decyloxynaphthalene was substituted for 6-(5'-benzyloxy-2'-pyrimidyl)-2-n-octyloxynaphthalene in Production Example 8, whereby 6-(5'-hydroxy-2'-pyrimidyl)-2-n-decyloxynaphthalene of 2.98 g was obtained (melting point: 159° C.).

Example 1: production of 6-(5'-benzyloxy-2'-pyrimidyl)-2-(2"-n-hexyloxyethoxy)naphthalene Suspended in N,N-dimethylformamide of 10 ml were 6-(5'-benzyloxy-2'-pyrimidyl)-2-hydroxynaphthalene of 3.28 g (10 mmole), tosylate of ethylene glycol mono-n-hexyl ether of 3.60 g (12 mmole) and potassium carbonate of 0.96 g, and they were reacted at 60° C. for 5 hours. After finishing the reaction, water was added, and the mixed solution was subjected to extraction with chloroform. Then, chloroform was distilled off, and the residue was refined with silica gel column chromatography (eluent: chloroform), whereby 6-(5'-benzyloxy-2'-pyrimidyl)-2-(2"-n-hexyloxyethoxy)-naphthalene of 4.14 g was obtained (melting point: 112° C.).

Example 2: production of 6-(5'-benzyloxy-2'-pyrimidyl)-2-(2"-n-butoxyethoxy)naphthalene The same procedure as described in Example 1 was repeated, except that tosylate of ethylene glycol mono-n-butyl ether was substituted for tosylate of ethylene glycol mono-n-hexyl ether in Example 1, whereby 6-(5'-benzyloxy-2'-pyrimidyl)-2-(2"-n-butoxyethoxy) naphthalene of 3.67 g was obtained (melting point: 119° C.).

Example 3: production of 6-(5'-benzyloxy-2'-pyrimidyl)-2-n-octylcarnbonyloxynaphthalene Triethylamine of 1.11 g was dropwise added to a solution of 6-(5'-benzyloxy-2'-pyrimidyl)-2-hydroxy-naphthalene of 3.28 g (10 mmole), pelargonoyl chloride of 2.11 g (11 mmole) and chloroform of 30 ml while cooling on ice, and then the reaction was continued at room temperature for 5 hours. After finishing the reaction, a hydrochloric acid aqueous solution was added for neutralization, and an organic layer was separated and washed with water. Then, chloroform was distilled off, and the residue was refined with silica gel column chromatography (eluent: chloroform), whereby 6-(5'-benzyloxy-2'-pyrimidyl)-2-n-octylcarnbonyloxy-naphthalene of 4.19 g was obtained. The phase transition temperatures (° C) of this compound are shown below:

Example 4: production of 6-(5'-benzyloxy-2'-pyrimidyl)-2-n-octyloxycarbonyloxynaphthalene The same procedure as described in Example 3 was repeated, except that n-octyl chloroformate was substituted for pelargonoyl chloride in Example 3, whereby 6-(5'-benzyloxy-2'-pyrimidyl)-2-n-octyloxycarbonyloxynaphthalene of 4.45 g was obtained. The phase transition temperatures (° C.) of this compound are shown below:

Example 5: production of 6-(5'-benzyloxy-2'-pyrimidyl)-2-{4''-[2-(2-n-hexyloxyethoxy)ethoxy]phenylcarbonyloxy}-naphthalene Dissolved in chloroform of 30 ml were 6-(5'-benzyloxy-2'-pyrimidyl)-2-hydroxynaphthalene of 3.28 g (10 mmole), 4-[2'-(2''-n-hexyloxyethoxy)ethoxy]benzoic acid of 3.10 g (10 mmole), 4-pyrrolidinopyridine of 0.20 g and DCC of 2.06 g, and they were reacted at room temperature for 5 hours. After finishing the reaction, insolubles were filtrated. Then, chloroform was distilled off, and the residue was refined with silica gel column chromatography (eluent: chloroform), whereby 6-(5'-benzyloxy-2'-pyrimidyl)-2-{4''-[2-(2-n-hexyloxyethoxy)ethoxy]phenylcarbonyloxy}naphthalene of 5.83 g was obtained. The phase transition temperatures (° C.) of this compound are shown below:

Example 6: production of 6-(5'-benzyloxy-2'-pyrimidyl)-2-[4''-(2-n-hexyloxyethoxy)phenylcarbonyloxy]naphthalene The same procedure as described in Example 5 was repeated, except that 4-(2'-n-hexyloxyethoxy)benzoic acid was substituted for 4-[2'-(2''-n-hexyloxyethoxy)ethoxy]-benzoic acid in Example 5, whereby 6-(5'-benzyloxy-2'-pyrimidyl)-2-[4''-(2-n-hexyloxyethoxy)phenylcarbonyloxy]-naphthalene of 4.91 g was obtained. The phase transition temperatures (° C.) of this compound are shown below:

Example 7: production of 6-(5'-hydroxy-2'-pyrimidyl)-2-(2''-n-hexyloxyethoxy)naphthalene Dissolved in ethyl acetate of 100 ml was 6-(5'-benzyloxy-2'-pyrimidyl)-2-(2''-n-hexyloxyethoxy)naphthalene of 3.76 g (8 mmole) and 50 weight % hydrous Pd/C of 0.37 g was added thereto. The suspension was stirred for 8 hours under a hydrogen atmosphere, and then Pd/C was removed by filtration. Ethyl acetate was distilled off from the filtrate to obtain 6-(5'-hydroxy-2'-pyrimidyl)-2-(2''-n-hexyloxyethoxy)naphthalene of 2.97 g (melting point: 143° C.).

Example 8: production of 6-(5'-hydroxy-2'-pyrimidyl)-2-(2''-n-butyloxyethoxy)naphthalene The same procedure as described in Example 7 was repeated, except that 6-(5'-benzyloxy-2'-pyrimidyl)-2-(2''-n-butoxyethoxy)naphthalene was substituted for 6-(5'-benzyloxy-2'-pyrimidyl)-2-(2''-n-hexyloxyethoxy)naphthalene in Example 7, whereby 6-(5'-hydroxy-2'-pyrimidyl)-2-(2''-n-butoxyethoxy)naphthalene of 2.98 g was obtained (melting point: 146° C.).

Example 9: production of 6-(5'-hydroxy-2'-pyrimidyl)-2-n-octylcarbonyloxynaphthalene The same procedure as described in Example 7 was repeated, except that 6-(5'-benzyloxy-2'-pyrimidyl)-2-n-octylcarbonyloxynaphthalene was substituted for 6-(5'-benzyloxy-2'-pyrimidyl)-2-(2''-n-hexyloxyethoxy)naphthalene in Example 7, whereby 6-(5'-hydroxy-2'-pyrimidyl)-2-n-octylcarbonyloxynaphthalene of 3.10 g was obtained (melting point: 138° C.).

Example 10: production of 6-(5'-hydroxy-2'-pyrimidyl)-2-n-octyloxycarbonyloxynaphthalene The same procedure as described in Example 7 was repeated, except that 6-(5'-benzyloxy-2'-pyrimidyl)-2-n-octyloxycarbonyloxynaphthalene was substituted for 6-(5'-benzyloxy-2'-pyrimidyl)-2-(2''-n-hexyloxyethoxy)naphthalene in Example 7, whereby 6-(5'-hydroxy-2'-pyrimidyl)-2-n-octyloxycarbonyloxynaphthalene of 3.10 g was obtained (melting point: 143° C.).

Example 11: production of 6-(5'-hydroxy-2'-pyrimidyl)-2-{4''-[2-(2-n-hexyloxyethoxy)ethoxy]phenylcarbonyloxy}naphthalene The same procedure as described in Example 7 was repeated, except that 6-(5'-benzyloxy-2'-pyrimidyl)-2-{4''-[2-(2-n-hexyloxyethoxy)ethoxy]phenylcarbonyloxy}naphthalene was substituted for 6-(5'-benzyloxy-2'-pyrimidyl)-2-(2''-n-hexyloxyethoxy)naphthalene in Example 7, whereby 6-(5'-hydroxy-2'-pyrimidyl)-2-{4''-[2-(2-n-hexyloxyethoxy)ethoxy]-phenylcarbonyloxy}naphthalene of 4.13 g was obtained (melting point: 133° C.).

Example 12: production of 6-(5'-hydroxy-2'-pyrimidyl)-2-{4''-[2-n-hexyloxyethoxy)phenylcarbonyloxy}naphthalene The same procedure as described in Example 7 was repeated, except that 6-(5'-benzyloxy-2'-pyrimidyl)-2-[4''-(2-n-hexyloxyethoxy)phenylcarbonyloxy}naphthalene was substituted for 6-(5'-benzyloxy-2'-pyrimidyl)-2-(2''-n-hexyloxyethoxy)naphthalene in Example 7, whereby 6-(5'-hydroxy-2'-pyrimidyl)-2-{4''-(2-n-hexyloxyethoxy)phenylcarbonyloxy}naphthalene of 4.13 g was obtained (melting point: 143° C.).

Example 13: production of Exemplified Compound 13

Dissolved in acetic anhydride of 90 ml were 6-(5'-n-octyloxy-2'-pyrimidyl)-2-hydroxynaphthalene of 8.78 g (25 mmole) and sodium acetate of 63 mg, and they were reacted at 100° C. for 30 minutes. After finishing the reaction, water was added, and the mixed solution was subjected to extraction with toluene. A toluene layer was separated and washed with water, and then toluene was distilled off to obtain a white solid. The resulting white solid was refined with silica gel column chromatography (eluent: toluene), and further, recrystallization was carried out twice from isopropanol, whereby Exemplified Compound 13 of 8.00 g was obtained in the form of colorless crystal. The phase transition temperatures of this compound are shown in Table 4.

$^1$H-NMR (CDCl$_3$; ppm) δ=0.8 to 2.0 (m, 15H), 2.3 (s, 3H), 4.1 (t, 2H), 7.3 (m, 1H), 7.5 (d, 1H), 8.0 (t, 2H), 8.4 (m, 3H), 8.9 (s, 1H)

Example 14: production of Exemplified Compound 14

Dissolved in chloroform of 10 ml were 6-(5'-n-decyl-2'-pyrimidyl)-2-hydroxynaphthalene of 361 mg (1.0 mmole), palmitic acid of 256 mg (1.0 mmole), 4-pyrrolidinopyridine of 21 mg and DCC of 206 mg, and the solution was stirred at room temperature for 15 hours. Then, insolubles were filtrated, and chloroform was distilled off. The residue was refined with silica gel column chromatography (eluent: chloroform), and further, recrystallization was carried out twice from isopropanol, whereby Exemplified Compound 14 of 492 mg was obtained in the form of colorless crystal. The phase transition temperatures of this compound are shown in Table 4.

$^1$H-NMR (CDCl$_3$; ppm) δ=0.8 to 1.8 (m, 48H), 2.6 (dt, 4H), 7.2 (d, 2H), 7.4 (d, 2H), 7.8 (s, 1H), 7.2 (m, 2H), 7.9 (t, 2H), 8.5 (d, 1H), 8.6 (s, 2H), 8.9 (s, 1H)

Examples 15 to 50:

Used were 6-(5'-substituted-2'-pyrimidyl)-2-hydroxynaphthalene shown in Table 3 or 6-(5'-hydroxy-2'-pyrimidyl)-2-substituted naphthalene and various carboxylic acids to produce the pyrimidine compounds according to the procedure described in Example 14. The phase transition temperatures of these compounds are shown in Table 4.

A compound represented by Formula (10) of 5.0 weight % was added as a chiral component to the compound obtained in Example 31, and the tilt angle (θ) was measured:

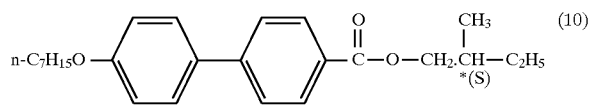

Figure 2:
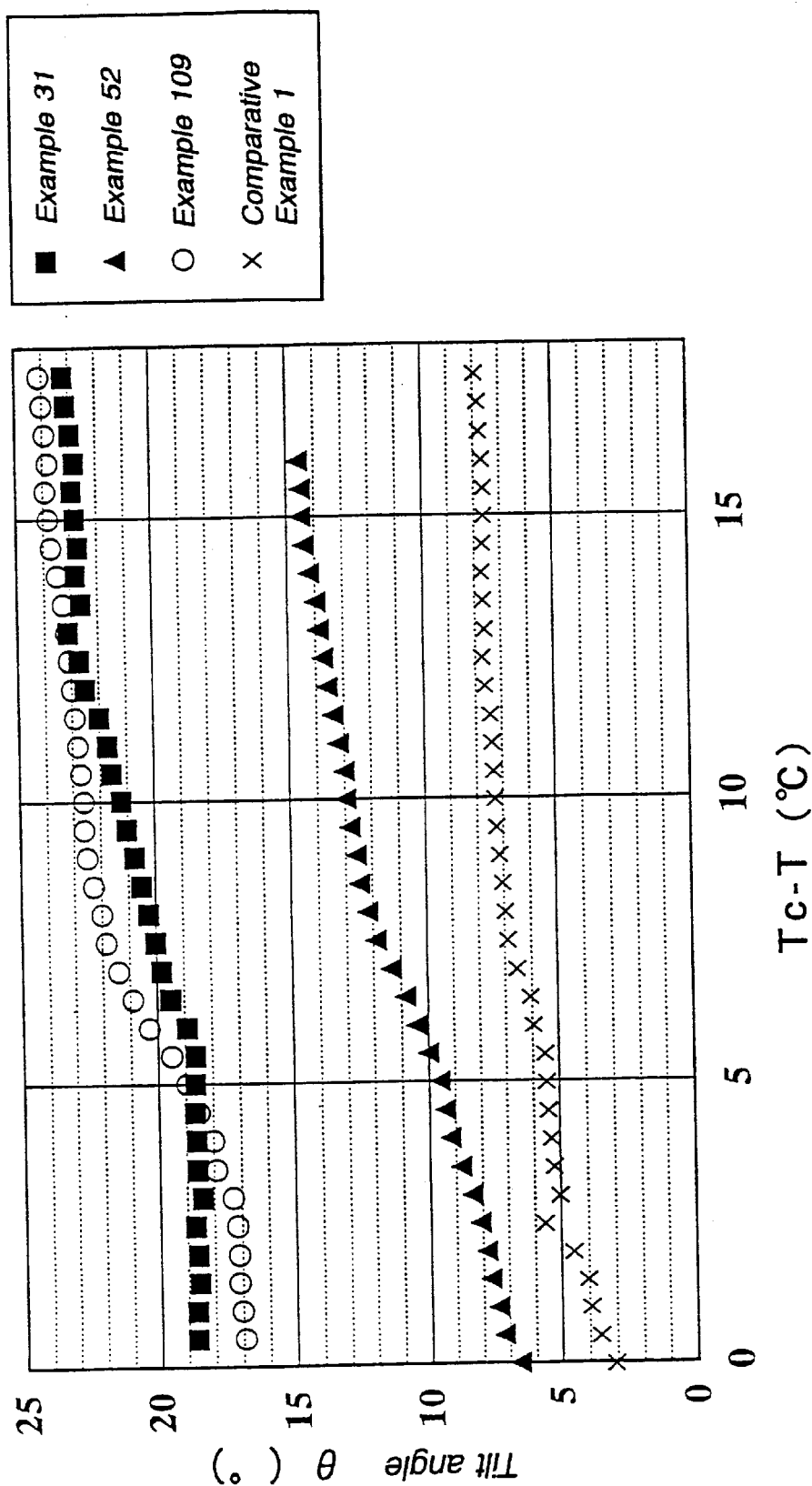
FIG. 2 is a graph showing the tilt angles and their temperature dependency of the compounds of examples and a comparative example.

The tilt angle (θ) was determined from a difference (2θ) between two angles residing in switching states, which was observed under a polarizing microscope when applying a rectangular wave (1 Hz) of ±10 V, wherein a glass-made test cell having a cell gap of about 2 μm and comprising ITO electrodes and rubbed oriented films of polyvinyl alcohol (PVA) was used and filled with a liquid crystal compound. The results thereof are shown in FIG. 2, wherein Tc represents temperatures at which the phases are converted to the Sc* phases in a temperature descending step, and T represents measuring temperatures. It is apparent from FIG. 2 that the pyrimidine compounds of the present invention have relatively large tilt angles (about 20°) and a temperature dependency of the tilt angles (change in tilt angles due to a change in temperature) is small. The observation of the test cells under the polarizing microscope revealed a good and even orientation state.

Comparative Example 1

For the sake of comparison, the compound of Formula (11) (the compound described in Japanese Patent Application No. 6-40985) (1994) was produced to determine the tilt angle. It was measured in the same manner as the tilt angle of the compound produced in Example 31 was determined. The results thereof are shown in FIG. 2. As apparent from FIG. 2, the compound of Formula (11) has a relatively small tilt angle.

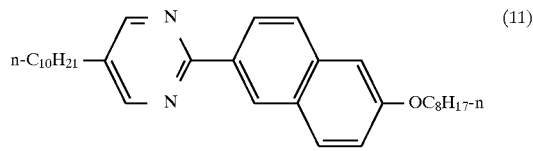

Example 51: production of Exemplified Compound 183

Dissolved in tetrahydrofuran of 16 ml were 6-(5'-n-decyloxycarbonyl-2'-pyrimidyl)-2-hydroxynaphthalene of 406 mg (1.0 mmole), n-decyl alcohol of 158 mg (1.0 mmole) and triphenylphosphine of 262 mg, and diethylazocarboxylic acid of 0.19 ml was added to this solution while cooling on ice. Then, they were reacted at room temperature for 12 hours. After finishing the reaction, tetrahydrofuran was distilled off, and the residue was refined with silica gel column chromatography (eluent: chloroform). Further, recrystallization was carried out twice from methanol-ethyl acetate, whereby Exemplified Compound 183 of 415 mg was obtained in the form of colorless crystal. The phase transition temperatures of this compound are shown in Table 4.

Example 52: production of Exemplified Compound 202

Triethylamine of 111 mg was dropwise added to a solution of 6-(5'-n-decyl-2'-pyrimidyl)-2-hydroxy-naphthalene of 389 mg (1.0 mmole), n-octyl chloroformate of 212 mg (1.1 mmole) and chloroform of 10 ml while cooling on ice, and then the reaction was continued at room temperature for 5 hours. After finishing the reaction, a hydrochloric acid aqueous solution was added for neutralization, and an organic layer was separated and washed with water. Then, chloroform was distilled off, and the residue was refined with silica gel column chromatography (eluent: chloroform), followed by carrying out recrystallization twice from methanol, whereby Exemplified Compound 202 of 440 mg was obtained in the form of colorless crystal. The phase transition temperatures of this compound are shown in Table 4.

The tilt angle of the above compound was measured in the same manner as the tilt angle of the compound produced in Example 31 was determined. The results thereof are shown in FIG. 2. As apparent from FIG. 2, the pyrimidine compound of the present invention has a larger tilt angle than those of conventional compounds. The observation of the test cell under the polarizing microscope revealed a good and even orientation state.

Examples 53 to 60:

Used were 6-(5'-substituted-2'-pyrimidyl)-2-hydroxynaphthalene shown in Table 3 or 6-(5'-hydroxy-2'-pyrimidyl)-2-substituted naphthalene to produce the pyrimidine compounds according to the procedure described in Example 52. The phase transition temperatures of these compounds are shown in Table 4.

Example 61: production of Exemplified Compound 279

Suspended in N,N-dimethylformamide of 2 ml were 6-(5'-n-octyloxy-2'-pyrimidyl)-2-hydroxynaphthalene of 350 mg (1.0 mmole) and potassium carbonate of 138 mg, and added thereto was a solution prepared by dissolving 4-(3',5',5'-trimethylhexyloxy)benzyl bromide of 313 mg in N,N-dimethylformamide of 3 ml. After stirring for 4 hours, chloroform and hydrochloric acid were added, and a chloroform layer was separated. Further, the chloroform layer was washed with water, and then chloroform was distilled off. The residue was refined with silica gel column chromatography (eluent: toluene), and further, recrystallization was carried out twice from isopropanol, whereby Exemplified Compound 279 of 466 mg was obtained in the form of colorless crystal. The phase transition temperatures of this compound are shown in Table 4.

$^1$H-NMR (CDCl$_3$; ppm) δ=0.9 to 1.8 (m, 32H), 3.9 (t, 2H), 4.1 (t, 2H), 5.1 (s, 2H), 6.9 (d, 2H), 7.2 (m, 3H), 7.4 (d, 2H), 7.8 (dd, 2H), 8.4 (d, 1H), 8.5 (s, 1H), 8.8 (s, 1H)

Examples 62 to 69:

Used were 6-(5'-substituted-2'-pyrimidyl)-2-hydroxynaphthalene shown in Table 3 or 6-(5'-hydroxy-2'-pyrimidyl)-2-substituted naphthalene and 4-substituted-benzyl bromide to produce the pyrimidine compounds according to the procedure described in Example 61. The phase transition temperatures of these compounds are shown in Table 4.

Example 70: production of Exemplified Compound 375

Dissolved in chloroform of 10 ml were 6-(5'-n-decyl-2'-pyrimidyl)-2-hydroxynaphthalene of 361 mg (1.0 mmole), 4-n-undecyloxybenzoic acid of 306 mg (1.0 mmole), 4-pyrrolidinopyridine of 21 mg and DCC of 206 mg, and the solution was stirred at room temperature for 15 hours. Then, insolubles were filtrated off, and chloroform was distilled off. The residue was refined with silica gel column chromatography (eluent: chloroform), and then recrystallization was carried out twice from isopropanol, whereby Exemplified Compound 375 of 492 mg was obtained in the form of colorless crystal. The phase transition temperatures of this compound are shown in Table 4.

$^1$H-NMR (CDCl$_3$; ppm) δ=0.9 to 1.8 (m, 44H), 2.7 (t, 2H), 4.1 (t, 2H), 7.0 (d, 2H), 7.4 (d, 2H), 7.8 (s, 1H), 8.0 (d, 1H), 8.1 (d, 1H), 8.2 (d, 2H), 8.6 (d, 1H), 8.7 (s, 2H), 9.0 (s, 1H)

Examples 71 to 89:

Used were 6-(5'-substituted-2'-pyrimidyl)-2-hydroxynaphthalene shown in Table 3 or 6-(5'-hydroxy-2'-pyrimidyl)-2-substituted naphthalene and 4-substituted benzoic acid, 4-substituted-cyclohexanecarboxylic acid or 6-substituted nicotinic acid to produce the pyrimidine compounds according to the procedure described in Example 70. The phase transition temperatures of these compounds are shown in Table 4.

The tilt angle of the compound produced in Example 79 was measured in the same manner as the tilt angle of the compound produced in Example 31 was determined. The results thereof are shown below.

Tilt angle (°) 37.5 [Tc-10° C.] 41.3 [Tc-20° C.]wherein Tc represents temperature at which the phase is converted to the Sc phase in a temperature descending step.

It can be found that the pyrimidine compound of the present invention has a large tilt angle.

Example 90: production of Exemplified Compound 498

Dissolved in tetrahydrofuran of 5 ml were 6-[5'-(4"-n-octyloxyphenyl)-2'-pyrimidyl]-2-hydroxy naphthalene of 426 mg (1.0 mmole), 3,5,5-trimethylhexanol of 144 mg and triphenylphosphine of 262 mg, and the solution was cooled on ice. Diethylazodicarboxylic acid of 0.19 ml was added thereto, and the solution was stirred at room temperature for 15 hours. Then, tetrahydrofuran was distilled off, and the residue was refined with silica gel column chromatography (eluent: toluene). Further, recrystallization was carried out twice from isopropanolethyl acetate, whereby Exemplified Compound 498 of 425 mg was obtained in the form of colorless crystal. The phase transition temperatures of this compound are shown in Table 4.

$^1$H-NMR (CDCl$_3$; ppm) δ=0.8 to 1.9 (m, 32H), 4.0 (t, 2H), 4.1 (t, 2H), 7.0 (d, 2H), 7.2 (m, 2H), 7.6 (d, 2H), 7.8 (dd, 2H), 8.5 (d, 1H), 8.9 (s, 1H), 9.0 (s, 1H)

Examples 91 to 92:

The pyrimidine compounds were produced in the same manner as described in Example 90, except that R-2-octanol and S-(+)-4-methyl-1-hexanol were substituted for 3,5,5-trimethylhexanol. The phase transition temperatures of these compounds are shown in Table 4.

Example 93: production of Exemplified Compound 494

Exemplified Compound 494 was produced in the same manner as described in Example 13, except that 6-[5'-(4"-n-octyloxyphenyl)-2'-pyrimidyl]-2-hydroxynaphthalene was substituted for 6-(5'-n-octyloxy-2'-pyrimidyl)-2-hydroxynaphthalene. The phase transition temperatures of these compounds are shown in Table 4.

Example 94: production of Exemplified Compound 672

Dissolved in tetrahydrofuran of 16 ml were 6-(5'-n-octyloxy-2'-pyrimidyl)-2-hydroxynaphthalene of 350 mg, ethylene glycol mono-n-hexyl ether of 161 mg and triphenylphosphine of 262 mg, and diethylazo-dicarboxylic acid of 0.19 ml was added to this solution while cooling on ice, followed by reacting them at room temperature for 12 hours. Then, tetrahydrofuran was distilled off, and the residue was refined with silica gel column chromatography (eluent: toluene). Further, recrystallization was carried out twice from methanol, whereby Exemplified Compound 672 of 366 mg was obtained in the form of colorless crystal. The phase transition temperatures of this compound are shown in Table 4.

$^1$H-NMR (CDCl$_3$; ppm) δ=0.7 to 1.8 (m, 26H), 3.48 (t, 2H), 3.5 to 4.4 (m, 6H), 7.0 to 7.3 (m, 2H), 7.7 to 8.0 (m, 2H), 8.4 (bs, 1H), 8.48 (s, 2H), 8.8 (bs, 1H)

Examples 95 to 100:

Used were 6-(5'-substituted-2'-pyrimidyl)-2-hydroxynaphthalene shown in Table 3 or 6-(5'-hydroxy-2'-pyrimidyl)-2-substituted naphthalene and alkoxyalcohols to produce the pyrimidine compounds according to the procedure described in Example 94. The phase transition temperatures of these compounds are shown in Table 4.

Example 101: production of Exemplified Compound 673

Suspended in N,N-dimethylformamide of 5 ml were 6-(5'-n-teradecyloxy-2'-pyrimidyl)-2-hydroxynaphthalene of 433 mg, tosylate of diethylene glycol monohexyl ether of 413 mg and potassium carbonate of 140 mg, and the suspension was heated to 60° C. and stirred for 12 hours. Then, chloroform of 20 ml and ½normal hydrochloric acid were added to the reaction solution to neutralize. A chloroform layer was separated and washed with water twice. Then, chloroform was distilled off, and the residue was refined with silica gel column chromatography (eluent: chloroform/hexane/ethyl acetate=10:3:1 vol/vol/vol). Further, recrystallization was repeated twice from methanol, whereby Exemplified Compound 673 of 398 mg was obtained in the form of colorless crystal. The phase transition temperatures of this compound are shown in Table 4.

$^1$H-NMR (CDCl$_3$; ppm) δ=0.7 to 1.6 (m, 38H), 3.48 (t, 2H), 3.5 to 4.48 (m, 10H), 7.1 to 7.3 (m, 2H), 7.7 to 8.0 (m, 2H), 8.4 to 8.6 (m, 1H), 8.64 (s, 2H), 8.8 (bs, 1H)

Examples 102 to 122:

Used were 6-(5'-substituted-2'-pyrimidyl)-2-hydroxynaphthalene shown in Table 3 or 6-(5'-hydroxy-2-pyrimidyl)-2-substituted naphthalene and tosylates of alkoxyalcohols to produce the pyrimidine compounds according to the procedure described in Example 101. The phase transition temperatures of these compounds are shown in Table 4.

The tilt angle of the compound produced in Example 109 was measured in the same manner as the tilt angle of the compound produced in Example 31 was determined. The results thereof are shown in FIG. 2. It is apparent from FIG. 2 that the pyrimidine compound of the present invention has a relatively large tilt angle (about 20°) and a temperature dependency of tilt angles is small. The observation of the test cell under a polarizing microscope revealed the good and even orientation state.

TABLE 4

| Example No. | Structure | C | $S_X$ | $S_C$ | $S_A$ | N | I |
|---|---|---|---|---|---|---|---|
| 13 | naphthalene with pyrimidine, n-C$_8$H$_{17}$O– and –OC(=O)CH$_3$ | ● 95 | — | ● 103 | ● 127 | ● 129 | ● |
| 14 | naphthalene with pyrimidine, n-C$_{10}$H$_{21}$– and –OC(=O)C$_{15}$H$_{31}$-n | ● 63 | ● 78 | ● 92 | ● 96 | — | ● |
| 15 | naphthalene with pyrimidine, n-C$_{12}$H$_{25}$O– and –OC(=O)C$_{15}$H$_{31}$-n | ● 72 | ● (55) | ● 95 | ● 121 | — | ● |
| 16 | naphthalene with pyrimidine, n-C$_{14}$H$_{29}$O– and –OC(=O)C$_{15}$H$_{31}$-n | ● 67 | ● 100 | ● 118 | ● 121 | — | ● |
| 17 | naphthalene with pyrimidine, n-C$_8$H$_{17}$– and –OC(=O)C$_{15}$H$_{31}$-n | ● 84 | — | ● (78) | ● 85 | ● 91 | ● |
| 18 | naphthalene with pyrimidine, n-C$_8$H$_{17}$O– and –OC(=O)C$_{15}$H$_{31}$-n | ● 87 | — | ● 101 | ● 116 | ● 117 | ● |

Phase transition temperature (°C.)

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 19 | (CH$_3$)$_3$CCH$_2$CH(CH$_3$)CH$_2$—[pyrimidine]—[naphthalene]—O—C(=O)—C$_{15}$H$_{31-n}$ | ● 65 | — | — | — | — | ● |
| 20 | (CH$_3$)$_3$CCH$_2$CH(CH$_3$)CH$_2$CH$_2$O—[pyrimidine]—[naphthalene]—O—C(=O)—C$_{15}$H$_{31-n}$ | ● 59 | — | — | — | — | ● |
| 21 | n-C$_{10}$H$_{21}$—[pyrimidine]—[naphthalene]—O—C(=O)—C$_9$H$_{19-n}$ | ● 69 | ● 74 | ● 95 | ● 97 | ● 99 | ● |
| 22 | n-C$_{10}$H$_{21}$—[pyrimidine]—[naphthalene]—O—C(=O)—C$_{10}$H$_{21-n}$ | ● 69 | ● 82 | ● 97 | ● 98 | ● 99 | ● |
| 23 | n-C$_{10}$H$_{21}$—[pyrimidine]—[naphthalene]—O—C(=O)—C$_{11}$H$_{23-n}$ | ● 71 | ● 83 | ● 95 | ● 96 | ● 99 | ● |
| 24 | n-C$_{10}$H$_{21}$—[pyrimidine]—[naphthalene]—O—C(=O)—C$_{12}$H$_{25-n}$ | ● 77 | ● 84 | ● 97 | ● 98 | — | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 25 | n-C$_{10}$H$_{21}$–[naphthalene-CH=N-N=CH]–O–C(=O)–C$_{13}$H$_{27}$-n | ● 73 | ● 86 | ● 96 | ● 98 | — | ● |
| 26 | n-C$_{10}$H$_{21}$–[naphthalene-CH=N-N=CH]–O–C(=O)–C$_{14}$H$_{29}$-n | ● 82 | ● (71) | ● 94 | ● 97 | — | ● |
| 27 | n-C$_{10}$H$_{21}$–[naphthalene-CH=N-N=CH]–O–C(=O)–C$_{17}$H$_{35}$-n | ● 80 | ● (73) | ● 93 | ● 94 | — | ● |
| 28 | n-C$_{10}$H$_{21}$–[naphthalene-CH=N-N=CH]–O–C(=O)–C$_{18}$H$_{37}$-n | ● 82 | ● (75) | ● 92 | ● 93 | — | ● |
| 29 | n-C$_{10}$H$_{21}$–[naphthalene-CH=N-N=CH]–O–C(=O)–C$_{19}$H$_{29}$-n | ● 83 | ● (82) | ● 91 | ● 93 | — | ● |
| 30 | n-C$_{10}$H$_{21}$–[naphthalene-CH=N-N=CH]–O–C(=O)–C$_{21}$H$_{43}$-n | ● 78 | — | ● 90 | ● 91 | — | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 31 | naphthalene with pyrimidine bearing n-$C_{12}H_{25}$ and ester O-CO-$C_9H_{19}$-n | ● 69 | ● 83 | ● 102 | — | — | ● |
| 32 | naphthalene with pyrimidine bearing n-$C_{12}H_{25}$ and ester O-CO-$C_{11}H_{23}$-n | ● 76 | — | ● 102 | — | — | ● |
| 33 | naphthalene with pyrimidine bearing n-$C_{10}H_{21}$ and ester O-CO-$(CH_2)_8CH=CH_2$ | ● 56 | ● 88 | ● 89 | ● 92 | ● 95 | ● |
| 34 | naphthalene with pyrimidine bearing n-$C_{12}H_{25}$ and ester O-CO-$(CH_2)_8CH=CH_2$ | ● 58 | ● 64 | ● 95 | ● 97 | — | ● |
| 35 | naphthalene with pyrimidine bearing n-$C_{12}H_{25}$ and ester O-CO-$C_{15}H_{31}$-n | ● 83 | — | ● 100 | — | — | ● |
| 36 | naphthalene with pyrimidine bearing n-$C_{10}H_{21}$ and ester O-CO-$C_8H_{17}$-n | ● 67 | — | ● 96 | ● 97 | ● 99 | ● |

TABLE 4-continued
| Example No. | Structure | Phase transition temperature (°C.) | | | | | |
|---|---|---|---|---|---|---|---|
| | | C | $S_X$ | $S_C$ | $S_A$ | N | I |
| 37 | 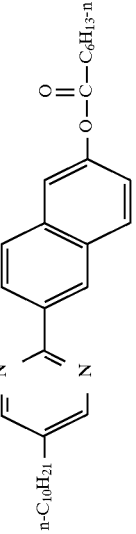 | ● 67 | — | ● 92 | ● 96 | ● 98 | ● |
| 38 | 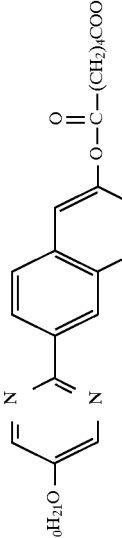 | ● 82 | — | ● (80) | ● 105 | ● 110 | ● |
| 39 | 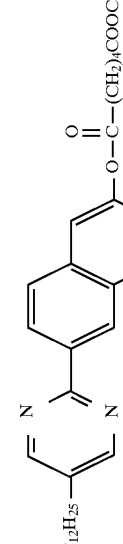 | ● 61 | ● (43) | ● 73 | ● 82 | — | ● |
| 40 | 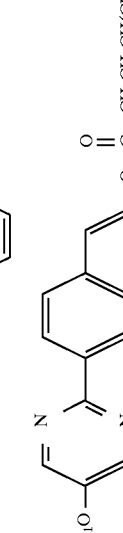 | ● 78 | — 72 | Sc* ● 98 | ● 114 | — | ● |
| 41 | 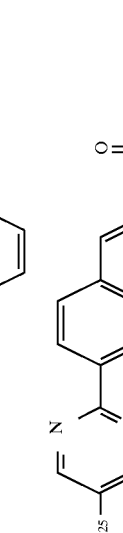 | ● 64 | — | Sc* ● (52) | ● 87 | — | ● |
| 42 | 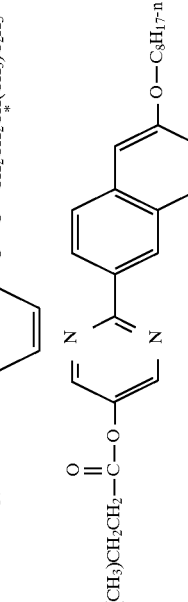 | ● 104 | — | — | — | N* ● (103) | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 43 | naphthalene with $C_2H_5CH(CH_3)CH_2CH_2$-* pyrimidine-COO- and -O-CH$_2$CH$_2$OC$_6$H$_{13}$-n | ● 56 | — | — | — | — | ● |
| 44 | naphthalene with n-C$_9$H$_{19}$-COO- pyrimidine and -O-C$_{10}$H$_{21}$-n | ● 88 | — | — | ● 118 | ● 128 | ● |
| 45 | naphthalene with n-C$_9$H$_{19}$-COO- pyrimidine and -O-CH$_2$CH$_2$OC$_6$H$_{13}$-n | ● 94 | — | — | ● 95 | ● 98 | ● |
| 46 | naphthalene with n-C$_{15}$H$_{31}$-COO- pyrimidine and -O-C$_{10}$H$_{21}$-n | ● 76 | — | — | ● 126 | — | ● |
| 47 | naphthalene with n-C$_{15}$H$_{31}$-COO- pyrimidine and -O-CH$_2$CH$_2$OC$_6$H$_{13}$-n | ● 93 | — | ● 93 | ● 108 | — | ● |
| 48 | naphthalene with n-C$_9$H$_{19}$-COO- pyrimidine and -O-C(=O)-C$_8$H$_{17}$-n | ● 66 | ● 70 | ● 108 | ● 123 | ● 132 | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 49 | n-C$_{12}$H$_{25}$—C(=O)—O—[naphthalene]—CH=N—N=CH—[naphthalene]—O—C(=O)—C$_8$H$_{17}$-n | ● 67 | — | ● 85 | ● 113 | ● 117 | ● |
| 50 | n-C$_{10}$H$_{21}$—O—C(=O)—[naphthalene]—CH=N—N=CH—[naphthalene]—O—C(=O)—C$_9$H$_{19}$-n | ● 127 | — | — | — | — | ● |
| 51 | n-C$_{10}$H$_{21}$—O—C(=O)—[naphthalene]—CH=N—N=CH—[naphthalene]—O—C$_{10}$H$_{21}$-n | ● 115 | — | — | — | — | ● |
| 52 | n-C$_{12}$H$_{25}$—[naphthalene]—CH=N—N=CH—[naphthalene]—O—C(=O)—C$_8$H$_{17}$-n | ● 46 | ● 65 | ● 80 | ● 85 | ● 88 | ● |
| 53 | n-C$_8$H$_{17}$—O—[naphthalene]—CH=N—N=CH—[naphthalene]—O—C(=O)—C$_8$H$_{17}$-n | ● 47 | ● 63 | ● 90 | ● 98 | ● 116 | ● |
| 54 | n-C$_{10}$H$_{21}$—O—[naphthalene]—CH=N—N=CH—[naphthalene]—O—C(=O)—C$_8$H$_{17}$-n | ● 49 | ● 86 | ● 99 | ● 107 | ● 115 | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 55 | n-C₁₄H₂₉—O—[pyrimidine]—[naphthalene]—O—CO—C₈H₁₇-n | ● 53 | ● 90 | ● 105 | ● 114 | — | ● |
| 56 | n-C₈H₁₇—O—CO—[pyrimidine]—[naphthalene]—O—CH₂CH₂OC₆H₁₃-n | ● 88 | — | — | — | ● (80) | ● |
| 57 | n-C₈H₁₇—O—CO—[pyrimidine]—[naphthalene]—O—C₁₀H₂₁-n | ● 100 | — | — | — | ● (114) | ● |
| 58 | n-C₈H₁₇—O—CO—[pyrimidine]—[naphthalene]—O—CO—C₈H₁₇-n | ● 74 | — | ● 74 | ● 88 | ● 116 | ● |
| 59 | n-C₈H₁₇—O—CO—[pyrimidine]—[naphthalene]—O—CO—C₈H₁₇-n | ● 72 | — | — | — | ● 104 | ● |
| 60 | n-C₁₀H₂₁—O—CO—[pyrimidine]—[naphthalene]—O—CO—C₈H₁₇-n | ● 116 | — | — | — | — | ● |

TABLE 4-continued

| Example No. | Structure | C | $S_X$ | $S_C$ | $S_A$ | N | I |
|---|---|---|---|---|---|---|---|
| 61 | n-C$_8$H$_{17}$—O—[pyrimidine]—[naphthalene]—O—CH$_2$—[phenyl]—O—CH$_2$CH$_2$CH(CH$_3$)CH$_2$C(CH$_3$)$_3$ | ● 101 | — | ● 138 | ● 139 | ● 146 | ● |
| 62 | n-C$_8$H$_{17}$—O—[pyrimidine]—[naphthalene]—O—CH$_2$—[phenyl]—O—C$_{12}$H$_{25}$-n | ● 122 | — | ● 156 | — | ● 165 | ● |
| 63 | n-C$_{14}$H$_{29}$—O—[pyrimidine]—[naphthalene]—O—CH$_2$—[phenyl]—O—CH$_2$CH$_2$CH(CH$_3$)CH$_2$C(CH$_3$)$_3$ | ● 101 | — | ● 143 | — | — | ● |
| 64 | n-C$_{10}$H$_{21}$—[pyrimidine]—[naphthalene]—O—CH$_2$—[phenyl]—O—CH$_2$CH$_2$CH(CH$_3$)CH$_2$C(CH$_3$)$_3$ | ● 118 | — | ● (110) | ● 122 | — | ● |
| 65 | n-C$_{10}$H$_{21}$—[pyrimidine]—[naphthalene]—O—CH$_2$—[phenyl]—O—C$_{12}$H$_{25}$-n | ● 112 | — | ● 142 | ● 146 | — | ● |
| 66 | (CH$_3$)$_3$CCH$_2$CH(CH$_3$)CH$_2$—[pyrimidine]—[naphthalene]—O—CH$_2$—[phenyl]—O—CH$_2$CH$_2$CH(CH$_3$)CH$_2$C(CH$_3$)$_3$ | ● 126 | — | — | — | — | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 67 | (CH$_3$)$_3$CH$_2$CH(CH$_3$)CH$_2$–[pyrimidine]–O–CH$_2$–[naphthyl]–O–[phenyl]–O–C$_{12}$H$_{25}$-n | ● 121 | — | — | — | — | ● |
| 68 | (CH$_3$)$_3$CH$_2$CH(CH$_3$)CH$_2$CH$_2$–O–[phenyl]–CH$_2$–O–[pyrimidine]–[naphthyl]–O–C$_8$H$_{17}$-n | ● 119 | — | ● 139 | ● 142 | — | ● |
| 69 | n-C$_{12}$H$_{25}$–O–[phenyl]–CH$_2$–O–[pyrimidine]–[naphthyl]–O–C$_8$H$_{17}$-n | ● 112 | ● (101) | ● 145 | ● 175 | — | ● |
| 70 | n-C$_{10}$H$_{21}$–[pyrimidine]–[naphthyl]–O–C(=O)–[phenyl]–O–C$_{12}$H$_{25}$-n | ● 88 | — | ● 115 | ● 116 | ● 190 | ● |
| 71 | n-C$_{12}$H$_{25}$–[pyrimidine]–[naphthyl]–O–C(=O)–[phenyl(OH)]–O–C$_{10}$H$_{21}$-n | ● 82 | ● 110 | — | — | — 164 | ● |
| 72 | n-C$_{12}$H$_{25}$–[pyrimidine]–[naphthyl]–O–C(=O)–[phenyl]–O–CH$_2$CH$_2$OC$_6$H$_{13}$-n | ● 75 | — | ● (56) | ● 105 | ● 187 | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 73 | n-C$_{10}$H$_{21}$—pyrazine—naphthalene—OC(O)—C$_6$H$_3$F—O—C$_{11}$H$_{23}$-n | ● 94 | — | ● 138 | — | — | ● |
| 74 | n-C$_{10}$H$_{21}$—O—pyrazine—naphthalene—OC(O)—C$_6$H$_4$—O—CH$_2$CH$_2$OC$_6$H$_{13}$-n | ● 84 | — | ● 92 | — | ● 156 | ● |
| 75 | n-C$_{10}$H$_{21}$—O—pyrazine—naphthalene—C(O)O—C$_6$H$_4$—O—C$_{10}$H$_{21}$-n | ● 81 | — | ● 138 | — | ● 209 | ● |
| 76 | C$_2$H$_5$CH(CH$_3$)CH$_2$CH$_2$—O—pyrazine—naphthalene—C(O)O—C$_6$H$_4$—O—(CH$_2$CH$_2$O)$_2$C$_6$H$_{13}$-n | ● 69 | — | — | — | N* ● 129 | ● |
| 77 | n-C$_6$H$_{13}$OCH$_2$CH$_2$—O—pyrazine—naphthalene—OC(O)—C$_6$H$_4$—OC(O)—C$_8$H$_{17}$-n | ● 91 | — | — | — 139 | N ● 193 | ● |
| 78 | n-C$_{11}$H$_{23}$—O—C$_6$H$_3$F—pyrazine—naphthalene—OC(O)—C$_8$H$_{17}$-n | ● 103 | — | ● 189 | — | ● 205 | ● |

TABLE 4-continued

| Example No. | Structure | C | $S_X$ | $S_C$ | $S_A$ | N | I |
|---|---|---|---|---|---|---|---|
| 79 | | ● 102 | — | ● 197 | ● 204 | ● 228 | ● |
| 80 | | ● 98 | — | ● 125 | — | ● 176 | ● |
| 81 | | ● 79 | — | ● 93 | — | ● 168 | ● |
| 82 | | ● 138 | — | — | — | — | ● |
| 83 | | ● 134 | — | ● | — | — | ● |
| 84 | | ● 137 | — | — | — | — | ● |

Phase transition temperature (°C.)

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 85 | | ● 133 | — | — | — | — | ● |
| 86 | | ● 100 | — | ● 100 | ● 125 | ● 200 | ● |
| 87 | | ● 97 | — | ● 128 | ● 132 | ● 191 | ● |
| 88 | | ● 105 | — | — | — | ● 238 | ● |
| 89 | | ● 163 | ● 130 | ● 143 | ● 159 | ● 202 | ● |
| 90 | | ● 102 | ● 181 | ● 193 | ● 198 | ● 200 | ● |

$S_C^*$

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 91 | n-C$_8$H$_{17}$—O—[phenyl]—CH=N—N=CH—[naphthyl]—O—CH(CH$_3$)C$_6$H$_{13}$-n (*) | ● 104 | ● (68) | ● 155 | ● 177 | — | ● |
| 92 | n-C$_8$H$_{17}$—O—[phenyl]—CH=N—N=CH—[naphthyl]—O—CH$_2$CH$_2$CH$_2$CH(CH$_3$)C$_2$H$_5$ (*) | ● 116 | ● 170 | $S_C$* ● 217 | ● 222 | N* ● 230 | ● |
| 93 | n-C$_8$H$_{17}$—O—[phenyl]—CH=N—N=CH—[naphthyl]—O—C(=O)—CH$_3$ | ● 137 | ● (105) | ● 164 | ● 247 | ● 272 | ● |
| 94 | n-C$_8$H$_{17}$—O—[pyridyl]—CH=N—N=CH—[naphthyl]—O—CH$_2$CH$_2$OC$_6$H$_{13}$-n | ● 102 | — | — | ● 98 | ● 129 | ● |
| 95 | n-C$_{10}$H$_{21}$—[pyridyl]—CH=N—N=CH—[naphthyl]—O—CH$_2$CH$_2$OC$_6$H$_{13}$-n | ● 75 | — | — | — | — | ● |
| 96 | n-C$_{10}$H$_{21}$—[pyridyl]—CH=N—N=CH—[naphthyl]—O—CH$_2$CH$_2$OCH$_2$CH$_2$OC$_6$H$_{13}$-n | ● 71 | — | — | — | — | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 97 | n-C$_{10}$H$_{21}$–[pyrimidine]–[naphthalene]–O–(CH$_2$CH$_2$O)$_3$C$_4$H$_9$-n | ● 72 | — | — | — | — | ● |
| 98 | (CH$_3$)$_3$CCH(CH$_3$)CH$_2$–[pyrimidine]–[naphthalene]–O–CH$_2$CH$_2$OCH$_2$CH$_2$OC$_6$H$_{13}$-n | ● 62 | — | — | — | — | ● |
| 99 | n-C$_{12}$H$_{25}$–[pyrimidine]–[naphthalene]–O–CH$_2$CH$_2$OCH$_2$CH$_2$Cl | ● 117 | — | — | — | — | ● |
| 100 | n-C$_{10}$H$_{21}$O–[pyrimidine]–[naphthalene]–O–CH$_2$CH$_2$OCH$_2$CH$_2$Cl | ● 92 | — | ● (61) | ● 96 | ● 104 | ● |
| 101 | n-C$_{14}$H$_{29}$O–[pyrimidine]–[naphthalene]–O–CH$_2$CH$_2$OCH$_2$CH$_2$OC$_6$H$_{13}$-n | ● 54 | — | ● 66 | ● 80 | — | ● |
| 102 | n-C$_{14}$H$_{29}$O–[pyrimidine]–[naphthalene]–O–(CH$_2$CH$_2$O)$_3$C$_4$H$_9$-n | ● 65 | — | ● (49) | ● 69 | — | ● |

TABLE 4-continued

| Example No. | Structure | Phase transition temperature (°C.) | | | | | |
|---|---|---|---|---|---|---|---|
| | | C | $S_X$ | $S_C$ | $S_A$ | N | I |
| 103 | n-$C_{12}H_{25}$—O—[pyrimidine]—[naphthalene]—O—$CH_2CH_2OCH_2CH_2OC_6H_{13}$-n | ● 52 | — | ● 77 | ● 82 | — | ● |
| 104 | n-$C_{12}H_{25}$—O—[pyrimidine]—[naphthalene]—O—$(CH_2CH_2O)_3C_4H_9$-n | ● 58 | — | ● 61 | ● 70 | — | ● |
| 105 | n-$C_8H_{17}$—O—[pyrimidine]—[naphthalene]—O—$CH_2CH_2OCH_2CH_2OC_6H_{13}$-n | ● 63 | — | ● 68 | ● 75 | ● 76 | ● |
| 106 | $(CH_3)_3CCH(CH_3)CH_2CH_2$—O—[pyrimidine]—[naphthalene]—O—$CH_2CH_2OCH_2CH_2OC_6H_{13}$-n | ● 83 | — | — | — | — | ● |
| 107 | n-$C_{12}H_{25}$—O—[pyrimidine]—[naphthalene]—O—$CH_2CH_2OC_6H_{13}$-n | ● 60 | — | ● 78 | ● 99 | — | ● |
| 108 | n-$C_{14}H_{29}$—O—[pyrimidine]—[naphthalene]—O—$CH_2CH_2OC_2H_5$ | ● 85 | — | ● 94 | ● 105 | — | ● |

TABLE 4-continued
| Example No. | | Phase transition temperature (°C.) | | | | | |
|---|---|---|---|---|---|---|---|
| | | C | $S_X$ | $S_C$ | $S_A$ | N | I |
| 109 | 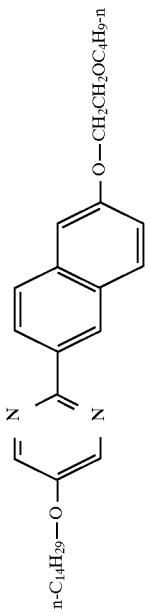 | ● 72 | — | ● 87 | ● 102 | — | ● |
| 110 | 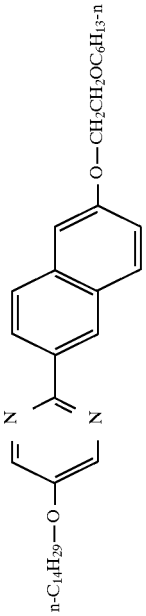 | ● 51 | — | ● 91 | ● 101 | — | ● |
| 111 | 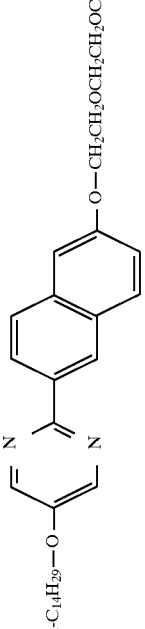 | ● 85 | — | ● (65) | ● 90 | — | ● |
| 112 | 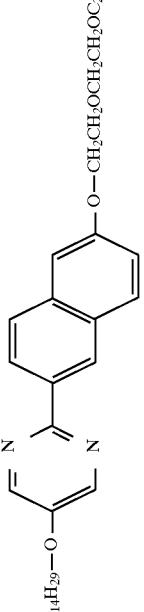 | ● 82 | — | ● (78) | ● 90 | — | ● |
| 113 | 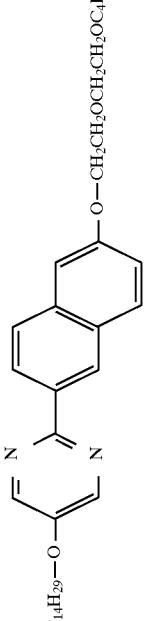 | ● 67 | — | ● 79 | ● 86 | — | ● |
| 114 | 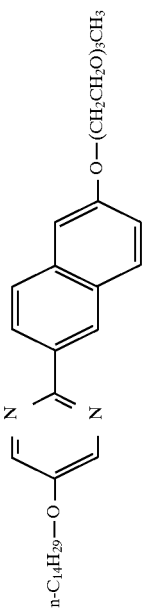 | ● 78 | — | ● (76) | ● 78 | — | ● |

TABLE 4-continued

| Example No. | Structure | C | $S_X$ | $S_C$ | $S_A$ | N | I |
|---|---|---|---|---|---|---|---|
| 115 | n-C$_{14}$H$_{29}$—O—[pyrimidine]—[naphthalene]—O—(CH$_2$CH$_2$O)$_3$C$_2$H$_5$ | ● 66 | — | ● 70 | ● 75 | — | ● |
| 116 | n-C$_{14}$H$_{29}$—O—[pyrimidine]—[naphthalene]—O—CH$_2$CH$_2$OCH(CH$_3$)$_2$ | ● 88 | — | ● 93 | ● 101 | — | ● |
| 117 | n-C$_{14}$H$_{29}$—O—[pyrimidine]—[naphthalene]—O—CH$_2$CH$_2$OCH$_2$CH=CH$_2$ | ● 83 | — | ● 88 | ● 103 | — | ● |
| 118 | n-C$_{14}$H$_{29}$—O—[pyrimidine]—[naphthalene]—O—CH$_2$CH$_2$OCH$_2$CH(CH$_3$)$_2$ | ● 79 | — | ● 86 | ● 102 | — | ● |
| 119 | n-C$_6$H$_{13}$OCH$_2$CH$_2$OCH$_2$CH$_2$—O—[pyrimidine]—[naphthalene]—O—C$_8$H$_{17}$-n | ● 57 | — | — | — | — | ● |
| 120 | n-C$_6$H$_{13}$OCH$_2$CH$_2$—O—[pyrimidine]—[naphthalene]—O—C$_{10}$H$_{21}$-n | ● 74 | — | — | ● (71) | ● 84 | ● |

TABLE 4-continued
| Example No. | | Phase transition temperature (°C.) | | | | |
|---|---|---|---|---|---|---|
| | | C | $S_X$ | $S_C$ | $S_A$ | N | I |
| 121 | (CH$_3$)$_3$CCH$_2$CH(CH$_3$)CH$_2$CH$_2$—O—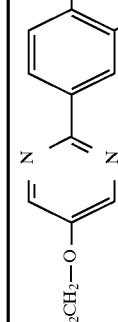—O—(CH$_2$)$_6$OCH$_2$CH(C$_2$H$_5$)C$_4$H$_9$-n | ● 8 | — | — | — | ● −18 | ● |
| 122 | n-C$_4$H$_9$CH(CH$_3$)CH$_2$—O—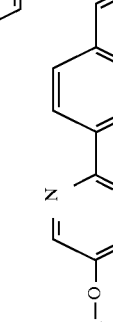—O—(CH$_2$)$_6$OCH$_2$CH(C$_2$H$_5$)C$_4$H$_9$-n | ● <−40 | — | — | — | — | ● |

Example 123: preparation of liquid crystal composition

The following compounds were blended in the folowing ratio and heated at 100° C. to melt, whereby a liquid crystal composition (ferroelectric liquid crystal composition) was prepared.

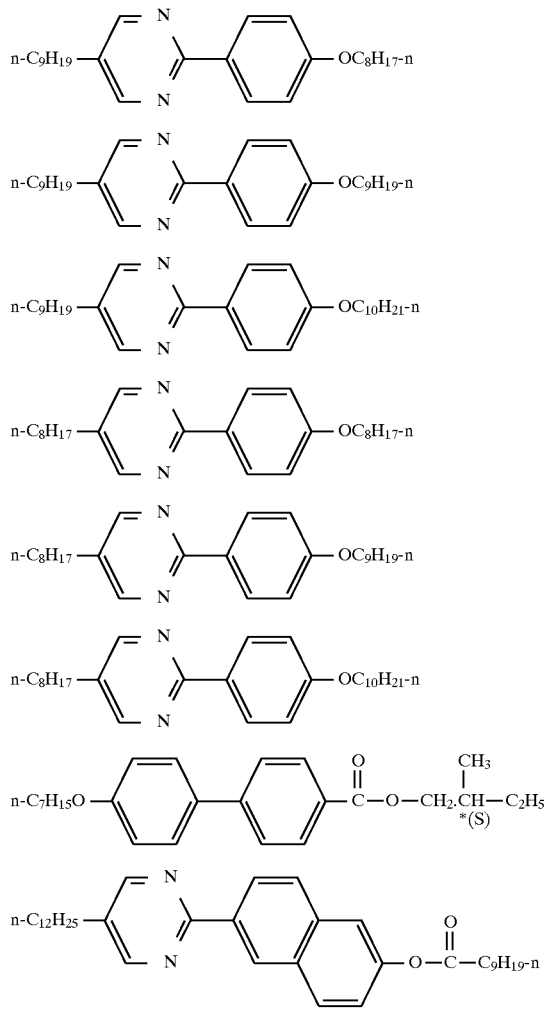

12.6 wt %

12.4 wt %

12.4 wt %

12.4 wt %

12.7 wt %

12.6 wt %

4.0 wt %

20.9 wt %

The phase transition temperatures (° C.) of this liquid crystal composition are shown below:

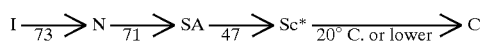

Example 124: preparation of liquid crystal element

Two sheets of glass plates each having a thickness of 1.1 mm were prepared. ITO films were formed on the respective glass plates, and surface treatment was further provided thereon. A liquid crystal orienting agent (CRD 8616 manufactured by Sumitomo Bakelite Co., Ltd.) was spin-coated on the glass plates provided with the ITO film, and after forming a film, the glass plates were pre-baked at 70° C., followed by further baking at 200° C. for one hour. This oriented films were subjected to rubbing treatment. Then, they were washed with isopropyl alcohol, and silica beads having an average particle diameter of 2 μm were sprayed on one glass plate. Thereafter, the glass plates were stuck together with a sealant so that the respective rubbing treatment axes were crossed parallel to each other to prepare a cell as shown in FIG. 1. This cell was charged with the liquid crystal composition prepared in Example 123 to prepare a liquid crystal element. This liquid crystal element was interposed between two sheets of polarizing plates disposed in a cross-nicol state, and a voltage of ±10 V was applied to observe a clear switching phenomenon. Further, observation under a polarizing microscope revealed a good and even orientation state. The optical response time (variation in transmitted light quantity: 10 to 90%) and the tilt angle were measured. The results thereof are shown in Table 5.

Comparative Example 2

For the sake of comparison, the compound of Formula (12) (described in Japanese Patent Application Laid-Open No. 6-228057) (1994) was produced to prepare a liquid crystal composition comprising the following compounds:

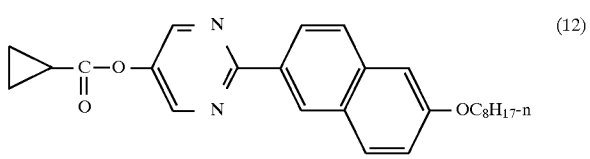

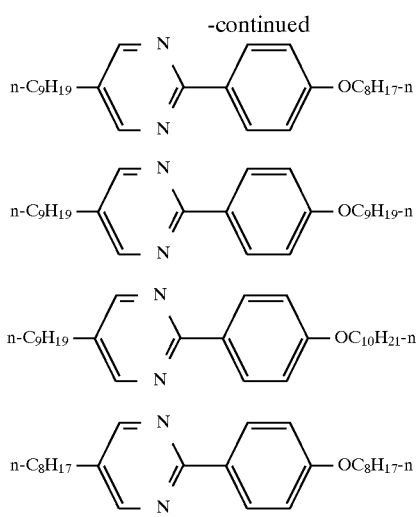

13.4 wt %

13.2 wt %

13.1 wt %

13.2 wt %

-continued 13.7 wt %

13.4 wt %

4.2 wt %

16.0 wt %

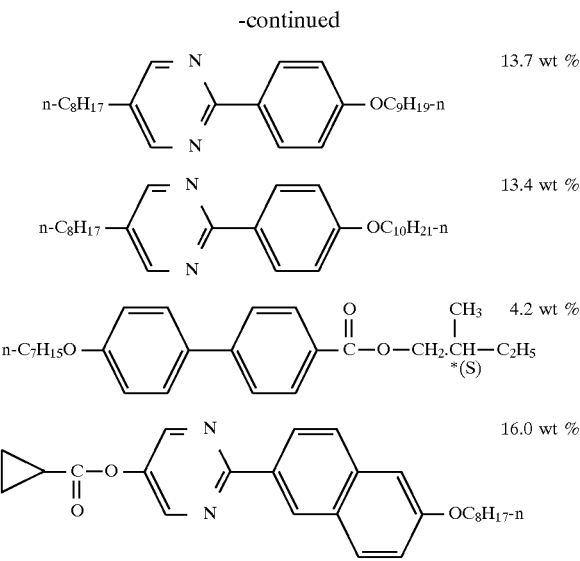

The phase of this liquid crystal composition was changed from an isotropic phase to an N phase at 69° C., and a part thereof was crystallized at 58° C. The crystalline phase and the SA phase were present together at about 53° C., and therefore this liquid crystal composition could not be used for a liquid crystal element.

Example 125: preparation of liquid crystal composition

The following compounds were used in the following mixed ratio to prepare a liquid crystal composition (ferroelectric liquid crystal composition) in the same manner as in Example 123.

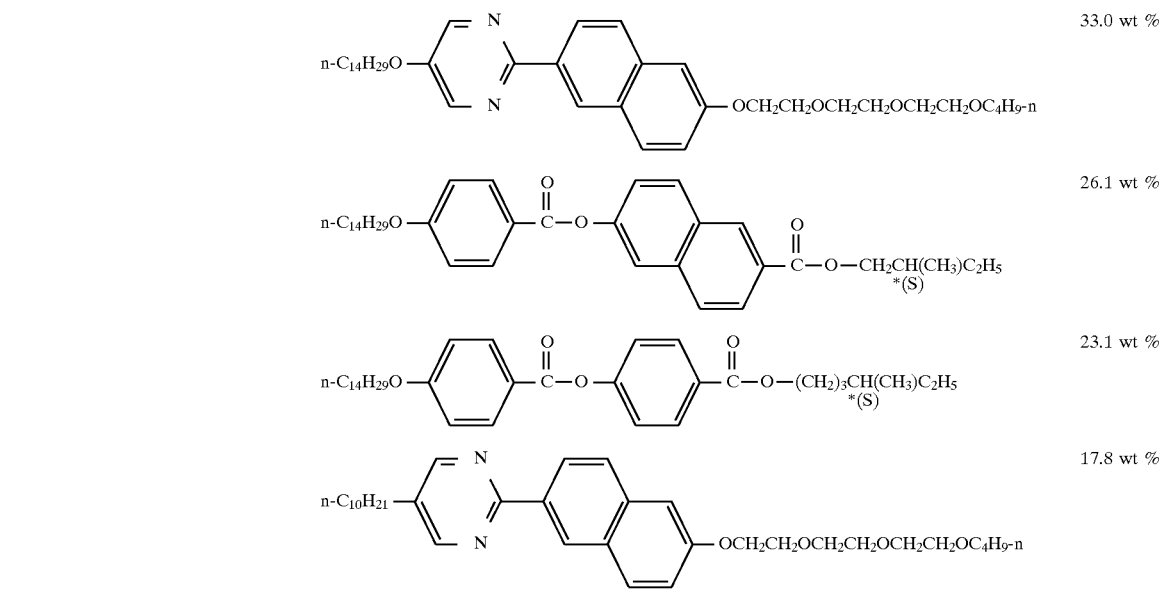

33.0 wt %

26.1 wt %

23.1 wt %

17.8 wt %

The phase transition temperatures (°C.) of this liquid crystal composition are shown below:

Example 126: preparation of liquid crystal element

A liquid crystal element was prepared in the same manner as in Example 124, except that in Example 124, the liquid crystal composition prepared in Example 125 was substituted for the liquid crystal composition prepared in Example 123. Observation under a polarizing microscope revealed a good and even orientation state. The results obtained by measuring the optical response time and the tilt angle are shown in Table 5.

Example 127: preparation of liquid crystal composition

The following compounds were used in the following mixed ratio to prepare a liquid crystal composition (ferroelectric liquid crystal composition) in the same manner as in Example 123.

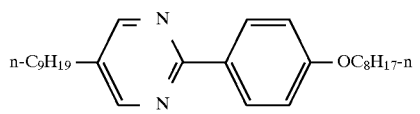  12.9 wt %

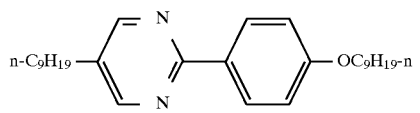  12.7 wt %

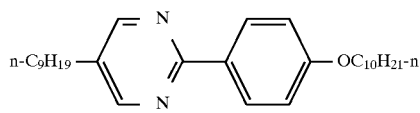  12.7 wt %

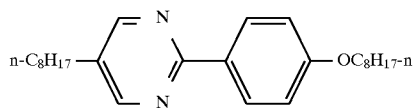  12.7 wt %

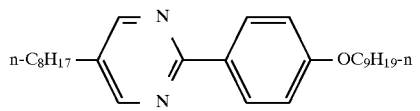  13.1 wt %

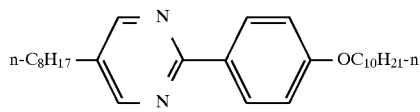  12.9 wt %

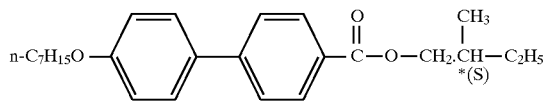  4.1 wt %

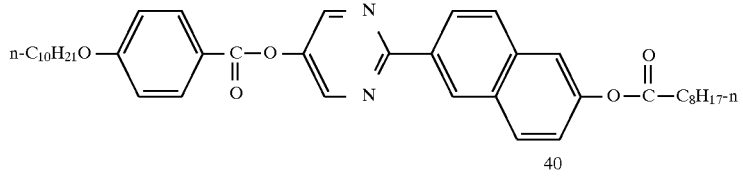  19.0 wt %

The phase transition temperatures (° C.) of this liquid crystal composition are shown below:

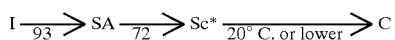

Example 128: preparation of liquid crystal element

A liquid crystal element was prepared in the same manner as in Example 124, except that in Example 124, the liquid crystal composition prepared in Example 127 was substituted for the liquid crystal composition prepared in Example 123. Observation under a polarizing microscope revealed a good and even orientation state. The results of measurement of the optical response time and the tilt angle are shown in Table 5.

Comparative Example 3

For the sake of comparison, a liquid crystal composition containing the compound produced in Comparative Example 1 was prepared.

The phase transition temperatures (°C.) of this liquid crystal composition are shown below:

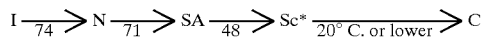

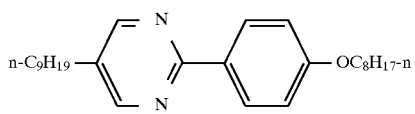  12.9 wt %

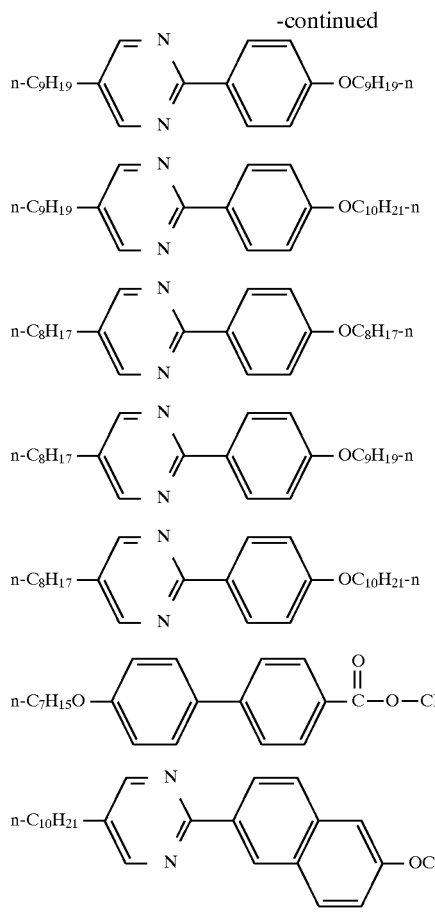

| | |
|---|---|
| | 12.7 wt % |
| | 12.7 wt % |
| | 12.7 wt % |
| | 13.1 wt % |
| | 12.9 wt % |
| | 4.1 wt % |
| | 18.9 wt % |

Further, a liquid crystal element was prepared in the same manner as in Example 124 to measure the optical response time and the tilt angle. The results thereof are shown in Table 5.

It is apparent from the results shown in Table 5 that the liquid crystal composition of the present invention has a large tilt angle and a short response time as compared with those of the liquid crystal composition prepared in Comparative Example 3.

TABLE 5

| | Response time (msec) | | | Tilt angle (°) | | |
|---|---|---|---|---|---|---|
| | Tc-5° C. | Tc-10° C. | Tc-15° C. | Tc-5° C. | Tc-10° C. | Tc-15° C. |
| Example 124 | 0.111 | 0.302 | 0.359 | 14.5 | 16.5 | 21.4 |
| Example 126 | 0.125 | 0.298 | 0.466 | 16.5 | 17.5 | 21.4 |
| Example 128 | 0.142 | 0.322 | 0.451 | 14.4 | 15.5 | 17.6 |
| Comparative Example 3 | 0.252 | 0.473 | 0.544 | 4.2 | 5.3 | 5.5 |

What is claimed is:

1. A pyrimidine compound represented by the following Formula (1):

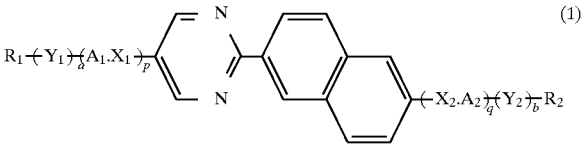

wherein $R_1$, and $R_2$ each represent a linear or branched alkyl group or alkyoxyl group having 1 to 24 carbon atoms or a linear or branched alkenyl group alkenyloxy group having 2 to 24 carbon atoms and each group may be substituted with halogen atoms; the —$CH_2$— groups which are present in said alkyl group, alkoxy group, alkyenyl group and alkenyloxy group, provided that the adjacent —$CH_2$— groups and the —$CH_2$— groups bonded to $Y_1$, $Y_2$ or an aromatic ring are excluded, may be substituted with an oxygen atom, a sulfur atom, a —CO— group, a —COO— group, or a —OCO— group; $R_1$ and $R_2$ may have asymmetric carbon atoms, and said asymmetric carbon atoms may be optically active; $A_1$ and $A_2$ each represent a substituted or unsubstituted 1,4-phenylene group, a pyridine-2,5-diyl group or a trans-1,4-cyclohexylene group; $X_1$ and $X_2$ each represent a connecting group selected from a single bond, a —COO— group, a —OCO— group, a —OCH$_2$— group and a —CH$_2$O— group; $Y_1$ and $Y_2$ each represent a —COO— group or a —OCO— group, provided that when $Y_1$ is a —OCO— group, $R_1$ is not a linear or branched alkoxyl group or alkenyloxy group, and when $Y_2$ is a —COO— group, $R_2$ is not a linear or branched alkoxyl group or alkenyloxy group; and a, b, p and q each represent 0 or 1, provided that a+b+p and q is not 0 and that when a, p and q each are 0, $R_2$ is an alkyl group having no optically active asymmetric carbon atoms, or an alkoxy group, alkenyl group or alkenyloxy group each of which may have optically active asymmetric carbons.

2. A pyrimidine compound as described in claim 1, having liquid crystallinity.

3. A pyrimidine compound as described in claim 1, wherein $R_1$ and $R_2$ in Formula (1) each are an alkyl group, alkoxyl group, alkenyl group or alkenyloxy group having no halogen atom.

4. A pyrimidine compound as described in claim 3, wherein both of $R_1$ and $R_2$ in Formula (1) are an alkyl group, alkoxyl group, alkenyl group or alkenyloxy group having no optically active carbon atoms.

5. A pyrimidine compound as described in claim 1, wherein $A_1$ and $A_2$ in Formula (1) are a substituted or unsubstituted 1,4-phenylene group.

6. A pyrimidine compound as described in claim 2, wherein a+b+p+q is 1 or 2.

7. A pyrimidine compound as described in claim 1, wherein both of $R_1$ and $R_2$ in Formula (1) are an alkyl group, alkoxyl group, alkenyl group or alkenyloxy group having no optically active carbon atoms.

8. A pyrimidine compound as described in claim 1, wherein a+b+p+q is 1 or 2.

9. A liquid crystal composition containing at least one of the pyrimidine compounds as described in claim 1.

10. A liquid crystal element comprising the liquid crystal composition as described in claim 9 disposed between a pair of electrode substrates.

11. A pyrimidine compound represented by the following Formula (2):

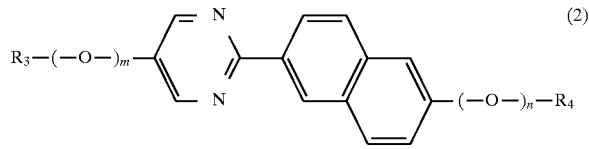

wherein $R_3$ and $R_4$ each represent a linear or branched alkyl group or alkenyl group having 3 to 24 carbon atoms and having no optically active carbon atoms, and each group may be substituted with halogen atoms; m and n each represent 0 or 1; at least one —CH$_2$— group present in the alkyl group or alkenyl group of at least one of $R_3$ and $R_4$ is substituted with an oxygen atom, provided that the adjacent —CH$_2$— groups and the —CH$_2$— groups bonded to oxygen atoms or aromatic rings are excluded.

12. A pyrimidine compound as described in claim 11, wherein m+n in Formula (2) is 1 or 2.

13. A pyrimidine compound as described in claim 11, wherein $R_4$ in Formula (2) is an alkyl group or alkenyl group having at least one oxygen atom.

14. A liquid crystal composition containing at least one of the pyrimidine compounds as described in claim 11.

15. A liquid crystal element comprising the liquid crystal composition as described in claim 14 disposed between a pair of electrode substrates.

16. A pyrimidine compound represented by the following Formula (3) or 4:

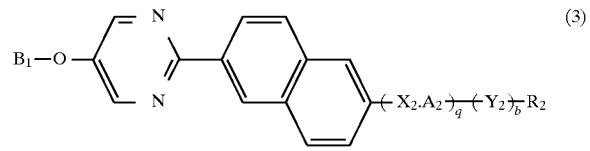

wherein $B_1$ represents a hydrogen atom or a benzyl group; $R_2$ represents a linear or branched alkyl group or alkoxyl group having 1 to 24 carbon atoms or a linear or branched alkenyl group or alkenyloxy group having 2 to 24 carbon atoms and each group may be substituted with halogen atoms; the —CH$_2$— groups (provided that the adjacent —CH$_2$— groups and the —CH$_2$— groups bonded to $Y_1$, $Y_2$ or an aromatic ring are excluded) which are present in said alkyl group, alkoxyl group, alkenyl group and alkenyloxy group may be substituted with an oxygen atom, a sulfur atom, a —CO— group, a —COO— group and a —OCO— group; $R_2$ may have asymmetric carbon atoms, and said asymmetric carbon atoms may be optically active; $A_2$ represents a substituted or unsubstituted 1,4-phenylene group, a pyridine-2,5-diyl group or a trans-1,4-cyclohexylene group; $X_2$ represents a connecting group selected from a single bond, a —COO— group, a —OCO— group, a —OCH$_2$— group and a —CH$_2$O— group; $Y_2$ represents a —COO— group or a —OCO— group (provided that when $Y_2$ is a —COO— group, $R_2$ is not a linear or branched alkoxyl group or alkenyloxy group); and b and q each represent 0 or 1, provided that b+q is not 0;

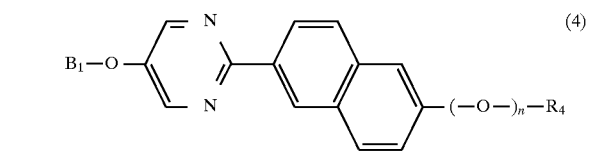

wherein $B_1$ represents a hydrogen atom or a benzyl group; $R_4$ represents a linear or branched alkyl group or alkenyl group which may be substituted with halogen atoms and has 3 to 24 carbon atoms; n represents 0 or 1; at least one —CH$_2$— group (provided that the adjacent —CH$_2$— groups and the —CH$_2$— groups bonded to oxygen atoms or aromatic rings are excluded) present in the alkyl group or alkenyl group of $R_4$ is substituted with an oxygen atom; and the branched alkyl group or alkenyl group may have asymmetric carbon atoms, and said carbon atoms may be optically active.

* * * * *